(12) United States Patent
Crooke et al.

(10) Patent No.: US 10,822,369 B2
(45) Date of Patent: Nov. 3, 2020

(54) COMPOUNDS AND METHODS FOR THE MODULATION OF PROTEINS

(71) Applicant: Ionis Pharmaceuticals, Inc., Carlsbad, CA (US)

(72) Inventors: Stanley T. Crooke, Carlsbad, CA (US); Xue-hai Liang, Del Mar, CA (US); Wen Shen, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 15 days.

(21) Appl. No.: 15/525,232

(22) PCT Filed: Nov. 16, 2015

(86) PCT No.: PCT/US2015/060938
§ 371 (c)(1),
(2) Date: May 8, 2017

(87) PCT Pub. No.: WO2016/077837
PCT Pub. Date: May 19, 2016

(65) Prior Publication Data
US 2018/0009837 A1 Jan. 11, 2018

Related U.S. Application Data

(60) Provisional application No. 62/233,183, filed on Sep. 25, 2015, provisional application No. 62/156,812, filed on May 4, 2015, provisional application No. 62/156,139, filed on May 1, 2015, provisional application No. 62/139,626, filed on Mar. 27, 2015, provisional application No. 62/080,223, filed on Nov. 14, 2014.

(51) Int. Cl.
*C07H 21/04* (2006.01)
*A61K 31/7088* (2006.01)
*C12N 15/113* (2010.01)
*C12N 15/67* (2006.01)
*C07H 21/00* (2006.01)
*C12P 19/34* (2006.01)

(52) U.S. Cl.
CPC ......... *C07H 21/04* (2013.01); *A61K 31/7088* (2013.01); *C07H 21/00* (2013.01); *C12N 15/113* (2013.01); *C12N 15/1137* (2013.01); *C12N 15/1138* (2013.01); *C12N 15/67* (2013.01); *C12P 19/34* (2013.01); *C12N 2310/11* (2013.01); *C12N 2310/315* (2013.01); *C12N 2310/3341* (2013.01); *C12N 2310/346* (2013.01); *C12Y 301/26004* (2013.01)

(58) Field of Classification Search
None
See application file for complete search history.

(56) References Cited

U.S. PATENT DOCUMENTS

| 7,718,625 | B2 | 5/2010 | Eichler et al. |
|---|---|---|---|
| 2002/0160976 | A1 | 10/2002 | Miles et al. |
| 2004/0110144 | A1* | 6/2004 | Bennett ............ C12N 15/1136 435/6.16 |
| 2005/0048549 | A1 | 3/2005 | Cao et al. |
| 2006/0166922 | A1 | 7/2006 | Eichler et al. |

FOREIGN PATENT DOCUMENTS

| WO | WO 1992/013070 | 8/1992 |
|---|---|---|
| WO | WO 2014/097226 | 6/2014 |
| WO | WO 2014/172698 | 10/2014 |
| WO | WO 2015/023937 | 2/2015 |
| WO | WO 2015/023938 | 2/2015 |
| WO | WO 2015/023939 | 2/2015 |
| WO | WO 2015/023941 | 2/2015 |
| WO | WO 2015/023975 | 2/2015 |

OTHER PUBLICATIONS

Babendure et al., "Control of mammalian translation by mRNA structure near caps" RNA (2006) 12: 851-861.
Caron et al., "Dual-acting riboswitch control of translation initiation and mRNA decay" Proc. Natl. Acad. Sci. USA (2012) 109(50): 3444-3453.
Lamping et al., "Small, synthetic, GC-rich mRNA stem-loop modules 5' proximal to the AUG start-codon predictably tune gene expression in yeast" Microb. Cell Fact. (2013) 12: 1-19.
Li et al., "MicroRNA-122 antagonism against hepatitis C virus genotypes 1-6 and reduced efficacy by host RNA insertion or mutations in the HCV 5' UTR" Proc Natl Acad Sci USA (2011) 108(12): 4991-4996.
Matsuda et al., "Determinants of initiation codon selection during translation in mammalian cells" PLOS One (2010) 5(11): 1-13.
Orom et al., "MicroRNA-10a binds the 5'UTR of ribosomal protein mRNAs and enhances their translation" Mol. Cell (2008) 30(4): 460-471.
Shabman et al., "An upstream open reading frame modulates ebola virus polymerase translation and virus replication" PLOS Pathog (2013) 9(1): 1-18.
Xue et al., "RNA regulons in Hox 5' UTRs confer ribosome specificity to gene regulation" Nature (2015) 517: 33-38.
Zammarchi et al., "5' UTR Control of Native ERG and of Tmprss2:ERG Variants Activity in Prostate Cancer" PLOS One (2013) 8(3): 1-14.
Bandyopadhyay et al., "Alzheimer's disease therapeutics targeted to the control of amyloid precursor protein translation: Maintenance of brain iron homeostasis" Biochem. Pharm. (2014) 88: 486-494.

(Continued)

*Primary Examiner* — Kimberly Chong
(74) *Attorney, Agent, or Firm* — McNeill Baur PLLC

(57) ABSTRACT

In certain embodiments, the present disclosure provides compounds and methods of increasing the amount or activity of a target protein in a cell. In certain embodiments, the compounds comprise a translation suppression element inhibitor. In certain embodiments, the translation suppression element inhibitor is a uORF inhibitor. In certain embodiments, the uORF inhibitor is an antisense compound.

15 Claims, No Drawings

Specification includes a Sequence Listing.

(56) References Cited

OTHER PUBLICATIONS

Barbosa et al., "Gene Expression Regulation by Upstream Open Reading Frames and Human Disease" PLOS (2013) 9(8): 1-12.
Brenet et al., "Identification of secondary structure in the 5'-untranslated region of the human adrenomedullin mRNA with implications for the regulation of mRNA translation" Oncogene (2006) 25: 6510-6519.
Calvo et al., "Upstream open reading frames cause widespread reduction of protein expression and are polymorphic among humans" PNAS (2009) 106(18): 7507-7512.
Cazzola et al., "Hereditary Hyperferritinemia-Cataract Syndrome: Relationship Between Phenotypes and Specific Mutations in the Iron-Responsive Element of Ferritin Light-Chain mRNA" Blood (1997) 90(2): 814-821.
Cheng et al., "Functional activation of the cystic fibrosis trafficking mutant AF508-CFTR by overexpression" Am. Physiol. Soc. (1995): L615-L624.
Gillen et al., "microRNA regulation of expression of the cystic fibrosis transmembrane conductance regulator gene" Biochem. J. (2011) 438(1): 25-32.
Giordano et al., "Molecular and Functional Analysis of the Large 5'Promoter Region of CFTR Gene Revealed Pathogenic Mutations in CF and CFTR-Related Disorders" J. Mol. Diagn. (2013) 15(3): 331-340.
International Search Report for PCT/US15/60938 dated Feb. 4, 2016.
Jenkins et al., "A Conserved Stem Loop Motif in the 5'Untranslated Region Regulates Transforming Growth Factor-β1 Translation" PLOS One (2010) 5(8): 1-12.
Lukowski et al., "CFTR mRNA expression is regulated by an upstream open reading frame and RNA secondary structure in its 5' untranslated region" Hum. Mol. Gen. (2014) 1-14.
Majdalani et al., "Regulation of RpoS by a novel small RNA: the chamcterization of RprA" Molecular Microbiology (2001) 39(5): 1382-1394.
Pendleton et al., "Regulation of Endothelial Argininosuccinate Synthase Expression and NO Production by an Upstream Open Reading Frame" J. Biol. Chem. (2005) 280(25): 24252-24260.
Rogers et al., "Differential utilization of upstream AUGs in the β-secretase mRNA suggests that a shunting mechanism regulates translation" PNAS (2004) 101(9): 2794-2799.
Schwanhausser et al., "Global quantification of mammalian gene expression control" Nature (2011) 473: 337-342.
Spitale et al., "Structural imprints in vivo decode RNA regulatory mechanisms" Nature (2015) 519: 486-503.
Swiatkowska et al., "The Role of Structural Elements of the 5'-Terminal Region of p53 mRNA in Translation under Stress Conditions Assayed by the Antisense Oligonucleotide Approach" PLOS One (2015): 1-20.
Wang "The Principles of MiRNA—Masking Antisense Oligonucleotides Technology" Chapter 3, Methods in Molecular Biology (2011) 676: 43-49.
Xiao et al., "Novel Approaches for Gene-Specific Interference Via Manipulating Actions of MicroRNAs: Examination on the Pacemaker Channel Genes HCN2 and HCN4" J. Cell. Physiol. (2007): 285-292.
Dvir et al., "Deciphering the rules by which 5'-UTR sequences affect protein expression in yeast" Proc Natl Acad Sci USA (2013) 110(30): E2792-E2801.
Extended EP Search Report for 15859580.1 dated Jun. 19, 2018.
Hinnebusch et al., "Translational control by 5'-untranslated regions of eukaryotic mRNAs" Science (2016) 352(6292): 1413-1416.
Liang et al., "Translation efficiency of mRNAs is increased by antisense oligonucleotides targeting upstream open reading frames" Nat Biotechnol (2016) 34(8): 875-880.
Liang et al., "Antisense oligonucleotides targeting translation inhibitory elements in 5' UTRs can selectively increase protein levels" Nucleic Acids Res (2017) 45(16): 9528-9546.
Morris et al., "Upstream open reading frames as regulators of mRNA translation" Mol Cell Biol (2000) 20(23): 8635-8642.
Wethmar "The regulatory potential of upstream open reading frames in eukaryotic gene expression" Wiley Interdiscip Rev RNA (2014) 5(6): 765-778.
Zhang et al., "The 5'-untranslated region of multidrug resistance associated protein 2 (MRP2; ABCC2) regulates downstream open reading frame expression through translational regulation" Mol Pharmacol (2010) 77(2): 237-246.

\* cited by examiner

COMPOUNDS AND METHODS FOR THE MODULATION OF PROTEINS

SEQUENCE LISTING

The present application is being filed along with a Sequence Listing in electronic format. The Sequence Listing is provided as a file entitled CORE0132USASEQ_ST25.txt, created May 8, 2017, which is 72 Kb in size. The information in the electronic format of the sequence listing is incorporated herein by reference in its entirety.

BACKGROUND

Translation of a polypeptide or protein encoded by an mRNA typically begins at the start codon of the primary open reading frame (pORF) of the mRNA. Some mRNA transcripts also comprise one or more additional start codons. Such additional start codons may be upstream of the pORF start codon. Such an additional start codon that is upstream of a pORF is referred to as an upstream open reading frame (uORF) start site. The potential role of additional start sites in regulating translation of pORF protein products has been discussed previously (see Barbosa et al. PLOS Genetics. 9, e1003529 (2013)) which is hereby incorporated by reference in its entirety. Mutations that introduce or eliminate an additional start codon (a uORF start codon) in a transcript can disrupt regulation of its translation and can lead to disease (see Calvo et al. Proc. Natl. Acad. Sci. 106, 7507 (2009)) which is hereby incorporated by reference in its entirety.

Antisense technology is an effective means for modulating the expression of one or more specific gene products and can therefore prove to be uniquely useful in a number of therapeutic, diagnostic, and research applications. Chemically modified nucleosides may be incorporated into antisense compounds to enhance one or more properties, such as nuclease resistance, pharmacokinetics or affinity for a target nucleic acid. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients. For another example, an antisense compound targeting ApoB, KYNAMRO™, has been approved by the U.S. Food and Drug Administration (FDA) as an adjunct treatment to lipid-lowering medications and diet to reduce low density lipoprotein-cholesterol (LDL-C), ApoB, total cholesterol (TC), and non-high density lipoprotein-cholesterol (non HDL-C) in patients with homozygous familial hypercholesterolemia (HoFH).

SUMMARY

The present disclosure provides compounds that interact with the 5'-UTR of a target transcript to increase translation of a target protein. It was discovered that certain compounds that interact with the 5'-UTR can increase translation of a given target transcript. For example, in certain embodiments, the present disclosure provides antisense compounds targeted to one or more regions of the 5'-UTR. These regions of the 5'-UTR may include a translation suppression element, such as a stem-loop structure or a uORF. When the antisense compounds interact with the translation suppression element in the 5'-UTR, the antisense compounds increase translation of the target transcript. One aspect of the invention is the increase in expression through contacting a cell with an agent targets a translation suppression element in the 5'-UTR. In certain embodiments, antisense compounds targeted to the 5'-UTR increase expression of a given target protein by disrupting a translation suppression element within the 5'-UTR.

Antisense oligonucleotide technology has been used most often to reduce the amount an mRNA via antisense induced RNase H cleavage or to alter splicing of a pre-mRNA transcript in a cell. In certain embodiments, the present disclosure provides antisense compounds that increase expression of a target protein in a cell. In this manner, antisense oligonucleotides may be used to increase the expression of a desired protein in a cell. In certain embodiments, an increase in the expression of a target protein in a cell is achieved by having the antisense compound reduce ribosomal recognition of one or more upstream open reading frames. In certain embodiments, recognition of an upstream open reading frame reduces expression of a target protein in a cell. Therefore, in certain embodiments, targeting the upstream open reading frame, or the nucleobase sequence upstream or downstream of the upstream open reading frame, reduces ribosomal recognition of the upstream open reading frame and thereby increases expression of one or more target proteins. Therefore, in certain embodiments, targeting the upstream open reading frame, or the nucleobase sequence upstream or downstream of the upstream open reading frame, reduces ribosomal recognition of the upstream open reading frame and thereby increases ribosomal recognition of a start codon in the primary open reading frame.

In certain embodiments, the present invention uses antisense compounds to increase expression of a target protein. In certain instances, a transcript encoding a protein of interest includes a pORF and one or more additional start sites, such as uORF start sites. In certain embodiments, the present disclosure provides modified oligonucleotides that are complementary to the target transcript at or near such uORF start sites. Antisense compounds designed to reduce the amount of a target protein typically induce cleavage of the target transcript (e.g., through recruitment of RNase H). In contrast, in certain embodiments of the present invention, modified oligonucleotides are not designed to elicit cleavage. Rather, in certain such embodiments, the modified oligonucleotides of the present invention mask a uORF start site in favor of increased translation at a pORF start site. In certain embodiments, the modified oligonucleotides of the present invention disrupt initiation of translation at a uORF start site and, in certain embodiments, thereby increase translation of the target protein. In certain embodiments, modified oligonucleotides of the present invention disrupt the regulatory function of the 5'-UTR. In certain such embodiments, translation of the desired protein is increased. In certain embodiments, modified oligonucleotides of the present invention recruit proteins to the transcript that interfere with initiation of translation at the uORF start site. In certain embodiments, antisense compounds of the invention result in decreased translation of a uORF polypeptide.

The present disclosure provides methods of increasing translation of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing translation of the target protein in the cell.

The present disclosure provides methods of decreasing suppression of translation of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby decreasing suppression of translation of the target protein in the cell.

The present disclosure provides methods of increasing the amount or activity of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing the amount or activity of the target protein in the cell.

The present disclosure provides methods of increasing the amount a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing expression of the target protein in the cell.

The present disclosure provides the following non-limiting numbered embodiments:

Embodiment 1

A method of increasing the amount or activity of a target protein in a cell, comprising contacting the cell with a uORF inhibitor, wherein the target protein is encoded by a target transcript comprising at least one uORF start site; and thereby increasing the amount or activity of the target protein in the cell.

Embodiment 2

A method of increasing expression of a target protein in a cell, comprising contacting the cell with a uORF inhibitor, wherein the target protein is encoded by a target transcript comprising at least one uORF start site; and thereby increasing expression of the target protein in the cell.

Embodiment 3

A method of increasing translation a target protein in a cell, comprising contacting the cell with a uORF inhibitor, wherein the target protein is encoded by a target transcript comprising at least one uORF start site; and thereby increasing translation of the target protein in the cell.

Embodiment 4

A method of decreasing suppression of translation a target protein in a cell, comprising contacting the cell with a uORF inhibitor, wherein the target protein is encoded by a target transcript comprising at least one uORF start site; and thereby decreasing suppression of translation of the target protein in the cell.

Embodiment 5

A method of decreasing translation of a uORF polypeptide in a cell, comprising contacting the cell with a uORF inhibitor; and thereby decreasing translation of the uORF polypeptide in the cell.

Embodiment 6

The method of any of embodiments 1-5, wherein the uORF inhibitor is a small molecule.

Embodiment 7

The method of any of embodiments 1-5, wherein the uORF inhibitor is an antibody.

Embodiment 8

The method of any of embodiments 1-5, wherein the uORF inhibitor is a peptide.

Embodiment 9

The method of any of embodiments 1-5, wherein the uORF inhibitor is a nucleic acid.

Embodiment 10

The method of any of embodiments 1-5, wherein the uORF inhibitor is an siRNA.

Embodiment 11

The method of any of embodiments 1-5, wherein the uORF inhibitor is an antisense compound.

Embodiment 12

The method of embodiment 11, wherein the antisense compound is a modified oligonucleotide.

Embodiment 13

A method of increasing the amount or activity of a target protein in a cell, comprising contacting the cell with an antisense compound comprising a modified oligonucleotide, wherein the target protein is encoded by a target transcript comprising at least one uORF start site and wherein the modified oligonucleotide is complementary to a target site within a uORF start site region of the target transcript; and thereby increasing the amount or activity of the target protein in the cell.

Embodiment 14

A method of increasing expression of a target protein in a cell, comprising contacting the cell with an antisense compound comprising a modified oligonucleotide, wherein the target protein is encoded by a target transcript comprising at least one uORF start site and wherein the modified oligonucleotide is complementary to target site within a uORF start site region of the target transcript; and thereby increasing expression of the target protein in the cell.

Embodiment 15

A method of increasing translation a target protein in a cell, comprising contacting the cell with an antisense compound comprising a modified oligonucleotide, wherein the target protein is encoded by a target transcript comprising at least one uORF start site and wherein the modified oligonucleotide is complementary to a target site within a uORF start site region of the target transcript; and thereby increasing translation of the target protein in the cell.

Embodiment 16

A method of decreasing suppression of translation a target protein in a cell, comprising contacting the cell with an antisense compound comprising a modified oligonucleotide, wherein the target protein is encoded by a target transcript comprising at least one uORF start site and wherein the modified oligonucleotide is complementary to a target site within a uORF start site region of the target transcript; and thereby decreasing suppression of translation of the target protein in the cell.

Embodiment 17

A method of decreasing translation of a uORF polypeptide in a cell, comprising contacting the cell with an antisense compound comprising a modified oligonucleotide complementary to a target site within a uORF region of the target transcript; and thereby decreasing translation of the uORF polypeptide in the cell.

Embodiment 18

The method of any of embodiments 1-17, wherein the uORF start site region is the 5' untranslated region.

Embodiment 19

The method of any of embodiments 13-18, wherein the target site comprises the uORF start site.

Embodiment 20

The method of any of embodiments 13-19, wherein the target site region consists of the uORF start site and the 100 nucleosides upstream and the 100 nucleosides downstream of the uORF start site.

Embodiment 21

The method of any of embodiments 13-19, wherein the target site region consists of the uORF start site and the 75 nucleosides upstream and the 75 nucleosides downstream of the uORF start site.

Embodiment 22

The method of any of embodiments 13-19, wherein the target site region consists of the uORF start site and the 50 nucleosides upstream and the 50 nucleosides downstream of the uORF start site.

Embodiment 23

The method of any of embodiments 13-19, wherein the target site region consists of the uORF start site and the 30 nucleosides upstream and the 30 nucleosides downstream of the uORF start site.

Embodiment 24

The method of any of embodiments 13-19, wherein the target site region consists of the uORF start site and the 20 nucleosides upstream and the 20 nucleosides downstream of the uORF start site.

Embodiment 25

The method of any of embodiments 13-19, wherein the target site region consists of the uORF start site and the 15 nucleosides upstream and the 15 nucleosides downstream of the uORF start site.

Embodiment 26

The method of any of embodiments 13-25, wherein the uORF start site is a wild-type uORF start site.

Embodiment 27

The method of any of embodiments 13-25, wherein the uORF start site is a mutant uORF start site.

Embodiment 28

The method of any of embodiments 13-27, wherein the target transcript comprises more than one uORF region.

Embodiment 29

The method of any of embodiments 13-27, wherein the target transcript comprises two uORF regions.

Embodiment 30

The method of any of embodiments 13-29, wherein the uORF start site comprises a weak Kozak sequence.

Embodiment 31

The method of any of embodiments 13-29, wherein the uORF start site comprises a strong Kozak sequence.

Embodiment 32

The method of any of embodiments 13-31, wherein the uORF start site has a non-canonical start codon.

Embodiment 33

The method of embodiment 32, wherein the non-canonical start codon is AUU.

Embodiment 34

The method of any of embodiments 13-33, wherein the target transcript encodes RNase H1.

Embodiment 35

The method of any of embodiments 13-34, wherein the target transcript is encoded by a gene selected from the genes in Table 1 or Table 2.

Embodiment 36

The method of any of embodiments 12-35, wherein the modified oligonucleotide has a nucleobase sequence comprising the nucleobases CAT.

Embodiment 37

The method of any of embodiments 12-35, wherein the modified oligonucleotide has a nucleobase sequence wherein the first three of the 5'-most nucleobases are CAT.

Embodiment 38

The method of any of embodiments 12-35, wherein the modified oligonucleotide has a nucleobase sequence wherein the $2^{nd}$, $3^{rd}$, and $4^{th}$ nucleobases from the 5'-most terminal nucleobase are CAT.

Embodiment 39

The method of any of embodiments 12-35, wherein the modified oligonucleotide has a nucleobase sequence wherein the $3^{rd}$, $4^{th}$, and $5^{th}$ nucleobases from the 5'-most terminal nucleobase are CAT.

Embodiment 40

The method of any of embodiments 12-35, wherein the modified oligonucleotide has a nucleobase sequence wherein the $4^{th}$, $5^{th}$, and $6^{th}$ nucleobases from the 5'-most terminal nucleobase are CAT.

Embodiment 41

The method of any of embodiments 12-35, wherein the modified oligonucleotide has a nucleobase sequence wherein the $5^{th}$, $6^{th}$, and $7^{th}$ nucleobases from the 5'-most terminal nucleobase are CAT.

Embodiment 42

The method of any of embodiments 12-35, wherein the modified oligonucleotide has a nucleobase sequence wherein the $6^{th}$, $7^{th}$, and $8^{th}$ nucleobases from the 5'-most terminal nucleobase are CAT.

Embodiment 43

The method of any of embodiments 12-35, wherein the modified oligonucleotide has a nucleobase sequence wherein the $7^{th}$, $8^{th}$, and $9^{th}$ nucleobases from the 5'-most terminal nucleobase are CAT.

Embodiment 44

The method of any of embodiments 12-35, wherein the modified oligonucleotide has a nucleobase sequence wherein the first three of the 3'-most nucleobases are CAT.

Embodiment 45

The method of any of embodiments 12-35, wherein the modified oligonucleotide has a nucleobase sequence wherein the $2^{nd}$, $3^{rd}$, and $4^{th}$ nucleobases from the 3'-most terminal nucleobase are CAT.

Embodiment 46

The method of any of embodiments 12-35, wherein the modified oligonucleotide has a nucleobase sequence wherein the $3^{rd}$, $4^{th}$, and $5^{th}$ nucleobases from the 3'-most terminal nucleobase are CAT.

Embodiment 47

The method of any of embodiments 12-35, wherein the modified oligonucleotide has a nucleobase sequence wherein the $4^{th}$, $5^{th}$, and $6^{th}$ nucleobases from the 3'-most terminal nucleobase are CAT.

Embodiment 48

The method of any of embodiments 12-35, wherein the modified oligonucleotide has a nucleobase sequence wherein the $5^{th}$, $6^{th}$, and $7^{th}$ nucleobases from the 3'-most terminal nucleobase are CAT.

Embodiment 49

The method of any of embodiments 12-35, wherein the modified oligonucleotide comprises a nucleobase sequence complementary to a Kozak sequence.

Embodiment 50

The method of any of embodiments 12-35, wherein the modified oligonucleotide has a nucleobase sequence comprising at least 8 contiguous nucleobases complementary to the uORF region of SEQ ID NOs: 1 or 2.

Embodiment 51

The method of any of embodiments 12-35, wherein the modified oligonucleotide has a nucleobase sequence comprising at least 8 contiguous nucleobases of any of the nucleobase sequences of SEQ ID NOs: 3, 4, 5, 6, 7, 8, 9, 10, 11, 12, 13, 14, 15, 16, 17 or 18.

Embodiment 52

The method of any of embodiments 12-35, wherein the modified oligonucleotide has a nucleobase sequence comprising at least 10 contiguous nucleobases of any of the nucleobase sequences of SEQ ID NOs: 3, 4, 5, 6, 7, 8, 9, 10, 11, 12, 13, 14, 15, 16, 17 or 18.

Embodiment 53

The method of any of embodiments 12-35, wherein the modified oligonucleotide has a nucleobase sequence comprising at least 12 contiguous nucleobases of any of the nucleobase sequences of SEQ ID NOs: 3, 4, 5, 6, 7, 8, 9, 10, 11, 12, 13, 14, 15, 16, 17 or 18.

Embodiment 54

The method of any of embodiments 12-35, wherein the modified oligonucleotide has a nucleobase sequence comprising at least 14 contiguous nucleobases of any of the nucleobase sequences of SEQ ID NOs: 3, 4, 5, 6, 7, 8, 9, 10, 11, 12, 13, 14, 15, 16, 17 or 18.

Embodiment 55

The method of any of embodiments 12-35, wherein the modified oligonucleotide has a nucleobase sequence consisting of the nucleobase sequence of any of SEQ ID NOs: 3, 4, 5, 6, 7, 8, 9, 10, 11, 12, 13, 14, 15, 16, 17 or 18.

Embodiment 56

The method of any of embodiments 12-55, wherein the modified oligonucleotide consists of 10 to 40 linked nucleosides.

Embodiment 57

The method of any of embodiments 12-55, wherein the modified oligonucleotide consists of 12 to 22 linked nucleosides.

Embodiment 58

The method of any of embodiments 12-55, wherein the modified oligonucleotide consists of 15 to 22 linked nucleosides.

Embodiment 59

The method of any of embodiments 12-55, wherein the modified oligonucleotide consists of 18 to 20 linked nucleosides.

Embodiment 60

The method of any of embodiments 12-59, wherein the modified oligonucleotide comprises at least one modified nucleoside.

Embodiment 61

The method of embodiment 60, wherein at least one modified nucleoside comprises a modified sugar moiety.

Embodiment 62

The method of embodiment 61, wherein at least one modified sugar moiety is a 2'-substituted sugar moiety.

Embodiment 63

The method of embodiment 62, wherein the 2'-substitutent of at least one 2'-substituted sugar moiety is selected from among: 2'-OMe, 2'-F, and 2'-MOE.

Embodiment 64

The method of any of embodiments 60-63, wherein the 2'-substituent of at least one 2'-substituted sugar moiety is a 2'-MOE.

Embodiment 65

The method of any of embodiments 60-61, wherein at least one modified sugar moiety is a bicyclic sugar moiety.

Embodiment 66

The method of embodiment 65, wherein at least one bicyclic sugar moiety is LNA or cEt.

Embodiment 67

The method of any of embodiments 61-66, wherein at least one sugar moiety is a sugar surrogate.

Embodiment 68

The method of embodiment 67, wherein at least one sugar surrogate is a morpholino.

Embodiment 69

The method of embodiment 67, wherein at least one sugar surrogate is a modified morpholino.

Embodiment 70

The method of embodiment 67, wherein at least one sugar surrogate is a peptide nucleic acid.

Embodiment 71

The method of any of embodiment 60-70, wherein the modified oligonucleotide comprises at least 5 modified nucleosides, each independently comprising a modified sugar moiety.

Embodiment 72

The method of any of embodiment 60-70, wherein the modified oligonucleotide comprises at least 6 modified nucleosides, each independently comprising a modified sugar moiety.

Embodiment 73

The method of any of embodiment 60-70, wherein the modified oligonucleotide comprises at least 7 modified nucleosides, each independently comprising a modified sugar moiety.

Embodiment 74

The method of any of embodiment 60-70, wherein the modified oligonucleotide comprises at least 8 modified nucleosides, each independently comprising a modified sugar moiety.

Embodiment 75

The method of any of embodiment 60-70, wherein the modified oligonucleotide comprises at least 9 modified nucleosides, each independently comprising a modified sugar moiety.

Embodiment 76

The method of embodiment 60-70, wherein the modified oligonucleotide comprises at least 10 modified nucleosides, each independently comprising a modified sugar moiety.

Embodiment 77

The method of any of embodiments 60-76, wherein each nucleoside of the modified oligonucleotide is a modified nucleoside or an unmodified nucleoside.

Embodiment 78

The method of embodiment 77, wherein each unmodified nucleoside is a 2'-deoxy nucleoside.

Embodiment 79

The method of any of embodiments 77-78, wherein the modified oligonucleotide comprises at least 6 2'-deoxy nucleosides.

Embodiment 80

The method of any of embodiments 77-78, wherein the modified oligonucleotide comprises at least 7 2'-deoxy nucleosides.

Embodiment 81

The method of any of embodiments 77-78, wherein the modified oligonucleotide comprises at least 8 2'-deoxy nucleosides.

Embodiment 82

The method of any of embodiments 77-78, wherein the modified oligonucleotide comprises at least 9 2'-deoxy nucleosides.

Embodiment 83

The method of any of embodiments 77-78, wherein the modified oligonucleotide comprises at least 10 2'-deoxy nucleosides.

Embodiment 84

The method of any of embodiments 79-83, wherein the modified oligonucleotide contains no more than 4 contiguous 2'-deoxy nucleosides.

Embodiment 85

The method of any of embodiments 77-78, wherein the modified oligonucleotide comprises at least 15 modified nucleosides, each independently comprising a modified sugar moiety.

Embodiment 86

The method of embodiment 85, wherein each nucleoside of the modified oligonucleotide is a modified nucleoside, each independently comprising a modified sugar moiety.

Embodiment 87

The method of any of embodiments 60-86, wherein the modified oligonucleotide comprises at least two modified nucleosides comprising modified sugar moieties that are the same as one another.

Embodiment 88

The method of any of embodiments 60-86, wherein the modified oligonucleotide comprises at least two modified nucleosides comprising modified sugar moieties that are different from one another.

Embodiment 89

The method of any of embodiments 60-86, wherein the modified oligonucleotide comprises a modified region of at least 5 contiguous modified nucleosides.

Embodiment 90

The method of embodiment 89, wherein the modified oligonucleotide comprises a modified region of at least 10 contiguous modified nucleosides.

Embodiment 91

The method of embodiment 89, wherein the modified oligonucleotide comprises a modified region of at least 15 contiguous modified nucleosides.

Embodiment 92

The method of embodiment 89, wherein the modified oligonucleotide comprises a modified region of at least 18 contiguous modified nucleosides.

Embodiment 93

The method of embodiment 89, wherein the modified oligonucleotide comprises a modified region of at least 20 contiguous modified nucleosides.

Embodiment 94

The method of any of embodiments 90-93, wherein each modified nucleoside of the modified region has a modified sugar moiety independently selected from among: 2'-F, 2'-OMe, 2'-MOE, cEt, LNA, morpholino, modified morpholino, and peptide nucleic acid.

Embodiment 95

The method of any of embodiments 90-94, wherein the modified nucleosides of the modified region each comprise the same modification as one another.

Embodiment 96

The method of embodiment 95, wherein the modified nucleosides of the modified region each comprise the same 2'-substituted sugar moiety.

Embodiment 97

The method of embodiment 95, wherein the 2'-substituted sugar moiety of the modified nucleosides of the region of modified nucleosides is selected from 2'-F, 2'-OMe, and 2'-MOE.

Embodiment 98

The method of embodiment 96, wherein the 2'-substituted sugar moiety of the modified nucleosides of the region of modified nucleosides is 2'-MOE.

Embodiment 99

The method of embodiment 95, wherein the modified nucleosides of the region of modified nucleosides each comprise the same bicyclic sugar moiety.

Embodiment 100

The method of embodiment 99, wherein the bicyclic sugar moiety of the modified nucleosides of the region of modified nucleosides is selected from LNA and cEt.

Embodiment 101

The method of embodiment 95, wherein the modified nucleosides of the region of modified nucleosides each comprises a sugar surrogate.

Embodiment 102

The method of embodiment 101, wherein the sugar surrogate of the modified nucleosides of the region of modified nucleosides is a morpholino.

Embodiment 103

The method of embodiment 101, wherein the sugar surrogate of the modified nucleosides of the region of modified nucleosides is a modified morpholino.

Embodiment 104

The method of embodiment 101, wherein the sugar surrogate of the modified nucleosides of the region of modified nucleosides is a peptide nucleic acid.

Embodiment 105

The method of any of embodiments 60-104, wherein the modified nucleotide comprises no more than 4 contiguous naturally occurring nucleosides.

Embodiment 106

The method of any of embodiments 60-107, wherein each nucleoside of the modified oligonucleotide is a modified nucleoside.

Embodiment 107

The method of embodiment 106 wherein each modified nucleoside comprises a modified sugar moiety.

Embodiment 108

The method of embodiment 107, wherein the modified nucleosides of the modified oligonucleotide comprise the same modification as one another.

Embodiment 109

The method of embodiment 108, wherein the modified nucleosides of the modified oligonucleotide each comprise the same 2'-substituted sugar moiety.

Embodiment 110

The method of embodiment 109, wherein the 2'-substituted sugar moiety of the modified oligonucleotide is selected from 2'-F, 2'-OMe, and 2'-MOE.

Embodiment 111

The method of embodiment 110, wherein the 2'-substituted sugar moiety of the modified oligonucleotide is 2'-MOE.

Embodiment 112

The method of embodiment 110, wherein the 2'-substituted sugar moiety of the modified oligonucleotide is 2'-OMe.

Embodiment 113

The method of embodiment 108, wherein the modified nucleosides of the modified oligonucleotide each comprise the same bicyclic sugar moiety.

Embodiment 114

The method of embodiment 113, wherein the bicyclic sugar moiety of the modified oligonucleotide is selected from LNA and cEt.

Embodiment 115

The method of embodiment 98, wherein the modified nucleosides of the modified oligonucleotide each comprises a sugar surrogate.

Embodiment 116

The method of embodiment 115, wherein the sugar surrogate of the modified oligonucleotide is a morpholino.

Embodiment 117

The method of embodiment 115, wherein the sugar surrogate of the modified oligonucleotide is a modified morpholino.

Embodiment 118

The method of embodiment 115, wherein the sugar surrogate of the modified oligonucleotide is a peptide nucleic acid.

Embodiment 119

The method of any of embodiments 60-118, wherein the modified oligonucleotide comprises at least one modified internucleoside linkage.

Embodiment 120

The method of embodiment 119, wherein the modified internucleoside linkage is a phosphorothioate internucleoside linkage.

Embodiment 121

The method of embodiment 119 or 120, wherein each internucleoside linkage is either a phosphodiester internucleoside linkage or a phosphorothioate internucleoside linkage.

Embodiment 122

The method of embodiment 119, wherein each internucleoside linkage is a modified internucleoside linkage.

Embodiment 123

The method of embodiment 119 or 120, comprising at least one phosphorothioate internucleoside linkage.

Embodiment 124

The method of embodiment 119, wherein each internucleoside linkage is a modified internucleoside linkage and wherein each internucleoside linkage comprises the same modification.

Embodiment 125

The method of embodiment 122, wherein each internucleoside linkage is a phosphorothioate internucleoside linkage.

Embodiment 126

The method of any of embodiments 60-125, wherein the antisense compound comprises at least one conjugate group.

Embodiment 127

The method of embodiment 126, wherein the conjugate group comprises Gal-NAc.

Embodiment 128

The method of any of embodiments 60-126, wherein the antisense compound consists of the modified oligonucleotide.

Embodiment 129

The method of any of embodiments 13-128, wherein the expression, translation, or amount or activity of the target protein is increased by at least 10%.

Embodiment 130

The method of any of embodiments 13-128, wherein the expression, translation, or amount or activity of the target protein is increased by at least 20%.

Embodiment 131

The method of any of embodiments 13-128, wherein the expression, translation, or amount or activity of the target protein is increased by at least 30%.

Embodiment 132

The method of any of embodiments 13-128, wherein the expression, translation, or amount or activity of the target protein is increased by at least 50%.

Embodiment 133

The method of any of embodiments 13-128, wherein the expression, translation, or amount or activity of the target protein is increased by at least 100%.

Embodiment 134

The method of any of embodiments 13-128, wherein the expression, translation, or amount or activity of the target protein is increased by at least 120%.

Embodiment 135

The method of any of embodiments 13-128, wherein the expression, translation, or amount or activity of the target protein is increased by at least 150%.

Embodiment 136

The method of any of embodiments 1-135, wherein the cell is in vitro.

Embodiment 137

The method of any of embodiments 1-135, wherein the cell is in a subject.

Embodiment 138

The method of embodiment 137, wherein the subject has a disease or condition and wherein at least one symptom of the disease or condition is ameliorated.

Embodiment 139

The method of embodiment 137 or 138, wherein the cell is in an animal.

Embodiment 140

The method of embodiment 139, wherein the animal is a human.

Embodiment 141

An antisense compound comprising a modified oligonucleotide consisting of 10-30 linked nucleosides having a nucleobase sequence complementary to a target site within a uORF start site region of a target transcript and wherein the modified oligonucleotide does not have more than four contiguous unmodified 2'-deoxy nucleosides.

Embodiment 142

The antisense compound of embodiments 141, wherein the uORF start site region is the 5' untranslated region.

Embodiment 143

The antisense compound of any of embodiments 141-142, wherein the target site comprises the uORF start site.

Embodiment 144

The antisense compound of any of embodiments 141-143, wherein the target site is within 50 nucleosides upstream or downstream of the uORF start site.

Embodiment 145

The antisense compound of any of embodiments 141-143, wherein the target site is within 40 nucleosides upstream or downstream of the uORF start site.

Embodiment 146

The antisense compound of any of embodiments 141-143, wherein the target site is within 30 nucleosides upstream or downstream of the uORF start site.

Embodiment 147

The antisense compound of any of embodiments 141-143, wherein the target site is within 20 nucleosides upstream or downstream of the uORF start site.

Embodiment 148

The antisense compound of any of embodiments 141-143, wherein the target site is within 10 nucleosides upstream or downstream of the uORF start site.

Embodiment 149

The antisense compound of any of embodiments 141-143, wherein the target site is within 5 nucleosides upstream or downstream of the uORF start site.

Embodiment 150

The antisense compound of any of embodiments 141-143, wherein the target site comprises a wild-type uORF region.

Embodiment 151

The antisense compound of any of embodiments 141-143, wherein the target site comprises a uORF region that arises from a mutation.

Embodiment 152

The antisense compound of any of embodiments 141-143, wherein the target transcript comprises more than one uORF region.

Embodiment 153

The antisense compound of any of embodiments 141-143, wherein the target transcript comprises two uORF regions.

Embodiment 154

The antisense compound of any of embodiments 141-143, wherein the uORF start site region comprises a weak Kozak sequence.

Embodiment 155

The antisense compound of any of embodiments 141-143, wherein the uORF start site region comprises a strong Kozak sequence.

Embodiment 156

The antisense compound of any of embodiments 141-143, wherein the uORF start site has a non-canonical start codon.

Embodiment 157

The antisense compound of embodiment 156, wherein the non-canonical start codon is AUU.

Embodiment 158

The antisense compound of any of embodiments 141-157, wherein the target transcript encodes RNase H1.

Embodiment 159

The antisense compound of any of embodiments 141-157, wherein the target transcript encodes a protein translated from a gene selected from the genes in Table 1 or Table 2.

Embodiment 160

The antisense compound of any of embodiments 141-159, wherein the modified oligonucleotide has a nucleobase sequence comprising the nucleobases CAT.

Embodiment 161

The antisense compound of any of embodiments 141-159, wherein the modified oligonucleotide has a nucleobase sequence wherein the first three of the 5'-most nucleobases are CAT.

Embodiment 162

The antisense compound of any of embodiments 141-159, wherein the modified oligonucleotide has a nucleobase sequence wherein the $2^{nd}$, $3^{rd}$, and $4^{th}$ nucleobases from the 5'-most terminal nucleobase are CAT.

Embodiment 163

The antisense compound of any of embodiments 141-159, wherein the modified oligonucleotide has a nucleobase sequence wherein the $3^{rd}$, $4^{th}$, and $5^{th}$ nucleobases from the 5'-most terminal nucleobase are CAT.

Embodiment 164

The antisense compound of any of embodiments 141-159, wherein the modified oligonucleotide has a nucleobase sequence wherein the $4^{th}$, $5^{th}$, and $6^{th}$ nucleobases from the 5'-most terminal nucleobase are CAT.

Embodiment 165

The antisense compound of any of embodiments 141-159, wherein the modified oligonucleotide has a nucleobase sequence wherein the $5^{th}$, $6^{th}$, and $7^{th}$ nucleobases from the 5'-most terminal nucleobase are CAT.

Embodiment 166

The antisense compound of any of embodiments 141-159, wherein the modified oligonucleotide has a nucleobase sequence wherein the $6^{th}$, $7^{th}$, and $8^{th}$ nucleobases from the 5'-most terminal nucleobase are CAT.

Embodiment 167

The antisense compound of any of embodiments 141-159, wherein the modified oligonucleotide has a nucleobase sequence wherein the 7$^{th}$, 8$^{th}$, and 9$^{th}$ nucleobases from the 5'-most terminal nucleobase are CAT.

Embodiment 168

The antisense compound of any of embodiments 141-167, wherein the modified oligonucleotide has a nucleobase sequence complementary to a Kozak sequence.

Embodiment 169

The antisense compound of any of embodiments 141-168, wherein the modified oligonucleotide has a nucleobase sequence comprising at least 8 contiguous nucleobases complementary to the uORF region of SEQ ID NOs: 1 or 2.

Embodiment 170

The antisense compound of any of embodiments 141-168, wherein the modified oligonucleotide has a nucleobase sequence comprising at least 8 contiguous nucleobases of any of the nucleobase sequences of SEQ ID NOs: 3, 4, 5, 6, 7, 8, 9, 10, 11, 12, 13, 14, 15, 16, 17 or 18.

Embodiment 171

The antisense compound of any of embodiments 141-168, wherein the modified oligonucleotide has a nucleobase sequence comprising at least 10 contiguous nucleobases of any of the nucleobase sequences of SEQ ID NOs: 3, 4, 5, 6, 7, 8, 9, 10, 11, 12, 13, 14, 15, 16, 17 or 18.

Embodiment 172

The antisense compound of any of embodiments 141-168, wherein the modified oligonucleotide has a nucleobase sequence comprising at least 12 contiguous nucleobases of any of the nucleobase sequences of SEQ ID NOs: 3, 4, 5, 6, 7, 8, 9, 10, 11, 12, 13, 14, 15, 16, 17 or 18.

Embodiment 173

The antisense compound of any of embodiments 141-168, wherein the modified oligonucleotide has a nucleobase sequence comprising at least 14 contiguous nucleobases of any of the nucleobase sequences of SEQ ID NOs: 3, 4, 5, 6, 7, 8, 9, 10, 11, 12, 13, 14, 15, 16, 17 or 18.

Embodiment 174

The antisense compound of any of embodiments 141-168, wherein the modified oligonucleotide has a nucleobase sequence consisting of the nucleobase sequence of any of SEQ ID NOs: 3, 4, 5, 6, 7, 8, 9, 10, 11, 12, 13, 14, 15, 16, 17 or 18.

Embodiment 175

The antisense compound of any of embodiments 141-174, wherein the modified oligonucleotide consists of 10 to 40 linked nucleosides.

Embodiment 176

The antisense compound of any of embodiments 141-174, wherein the modified oligonucleotide consists of 12 to 22 linked nucleosides.

Embodiment 177

The antisense compound of any of embodiments 141-174, wherein the modified oligonucleotide consists of 15 to 22 linked nucleosides.

Embodiment 178

The antisense compound of any of embodiments 141-174, wherein the modified oligonucleotide consists of 18 to 20 linked nucleosides.

Embodiment 179

The antisense compound of any of embodiments 141-174, wherein the modified oligonucleotide comprises at least one modified nucleoside.

Embodiment 180

The antisense compound of any of embodiments 175-179, wherein at least one modified nucleoside comprises a modified sugar moiety.

Embodiment 181

The antisense compound of embodiment 180, wherein at least one modified sugar moiety is a 2'-substituted sugar moiety.

Embodiment 182

The antisense compound of embodiment 181, wherein the 2'-substituent of at least one 2'-substituted sugar moiety is selected from among: 2'-OMe, 2'-F, and 2'-MOE.

Embodiment 183

The antisense compound of any of embodiments 179-182, wherein the 2'-substituent of at least one 2'-substituted sugar moiety is a 2'-MOE.

Embodiment 184

The antisense compound of any of embodiments 179-180, wherein at least one modified sugar moiety is a bicyclic sugar moiety.

Embodiment 185

The antisense compound of embodiment 184, wherein at least one bicyclic sugar moiety is LNA or cEt.

Embodiment 186

The antisense compound of any of embodiments 179-185, wherein at least one sugar moiety is a sugar surrogate.

Embodiment 187

The antisense compound of embodiment 186, wherein at least one sugar surrogate is a morpholino.

Embodiment 188

The antisense compound of embodiment 186, wherein at least one sugar surrogate is a modified morpholino.

Embodiment 189

The antisense compound of embodiment 186, wherein at least one sugar surrogate is a peptide nucleic acid.

Embodiment 190

The antisense compound of any of embodiment 179-189, wherein the modified oligonucleotide comprises at least 5 modified nucleosides, each independently comprising a modified sugar moiety.

Embodiment 191

The antisense compound of any of embodiment 179-189, wherein the modified oligonucleotide comprises at least 6 modified nucleosides, each independently comprising a modified sugar moiety.

Embodiment 192

The antisense compound of any of embodiment 179-189, wherein the modified oligonucleotide comprises at least 7 modified nucleosides, each independently comprising a modified sugar moiety.

Embodiment 193

The antisense compound of any of embodiment 179-189, wherein the modified oligonucleotide comprises at least 8 modified nucleosides, each independently comprising a modified sugar moiety.

Embodiment 194

The antisense compound of any of embodiment 179-189, wherein the modified oligonucleotide comprises at least 9 modified nucleosides, each independently comprising a modified sugar moiety.

Embodiment 195

The antisense compound of embodiment 179-189, wherein the modified oligonucleotide comprises at least 10 modified nucleosides, each independently comprising a modified sugar moiety.

Embodiment 196

The antisense compound of any of embodiments 179-195, wherein each nucleoside of the modified oligonucleotide is a modified nucleoside or an unmodified nucleoside.

Embodiment 197

The antisense compound of embodiment 196, wherein each unmodified nucleoside is a 2'-deoxy nucleoside.

Embodiment 198

The antisense compound of any of embodiments 196-197, wherein the modified oligonucleotide comprises at least 6 2'-deoxy nucleosides.

Embodiment 199

The antisense compound of any of embodiments 196-197, wherein the modified oligonucleotide comprises at least 7 2'-deoxy nucleosides.

Embodiment 200

The antisense compound of any of embodiments 196-197, wherein the modified oligonucleotide comprises at least 8 2'-deoxy nucleosides.

Embodiment 201

The antisense compound of any of embodiments 196-197, wherein the modified oligonucleotide comprises at least 9 2'-deoxy nucleosides.

Embodiment 202

The antisense compound of any of embodiments 196-197, wherein the modified oligonucleotide comprises at least 10 2'-deoxy nucleosides.

Embodiment 203

The antisense compound of any of embodiments 198-1202, wherein the modified oligonucleotide contains no more than 4 contiguous 2'-deoxy nucleosides.

Embodiment 204

The antisense compound of any of embodiments 196-197, wherein the modified oligonucleotide comprises at least 15 modified nucleosides, each independently comprising a modified sugar moiety.

Embodiment 205

The antisense compound of embodiment 204, wherein each nucleoside of the modified oligonucleotide is a modified nucleoside, each independently comprising a modified sugar moiety.

Embodiment 206

The antisense compound of any of embodiments 141-205, wherein the modified oligonucleotide comprises at least two modified nucleosides comprising modified sugar moieties that are the same as one another.

Embodiment 207

The antisense compound of any of embodiments 141-205, wherein the modified oligonucleotide comprises at least two modified nucleosides comprising modified sugar moieties that are different from one another.

Embodiment 208

The antisense compound of any of embodiments 141-204, wherein the modified oligonucleotide comprises a modified region of at least 5 contiguous modified nucleosides.

Embodiment 209

The antisense compound of embodiment 208, wherein the modified oligonucleotide comprises a modified region of at least 10 contiguous modified nucleosides.

Embodiment 210

The antisense compound of embodiment 208, wherein the modified oligonucleotide comprises a modified region of at least 15 contiguous modified nucleosides.

Embodiment 211

The antisense compound of embodiment 208, wherein the modified oligonucleotide comprises a modified region of at least 18 contiguous modified nucleosides.

Embodiment 212

The antisense compound of embodiment 208, wherein the modified oligonucleotide comprises a modified region of at least 20 contiguous modified nucleosides.

Embodiment 213

The antisense compound of any of embodiments 209-212, wherein each modified nucleoside of the modified region has a modified sugar moiety independently selected from among: 2'-F, 2'-OMe, 2'-MOE, cEt, LNA, morpholino, modified morpholino, and peptide nucleic acid.

Embodiment 214

The antisense compound of any of embodiments 209-213, wherein the modified nucleosides of the modified region each comprise the same modification as one another.

Embodiment 215

The antisense compound of embodiment 214, wherein the modified nucleosides of the modified region each comprise the same 2'-substituted sugar moiety.

Embodiment 216

The antisense compound of embodiment 214, wherein the 2'-substituted sugar moiety of the modified nucleosides of the region of modified nucleosides is selected from 2'-F, 2'-OMe, and 2'-MOE.

Embodiment 217

The antisense compound of embodiment 215, wherein the 2'-substituted sugar moiety of the modified nucleosides of the region of modified nucleosides is 2'-MOE.

Embodiment 218

The antisense compound of embodiment 214, wherein the modified nucleosides of the region of modified nucleosides each comprise the same bicyclic sugar moiety.

Embodiment 219

The antisense compound of embodiment 218, wherein the bicyclic sugar moiety of the modified nucleosides of the region of modified nucleosides is selected from LNA and cEt.

Embodiment 220

The antisense compound of embodiment 214, wherein the modified nucleosides of the region of modified nucleosides each comprises a sugar surrogate.

Embodiment 221

The antisense compound of embodiment 220, wherein the sugar surrogate of the modified nucleosides of the region of modified nucleosides is a morpholino.

Embodiment 222

The antisense compound of embodiment 220, wherein the sugar surrogate of the modified nucleosides of the region of modified nucleosides is a modified morpholino.

Embodiment 223

The antisense compound of embodiment 220, wherein the sugar surrogate of the modified nucleosides of the region of modified nucleosides is a peptide nucleic acid.

Embodiment 224

The antisense compound of any of embodiments 141-204, or 206 to 223, wherein the modified nucleotide comprises no more than 4 contiguous naturally occurring nucleosides.

Embodiment 225

The antisense compound of any of embodiments 141-196, wherein each nucleoside of the modified oligonucleotide is a modified nucleoside.

Embodiment 226

The antisense compound of embodiment 225 wherein each modified nucleoside comprises a modified sugar moiety.

Embodiment 227

The antisense compound of embodiment 226, wherein the modified nucleosides of the modified oligonucleotide comprise the same modification as one another.

Embodiment 228

The antisense compound of embodiment 227, wherein the modified nucleosides of the modified oligonucleotide each comprise the same 2'-substituted sugar moiety.

Embodiment 229

The antisense compound of embodiment 228, wherein the 2'-substituted sugar moiety of the modified oligonucleotide is selected from 2'-F, 2'-OMe, and 2'-MOE.

Embodiment 230

The antisense compound of embodiment 229, wherein the 2'-substituted sugar moiety of the modified oligonucleotide is 2'-MOE.

Embodiment 231

The antisense compound of embodiment 229, wherein the 2'-substituted sugar moiety of the modified oligonucleotide is 2'-OMe.

Embodiment 232

The antisense compound of embodiment 227, wherein the modified nucleosides of the modified oligonucleotide each comprise the same bicyclic sugar moiety.

Embodiment 233

The antisense compound of embodiment 232, wherein the bicyclic sugar moiety of the modified oligonucleotide is selected from LNA and cEt.

Embodiment 234

The antisense compound of embodiment 227, wherein the modified nucleosides of the modified oligonucleotide each comprises a sugar surrogate.

Embodiment 235

The antisense compound of embodiment 234, wherein the sugar surrogate of the modified oligonucleotide is a morpholino.

Embodiment 236

The antisense compound of embodiment 234, wherein the sugar surrogate of the modified oligonucleotide is a modified morpholino.

Embodiment 237

The antisense compound of embodiment 234, wherein the sugar surrogate of the modified oligonucleotide is a peptide nucleic acid.

Embodiment 238

The antisense compound of any of embodiments 141-237, wherein the modified oligonucleotide comprises at least one modified internucleoside linkage.

Embodiment 239

The antisense compound of embodiment 238, wherein each internucleoside linkage is a modified internucleoside linkage.

Embodiment 240

The antisense compound of embodiment 238 or 239, comprising at least one phosphorothioate internucleoside linkage.

Embodiment 241

The antisense compound of embodiment 238 or 239, wherein each internucleoside linkage is a phosphorothioate linkage or a phosphodiester internucleoside linkage.

Embodiment 242

The antisense compound of embodiment 238, wherein each internucleoside linkage is a modified internucleoside linkage and wherein each internucleoside linkage comprises the same modification.

Embodiment 243

The antisense compound of embodiment 242, wherein each internucleoside linkage is a phosphorothioate internucleoside linkage.

Embodiment 244

The antisense compound of any of embodiments 141-243, comprising at least one conjugate group.

Embodiment 245

The antisense compound of embodiment 244, wherein the conjugate group comprises Gal-NAc.

Embodiment 246

The antisense compound of any of embodiments 141-243, consisting of the modified oligonucleotide.

Embodiment 247

The antisense compound of any of embodiments 141-246, wherein the antisense compound increases translation of the target protein.

Embodiment 248

The antisense compound of any of embodiments 141-247, wherein the antisense compound does not relieve suppression of transcription.

Embodiment 249

The antisense compound of any of embodiments 141-248, wherein the antisense compound does not modulate splicing of the target transcript.

Embodiment 250

A pharmaceutical composition comprising the antisense compound of any of embodiments 141-249 and at least one pharmaceutically acceptable carrier or diluent.

Embodiment 251

A method of increasing the amount or activity of a target protein in a cell, comprising contacting the cell with the antisense compound or composition of any of embodiments 141-250.

Embodiment 252

A method of increasing expression of a target protein in a cell, comprising contacting the cell with the antisense compound or composition of any of embodiments 141-250.

Embodiment 253

A method of increasing translation a target protein in a cell, comprising contacting the cell with the antisense compound or composition of any of embodiments 141-250.

Embodiment 254

A method of decreasing suppression of translation a target protein in a cell, comprising contacting the cell with the antisense compound or composition of any of embodiments 141-250.

Embodiment 255

A method of decreasing translation of a uORF polypeptide in a cell, comprising contacting the cell with an antisense compound or composition of any of embodiments 141-250.

Embodiment 256

The method of any of embodiments 251-255, wherein the cell is in vitro.

Embodiment 257

The method of any of embodiments 251-255, wherein the cell is in an animal.

Embodiment 258

The method of embodiment 257, wherein the animal is a human.

Embodiment 259

A method of administering the antisense compound or composition of any of embodiments 141-250 to a subject in need thereof.

Embodiment 260

A method of treating a disease or condition, comprising administering the antisense compound or composition of any of embodiments 141-250 to a subject in need thereof.

Embodiment 261

The method of embodiment 260, wherein administering the antisense compound or composition of any of claims 141-250 to a subject in need thereof ameliorates one or more symptoms of the disease or condition

Embodiment 262

The method of any of embodiments 259-261, wherein the subject is a human.

Embodiment 263

Use of the antisense compound or composition of any of embodiments 141-250 for the treatment of a disease or condition.

Embodiment 264

Use of the antisense compound or composition of any of embodiments 141-250 for the preparation of a medicament for the treatment of a disease or condition.

Embodiment 265

A method of increasing translation of a target protein in a cell, comprising contacting the cell with a translation suppression element inhibitor, wherein the target protein is encoded by a target transcript comprising at least one translation suppression element; and thereby increasing translation of the target protein in a cell.

Embodiment 266

A method of decreasing suppression of translation a target protein in a cell, comprising contacting the cell with a translation suppression element inhibitor, wherein the target protein is encoded by a target transcript comprising at least one translation suppression element; and thereby decreasing suppression of translation of the target protein in a cell.

Embodiment 267

A method of increasing the amount or activity of a target protein in a cell, comprising contacting the cell with a translation suppression element inhibitor, wherein the target protein is encoded by a target transcript comprising at least one translation suppression element; and thereby increasing the amount or activity of the target protein in the cell.

Embodiment 268

A method of increasing expression of a target protein in a cell, comprising contacting the cell with a translation suppression element inhibitor, wherein the target protein is encoded by a target transcript comprising at least one translation suppression element; and thereby increasing the expression of the target protein in a cell.

Embodiment 269

The method of any of embodiments 265-268, wherein the translation suppression element inhibitor is a small molecule.

Embodiment 270

The method of any of embodiments 265-268, wherein the translation suppression element inhibitor is an antibody.

Embodiment 271

The method of any of embodiments 265-268, wherein the translation suppression element inhibitor is a peptide.

Embodiment 272

The method of any of embodiments 265-268, wherein the translation suppression element inhibitor is a nucleic acid.

Embodiment 273

The method of any of embodiments 265-268, wherein the translation suppression element inhibitor is an siRNA.

Embodiment 274

The method of any of embodiments 265-268, wherein the translation suppression element inhibitor is an antisense compound.

Embodiment 275

The method of embodiment 274, wherein the antisense compound is a modified oligonucleotide.

Embodiment 276

A method of increasing translation of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing translation of the target protein in the cell.

Embodiment 277

A method of decreasing suppression of translation of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby decreasing suppression of translation of the target protein in the cell.

Embodiment 278

A method of increasing the amount or activity of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing the amount or activity of the target protein in the cell.

Embodiment 279

A method of increasing expression of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing expression of the target protein in the cell.

Embodiment 280

The method of any of embodiments 276-279, wherein the translation suppression element region is the 5' untranslated region.

Embodiment 281

The method of any of embodiments 276-280, wherein the target transcript encodes RNase H1.

Embodiment 282

The method of any of embodiments 276-280, wherein the target transcript does not encode RNase H1.

Embodiment 283

The method of any of embodiments 276-281, wherein the modified oligonucleotide has a nucleobase sequence comprising at least 8 contiguous nucleobases of any of the nucleobase sequences of SEQ ID NOs: 8, 9, 11, or 12.

Embodiment 284

The method of any of embodiments 276-281, wherein the modified oligonucleotide has a nucleobase sequence comprising at least 10 contiguous nucleobases of any of the nucleobase sequences of SEQ ID NOs: 8, 9, 11, or 12.

Embodiment 285

The method of any of embodiments 276-281, wherein the modified oligonucleotide has a nucleobase sequence comprising at least 12 contiguous nucleobases of any of the nucleobase sequences of SEQ ID NOs: 8, 9, 11, or 12.

Embodiment 286

The method of any of embodiments 276-281, wherein the modified oligonucleotide has a nucleobase sequence comprising at least 14 contiguous nucleobases of any of the nucleobase sequences of SEQ ID NOs: 8, 9, 11, or 12.

Embodiment 287

The method of any of embodiments 276-281, wherein the modified oligonucleotide has a nucleobase sequence consisting of the nucleobase sequence of any of SEQ ID NOs: 8, 9, 11, or 12.

Embodiment 288

The method of any of embodiments 276-282, wherein the modified oligonucleotide has a nucleobase sequence wherein at least 35% all the nubcleobases are G or C nucleobases.

Embodiment 289

The method of any of embodiments 276-282, wherein the modified oligonucleotide has a nucleobase sequence wherein at least 40% all the nubcleobases are G or C nucleobases.

Embodiment 290

The method of any of embodiments 276-282, wherein the modified oligonucleotide has a nucleobase sequence wherein at least 45% all the nubcleobases are G or C nucleobases.

Embodiment 291

The method of any of embodiments 276-282, wherein the modified oligonucleotide has a nucleobase sequence wherein at least 50% all the nubcleobases are G or C nucleobases.

Embodiment 292

The method of any of embodiments 276-282, wherein the modified oligonucleotide has a nucleobase sequence wherein at least 55% all the nubcleobases are G or C nucleobases.

Embodiment 293

The method of any of embodiments 276-282, wherein the modified oligonucleotide has a nucleobase sequence wherein at least 60% all the nubcleobases are G or C nucleobases.

Embodiment 294

The method of any of embodiments 276-282, wherein the modified oligonucleotide has a nucleobase sequence wherein at least 65% all the nubcleobases are G or C nucleobases.

Embodiment 295

The method of any of embodiments 276-282, wherein the modified oligonucleotide has a nucleobase sequence wherein at least 70% all the nubcleobases are G or C nucleobases.

Embodiment 296

The method of any of embodiments 276-282, wherein at least a portion of the nucleobase sequence of the modified oligonucleotide is complementary to a G-quartet.

Embodiment 297

The method of any of embodiments 276-295, wherein the modified oligonucleotide has a nucleobase sequence that is not complementary to a G-quartet.

Embodiment 298

The method of any of embodiments 276-297, wherein the modified oligonucleotide consists of 10 to 40 linked nucleosides.

Embodiment 299

The method of any of embodiments 276-297, wherein the modified oligonucleotide consists of 12 to 22 linked nucleosides.

Embodiment 300

The method of any of embodiments 276-297, wherein the modified oligonucleotide consists of 15 to 22 linked nucleosides.

Embodiment 301

The method of any of embodiments 276-297, wherein the modified oligonucleotide consists of 18 to 20 linked nucleosides.

Embodiment 302

The method of any of embodiments 276-297, wherein the modified oligonucleotide comprises at least one modified nucleoside.

Embodiment 303

The method of embodiment 302, wherein at least one modified nucleoside comprises a modified sugar moiety.

Embodiment 304

The method of embodiment 303, wherein at least one modified sugar moiety is a 2'-substituted sugar moiety.

Embodiment 305

The method of embodiment 304, wherein the 2'-substitutent of at least one 2'-substituted sugar moiety is selected from among: 2'-OMe, 2'-F, and 2'-MOE.

Embodiment 306

The method of any of embodiments 302-305, wherein the 2'-substituent of at least one 2'-substituted sugar moiety is a 2'-MOE.

Embodiment 307

The method of any of embodiments 302-305, wherein the 2'-substituent of at least one 2'-substituted sugar moiety is not 2'OMe.

Embodiment 308

The method of any of embodiments 302-303, wherein at least one modified sugar moiety is a bicyclic sugar moiety.

Embodiment 309

The method of embodiment 308, wherein at least one bicyclic sugar moiety is LNA or cEt.

Embodiment 310

The method of any of embodiments 301-308, wherein at least one sugar moiety is a sugar surrogate.

Embodiment 311

The method of embodiment 303, wherein at least one sugar surrogate is a morpholino.

Embodiment 312

The method of embodiment 310, wherein at least one sugar surrogate is a modified morpholino.

Embodiment 313

The method of embodiment 310, wherein at least one sugar surrogate is a peptide nucleic acid.

Embodiment 314

The method of any of embodiment 302-313, wherein the modified oligonucleotide comprises at least 5 modified nucleosides, each independently comprising a modified sugar moiety.

Embodiment 315

The method of any of embodiment 302-313, wherein the modified oligonucleotide comprises at least 6 modified nucleosides, each independently comprising a modified sugar moiety.

Embodiment 316

The method of any of embodiment 302-313, wherein the modified oligonucleotide comprises at least 7 modified nucleosides, each independently comprising a modified sugar moiety.

Embodiment 317

The method of any of embodiment 302-313, wherein the modified oligonucleotide comprises at least 8 modified nucleosides, each independently comprising a modified sugar moiety.

Embodiment 318

The method of any of embodiment 302-313, wherein the modified oligonucleotide comprises at least 9 modified nucleosides, each independently comprising a modified sugar moiety.

Embodiment 319

The method of embodiment 302-313, wherein the modified oligonucleotide comprises at least 10 modified nucleosides, each independently comprising a modified sugar moiety.

Embodiment 320

The method of any of embodiments 302-319, wherein each nucleoside of the modified oligonucleotide is a modified nucleoside or an unmodified nucleoside.

Embodiment 321

The method of embodiment 320, wherein each unmodified nucleoside is a 2'-deoxy nucleoside.

Embodiment 322

The method of any of embodiments 320-321, wherein the modified oligonucleotide comprises at least 6 2'-deoxy nucleosides.

Embodiment 323

The method of any of embodiments 320-321, wherein the modified oligonucleotide comprises at least 7 2'-deoxy nucleosides.

Embodiment 324

The method of any of embodiments 320-321, wherein the modified oligonucleotide comprises at least 8 2'-deoxy nucleosides.

Embodiment 325

The method of any of embodiments 320-321, wherein the modified oligonucleotide comprises at least 9 2'-deoxy nucleosides.

Embodiment 326

The method of any of embodiments 320-321, wherein the modified oligonucleotide comprises at least 10 2'-deoxy nucleosides.

Embodiment 327

The method of any of embodiments 322-326, wherein the modified oligonucleotide contains no more than 4 contiguous 2'-deoxy nucleosides.

Embodiment 328

The method of any of embodiments 322-326, wherein the modified oligonucleotide comprises at least 15 modified nucleosides, each independently comprising a modified sugar moiety.

Embodiment 329

The method of embodiment 320, wherein each nucleoside of the modified oligonucleotide is a modified nucleoside, each independently comprising a modified sugar moiety.

Embodiment 330

The method of any of embodiments 303-329, wherein the modified oligonucleotide comprises at least two modified nucleosides comprising modified sugar moieties that are the same as one another.

Embodiment 331

The method of any of embodiments 303-329, wherein the modified oligonucleotide comprises at least two modified nucleosides comprising modified sugar moieties that are different from one another.

Embodiment 332

The method of any of embodiments 303-329, wherein the modified oligonucleotide comprises a modified region of at least 5 contiguous modified nucleosides.

Embodiment 333

The method of embodiment 332, wherein the modified oligonucleotide comprises a modified region of at least 10 contiguous modified nucleosides.

Embodiment 334

The method of embodiment 332, wherein the modified oligonucleotide comprises a modified region of at least 15 contiguous modified nucleosides.

Embodiment 335

The method of embodiment 332, wherein the modified oligonucleotide comprises a modified region of at least 18 contiguous modified nucleosides.

Embodiment 336

The method of embodiment 332, wherein the modified oligonucleotide comprises a modified region of at least 20 contiguous modified nucleosides.

Embodiment 337

The method of any of embodiments 332-336, wherein each modified nucleoside of the modified region has a modified sugar moiety independently selected from among: 2'-F, 2'-OMe, 2'-MOE, cEt, LNA, morpholino, modified morpholino, and peptide nucleic acid.

Embodiment 338

The method of any of embodiments 332-337, wherein the modified nucleosides of the modified region each comprise the same modification as one another.

Embodiment 339

The method of embodiment 338, wherein the modified nucleosides of the modified region each comprise the same 2'-substituted sugar moiety.

Embodiment 340

The method of embodiment 338, wherein the 2'-substituted sugar moiety of the modified nucleosides of the region of modified nucleosides is selected from 2'-F, 2'-OMe, and 2'-MOE.

Embodiment 341

The method of embodiment 339, wherein the 2'-substituted sugar moiety of the modified nucleosides of the region of modified nucleosides is 2'-MOE.

Embodiment 342

The method of embodiment 338, wherein the modified nucleosides of the region of modified nucleosides each comprise the same bicyclic sugar moiety.

Embodiment 343

The method of embodiment 342, wherein the bicyclic sugar moiety of the modified nucleosides of the region of modified nucleosides is selected from LNA and cEt.

Embodiment 344

The method of embodiment 338, wherein the modified nucleosides of the region of modified nucleosides each comprises a sugar surrogate.

Embodiment 345

The method of embodiment 344, wherein the sugar surrogate of the modified nucleosides of the region of modified nucleosides is a morpholino.

Embodiment 346

The method of embodiment 344, wherein the sugar surrogate of the modified nucleosides of the region of modified nucleosides is a modified morpholino.

Embodiment 347

The method of embodiment 344, wherein the sugar surrogate of the modified nucleosides of the region of modified nucleosides is a peptide nucleic acid.

Embodiment 348

The method of any of embodiments 338-347, wherein the modified nucleotide comprises no more than 4 contiguous naturally occurring nucleosides.

Embodiment 349

The method of any of embodiments 338-347, wherein each nucleoside of the modified oligonucleotide is a modified nucleoside.

Embodiment 350

The method of embodiment 349 wherein each modified nucleoside comprises a modified sugar moiety.

Embodiment 351

The method of embodiment 350, wherein the modified nucleosides of the modified oligonucleotide comprise the same modification as one another.

Embodiment 352

The method of embodiment 351, wherein the modified nucleosides of the modified oligonucleotide each comprise the same 2'-substituted sugar moiety.

Embodiment 353

The method of embodiment 352, wherein the 2'-substituted sugar moiety of the modified oligonucleotide is selected from 2'-F, 2'-OMe, and 2'-MOE.

Embodiment 354

The method of embodiment 353, wherein the 2'-substituted sugar moiety of the modified oligonucleotide is 2'-MOE.

Embodiment 355

The method of embodiment 353, wherein the 2'-substituted sugar moiety of the modified oligonucleotide is 2'-OMe.

Embodiment 356

The method of embodiment 351, wherein the modified nucleosides of the modified oligonucleotide each comprise the same bicyclic sugar moiety.

Embodiment 357

The method of embodiment 356, wherein the bicyclic sugar moiety of the modified oligonucleotide is selected from LNA and cEt.

Embodiment 358

The method of embodiment 349-350, wherein the modified nucleosides of the modified oligonucleotide each comprises a sugar surrogate.

Embodiment 359

The method of embodiment 358, wherein the sugar surrogate of the modified oligonucleotide is a morpholino.

Embodiment 360

The method of embodiment 358, wherein the sugar surrogate of the modified oligonucleotide is a modified morpholino.

Embodiment 361

The method of embodiment 358, wherein the sugar surrogate of the modified oligonucleotide is a peptide nucleic acid.

Embodiment 362

The method of any of embodiments 276-361, wherein the modified oligonucleotide comprises at least one modified internucleoside linkage.

Embodiment 363

The method of embodiment 361, wherein the modified internucleoside linkage is a phosphorothioate internucleoside linkage.

Embodiment 364

The method of embodiment 362 or 363, wherein each internucleoside linkage is either a phosphodiester internucleoside linkage or a phosphorothioate internucleoside linkage.

Embodiment 365

The method of embodiment 362, wherein each internucleoside linkage is a modified internucleoside linkage.

Embodiment 366

The method of embodiment 362 or 363, comprising at least one phosphorothioate internucleoside linkage.

Embodiment 367

The method of embodiment 362, wherein each internucleoside linkage is a modified internucleoside linkage and wherein each internucleoside linkage comprises the same modification.

Embodiment 368

The method of embodiment 363, wherein each internucleoside linkage is a phosphorothioate internucleoside linkage.

Embodiment 369

The method of any of embodiments 276-368, wherein the antisense compound comprises at least one conjugate group.

Embodiment 370

The method of embodiment 369, wherein the conjugate group comprises Gal-NAc.

Embodiment 371

The method of any of embodiments 276-368, wherein the antisense compound consists of the modified oligonucleotide.

Embodiment 372

The method of any of embodiments 276-371, wherein the expression, translation, or amount or activity of the target protein is increased by at least 10%.

Embodiment 373

The method of any of embodiments 276-371, wherein the expression, translation, or amount or activity of the target protein is increased by at least 20%.

Embodiment 374

The method of any of embodiments 276-371, wherein the expression, translation, or amount or activity of the target protein is increased by at least 30%.

Embodiment 375

The method of any of embodiments 276-371, wherein the expression, translation, or amount or activity of the target protein is increased by at least 50%.

Embodiment 376

The method of any of embodiments 276-371, wherein the expression, translation, or amount or activity of the target protein is increased by at least 100%.

Embodiment 377

The method of any of embodiments 276-371, wherein the expression, translation, or amount or activity of the target protein is increased by at least 120%.

Embodiment 378

The method of any of embodiments 276-371, wherein the expression, translation, or amount or activity of the target protein is increased by at least 150%.

Embodiment 379

The method of any of embodiments 265-378, wherein the cell is in vitro.

Embodiment 380

The method of any of embodiments 265-378, wherein the cell is in a subject.

Embodiment 381

The method of embodiment 380, wherein the subject has a disease or condition and wherein at least one symptom of the disease or condition is ameliorated.

Embodiment 382

The method of embodiment 380 or 381, wherein the cell is in an animal.

Embodiment 383

The method of embodiment 382, wherein the animal is a human.

Embodiment 384

An antisense compound comprising a modified oligonucleotide consisting of 10-30 linked nucleosides having a nucleobase sequence complementary to a target site within a translation suppression element region of a target transcript and wherein the modified oligonucleotide does not have more than four contiguous unmodified 2'-deoxy nucleosides.

Embodiment 385

The antisense compound of embodiments 384, wherein the translation suppression element region is the 5' untranslated region.

Embodiment 386

A method of increasing the amount or activity of a target protein in a cell, comprising contacting the cell with a uORF inhibitor, wherein the target protein is encoded by a target transcript comprising at least one uORF start site; and thereby increasing the amount or activity of the target protein in the cell.

Embodiment 387

A method of increasing expression of a target protein in a cell, comprising contacting the cell with a uORF inhibitor, wherein the target protein is encoded by a target transcript comprising at least one uORF start site; and thereby increasing expression of the target protein in the cell.

Embodiment 388

A method of increasing translation of a target protein in a cell, comprising contacting the cell with a uORF inhibitor, wherein the target protein is encoded by a target transcript comprising at least one uORF start site; and thereby increasing translation of the target protein in the cell.

Embodiment 389

A method of decreasing suppression of translation a target protein in a cell, comprising contacting the cell with a uORF inhibitor, wherein the target protein is encoded by a target transcript comprising at least one uORF start site; and thereby decreasing suppression of translation of the target protein in the cell.

Embodiment 390

A method of decreasing translation of a uORF polypeptide in a cell, comprising contacting the cell with a uORF inhibitor; and thereby decreasing translation of the uORF polypeptide in the cell.

Embodiment 391

The method of any of embodiments 386-390, wherein the uORF inhibitor is a small molecule.

Embodiment 392

The method of any of embodiments 386-390, wherein the uORF inhibitor is an antibody.

Embodiment 393

The method of any of embodiments 386-390, wherein the uORF inhibitor is a peptide.

Embodiment 394

The method of any of embodiments 386-390, wherein the uORF inhibitor is a nucleic acid.

Embodiment 395

The method of any of embodiments 386-390, wherein the uORF inhibitor is an siRNA.

Embodiment 396

The method of any of embodiments 386-390, wherein the uORF inhibitor is an antisense compound.

Embodiment 397

The method of embodiment 396, wherein the antisense compound is a modified oligonucleotide.

Embodiment 398

A method of increasing the amount or activity of a target protein in a cell, comprising contacting the cell with an antisense compound comprising a modified oligonucleotide, wherein the target protein is encoded by a target transcript comprising at least one uORF start site and wherein the modified oligonucleotide is complementary to a target site within a uORF start site region of the target transcript; and thereby increasing the amount or activity of the target protein in the cell.

Embodiment 399

A method of increasing expression of a target protein in a cell, comprising contacting the cell with an antisense compound comprising a modified oligonucleotide, wherein the target protein is encoded by a target transcript comprising at least one uORF start site and wherein the modified oligonucleotide is complementary to target site within a uORF start site region of the target transcript; and thereby increasing expression of the target protein in the cell.

Embodiment 400

A method of increasing translation of a target protein in a cell, comprising contacting the cell with an antisense compound comprising a modified oligonucleotide, wherein the target protein is encoded by a target transcript comprising at least one uORF start site and wherein the modified oligonucleotide is complementary to a target site within a uORF start site region of the target transcript; and thereby increasing translation of the target protein in the cell.

Embodiment 401

A method of decreasing suppression of translation of a target protein in a cell, comprising contacting the cell with an antisense compound comprising a modified oligonucleotide, wherein the target protein is encoded by a target transcript comprising at least one uORF start site and wherein the modified oligonucleotide is complementary to a target site within a uORF start site region of the target transcript; and thereby decreasing suppression of translation of the target protein in the cell.

Embodiment 402

A method of decreasing translation of a uORF polypeptide in a cell, comprising contacting the cell with an antisense compound comprising a modified oligonucleotide complementary to a target site within a uORF region of the target transcript; and thereby decreasing translation of the uORF polypeptide in the cell.

Embodiment 403

The method of any of embodiments 386-402, wherein the uORF start site region is the 5' untranslated region.

Embodiment 404

The method of any of embodiments 398-403, wherein the target site comprises the uORF start site.

Embodiment 405

The method of any of embodiments 398-404, wherein the target site region consists of the uORF start site and the 100 nucleosides upstream and the 100 nucleosides downstream of the uORF start site.

Embodiment 406

The method of any of embodiments 398-404, wherein the target site region consists of the uORF start site and the 75 nucleosides upstream and the 75 nucleosides downstream of the uORF start site.

Embodiment 407

The method of any of embodiments 398-404, wherein the target site region consists of the uORF start site and the 50 nucleosides upstream and the 50 nucleosides downstream of the uORF start site.

Embodiment 408

The method of any of embodiments 398-404, wherein the target site region consists of the uORF start site and the 30 nucleosides upstream and the 30 nucleosides downstream of the uORF start site.

Embodiment 409

The method of any of embodiments 398-404, wherein the target site region consists of the uORF start site and the 20 nucleosides upstream and the 20 nucleosides downstream of the uORF start site.

Embodiment 410

The method of any of embodiments 398-404, wherein the target site region consists of the uORF start site and the 15 nucleosides upstream and the 15 nucleosides downstream of the uORF start site.

Embodiment 411

The method of any of embodiments 398-404, wherein the target site region is downstream of the uORF start site.

Embodiment 412

The method of any of embodiments 398-404, wherein the target site region is 6 to 65 nucleobases downstream of the uORF start site.

Embodiment 413

The method of any of embodiments 398-404, wherein the target site region is 6 to 23 nucleobases downstream of the uORF start site.

Embodiment 414

The method of any of embodiments 398-404, wherein the target site region is 47 to 64 nucleobases downstream of the uORF start site.

Embodiment 415

The method of any of embodiments 398-414, wherein the uORF start site is a wild-type uORF start site.

Embodiment 416

The method of any of embodiments 398-414, wherein the uORF start site is a mutant uORF start site.

Embodiment 417

The method of any of embodiments 398-416, wherein the target transcript comprises more than one uORF region.

Embodiment 418

The method of any of embodiments 398-417, wherein the target transcript comprises two uORF regions.

Embodiment 419

The method of any of embodiments 398-418, wherein the uORF start site comprises a weak Kozak sequence.

Embodiment 420

The method of any of embodiments 398-418, wherein the uORF start site comprises a strong Kozak sequence.

Embodiment 421

The method of any of embodiments 398-420, wherein the uORF start site has a non-canonical start codon.

Embodiment 422

The method of embodiment 421, wherein the non-canonical start codon is AUU.

Embodiment 423

The method of any of embodiments 398-422, wherein the target transcript encodes RNase H1.

Embodiment 424

The method of any of embodiments 398-422, wherein the target transcript encodes LRPPRC.

Embodiment 425

The method of any of embodiments 398-422, wherein the target transcript encodes SFXN3.

Embodiment 426

The method of any of embodiments 398-422, wherein the target transcript encodes MRPL11.

Embodiment 427

The method of any of embodiments 398-422, wherein the target transcript encodes THPO.

Embodiment 428

The method of any of embodiments 398-422, wherein the target transcript encodes CFTR.

Embodiment 429

The method of any of embodiments 398-422, wherein the target transcript encodes a protein selected from the group consisting of La/SSB, NPM1, TCP1-alpha, TCP1-epsilon, TCP1-beta, HSP90-AA1, hsp90-AB, HSPA1L, RAN, IMPS, Annexin A2, FTCD/58K, PC4/SUB1, VARS, and DHX36.

Embodiment 430

The method of any of embodiments 398-422, wherein the target transcript is encoded by a gene selected from the genes in Table 1 or Table 2.

Embodiment 431

The method of any of embodiments 397-430, wherein the modified oligonucleotide has a nucleobase sequence 80% complementary to the target transcript.

Embodiment 432

The method of any of embodiments 397-430, wherein the modified oligonucleotide has a nucleobase sequence 85% complementary to the target transcript.

Embodiment 433

The method of any of embodiments 397-430, wherein the modified oligonucleotide has a nucleobase sequence 90% complementary to the target transcript.

Embodiment 434

The method of any of embodiments 397-430, wherein the modified oligonucleotide has a nucleobase sequence 95% complementary to the target transcript.

Embodiment 435

The method of any of embodiments 397-430, wherein the modified oligonucleotide has a nucleobase sequence 100% complementary to the target transcript.

Embodiment 436

The method of any of embodiments 397-430, wherein the modified oligonucleotide has a nucleobase having at least 1 mismatch relative to the target transcript.

Embodiment 437

The method of any of embodiments 397-430, wherein the modified oligonucleotide has a nucleobase having at least 2 mismatches relative to the target transcript.

Embodiment 438

The method of any of embodiments 397-430, wherein the modified oligonucleotide has a nucleobase having at least 3 mismatches relative to the target transcript.

Embodiment 439

The method of any of embodiments 397-430, wherein the modified oligonucleotide has a nucleobase sequence comprising the nucleobases CAT.

Embodiment 440

The method of any of embodiments 397-430, wherein the modified oligonucleotide has a nucleobase sequence wherein the first three of the 5'-most nucleobases are CAT.

Embodiment 441

The method of any of embodiments 397-430, wherein the modified oligonucleotide has a nucleobase sequence wherein the $2^{nd}$, $3^{rd}$, and $4^{th}$ nucleobases from the 5'-most terminal nucleobase are CAT.

Embodiment 442

The method of any of embodiments 397-430, wherein the modified oligonucleotide has a nucleobase sequence wherein the $3^{rd}$, $4^{th}$, and $5^{th}$ nucleobases from the 5'-most terminal nucleobase are CAT.

Embodiment 443

The method of any of embodiments 397-430, wherein the modified oligonucleotide has a nucleobase sequence wherein the $4^{th}$, $5^{th}$, and $6^{th}$ nucleobases from the 5'-most terminal nucleobase are CAT.

Embodiment 444

The method of any of embodiments 397-430, wherein the modified oligonucleotide has a nucleobase sequence wherein the $5^{th}$, $6^{th}$, and $7^{th}$ nucleobases from the 5'-most terminal nucleobase are CAT.

Embodiment 445

The method of any of embodiments 397-430, wherein the modified oligonucleotide has a nucleobase sequence wherein the $6^{th}$, $7^{th}$, and $8^{th}$ nucleobases from the 5'-most terminal nucleobase are CAT.

Embodiment 446

The method of any of embodiments 397-430, wherein the modified oligonucleotide has a nucleobase sequence wherein the $7^{th}$, $8^{th}$, and $9^{th}$ nucleobases from the 5'-most terminal nucleobase are CAT.

Embodiment 447

The method of any of embodiments 397-430, wherein the modified oligonucleotide has a nucleobase sequence wherein the first three of the 3'-most nucleobases are CAT.

Embodiment 448

The method of any of embodiments 397-430, wherein the modified oligonucleotide has a nucleobase sequence wherein the $2^{nd}$, $3^{rd}$, and $4^{th}$ nucleobases from the 3'-most terminal nucleobase are CAT.

Embodiment 449

The method of any of embodiments 397-430, wherein the modified oligonucleotide has a nucleobase sequence wherein the $3^{rd}$, $4^{th}$, and $5^{th}$ nucleobases from the 3'-most terminal nucleobase are CAT.

Embodiment 450

The method of any of embodiments 397-430, wherein the modified oligonucleotide has a nucleobase sequence wherein the $4^{th}$, $5^{th}$, and $6^{th}$ nucleobases from the 3'-most terminal nucleobase are CAT.

Embodiment 451

The method of any of embodiments 397-430, wherein the modified oligonucleotide has a nucleobase sequence wherein the $5^{th}$, $6^{th}$, and $7^{th}$ nucleobases from the 3'-most terminal nucleobase are CAT.

Embodiment 452

The method of any of embodiments 397-430, wherein the modified oligonucleotide comprises a nucleobase sequence complementary to a Kozak sequence.

Embodiment 453

The method of any of embodiments 397-430, wherein the modified oligonucleotide has a nucleobase sequence comprising at least 8 contiguous nucleobases complementary to the uORF region of SEQ ID NOs: 1 or 2.

Embodiment 454

The method of any of embodiments 397-430, wherein the modified oligonucleotide has a nucleobase sequence comprising at least 8 contiguous nucleobases of any of the nucleobase sequences of SEQ ID NOs: 3, 4, 5, 6, 7, 8, 9, 10, 11, 12, 13, 14, 15, 16, 17, 18, 21, 23, 25, 26, 27, 28, 29, 30, 31, 32, 33, 34, 35, 36, 37, 38, 39, 40, 41, 42, 44, 45, 52, 53, 54, 55, 56, 57, 58, 59, 60, 61, 62, 63, 64, 65, 66, 67, 68, 69, 70, 71, 72, 73, 74, 75, 76, 77, 82, or 83.

Embodiment 455

The method of any of embodiments 397-430, wherein the modified oligonucleotide has a nucleobase sequence comprising at least 10 contiguous nucleobases of any of the nucleobase sequences of SEQ ID NOs: 3, 4, 5, 6, 7, 8, 9, 10, 11, 12, 13, 14, 15, 16, 17, 18, 21, 23, 25, 26, 27, 28, 29, 30, 31, 32, 33, 34, 35, 36, 37, 38, 39, 40, 41, 42, 44, 45, 52, 53, 54, 55, 56, 57, 58, 59, 60, 61, 62, 63, 64, 65, 66, 67, 68, 69, 70, 71, 72, 73, 74, 75, 76, 77, 82, or 83.

Embodiment 456

The method of any of embodiments 397-430, wherein the modified oligonucleotide has a nucleobase sequence comprising at least 12 contiguous nucleobases of any of the nucleobase sequences of SEQ ID NOs: 3, 4, 5, 6, 7, 8, 9, 10, 11, 12, 13, 14, 15, 16, 17, 18, 21, 23, 25, 26, 27, 28, 29, 30, 31, 32, 33, 34, 35, 36, 37, 38, 39, 40, 41, 42, 44, 45, 52, 53, 54, 55, 56, 57, 58, 59, 60, 61, 62, 63, 64, 65, 66, 67, 68, 69, 70, 71, 72, 73, 74, 75, 76, 77, 82, or 83.

Embodiment 457

The method of any of embodiments 397-430, wherein the modified oligonucleotide has a nucleobase sequence comprising at least 14 contiguous nucleobases of any of the nucleobase sequences of SEQ ID NOs: 3, 4, 5, 6, 7, 8, 9, 10, 11, 12, 13, 14, 15, 16, 17, 18, 21, 23, 25, 26, 27, 28, 29, 30, 31, 32, 33, 34, 35, 36, 37, 38, 39, 40, 41, 42, 44, 45, 52, 53, 54, 55, 56, 57, 58, 59, 60, 61, 62, 63, 64, 65, 66, 67, 68, 69, 70, 71, 72, 73, 74, 75, 76, 77, 82, or 83.

Embodiment 458

The method of any of embodiments 397-430, wherein the modified oligonucleotide has a nucleobase sequence consisting of the nucleobase sequence of any of SEQ ID NOs: 3, 4, 5, 6, 7, 8, 9, 10, 11, 12, 13, 14, 15, 16, 17, 18, 21, 23, 25, 26, 27, 28, 29, 30, 31, 32, 33, 34, 35, 36, 37, 38, 39, 40, 41, 42, 44, 45, 52, 53, 54, 55, 56, 57, 58, 59, 60, 61, 62, 63, 64, 65, 66, 67, 68, 69, 70, 71, 72, 73, 74, 75, 76, 77, 82, or 83.

Embodiment 459

The method of any of embodiments 397-458, wherein the modified oligonucleotide consists of 10 to 40 linked nucleosides.

Embodiment 460

The method of any of embodiments 397-458, wherein the modified oligonucleotide consists of 12 to 22 linked nucleosides.

Embodiment 461

The method of any of embodiments 397-458, wherein the modified oligonucleotide consists of 15 to 22 linked nucleosides.

Embodiment 462

The method of any of embodiments 397-458, wherein the modified oligonucleotide consists of 18 to 20 linked nucleosides.

Embodiment 463

The method of any of embodiments 397-462, wherein the modified oligonucleotide comprises at least one modified nucleoside.

Embodiment 464

The method of embodiment 463, wherein at least one modified nucleoside comprises a modified sugar moiety.

Embodiment 465

The method of embodiment 464, wherein at least one modified sugar moiety is a 2'-substituted sugar moiety.

Embodiment 466

The method of embodiment 465, wherein the 2'-substitutent of at least one 2'-substituted sugar moiety is selected from among: 2'-OMe, 2'-F, and 2'-MOE.

Embodiment 467

The method of any of embodiments 463-466, wherein the 2'-substituent of at least one 2'-substituted sugar moiety is a 2'-MOE.

Embodiment 468

The method of any of embodiments 463-464, wherein at least one modified sugar moiety is a bicyclic sugar moiety.

Embodiment 469

The method of embodiment 468, wherein at least one bicyclic sugar moiety is LNA or cEt.

Embodiment 470

The method of any of embodiments 464-469, wherein at least one sugar moiety is a sugar surrogate.

Embodiment 471

The method of embodiment 470, wherein at least one sugar surrogate is a morpholino.

Embodiment 472

The method of embodiment 470, wherein at least one sugar surrogate is a modified morpholino.

Embodiment 473

The method of embodiment 470, wherein at least one sugar surrogate is a peptide nucleic acid.

Embodiment 474

The method of any of embodiment 463-473, wherein the modified oligonucleotide comprises at least 5 modified nucleosides, each independently comprising a modified sugar moiety.

Embodiment 475

The method of any of embodiment 463-473, wherein the modified oligonucleotide comprises at least 6 modified nucleosides, each independently comprising a modified sugar moiety.

Embodiment 476

The method of any of embodiment 463-473, wherein the modified oligonucleotide comprises at least 7 modified nucleosides, each independently comprising a modified sugar moiety.

Embodiment 477

The method of any of embodiment 463-473, wherein the modified oligonucleotide comprises at least 8 modified nucleosides, each independently comprising a modified sugar moiety.

Embodiment 478

The method of any of embodiment 463-473, wherein the modified oligonucleotide comprises at least 9 modified nucleosides, each independently comprising a modified sugar moiety.

Embodiment 479

The method of embodiment 463-473, wherein the modified oligonucleotide comprises at least 10 modified nucleosides, each independently comprising a modified sugar moiety.

Embodiment 480

The method of any of embodiments 463-479, wherein each nucleoside of the modified oligonucleotide is a modified nucleoside or an unmodified nucleoside.

Embodiment 481

The method of embodiment 480, wherein each unmodified nucleoside is a 2'-deoxy nucleoside.

Embodiment 482

The method of any of embodiments 480-481, wherein the modified oligonucleotide comprises at least 6 2'-deoxy nucleosides.

Embodiment 483

The method of any of embodiments 480-481, wherein the modified oligonucleotide comprises at least 7 2'-deoxy nucleosides.

Embodiment 484

The method of any of embodiments 480-481, wherein the modified oligonucleotide comprises at least 8 2'-deoxy nucleosides.

Embodiment 485

The method of any of embodiments 480-481, wherein the modified oligonucleotide comprises at least 9 2'-deoxy nucleosides.

Embodiment 486

The method of any of embodiments 480-481, wherein the modified oligonucleotide comprises at least 10 2'-deoxy nucleosides.

Embodiment 487

The method of any of embodiments 482-486, wherein the modified oligonucleotide contains no more than 4 contiguous 2'-deoxy nucleosides.

Embodiment 488

The method of any of embodiments 480-481, wherein the modified oligonucleotide comprises at least 15 modified nucleosides, each independently comprising a modified sugar moiety.

Embodiment 489

The method of embodiment 488, wherein each nucleoside of the modified oligonucleotide is a modified nucleoside, each independently comprising a modified sugar moiety.

Embodiment 490

The method of any of embodiments 463-489, wherein the modified oligonucleotide comprises at least two modified nucleosides comprising modified sugar moieties that are the same as one another.

Embodiment 491

The method of any of embodiments 463-489, wherein the modified oligonucleotide comprises at least two modified nucleosides comprising modified sugar moieties that are different from one another.

Embodiment 492

The method of any of embodiments 463-489, wherein the modified oligonucleotide comprises a modified region of at least 5 contiguous modified nucleosides.

Embodiment 493

The method of embodiment 492, wherein the modified oligonucleotide comprises a modified region of at least 10 contiguous modified nucleosides.

Embodiment 494

The method of embodiment 492, wherein the modified oligonucleotide comprises a modified region of at least 15 contiguous modified nucleosides.

Embodiment 495

The method of embodiment 492, wherein the modified oligonucleotide comprises a modified region of at least 18 contiguous modified nucleosides.

Embodiment 496

The method of embodiment 488, wherein the modified oligonucleotide comprises a modified region of at least 20 contiguous modified nucleosides.

Embodiment 497

The method of any of embodiments 493-496, wherein each modified nucleoside of the modified region has a modified sugar moiety independently selected from among: 2'-F, 2'-OMe, 2'-MOE, cEt, LNA, morpholino, modified morpholino, and peptide nucleic acid.

Embodiment 498

The method of any of embodiments 493-497, wherein the modified nucleosides of the modified region each comprise the same modification as one another.

Embodiment 499

The method of embodiment 498, wherein the modified nucleosides of the modified region each comprise the same 2'-substituted sugar moiety.

Embodiment 500

The method of embodiment 498, wherein the 2'-substituted sugar moiety of the modified nucleosides of the region of modified nucleosides is selected from 2'-F, 2'-OMe, and 2'-MOE.

Embodiment 501

The method of embodiment 500, wherein the 2'-substituted sugar moiety of the modified nucleosides of the region of modified nucleosides is 2'-MOE.

Embodiment 502

The method of embodiment 499, wherein the modified nucleosides of the region of modified nucleosides each comprise the same bicyclic sugar moiety.

Embodiment 503

The method of embodiment 502, wherein the bicyclic sugar moiety of the modified nucleosides of the region of modified nucleosides is selected from LNA and cEt.

Embodiment 504

The method of embodiment 498, wherein the modified nucleosides of the region of modified nucleosides each comprises a sugar surrogate.

Embodiment 505

The method of embodiment 504, wherein the sugar surrogate of the modified nucleosides of the region of modified nucleosides is a morpholino.

Embodiment 506

The method of embodiment 504, wherein the sugar surrogate of the modified nucleosides of the region of modified nucleosides is a modified morpholino.

Embodiment 507

The method of embodiment 504, wherein the sugar surrogate of the modified nucleosides of the region of modified nucleosides is a peptide nucleic acid.

Embodiment 508

The method of any of embodiments 463-507, wherein the modified nucleotide comprises no more than 4 contiguous naturally occurring nucleosides.

Embodiment 509

The method of any of embodiments 463-507, wherein each nucleoside of the modified oligonucleotide is a modified nucleoside.

Embodiment 510

The method of embodiment 509 wherein each modified nucleoside comprises a modified sugar moiety.

Embodiment 511

The method of embodiment 510 wherein each modified nucleoside comprises a modified sugar moiety, and wherein $1^{st}$ and $2^{nd}$ nucleosides from the 3'-most terminal nucleoside are bicyclic sugar moieties.

Embodiment 512

The method of embodiment 510 wherein each modified nucleoside comprises a modified sugar moiety, and wherein $1^{st}$, $2^{nd}$, and $3^{rd}$ nucleosides from the 3'-most terminal nucleoside are bicyclic sugar moieties.

Embodiment 513

The method of embodiment 510 wherein each modified nucleoside comprises a modified sugar moiety, and wherein $1^{st}$, $2^{nd}$, $3^{rd}$, and $4^{th}$ nucleosides from the 3'-most terminal nucleoside are bicyclic sugar moieties.

Embodiment 514

The method of embodiment 510 wherein each modified nucleoside comprises a modified sugar moiety, and wherein $1^{st}$, $2^{nd}$, $3^{rd}$, $4^{th}$ and $5^{th}$ nucleosides from the 3'-most terminal nucleoside are bicyclic sugar moieties.

Embodiment 515

The method of embodiment 510 wherein each modified nucleoside comprises a modified sugar moiety, and wherein $1^{st}$, $2^{nd}$, $3^{rd}$, $4^{th}$, $5^{th}$, and $6^{th}$ nucleosides from the 3'-most terminal nucleoside are bicyclic sugar moieties.

Embodiment 516

The method of embodiments 511-515 wherein the bicyclic sugar moiety of the modified oligonucleotide is selected from LNA and cEt.

Embodiment 517

The method of embodiment 515 wherein, each remaining nucleoside in the modified oligonucleotide comprises a modified sugar moiety selected from 2'-F, 2'-OMe, and 2'-MOE.

Embodiment 518

The method of embodiment 510 wherein each modified nucleoside comprises a modified sugar moiety, and wherein $1^{st}$ and $2^{nd}$ nucleosides from the 3'-most terminal nucleoside are 2'-F modified sugar moieties.

Embodiment 519

The method of embodiment 510 wherein each modified nucleoside comprises a modified sugar moiety, and wherein $1^{st}$, $2^{nd}$, and $3^{rd}$ nucleosides from the 3'-most terminal nucleoside are 2'-F modified sugar moieties.

Embodiment 520

The method of embodiment 510 wherein each modified nucleoside comprises a modified sugar moiety, and wherein 1st, 2nd, 3rd, and 4th nucleosides from the 3'-most terminal nucleoside are 2'-F modified sugar moieties.

Embodiment 521

The method of embodiment 510 wherein each modified nucleoside comprises a modified sugar moiety, and wherein 1st, 2nd, 3rd, 4th and 5th nucleosides from the 3'-most terminal nucleoside are 2'-F modified sugar moieties.

Embodiment 522

The method of embodiment 510 wherein each modified nucleoside comprises a modified sugar moiety, and wherein 1st, 2nd, 3rd, 4th, 5th, and 6th nucleosides from the 3'-most terminal nucleoside are 2'-F modified sugar moieties.

Embodiment 523

The method of embodiments 511-522, wherein each remaining nucleoside in the modified oligonucleotide comprises a modified sugar moiety selected from 2'-OMe and 2'-MOE.

Embodiment 524

The method of embodiment 509, wherein the modified nucleosides of the modified oligonucleotide comprise the same modification as one another.

Embodiment 525

The method of embodiment 524, wherein the modified nucleosides of the modified oligonucleotide each comprise the same 2'-substituted sugar moiety.

Embodiment 526

The method of embodiment 525, wherein the 2'-substituted sugar moiety of the modified oligonucleotide is selected from 2'-F, 2'-OMe, and 2'-MOE.

Embodiment 527

The method of embodiment 526, wherein the 2'-substituted sugar moiety of the modified oligonucleotide is 2'-MOE.

Embodiment 528

The method of embodiment 526, wherein the 2'-substituted sugar moiety of the modified oligonucleotide is 2'-OMe.

Embodiment 529

The method of embodiment 524, wherein the modified nucleosides of the modified oligonucleotide each comprise the same bicyclic sugar moiety.

Embodiment 530

The method of embodiment 529, wherein the bicyclic sugar moiety of the modified oligonucleotide is selected from LNA and cEt.

Embodiment 531

The method of embodiment 524, wherein the modified nucleosides of the modified oligonucleotide each comprises a sugar surrogate.

Embodiment 532

The method of embodiment 531, wherein the sugar surrogate of the modified oligonucleotide is a morpholino.

Embodiment 533

The method of embodiment 531, wherein the sugar surrogate of the modified oligonucleotide is a modified morpholino.

Embodiment 534

The method of embodiment 531, wherein the sugar surrogate of the modified oligonucleotide is a peptide nucleic acid.

Embodiment 535

The method of any of embodiments 397-534, wherein the modified oligonucleotide comprises at least one modified internucleoside linkage.

Embodiment 536

The method of embodiment 535, wherein the modified internucleoside linkage is a phosphorothioate internucleoside linkage.

Embodiment 537

The method of embodiment 535 or 536, wherein each internucleoside linkage is either a phosphodiester internucleoside linkage or a phosphorothioate internucleoside linkage.

Embodiment 538

The method of embodiment 537, wherein each internucleoside linkage is a modified internucleoside linkage.

Embodiment 539

The method of embodiment 535 or 536, comprising at least one phosphorothioate internucleoside linkage.

Embodiment 540

The method of embodiment 535, wherein each internucleoside linkage is a modified internucleoside linkage and wherein each internucleoside linkage comprises the same modification.

Embodiment 541

The method of embodiment 540, wherein each internucleoside linkage is a phosphorothioate internucleoside linkage.

Embodiment 542

The method of any of embodiments 397-541, wherein the antisense compound comprises at least one conjugate group.

Embodiment 543

The method of embodiment 542, wherein the conjugate group comprises Gal-NAc.

Embodiment 544

The method of any of embodiments 397-543, wherein the antisense compound consists of the modified oligonucleotide.

Embodiment 545

The method of any of embodiments 397-544, wherein the expression, translation, or amount or activity of the target protein is increased by at least 10%.

Embodiment 546

The method of any of embodiments 397-544, wherein the expression, translation, or amount or activity of the target protein is increased by at least 20%.

Embodiment 547

The method of any of embodiments 397-544, wherein the expression, translation, or amount or activity of the target protein is increased by at least 30%.

Embodiment 548

The method of any of embodiments 397-544, wherein the expression, translation, or amount or activity of the target protein is increased by at least 50%.

Embodiment 549

The method of any of embodiments 397-544, wherein the expression, translation, or amount or activity of the target protein is increased by at least 100%.

Embodiment 550

The method of any of embodiments 397-544, wherein the expression, translation, or amount or activity of the target protein is increased by at least 120%.

Embodiment 551

The method of any of embodiments 397-544, wherein the expression, translation, or amount or activity of the target protein is increased by at least 150%.

Embodiment 552

The method of any of embodiments 386-551, wherein the cell is in vitro.

Embodiment 553

The method of any of embodiments 386-551, wherein the cell is in a subject.

Embodiment 554

The method of embodiment 553, wherein the subject has a disease or condition and wherein at least one symptom of the disease or condition is ameliorated.

Embodiment 555

The method of embodiment 553 or 554, wherein the cell is in an animal.

Embodiment 556

The method of embodiment 555, wherein the animal is a human.

Embodiment 557

A method of increasing translation of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing translation of the target protein in the cell.

Embodiment 558

A method of decreasing suppression of translation of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby decreasing suppression of translation of the target protein in the cell.

Embodiment 559

A method of increasing the amount or activity of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing the amount or activity of the target protein in the cell.

Embodiment 560

A method of increasing expression of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing expression of the target protein in the cell.

Embodiment 561

The method of any of embodiments 557-560, wherein the translation suppression element region is the 5' untranslated region.

Embodiment 562

The method of any of embodiments 557-561, wherein the translation suppression element region contains one or more uORFs.

Embodiment 563

The method of any of embodiments 557-561, wherein the translation suppression element region contains one or more uORFs, but wherein the one or more uORFs do not suppress translation of the target transcript.

Embodiment 564

The method of any of embodiments 557-561, wherein the translation suppression element region does not contains a uORF.

Embodiment 565

The method of any of embodiments 557-563, wherein the target transcript encodes RNase H1.

Embodiment 566

The method of any of embodiments 557-561 or 564, wherein the target transcript encodes ACP1.

Embodiment 567

The method of any of embodiments 557-563, wherein the target transcript encodes LRPPRC.

Embodiment 568

The method of any of embodiments 557-563, wherein the target transcript encodes SFXN3.

Embodiment 569

The method of any of embodiments 557-563, wherein the target transcript encodes MRPL11.

Embodiment 570

The method of any of embodiments 557-563, wherein the target transcript encodes THPO.

Embodiment 571

The method of any of embodiments 557-563, wherein the target transcript encodes CFTR.

Embodiment 572

The method of any of embodiments 557-564, wherein the target transcript encodes a protein selected from the group consisting of La/SSB, NPM1, TCP1-alpha, TCP1-epsilon, TCP1-beta, HSP90-AA1, hsp90-AB, HSPA1L, RAN, IMPS, Annexin A2, FTCD/58K, PC4/SUB1, VARS, and DHX36.

Embodiment 573

The method of any of embodiments 557-564, wherein the target transcript does not encode RNase H1.

Embodiment 574

The method of any of embodiments 557-563, wherein the modified oligonucleotide has a nucleobase sequence comprising at least 8 contiguous nucleobases of any of the nucleobase sequences of SEQ ID NOs: 8, 9, 11, or 12.

Embodiment 575

The method of any of embodiments 557-563, wherein the modified oligonucleotide has a nucleobase sequence comprising at least 10 contiguous nucleobases of any of the nucleobase sequences of SEQ ID NOs: 8, 9, 11, or 12.

Embodiment 576

The method of any of embodiments 557-563, wherein the modified oligonucleotide has a nucleobase sequence comprising at least 12 contiguous nucleobases of any of the nucleobase sequences of SEQ ID NOs: 8, 9, 11, or 12.

Embodiment 577

The method of any of embodiments 557-563, wherein the modified oligonucleotide has a nucleobase sequence comprising at least 14 contiguous nucleobases of any of the nucleobase sequences of SEQ ID NOs: 8, 9, 11, or 12.

Embodiment 578

The method of any of embodiments 557-563, wherein the modified oligonucleotide has a nucleobase sequence consisting of the nucleobase sequence of any of SEQ ID NOs: 8, 9, 11, or 12.

Embodiment 579

The method of any of embodiments 557-561 or 564 or 566, wherein the modified oligonucleotide has a nucleobase sequence comprising at least 8 contiguous nucleobases of any of the nucleobase sequences of SEQ ID NOs: 79 or 80.

Embodiment 580

The method of any of embodiments 557-561 or 564 or 566, wherein the modified oligonucleotide has a nucleobase sequence comprising at least 10 contiguous nucleobases of any of the nucleobase sequences of SEQ ID NOs: 79 or 80.

Embodiment 581

The method of any of embodiments 557-561 or 564 or 566, wherein the modified oligonucleotide has a nucleobase sequence comprising at least 12 contiguous nucleobases of any of the nucleobase sequences of SEQ ID NOs: 79 or 80.

Embodiment 582

The method of any of embodiments 557-561 or 564 or 566, wherein the modified oligonucleotide has a nucleobase sequence comprising at least 14 contiguous nucleobases of any of the nucleobase sequences of SEQ ID NOs: 79 or 80.

Embodiment 583

The method of any of embodiments 557-561 or 564 or 566, wherein the modified oligonucleotide has a nucleobase sequence consisting of the nucleobase sequence of any of SEQ ID NOs: 79 or 80.

Embodiment 584

The method of any of embodiments 557-573, wherein the modified oligonucleotide has a nucleobase sequence wherein at least 35% all the nubcleobases are G or C nucleobases.

Embodiment 585

The method of any of embodiments 557-573, wherein the modified oligonucleotide has a nucleobase sequence wherein at least 40% all the nubcleobases are G or C nucleobases.

Embodiment 586

The method of any of embodiments 557-573, wherein the modified oligonucleotide has a nucleobase sequence wherein at least 45% all the nubcleobases are G or C nucleobases.

Embodiment 587

The method of any of embodiments 557-573, wherein the modified oligonucleotide has a nucleobase sequence wherein at least 50% all the nubcleobases are G or C nucleobases.

Embodiment 588

The method of any of embodiments 557-573, wherein the modified oligonucleotide has a nucleobase sequence wherein at least 55% all the nubcleobases are G or C nucleobases.

Embodiment 589

The method of any of embodiments 557-573, wherein the modified oligonucleotide has a nucleobase sequence wherein at least 60% all the nubcleobases are G or C nucleobases.

Embodiment 590

The method of any of embodiments 557-573, wherein the modified oligonucleotide has a nucleobase sequence wherein at least 65% all the nubcleobases are G or C nucleobases.

Embodiment 591

The method of any of embodiments 557-573, wherein the modified oligonucleotide has a nucleobase sequence wherein at least 70% all the nubcleobases are G or C nucleobases.

Embodiment 592

The method of any of embodiments 557-573, wherein at least a portion of the nucleobase sequence of the modified oligonucleotide is complementary to a G-quartet.

Embodiment 593

The method of any of embodiments 557-573, wherein the modified oligonucleotide has a nucleobase sequence that is not complementary to a G-quartet.

Embodiment 594

The method of any of embodiments 557-593, wherein the modified oligonucleotide consists of 10 to 40 linked nucleosides.

Embodiment 595

The method of any of embodiments 557-593, wherein the modified oligonucleotide consists of 12 to 22 linked nucleosides.

Embodiment 596

The method of any of embodiments 557-593, wherein the modified oligonucleotide consists of 15 to 22 linked nucleosides.

Embodiment 597

The method of any of embodiments 557-593, wherein the modified oligonucleotide consists of 18 to 20 linked nucleosides.

Embodiment 598

The method of any of embodiments 557-593, wherein the modified oligonucleotide comprises at least one modified nucleoside.

Embodiment 599

The method of embodiment 598, wherein at least one modified nucleoside comprises a modified sugar moiety.

Embodiment 600

The method of embodiment 599, wherein at least one modified sugar moiety is a 2'-substituted sugar moiety.

Embodiment 601

The method of embodiment 600, wherein the 2'-substituent of at least one 2'-substituted sugar moiety is selected from among: 2'-OMe, 2'-F, and 2'-MOE.

Embodiment 602

The method of any of embodiments 600-601, wherein the 2'-substituent of at least one 2'-substituted sugar moiety is a 2'-MOE.

Embodiment 603

The method of any of embodiments 600-602, wherein the 2'-substituent of at least one 2'-substituted sugar moiety is not 2'OMe.

Embodiment 604

The method of any of embodiments 598-603, wherein at least one modified sugar moiety is a bicyclic sugar moiety.

Embodiment 605

The method of embodiment 604, wherein at least one bicyclic sugar moiety is LNA or cEt.

Embodiment 606

The method of any of embodiments 598-605, wherein at least one sugar moiety is a sugar surrogate.

Embodiment 607

The method of embodiment 606, wherein at least one sugar surrogate is a morpholino.

Embodiment 608

The method of embodiment 606, wherein at least one sugar surrogate is a modified morpholino.

Embodiment 609

The method of embodiment 606, wherein at least one sugar surrogate is a peptide nucleic acid.

Embodiment 610

The method of any of embodiment 598-609, wherein the modified oligonucleotide comprises at least 5 modified nucleosides, each independently comprising a modified sugar moiety.

Embodiment 611

The method of any of embodiment 598-609, wherein the modified oligonucleotide comprises at least 6 modified nucleosides, each independently comprising a modified sugar moiety.

Embodiment 612

The method of any of embodiment 598-609, wherein the modified oligonucleotide comprises at least 7 modified nucleosides, each independently comprising a modified sugar moiety.

Embodiment 613

The method of any of embodiment 598-609, wherein the modified oligonucleotide comprises at least 8 modified nucleosides, each independently comprising a modified sugar moiety.

Embodiment 614

The method of any of embodiment 598-609, wherein the modified oligonucleotide comprises at least 9 modified nucleosides, each independently comprising a modified sugar moiety.

Embodiment 615

The method of embodiment 598-609, wherein the modified oligonucleotide comprises at least 10 modified nucleosides, each independently comprising a modified sugar moiety.

Embodiment 616

The method of any of embodiments 598-609, wherein each nucleoside of the modified oligonucleotide is a modified nucleoside or an unmodified nucleoside.

Embodiment 617

The method of embodiment 616, wherein each unmodified nucleoside is a 2'-deoxy nucleoside.

Embodiment 618

The method of any of embodiments 616-617, wherein the modified oligonucleotide comprises at least 6 2'-deoxy nucleosides.

Embodiment 619

The method of any of embodiments 616-617, wherein the modified oligonucleotide comprises at least 7 2'-deoxy nucleosides.

Embodiment 620

The method of any of embodiments 616-617, wherein the modified oligonucleotide comprises at least 8 2'-deoxy nucleosides.

Embodiment 621

The method of any of embodiments 616-617, wherein the modified oligonucleotide comprises at least 9 2'-deoxy nucleosides.

Embodiment 622

The method of any of embodiments 616-617, wherein the modified oligonucleotide comprises at least 10 2'-deoxy nucleosides.

Embodiment 623

The method of any of embodiments 616-622, wherein the modified oligonucleotide contains no more than 4 contiguous 2'-deoxy nucleosides.

Embodiment 624

The method of any of embodiments 598-623, wherein the modified oligonucleotide comprises at least 15 modified nucleosides, each independently comprising a modified sugar moiety.

Embodiment 625

The method of embodiment 624, wherein each nucleoside of the modified oligonucleotide is a modified nucleoside, each independently comprising a modified sugar moiety.

Embodiment 626

The method of any of embodiments 598-625, wherein the modified oligonucleotide comprises at least two modified nucleosides comprising modified sugar moieties that are the same as one another.

Embodiment 627

The method of any of embodiments 598-626, wherein the modified oligonucleotide comprises at least two modified nucleosides comprising modified sugar moieties that are different from one another.

Embodiment 628

The method of any of embodiments 598-627, wherein the modified oligonucleotide comprises a modified region of at least 5 contiguous modified nucleosides.

Embodiment 629

The method of embodiment 628, wherein the modified oligonucleotide comprises a modified region of at least 10 contiguous modified nucleosides.

Embodiment 630

The method of embodiment 628, wherein the modified oligonucleotide comprises a modified region of at least 15 contiguous modified nucleosides.

Embodiment 631

The method of embodiment 628, wherein the modified oligonucleotide comprises a modified region of at least 18 contiguous modified nucleosides.

Embodiment 632

The method of embodiment 628, wherein the modified oligonucleotide comprises a modified region of at least 20 contiguous modified nucleosides.

Embodiment 633

The method of any of embodiments 626-632, wherein each modified nucleoside of the modified region has a modified sugar moiety independently selected from among: 2'-F, 2'-OMe, 2'-MOE, cEt, LNA, morpholino, modified morpholino, and peptide nucleic acid.

Embodiment 634

The method of any of embodiments 628-633, wherein the modified nucleosides of the modified region each comprise the same modification as one another.

Embodiment 635

The method of embodiment 634, wherein the modified nucleosides of the modified region each comprise the same 2'-substituted sugar moiety.

Embodiment 636

The method of embodiment 635, wherein the 2'-substituted sugar moiety of the modified nucleosides of the region of modified nucleosides is selected from 2'-F, 2'-OMe, and 2'-MOE.

Embodiment 637

The method of embodiment 635, wherein the 2'-substituted sugar moiety of the modified nucleosides of the region of modified nucleosides is 2'-MOE.

Embodiment 638

The method of embodiment 634, wherein the modified nucleosides of the region of modified nucleosides each comprise the same bicyclic sugar moiety.

Embodiment 639

The method of embodiment 638, wherein the bicyclic sugar moiety of the modified nucleosides of the region of modified nucleosides is selected from LNA and cEt.

Embodiment 640

The method of embodiment 634, wherein the modified nucleosides of the region of modified nucleosides each comprises a sugar surrogate.

Embodiment 641

The method of embodiment 640, wherein the sugar surrogate of the modified nucleosides of the region of modified nucleosides is a morpholino.

Embodiment 642

The method of embodiment 640, wherein the sugar surrogate of the modified nucleosides of the region of modified nucleosides is a modified morpholino.

Embodiment 643

The method of embodiment 640, wherein the sugar surrogate of the modified nucleosides of the region of modified nucleosides is a peptide nucleic acid.

Embodiment 644

The method of any of embodiments 623-643, wherein the modified nucleotide comprises no more than 4 contiguous naturally occurring nucleosides.

Embodiment 645

The method of any of embodiments 626-644, wherein each nucleoside of the modified oligonucleotide is a modified nucleoside.

Embodiment 646

The method of embodiment 645 wherein each modified nucleoside comprises a modified sugar moiety.

Embodiment 647

The method of embodiment 646, wherein the modified nucleosides of the modified oligonucleotide comprise the same modification as one another.

Embodiment 648

The method of embodiment 647, wherein the modified nucleosides of the modified oligonucleotide each comprise the same 2'-substituted sugar moiety.

Embodiment 649

The method of embodiment 648, wherein the 2'-substituted sugar moiety of the modified oligonucleotide is selected from 2'-F, 2'-OMe, and 2'-MOE.

Embodiment 650

The method of embodiment 649, wherein the 2'-substituted sugar moiety of the modified oligonucleotide is 2'-MOE.

Embodiment 651

The method of embodiment 649, wherein the 2'-substituted sugar moiety of the modified oligonucleotide is 2'-OMe.

Embodiment 652

The method of embodiment 647, wherein the modified nucleosides of the modified oligonucleotide each comprise the same bicyclic sugar moiety.

Embodiment 653

The method of embodiment 652, wherein the bicyclic sugar moiety of the modified oligonucleotide is selected from LNA and cEt.

Embodiment 654

The method of embodiment 646-647, wherein the modified nucleosides of the modified oligonucleotide each comprises a sugar surrogate.

Embodiment 655

The method of embodiment 654, wherein the sugar surrogate of the modified oligonucleotide is a morpholino.

Embodiment 656

The method of embodiment 654, wherein the sugar surrogate of the modified oligonucleotide is a modified morpholino.

Embodiment 657

The method of embodiment 654, wherein the sugar surrogate of the modified oligonucleotide is a peptide nucleic acid.

Embodiment 658

The method of any of embodiments 557-657, wherein the modified oligonucleotide comprises at least one modified internucleoside linkage.

Embodiment 659

The method of embodiment 658, wherein the modified internucleoside linkage is a phosphorothioate internucleoside linkage.

Embodiment 660

The method of embodiment 658 or 659, wherein each internucleoside linkage is either a phosphodiester internucleoside linkage or a phosphorothioate internucleoside linkage.

Embodiment 661

The method of embodiment 658, wherein each internucleoside linkage is a modified internucleoside linkage.

Embodiment 662

The method of any of embodiments 557-657, comprising at least one phosphorothioate internucleoside linkage.

Embodiment 663

The method of embodiment 658, wherein each internucleoside linkage is a modified internucleoside linkage and wherein each internucleoside linkage comprises the same modification.

Embodiment 664

The method of embodiment 663, wherein each internucleoside linkage is a phosphorothioate internucleoside linkage.

Embodiment 665

The method of any of embodiments 557-664, wherein the antisense compound comprises at least one conjugate group.

Embodiment 666

The method of embodiment 665, wherein the conjugate group comprises Gal-NAc.

Embodiment 667

The method of any of embodiments 557-666, wherein the antisense compound consists of the modified oligonucleotide.

Embodiment 668

The method of any of embodiments 557-667, wherein the expression, translation, or amount or activity of the target protein is increased by at least 10%.

Embodiment 669

The method of any of embodiments 557-667, wherein the expression, translation, or amount or activity of the target protein is increased by at least 20%.

Embodiment 670

The method of any of embodiments 557-667, wherein the expression, translation, or amount or activity of the target protein is increased by at least 30%.

Embodiment 671

The method of any of embodiments 557-667, wherein the expression, translation, or amount or activity of the target protein is increased by at least 50%.

Embodiment 672

The method of any of embodiments 557-667, wherein the expression, translation, or amount or activity of the target protein is increased by at least 100%.

Embodiment 673

The method of any of embodiments 557-667, wherein the expression, translation, or amount or activity of the target protein is increased by at least 120%.

Embodiment 674

The method of any of embodiments 557-667, wherein the expression, translation, or amount or activity of the target protein is increased by at least 150%.

Embodiment 675

The method of any of embodiments 557-674, wherein the cell is in vitro.

Embodiment 676

The method of any of embodiments 557-674, wherein the cell is in a subject.

Embodiment 677

The method of embodiment 676, wherein the subject has a disease or condition and wherein at least one symptom of the disease or condition is ameliorated.

Embodiment 678

The method of embodiment 676 or 677, wherein the cell is in an animal.

Embodiment 679

The method of embodiment 678, wherein the animal is a human.

Embodiment 680

The compound or method of any preceeding embodiment, wherein the modified oligonucleotide does not activate RNase H when bound to a target transcript.

Embodiment 681

The compound or method of any preceeding embodiment, wherein the modified oligonucleotide is not a gapmer.

Embodiment 682

A method of increasing translation of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing translation of the target protein in the cell.

Embodiment 683

A method of decreasing suppression of translation of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby decreasing suppression of translation of the target protein in the cell.

Embodiment 684

A method of increasing the amount or activity of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing the amount or activity of the target protein in the cell.

Embodiment 685

A method of increasing expression of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing expression of the target protein in the cell.

Embodiment 686

The method of any of embodiments 682-685, wherein the translation suppression element region is the 5' untranslated region.

Embodiment 687

The method of any of embodiments 682-685, wherein the translation suppression element region is a stem-loop structure in the 5' untranslated region.

Embodiment 688

The method of any of embodiments 682-685, wherein the translation suppression element region is a stem in a stem-loop structure in the 5' untranslated region.

Embodiment 689

The method of any of embodiments 682-685, wherein the translation suppression element region is a loop in a stem-loop structure in the 5' untranslated region.

Embodiment 690

The method of any of embodiments 682-689, wherein the translation suppression element region contains one or more uORFs.

Embodiment 691

The method of any of embodiments 682-689, wherein the translation suppression element region contains one or more uORFs, but wherein the one or more uORFs do not suppress translation of the target transcript.

Embodiment 692

The method of any of embodiments 682-689, wherein the translation suppression element region does not contains a uORF.

Embodiment 693

The method of any of embodiments 682-691, wherein the target transcript encodes RNase H1.

Embodiment 694

The method of any of embodiments 682-692, wherein the target transcript encodes LDLr.

Embodiment 695

The method of any of embodiments 682-689, wherein the target transcript encodes ARF1.

Embodiment 696

The method of any of embodiments 682-692 or 694-695, wherein the modified oligonucleotide has a nucleobase sequence comprising at least 8 contiguous nucleobases of any of the nucleobase sequences of SEQ ID NOs: 80, 84, 85, 86, 87, 88, 89, 90, 92, 93, 95, 97, 99, or 100.

Embodiment 697

The method of any of embodiments 682-692 or 694-695, wherein the modified oligonucleotide has a nucleobase sequence comprising at least 10 contiguous nucleobases of any of the nucleobase sequences of SEQ ID NOs: 80, 84, 85, 86, 87, 88, 89, 90, 92, 93, 95, 97, 99, or 100.

Embodiment 698

The method of any of embodiments 682-692 or 694-695, wherein the modified oligonucleotide has a nucleobase sequence comprising at least 12 contiguous nucleobases of any of the nucleobase sequences of SEQ ID NOs: 80, 84, 85, 86, 87, 88, 89, 90, 92, 93, 95, 97, 99, or 100.

Embodiment 699

The method of any of embodiments 682-692 or 694-695, wherein the modified oligonucleotide has a nucleobase sequence comprising at least 14 contiguous nucleobases of any of the nucleobase sequences of SEQ ID NOs: 80, 84, 85, 86, 87, 88, 89, 90, 92, 93, 95, 97, 99, or 100.

Embodiment 700

The method of any of embodiments 682-692 or 694-695, wherein the modified oligonucleotide has a nucleobase sequence consisting of the nucleobase sequence of any of SEQ ID NOs: 80, 84, 85, 86, 87, 88, 89, 90, 92, 93, 95, 97, 99, or 100.

Embodiment 701

The method of any of embodiments 682-692 or 694-695, wherein the modified oligonucleotide has a nucleobase sequence consisting of the nucleobase sequence of any of SEQ ID NOs: 80, 84, 85, 86, 87, 88, 89, 90, 92, 93, 95, 97, 99, or 100.

Embodiment 702

The compound or method of any preceeding embodiment, wherein the modified oligonucleotide is not a gapmer.

Embodiment 703

The compound or method of any preceeding embodiment, wherein the target transcript is not: CFTR, FXN (Frataxin), HOTAIR, LAMA1, UTRN, EZH2, Suv3H1, NEST, DINO, Apoa1, SSPN, MERTK, MECP2, MBNL1, FMR1, CD247, PTEN, KLF4, ATP2A2, NFE2L2, FoxP3, ANRIL, SMN, HBF, ACTB, or EPO.

Embodiment 704

The compound or method of any preceeding embodiment, wherein the target transcript is not an epigenetic regulator.

Embodiment 705

The compound or method of any preceeding embodiment, wherein the target protein is not frataxin.

Embodiment 706

The compound or method of any preceeding embodiment, wherein the target transcript is not frataxin.

Embodiment 707

The compound or method of any preceeding embodiment, wherein the target transcript is not a lncRNA.

Embodiment 708

A pharmaceutical composition comprising a prodrug of any preceeding embodiment.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

Definitions

Unless otherwise indicated, the following terms have the following meanings:

As used herein, "target transcript" means a transcript that encodes a target protein. In certain embodiments, a target transcript contains a primary open reading frame that encodes a primary protein and one or more start sites at which translation of a polypeptide that is not the target protein may be initiated. In certain such embodiments, a target transcript contains a primary open reading frame and a uORF. In certain such embodiments, a target transcript contains a primary open reading frame and more than one uORF. In certain embodiments, a target transcript contains a primary open reading frame and does not contain a uORF. In certain embodiments, a target transcript contains a primary open reading frame and a translation suppression element.

As used herein, "translation suppression element," means any sequence and/or secondary structure in the 5'-UTR of a target transcript that reduces, inhibits, and/or suppresses translation of the target transcript. In certain embodiments, a translation suppression element comprises a uORF. In certain embodiments, a translation suppression element does not comprise a uORF. In certain embodiments, a translation suppression element comprises one or more stem-loops. In certain embodiments, a translation suppression element comprises greater than 60%, greater than 70%, or greater than 80% GC content. In certain embodiments, the translation suppression element is a uORF. In certain embodiments, the translation suppression element is a stem-loop.

As used herein, "translation suppression element inhibitor," means any means any agent capable of specifically inhibiting the activity of a translation suppression element. In certain embodiments, the activity of a translation suppression element inhibitor is suppression of translation of the pORF polypeptide or protein on the same transcript. For example, translation suppression element inhibitors include nucleic acids (including antisense compounds and siRNA), peptides, antibodies, small molecules, and other agents capable of inhibiting the amount or activity of a translation suppression element.

As used herein, "translation suppression element region" means a portion of the target transcript that comprises one or more translation suppression elements. In certain embodiments, a translation suppression element region comprises a uORF. In certain embodiments, a translation suppression element region comprises more than one uORF. In certain embodiments, a translation suppression element region comprises a uORF and at least one translation suppression element that is not a uORF. In certain embodiments, a translation suppression element region comprises a translation suppression element that is not a uORF and does not contain a uORF.

As used herein, "GC content" means the percentage of total nucleosides in a particular portion of a nucleic acid or oligonucleotide that are either G or C or that base pair with G or C.

As used herein, "consecutive GC nucleosides" or "consecutive GC nucleotides" means a portion of adjacent nucleosides in a nucleic acid or oligonucleotide that are all either G or C or that base pair with G or C.

As used herein, "target protein" means a protein that one desires to increase in amount, concentration, or activity. In certain embodiments, the target protein is encoded by the primary open reading frame of a target transcript.

As used herein, "target transcript" means a transcript that encodes a target protein. In certain embodiments, a target transcript contains a primary open reading frame that encodes a primary protein and one or more start sites at which translation of a polypeptide that is not the target protein may be initiated. In certain such embodiments, a target transcript contains a primary open reading frame and a uORF. In certain such embodiments, a target transcript contains a primary open reading frame and more than one uORF.

As used herein, "primary open reading frame" or "pORF" means the portion of the target transcript that encodes the primary protein associated with the transcript. In certain embodiments, the pORF encodes the target protein.

As used herein, "primary protein" means a protein encoded by a primary open reading frame.

As used herein, "target site" means the portion of the target transcript having a nucleobase sequence that is complementary to a portion of the nucleobase sequence of a modified oligonucleotide. In certain embodiments, the modified oligonucleotide is complementary to the target site across the entire length of the modified oligonucleotide.

As used herein, "start site" means a group of nucleobases on a transcript at which a ribosomal subunit is recruited. In certain embodiments, a start site may result in initiation of translation. In certain embodiments, a start site is an AUG codon. In certain embodiments, a start site is a non-canonical start codon.

As used herein, "upstream open reading frame start site" or "uORF start site" means a start site that is upstream of the pORF start codon. In certain embodiments, a uORF start site initiates translation of a polypeptide that is not the target protein.

As used herein, "uORF start site region" means a portion of the target transcript that comprises a uORF start site. In certain embodiments, a uORF start site region comprises a uORF start site and the 100 nucleosides upstream and downstream of the uORF start site. In certain embodiments, a uORF start site region comprises a uORF start site and the 75 nucleosides upstream and downstream of the uORF start site. In certain embodiments, a uORF start site region comprises a uORF start site and the 50 nucleosides upstream and downstream of the uORF start site. In certain embodiments, a uORF start site region comprises a uORF start site and the 30 nucleosides upstream and downstream of the uORF start site. In certain embodiments, a uORF start site region comprises a uORF start site and the 20 nucleosides upstream and downstream of the uORF start site. In certain embodiments, a uORF start site region comprises the 5' untranslated region. In certain embodiments, a uORF start site region consists of the 5'-UTR.

As used herein, "uORF" or "upstream open reading frame" means a portion of a target transcript that comprises a start site upstream of (i.e. 5' of) the pORF and an in frame termination codon. In certain embodiments, a uORF is the portion of the target transcript that is translated when translation is initiated at a uORF start site. In certain embodiments, a uORF does not overlap with a pORF. In certain embodiments, a uORF does overlap with a pORF. In certain embodiments a uORF overlaps with another uORF. In certain embodiments, a uORF is out of frame with a pORF.

As used herein, "wild-type uORF start site" means a uORF start site that does not arise from a mutation.

As used herein, "wild-type uORF start site region" means the uORF start site region of a wild-type uORF start site.

As used herein, "a uORF start site that arises from a mutation" means a uORF start site, where the same portion of the target transcript on the wild-type allele does not contain a uORF start site.

As used herein, "uORF polypeptide" means a polypeptide encoded by a uORF. In certain embodiments, a uORF polypeptide is a protein.

As used herein, "uORF inhibitor" means any agent capable of specifically inhibiting the activity of a uORF. In certain embodiments, the activity of a uORF is suppression of translation of the pORF polypeptide or protein on the same transcript. In certain embodiments, the activity of a uORF is suppression of translation of the pORF polypeptide or protein on a different transcript. For example, uORF specific inhibitors include nucleic acids (including antisense compounds and siRNA), peptides, antibodies, small molecules, and other agents capable of inhibiting the amount or activity of a uORF.

As used herein, "suppression of translation of a target protein in a cell," means that translation of the target protein is less than the translation of the target protein in the absence of one or more TSEs.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluoroine at the 2' position. Unless otherwise indicated, the fluorine in a 2'-F nucleoside is in the ribo position (replacing the OH of a natural ribose).

As used herein, "2'-(ara)-F" refers to a 2'-F substituted nucleoside, wherein the fluoro group is in the arabino position.

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligonucleotide which is capable of hybridizing to a complementary oligonucleotide. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage. Examples of modified oligonucleotides include single-stranded and double-stranded compounds, such as, antisense compounds, siRNAs, shRNAs, ssRNAs, and occupancy-based compounds.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, the sub-structures are nucleotides or nucleosides. In certain embodiments, an oligomeric compound comprises an oligonucleotide. In certain embodiments, an oligomeric compound consists of an oligonucleotide. In certain embodiments, an oligomeric compound consists of an antisense compound.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate group" means an atom or group of atoms bound to an oligonucleotide or oligomeric compound. In general, conjugate groups modify one or more properties of the oligonucleotide or oligomeric compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a measurable activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), translation, and post-translational modification.

As used herein, "translation" means the process in which a polypeptide (e.g. a protein) is translated from an mRNA. In certain embodiments, an increase in translation means an increase in the number of polypeptide (e.g. a protein) molecules that are made per copy of mRNA that encodes said polypeptide.

As used herein, "target nucleic acid" means a nucleic acid molecule to which an antisense compound is intended to hybridize.

As used herein, "mRNA" means an RNA molecule that encodes a protein.

As used herein, "pre-mRNA" means an RNA transcript that has not been fully processed into mRNA. Pre-RNA includes one or more intron.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense compound specifically hybridizes to more than one target site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "modification motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)R$_{aa}$), carboxyl (—C(O)O—R$_{aa}$), aliphatic groups, alicyclic groups, alkoxy, substituted oxy (—O—R$_{aa}$), aryl, aralkyl, heterocyclic radical, heteroaryl, heteroarylalkyl, amino (—N(R$_{bb}$)(R$_{cc}$)), imino (=NR$_{bb}$), amido (—C(O)N(R$_{bb}$)(R$_{cc}$) or —N(R$_{bb}$)C(O)R$_{aa}$), azido (—N$_3$), nitro (—NO$_2$), cyano (—CN), carbamido (—OC(O)N(R$_{bb}$)(R$_{cc}$) or —N(R$_{bb}$)C(O)OR$_{aa}$), ureido (—N(R$_{bb}$)C(O)N(R$_{bb}$)(R$_{cc}$)), thioureido (—N(R$_{bb}$)C(S)N(R$_{bb}$)—(R$_{cc}$)), guanidinyl (—N(R$_{bb}$)C(=NR$_{bb}$)N(R$_{bb}$)(R$_{cc}$)), amidinyl (—C(=NR$_{bb}$)N(R$_{bb}$)(R$_{cc}$) or —N(R$_{bb}$)C(=NR$_{bb}$)(R$_{aa}$)), thiol (—SR$_{bb}$), sulfinyl (—S(O)R$_{bb}$), sulfonyl (—S(O)$_2$R$_{bb}$) and sulfonamidyl (—S(O)$_2$N(R$_{bb}$)(R$_{cc}$) or —N(R$_{bb}$)S—(O)$_2$R$_{bb}$). Wherein each R$_{aa}$, R$_{bb}$ and R$_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "Intracerebroventricular" or "ICV" means administration into the ventricular system of the brain.

As used herein, "wherein the translation suppression element region comprises one and only one uORF," means that exactly one uORF is present in the translation suppression element region. In certain embodiments, exactly one uORF is present in the 5'-UTR.

The compounds described herein include variations in which one or more atoms are replaced with a non-radioactive isotope or radioactive isotope of the indicated element. For example, compounds herein that comprise hydrogen atoms encompass all possible deuterium substitutions for each of the 1H hydrogen atoms. Isotopic substitutions encompassed by the compounds herein include but are not limited to: 2H or 3H in place of 1H, 13C or 14C in place of 12C, 15N in place of 14N, 17O or 18O in place of 16O, and 33S, 34S, 35S, or 36S in place of 32S. In certain embodiments, non-radioactive isotopic substitutions may impart new properties on the oligomeric compound that are beneficial for use as a therapeutic or research tool. In certain embodiments, radioactive isotopic substitutions may make the compound suitable for research purposes such as imaging.

Certain Modified Oligonucleotides

In certain embodiments, the present invention provides antisense compounds. In certain embodiments, antisense compounds comprise a modified oligonucleotide. In certain embodiments, such antisense compounds comprise modified oligonucleotides and optionally one or more conjugate and/or terminal groups. In certain embodiments, an antisense compound consists of a modified oligonucleotide. In certain embodiments, modified oligonucleotides comprise one or more chemical modifications. Such chemical modifications include modifications of one or more nucleoside (including modifications to the sugar moiety and/or the nucleobase) and/or modifications to one or more internucleoside linkage.

a. Certain Modified Nucleosides

In certain embodiments, provided herein are antisense compounds comprising or consisting of oligonuleotides comprising at least one modified nucleoside. Such modified nucleosides comprise a modified sugar moeity, a modified nucleobase, or both a modified sugar moiety and a modified nucleobase.

i. Certain Sugar Moieties

In certain embodiments, antisense compounds of the invention comprise one or more modified nucleosides comprising a modified sugar moiety. Such antisense compounds comprising one or more sugar-modified nucleosides may have desirable properties, such as enhanced nuclease stability or increased binding affinity with a target nucleic acid relative to antisense compounds comprising only nucleosides comprising naturally occurring sugar moieties. In certain embodiments, modified sugar moieties are substituted sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-$OCH_3$ ("OMe" or "O-methyl"), and 2'-$O(CH_2)_2OCH_3$ ("MOE"). In certain embodiments, sugar substituents at the 2' position is selected from allyl, amino, azido, thio, O-allyl, O—$C_1$-$C_{10}$ alkyl, O—$C_1$-$C_{10}$ substituted alkyl; O—$C_1$-$C_{10}$ alkoxy; O—$C_1$-$C_{10}$ substituted alkoxy, $OCF_3$, $O(CH_2)_2SCH_3$, $O(CH_2)_2$—O—N(Rm)(Rn), and O—$CH_2$—C(=O)—N(Rm)(Rn), where each Rm and Rn is, independently, H or substituted or unsubstituted $C_1$-$C_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, O—$C_1$-$C_{10}$ alkoxy; O—$C_1$-$C_{10}$ substituted alkoxy, SH, CN, OCN, $CF_3$, $OCF_3$, O-alkyl, S-alkyl, N($R_m$)-alkyl; O-alkenyl, S-alkenyl, or N($R_m$)-alkenyl; O-alkynyl, S-alkynyl, N($R_m$)-alkynyl; O-alkylenyl-O-alkyl, alkynyl, alkaryl, aralkyl, O-alkaryl, O-aralkyl, $O(CH_2)_2SCH_3$, O—$(CH_2)_2$—O—N($R_m$)($R_n$) or O—$CH_2$—C(=O)—N($R_m$)($R_n$), where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O—(CH$_2$)$_2$—O—N(CH$_3$)$_2$, —O(CH$_2$)$_2$O(CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)$_3$-2', 4'-(CH$_2$)—O-2' (LNA); 4'-(CH$_2$)—S-2; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)-0-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., *J. Org. Chem.*, 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:
x is 0, 1, or 2;
n is 1, 2, 3, or 4;
each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and
each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio(4'-CH$_2$—S-2') BNA, (H) methylene-amino (4'-CH2-N(R)-2') BNA, (I) methyl carbocyclic (4'-CH$_2$—CH(CH$_3$)-2') BNA, (J) propylene carbocyclic (4'-(CH$_2$)$_3$-2') BNA, and (M) 4'-CH$_2$—O—CH$_2$-2' as depicted below.

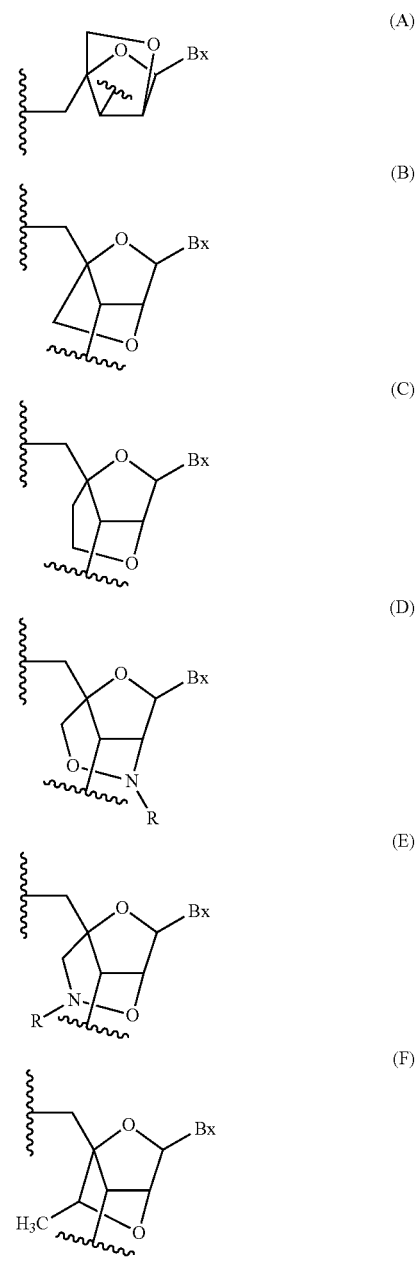

-continued

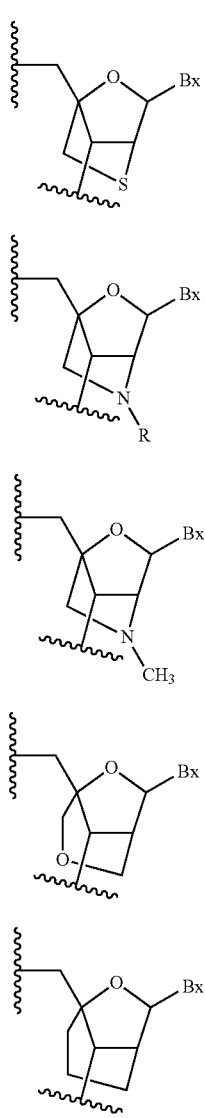

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfer, carbon or nitrogen atom. In certain such embodiments, such modified sugar moiety also comprises bridging and/or non-bridging substituents as described above. For example, certain sugar surrogates comprise a 4'-sulfer atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

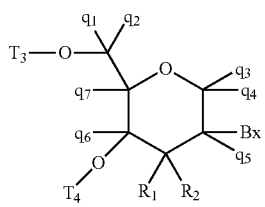

VII wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclic and tricyclic sugar and sugar surrogate ring systems are known in the art that can be used to modify nucleosides (see, e.g., review article: Leumann, J C, *Bioorganic & Medicinal Chemistry*, 2002, 10, 841-854).

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166,315; 5,185,444; and 5,034,506). As used here, the term "morpholino" means a sugar surrogate having the following structure:

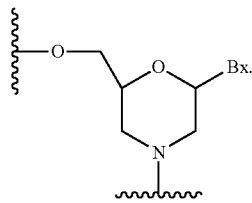

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

ii. Certain Modified Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

b. Certain Internucleoside Linkages

In certain embodiments, nucleosides may be linked together using any internucleoside linkage to form oligonucleotides. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—$CH_2$—$N(CH_3)$—O—$CH_2$—), thiodiester (—O—C(O)—S—), thionocarbamate (—O—C(O)(NH)—S—); siloxane (—O—$Si(H)_2$—O—); and N,N'-dimethylhydrazine (—$CH_2$—$N(CH_3)$—$N(CH_3)$—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

c. Certain Motifs

In certain embodiments, the invention provides modified oligonucleotides. In certain embodiments, modified oligonucleotides comprise one or more modified sugars. In certain embodiments, modified oligonucleotides comprise one or more modified nucleobases. In certain embodiments, modified oligonucleotides comprise one or more modified internucleoside linkages. In certain embodiments, the modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, a modified oligonucleotide may be described by its sugar modification motif, internucleoside linkage motif and/or nucleobase modification motif (as used herein, nucleobase modification motif describes the chemical modifications to the nucleobases independent of the sequence of nucleobases).

In certain embodiments, every sugar moiety of the modified oligonucleotides of the present invention is modified. In certain embodiments, modified oligonucleotides include one or more unmodified sugar moiety.

d. Certain Overall Lengths

In certain embodiments, the present invention provides modified oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides modified oligonucleotides which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a modified oligonucleotides has any of the above lengths.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

e. Certain Oligonucleotides

In certain embodiments, oligonucleotides of the present invention are characterized by their modification motif and overall length. In certain embodiments, such parameters are each independent of one another.

I. Certain Oligomeric Compounds

In certain embodiments, the invention provides oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, abasic nucleosides, modified or unmodified nucleosides, and two or more nucleosides that are independently modified or unmodified.

In certain embodiments, antisense compounds are provided wherein the 5'-terminal group comprises a 5'-terminal stabilized phosphate. A "5'-terminal stabilized phosphate" is a 5'-terminal phosphate group having one or more modifications that increase nuclease stability relative to a 5'-phosphate.

In certain embodiments, antisense compounds are provided wherein the 5'-terminal group has Formula IIe:

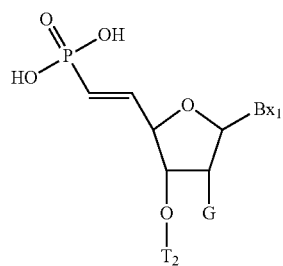

IIe wherein:

Bx is uracil, thymine, cytosine, 5-methyl cytosine, adenine or guanine;

T2 is a phosphorothioate internucleoside linking group linking the compound of Formula IIe to the oligomeric compound; and G is halogen, OCH3, OCF3, OCH2CH3, OCH2CF3, OCH2-CH=CH2, O(CH2)2-OCH3, O(CH2)2-O(CH2)2-N(CH3)2, OCH2C(=O)—N(H)CH3, OCH2C(=O)—N(H)—(CH2)2-N(CH3)2 or OCH2-N(H)—C(=NH)NH2.

In certain embodiments, antisense compounds are provided wherein said 5'-terminal compound has Formula IIe wherein G is F, OCH3 or O(CH2)2-OCH3.

In certain embodiments, the 5'-terminal group is a 5'-terminal stabilized phosphate comprising a vinyl phosphonate represented by Formula IIe above.

f. Certain Conjugate Groups

In certain embodiments, the oligonucleotides or oligomeric compounds as provided herein are modified by covalent attachment of one or more conjugate groups. In general, conjugate groups modify one or more properties of the attached oligonucleotide or oligomeric compound including but not limited to pharmacodynamics, pharmacokinetics, stability, binding, absorption, cellular distribution, cellular uptake, charge and clearance. As used herein, "conjugate group" means a radical group comprising a group of atoms that are attached to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties. Conjugate groups are routinely used in the chemical arts and can include a conjugate linker that covalently links the conjugate group to an oligonucleotide or oligomeric compound. In certain embodiments, conjugate groups include a cleavable moiety that covalently links the conjugate group to an oligonucleotide or oligomeric compound. In certain embodiments, conjugate groups include a conjugate linker and a cleavable moiety to covalently link the conjugate group to an oligonucleotide or oligomeric compound. In certain embodiments, a conjugate group has the general formula:

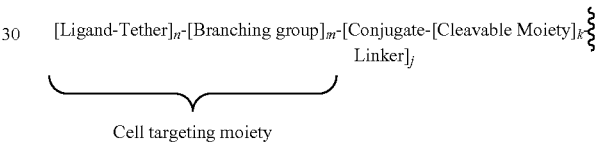

wherein n is from 1 to about 3, m is 0 when n is 1 or m is 1 when n is 2 or 3, j is 1 or 0, k is 1 or 0 and the sum of j and k is at least one.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

Conjugate groups are shown herein as radicals, providing a bond for forming covalent attachment to an oligomeric compound such as an oligonucleotide. In certain embodiments, the point of attachment on the oligomeric compound is at the 3'-terminal nucleoside or modified nucleoside. In certain embodiments, the point of attachment on the oligomeric compound is the 3'-oxygen atom of the 3'-hydroxyl group of the 3' terminal nucleoside or modified nucleoside. In certain embodiments, the point of attachment on the oligomeric compound is at the 5'-terminal nucleoside or modified nucleoside. In certain embodiments the point of attachment on the oligomeric compound is the 5'-oxygen atom of the 5'-hydroxyl group of the 5'-terminal nucleoside or modified nucleoside. In certain embodiments, the point of attachment on the oligomeric compound is at any reactive site on a nucleoside, a modified nucleoside or an internucleoside linkage.

As used herein, "cleavable moiety" and "cleavable bond" mean a cleavable bond or group of atoms that is capable of being split or cleaved under certain physiological conditions. In certain embodiments, a cleavable moiety is a cleavable bond. In certain embodiments, a cleavable moiety comprises a cleavable bond. In certain embodiments, a cleavable moiety is a group of atoms. In certain embodiments, a cleavable moiety is selectively cleaved inside a cell or sub-cellular compartment, such as a lysosome. In certain embodiments, a cleavable moiety is selectively cleaved by endogenous enzymes, such as nucleases. In certain embodiments, a cleavable moiety comprises a group of atoms having one, two, three, four, or more than four cleavable bonds.

In certain embodiments, conjugate groups comprise a cleavable moiety. In certain such embodiments, the cleavable moiety covalently attaches the oligomeric compound to the conjugate linker. In certain such embodiments, the cleavable moiety covalently attaches the oligomeric compound to the cell-targeting moiety.

In certain embodiments, a cleavable bond is selected from among: an amide, a polyamide, an ester, an ether, one or both esters of a phosphodiester, a phosphate ester, a carbamate, a di-sulfide, or a peptide. In certain embodiments, a cleavable bond is one of the esters of a phosphodiester. In certain embodiments, a cleavable bond is one or both esters of a phosphodiester. In certain embodiments, the cleavable moiety is a phosphodiester linkage between an oligomeric compound and the remainder of the conjugate group. In certain embodiments, the cleavable moiety comprises a phosphodiester linkage that is located between an oligomeric compound and the remainder of the conjugate group. In certain embodiments, the cleavable moiety comprises a phosphate or phosphodiester. In certain embodiments, the cleavable moiety is attached to the conjugate linker by either a phosphodiester or a phosphorothioate linkage. In certain embodiments, the cleavable moiety is attached to the conjugate linker by a phosphodiester linkage. In certain embodiments, the conjugate group does not include a cleavable moiety.

In certain embodiments, the cleavable moiety is a cleavable nucleoside or a modified nucleoside. In certain embodiments, the nucleoside or modified nucleoside comprises an optionally protected heterocyclic base selected from a purine, substituted purine, pyrimidine or substituted pyrimidine. In certain embodiments, the cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine.

In certain embodiments, the cleavable moiety is 2'-deoxy nucleoside that is attached to either the 3' or 5'-terminal nucleoside of an oligomeric compound by a phosphodiester linkage and covalently attached to the remainder of the conjugate group by a phosphodiester or phosphorothioate linkage. In certain embodiments, the cleavable moiety is 2'-deoxy adenosine that is attached to either the 3' or 5'-terminal nucleoside of an oligomeric compound by a phosphodiester linkage and covalently attached to the remainder of the conjugate group by a phosphodiester or phosphorothioate linkage. In certain embodiments, the cleavable moiety is 2'-deoxy adenosine that is attached to the 3'-oxygen atom of the 3'-hydroxyl group of the 3'-terminal nucleoside or modified nucleoside by a phosphodiester linkage. In certain embodiments, the cleavable moiety is 2'-deoxy adenosine that is attached to the 5'-oxygen atom of the 5'-hydroxyl group of the 5'-terminal nucleoside or modified nucleoside by a phosphodiester linkage. In certain embodiments, the cleavable moiety is attached to a 2'-position of a nucleoside or modified nucleoside of an oligomeric compound.

As used herein, "conjugate linker" in the context of a conjugate group means a portion of a conjugate group comprising any atom or group of atoms that covalently link the cell-targeting moiety to the oligomeric compound either directly or through the cleavable moiety. In certain embodiments, the conjugate linker comprises groups selected from alkyl, amino, oxo, amide, disulfide, polyethylene glycol, ether, thioether (—S—) and hydroxylamino (—O—N(H)—). In certain embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus linking group. In certain embodiments, the conjugate linker comprises at least one phosphodiester group. In certain embodiments, the conjugate linker includes at least one neutral linking group.

In certain embodiments, the conjugate linker is covalently attached to the oligomeric compound. In certain embodiments, the conjugate linker is covalently attached to the oligomeric compound and the branching group. In certain embodiments, the conjugate linker is covalently attached to the oligomeric compound and a tethered ligand. In certain embodiments, the conjugate linker is covalently attached to the cleavable moiety. In certain embodiments, the conjugate linker is covalently attached to the cleavable moiety and the branching group. In certain embodiments, the conjugate linker is covalently attached to the cleavable moiety and a tethered ligand. In certain embodiments, the conjugate linker includes one or more cleavable bonds. In certain embodiments, the conjugate group does not include a conjugate linker.

As used herein, "branching group" means a group of atoms having at least 3 positions that are capable of forming covalent linkages to two or more tether-ligands and the remainder of the conjugate group. In general a branching group provides a plurality of reactive sites for connecting tethered ligands to the oligomeric compound through the conjugate linker and/or the cleavable moiety. In certain embodiments, the branching group comprises groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, the branching group is covalently attached to the conjugate linker. In certain embodiments, the branching group is covalently attached to the cleavable moiety. In certain embodiments, the branching group is covalently attached to the conjugate linker and each of the tethered ligands. In certain embodiments, the branching group comprises one or more cleavable bond. In certain embodiments, the conjugate group does not include a branching group.

In certain embodiments, conjugate groups as provided herein include a cell-targeting moiety that has at least one tethered ligand. In certain embodiments, the cell-targeting moiety comprises two tethered ligands covalently attached to a branching group. In certain embodiments, the cell-targeting moiety comprises three tethered ligands covalently attached to a branching group.

As used herein, "tether" means a group of atoms that connect a ligand to the remainder of the conjugate group. In certain embodiments, each tether is a linear aliphatic group comprising one or more groups selected from alkyl, substituted alkyl, ether, thioether, disulfide, amino, oxo, amide, phosphodiester and polyethylene glycol groups in any combination. In certain embodiments, each tether is a linear aliphatic group comprising one or more groups selected from alkyl, ether, thioether, disulfide, amino, oxo, amide and polyethylene glycol groups in any combination. In certain embodiments, each tether is a linear aliphatic group comprising one or more groups selected from alkyl, substituted alkyl, phosphodiester, ether and amino, oxo, amide groups in any combination. In certain embodiments, each tether is a linear aliphatic group comprising one or more groups selected from alkyl, ether and amino, oxo, amide groups in any combination. In certain embodiments, each tether is a linear aliphatic group comprising one or more groups selected from alkyl, amino and oxo groups in any combination. In certain embodiments, each tether is a linear aliphatic group comprising one or more groups selected from alkyl and oxo groups in any combination. In certain embodiments, each tether is a linear aliphatic group comprising one or more groups selected from alkyl and phosphodiester in any combination. In certain embodiments, each tether comprises at least one phosphorus linking group or neutral linking group.

In certain embodiments, tethers include one or more cleavable bond. In certain embodiments, each tethered ligand is attached to a branching group. In certain embodiments, each tethered ligand is attached to a branching group through an amide group. In certain embodiments, each tethered ligand is attached to a branching group through an ether group. In certain embodiments, each tethered ligand is attached to a branching group through a phosphorus linking group or neutral linking group. In certain embodiments, each tethered ligand is attached to a branching group through a phosphodiester group. In certain embodiments, each tether is attached to a ligand through either an amide or an ether group. In certain embodiments, each tether is attached to a ligand through an ether group.

In certain embodiments, each tether comprises from about 8 to about 20 atoms in chain length between the ligand and the branching group. In certain embodiments, each tether comprises from about 10 to about 18 atoms in chain length between the ligand and the branching group. In certain embodiments, each tether comprises about 13 atoms in chain length.

In certain embodiments, the present disclosure provides ligands wherein each ligand is covalently attached to the remainder of the conjugate group through a tether. In certain embodiments, each ligand is selected to have an affinity for at least one type of receptor on a target cell. In certain embodiments, ligands are selected that have an affinity for at least one type of receptor on the surface of a mammalian liver cell. In certain embodiments, ligands are selected that have an affinity for the hepatic asialoglycoprotein receptor (ASGP-R). In certain embodiments, each ligand is a carbohydrate. In certain embodiments, each ligand is, independently selected from galactose, N-acetyl galactoseamine, mannose, glucose, glucosamone and fucose. In certain embodiments, each ligand is N-acetyl galactoseamine (GalNAc). In certain embodiments, the targeting moiety comprises 1 to 3 ligands. In certain embodiments, the targeting moiety comprises 3 ligands. In certain embodiments, the targeting moiety comprises 2 ligands. In certain embodiments, the targeting moiety comprises 1 ligand. In certain embodiments, the targeting moiety comprises 3 N-acetyl galactoseamine ligands. In certain embodiments, the targeting moiety comprises 2 N-acetyl galactoseamine ligands. In certain embodiments, the targeting moiety comprises 1 N-acetyl galactoseamine ligand.

In certain embodiments, each ligand is a carbohydrate, carbohydrate derivative, modified carbohydrate, multivalent carbohydrate cluster, polysaccharide, modified polysaccharide, or polysaccharide derivative. In certain embodiments, each ligand is an amino sugar or a thio sugar. For example, amino sugars may be selected from any number of compounds known in the art, for example glucosamine, sialic acid, α-D-galactosamine, N-Acetylgalactosamine, 2-acetamido-2-deoxy-D-galactopyranose (GalNAc), 2-Amino-3-O—[(R)-1-carboxyethyl]-2-deoxy-β-D-glucopyranose (β-muramic acid), 2-Deoxy-2-methylamino-L-glucopyranose, 4,6-Dideoxy-4-formamido-2,3-di-O-methyl-D-mannopyranose, 2-Deoxy-2-sulfoamino-D-glucopyranose and N-sulfo-D-glucosamine, and N-Glycoloyl-α-neuraminic acid. For example, thio sugars may be selected from the group consisting of 5-Thio-β-D-glucopyranose, Methyl 2,3,4-tri-O-acetyl-1-thio-6-O-trityl-α-D-glucopyranoside, 4-Thio-β-D-galactopyranose, and ethyl 3,4,6,7-tetra-O-acetyl-2-deoxy-1,5-dithio-α-D-gluco-heptopyranoside.

In certain embodiments, conjugate groups as provided herein comprise a carbohydrate cluster. As used herein, "carbohydrate cluster" means a portion of a conjugate group wherein two or more carbohydrate residues are attached to a branching group through tether groups. (see, e.g., Maier et al., "Synthesis of Antisense Oligonucleotides Conjugated to a Multivalent Carbohydrate Cluster for Cellular Targeting," *Bioconjugate Chemistry*, 2003, (14): 18-29, which is incorporated herein by reference in its entirety, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, (47): 5798-5808, for examples of carbohydrate conjugate clusters).

As used herein, "modified carbohydrate" means any carbohydrate having one or more chemical modifications relative to naturally occurring carbohydrates.

As used herein, "carbohydrate derivative" means any compound which may be synthesized using a carbohydrate as a starting material or intermediate.

As used herein, "carbohydrate" means a naturally occurring carbohydrate, a modified carbohydrate, or a carbohydrate derivative.

In certain embodiments, conjugate groups are provided wherein the cell-targeting moiety has the formula:

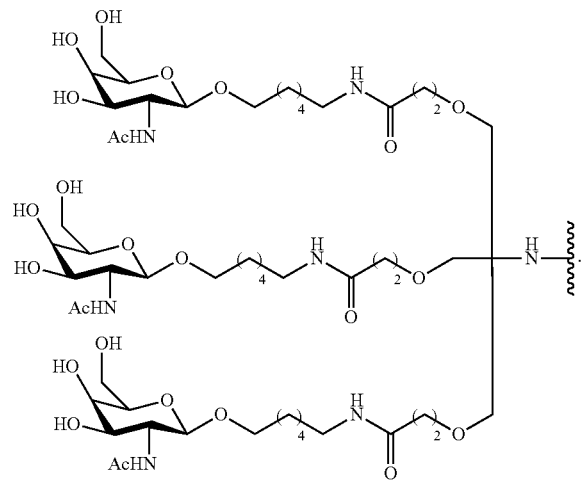

In certain embodiments, conjugate groups are provided wherein the cell-targeting moiety has the formula:

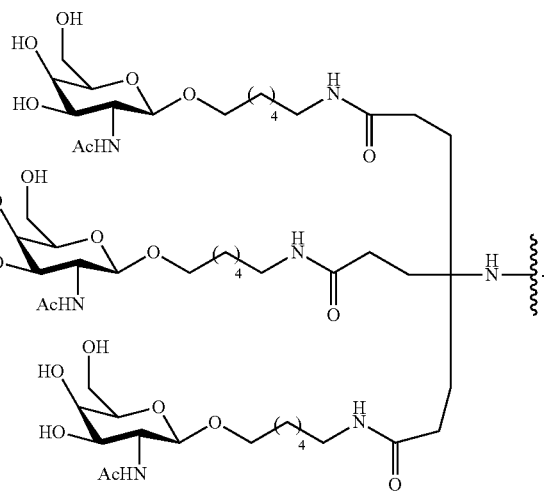

In certain embodiments, conjugate groups are provided wherein the cell-targeting moiety has the formula:

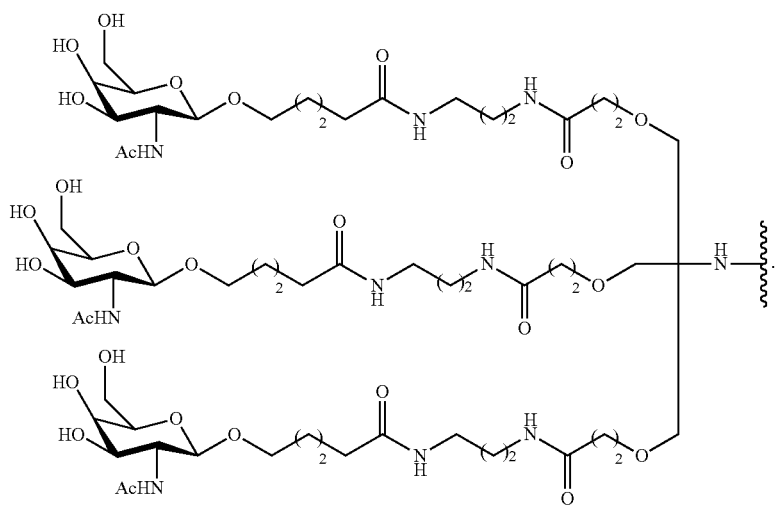

In certain embodiments, conjugate groups have the formula:

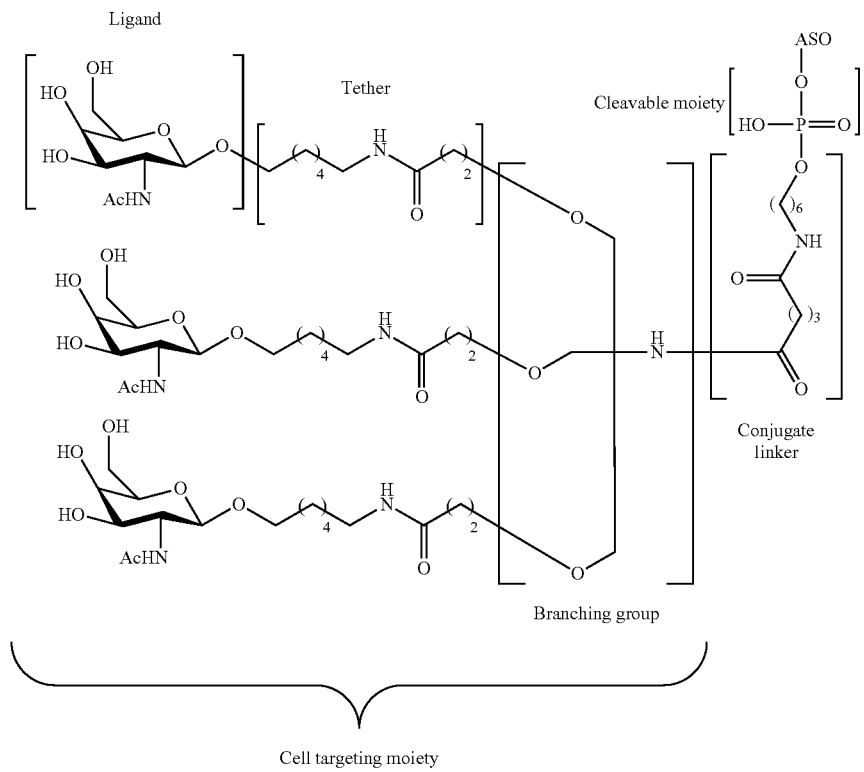

Representative United States patents, United States patent application publications, and international patent application publications that teach the preparation of certain of the above noted conjugate groups, conjugated oligomeric compounds such as antisense compounds comprising a conjugate group, tethers, conjugate linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, US 2006/0148740, US 2011/0123520, WO 2013/033230 and WO 2012/037254, each of which is incorporated by reference herein in its entirety.

Representative publications that teach the preparation of certain of the above noted conjugate groups, conjugated oligomeric compounds such as antisense compounds comprising a conjugate group, tethers, conjugate linkers, branching groups, ligands, cleavable moieties as well as other modifications include without limitation, BIESSEN et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852, BIESSEN et al., "Synthesis of Cluster Galactosides with High Affinity for the Hepatic Asialoglycoprotein Receptor" J. Med. Chem. (1995) 38:1538-1546, LEE et al., "New and more efficient multivalent glyco-ligands for asialoglycoprotein receptor of mammalian hepatocytes" Bioorganic & Medicinal Chemistry (2011) 19:2494-2500, RENSEN et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584, RENSEN et al., "Design and Synthesis of Novel N-Acetyl-galactosamine-Terminated Glycolipids for Targeting of Lipoproteins to the Hepatic Asialoglycoprotein Receptor" J. Med. Chem. (2004) 47:5798-5808, SLIEDREGT et al., "Design and Synthesis of Novel Amphiphilic Dendritic Galactosides for Selective Targeting of Liposomes to the Hepatic Asialoglycoprotein Receptor" J. Med. Chem. (1999) 42:609-618, and Valentijn et al., "Solid-phase synthesis of lysine-based cluster galactosides with high affinity for the Asialoglycoprotein Receptor" Tetrahedron, 1997, 53(2), 759-770, each of which is incorporated by reference herein in its entirety.

In certain embodiments, conjugate groups include without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

Some nonlimiting examples of conjugate linkers include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other connugate linkers include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a non-limiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3' end of an oligomeric compound, but before one or more terminal group nucleosides. In certain embodiments, conjugate groups are placed within a terminal group.

B. Antisense Compounds

In certain embodiments, modified oligonucleotides provided herein are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

a. Certain Antisense Compounds

In certain embodiments, a modified oligonucleotide described herein has a nucleobase sequence comprising at least 14 contiguous nucleobases of any of the nucleobase sequences of SEQ ID NOs: 3, 4, 5, 6, 7, 8, 9, 10, 11, 12, 13, 14, 15, 16, 26, 27, 28, 29, 30, 31, 32, 33, 34, 35, 36, 37, 38, 39, 40, 45, 54, 55, 56, 57, 58, 59, 60, 61, 62, 63, 64, 65, 66, 67, 68, 69, 70, 71, 72, 73, 74, 75, 76, or 77.

In certain embodiments, a modified oligonucleotide described herein has a nucleobase sequence comprising at least 14 contiguous nucleobases of any of the nucleobase sequences of SEQ ID NOs: 17, 18, 19, 41, or 32.

In certain embodiments, a modified oligonucleotide described herein has a nucleobase sequence comprising at least 14 contiguous nucleobases of any of the nucleobase sequences of SEQ ID NO: 21.

In certain embodiments, a modified oligonucleotide described herein has a nucleobase sequence comprising at least 14 contiguous nucleobases of any of the nucleobase sequences of SEQ ID NOs: 25 or 44.

In certain embodiments, a modified oligonucleotide described herein has a nucleobase sequence comprising at least 14 contiguous nucleobases of any of the nucleobase sequences of SEQ ID NO: 23.

In certain embodiments, a modified oligonucleotide described herein has a nucleobase sequence comprising at least 14 contiguous nucleobases of any of the nucleobase sequences of SEQ ID NOs: 79, 80, 84, 85, 86, 87, 88, 89, 90, 92, or 93.

In certain embodiments, a modified oligonucleotide described herein has a nucleobase sequence comprising at least 14 contiguous nucleobases of any of the nucleobase sequences of SEQ ID NOs: 82 or 83.

In certain embodiments, a modified oligonucleotide described herein has a nucleobase sequence comprising at least 14 contiguous nucleobases of any of the nucleobase sequences of SEQ ID NO: 95.

In certain embodiments, a modified oligonucleotide described herein has a nucleobase sequence comprising at least 14 contiguous nucleobases of any of the nucleobase sequences of SEQ ID NO: 97.

In certain embodiments, a modified oligonucleotide described herein has a nucleobase sequence comprising at least 14 contiguous nucleobases of any of the nucleobase sequences of SEQ ID NOs: 99, 101, 102, 103, or 104.

In certain embodiments, a modified oligonucleotide described herein has a nucleobase sequence consisting of the nucleobase sequence of any of SEQ ID NOs: 3, 4, 5, 6, 7, 8, 9, 10, 11, 12, 13, 14, 15, 16, 26, 27, 28, 29, 30, 31, 32, 33, 34, 35, 36, 37, 38, 39, 40, 45, 54, 55, 56, 57, 58, 59, 60, 61, 62, 63, 64, 65, 66, 67, 68, 69, 70, 71, 72, 73, 74, 75, 76, or 77.

In certain embodiments, a modified oligonucleotide described herein has a nucleobase sequence consisting of the nucleobase sequence of any of SEQ ID NOs: 17, 18, 19, 41, or 32.

In certain embodiments, a modified oligonucleotide described herein has a nucleobase sequence consisting of the nucleobase sequence of SEQ ID NO: 21.

In certain embodiments, a modified oligonucleotide described herein has a nucleobase sequence consisting of the nucleobase sequence of any of SEQ ID NOs: 25 or 44.

In certain embodiments, a modified oligonucleotide described herein has a nucleobase sequence consisting of the nucleobase sequence of SEQ ID NO: 23.

In certain embodiments, a modified oligonucleotide described herein has a nucleobase sequence consisting of the nucleobase sequence of any of SEQ ID NOs: 79, 80, 84, 85, 86, 87, 88, 89, 90, 92, or 93.

In certain embodiments, a modified oligonucleotide described herein has a nucleobase sequence consisting of the nucleobase sequence of any of SEQ ID NOs: 82 or 83.

In certain embodiments, a modified oligonucleotide described herein has a nucleobase sequence consisting of the nucleobase sequence of SEQ ID NO: 95.

In certain embodiments, a modified oligonucleotide described herein has a nucleobase sequence consisting of the nucleobase sequence of SEQ ID NO: 97.

In certain embodiments, a modified oligonucleotide described herein has a nucleobase sequence consisting of the nucleobase sequence of any of SEQ ID NOs: 99, 101, 102, 103, or 104.

In certain embodiments, the present disclosure provides methods for increasing the expression of RNAse H1 by contacting a cell with a modified oligonucleotide described herein has a nucleobase sequence comprising at least 14 contiguous nucleobases of any of the nucleobase sequences of SEQ ID NOs: 3, 4, 5, 6, 7, 8, 9, 10, 11, 12, 13, 14, 15, 16, 26, 27, 28, 29, 30, 31, 32, 33, 34, 35, 36, 37, 38, 39, 40, 45, 54, 55, 56, 57, 58, 59, 60, 61, 62, 63, 64, 65, 66, 67, 68, 69, 70, 71, 72, 73, 74, 75, 76, or 77.

In certain embodiments, the present disclosure provides methods for increasing the expression of LRPPRC by contacting a cell with a modified oligonucleotide described herein has a nucleobase sequence comprising at least 14 contiguous nucleobases of any of the nucleobase sequences of SEQ ID NOs: 17, 18, 19, 41, or 32.

In certain embodiments, the present disclosure provides methods for increasing the expression of SFXN3 by contacting a cell with a modified oligonucleotide described herein has a nucleobase sequence comprising at least 14 contiguous nucleobases of the nucleobase sequences of SEQ ID NO: 21.

In certain embodiments, the present disclosure provides methods for increasing the expression of THPO by contacting a cell with a modified oligonucleotide described herein has a nucleobase sequence comprising at least 14 contiguous nucleobases of any of the nucleobase sequences of SEQ ID NOs: 25 or 44.

In certain embodiments, the present disclosure provides methods for increasing the expression of MRPL11 by contacting a cell with a modified oligonucleotide described herein has a nucleobase sequence comprising at least 14 contiguous nucleobases of the nucleobase sequences of SEQ ID NO: 23.

In certain embodiments, the present disclosure provides methods for increasing the expression of ACP1 by contacting a cell with a modified oligonucleotide described herein has a nucleobase sequence comprising at least 14 contiguous nucleobases of any of the nucleobase sequences of SEQ ID NOs: 79, 80, 84, 85, 86, 87, 88, 89, 90, 92, or 93.

In certain embodiments, the present disclosure provides methods for increasing the expression of CFTR by contacting a cell with a modified oligonucleotide described herein has a nucleobase sequence comprising at least 14 contiguous nucleobases of any of the nucleobase sequences of SEQ ID NOs: 82 or 83.

In certain embodiments, the present disclosure provides methods for increasing the expression of ARF1 by contacting a cell with a modified oligonucleotide described herein has a nucleobase sequence comprising at least 14 contiguous nucleobases of the nucleobase sequences of SEQ ID NO: 95.

In certain embodiments, the present disclosure provides methods for increasing the expression of USP16 by contacting a cell with a modified oligonucleotide described herein has a nucleobase sequence comprising at least 14 contiguous nucleobases of the nucleobase sequences of SEQ ID NO: 97.

In certain embodiments, the present disclosure provides methods for increasing the expression of LDLr by contacting a cell with a modified oligonucleotide described herein has a nucleobase sequence comprising at least 14 contiguous nucleobases of any of the nucleobase sequences of SEQ ID NOs: 99, 101, 102, 103, or 104.

b. Certain Antisense Activities and Mechanisms

The 5'-UTR has emerged as playing an important role in the regulation of translation of many transcripts. In certain embodiments, the 5'-UTR contains translation suppression elements (TSEs), which serve to suppress translation of a target protein. In certain embodiments, translation suppression elements are uORFs. In certain embodiments, translation suppression elements are G-quartets. In certain embodiments, translation suppression elements are stem-loops. Disruption of a TSE will decrease the TSE's suppression of translation of a given transcript and will therefore result in an increase in translation of a target protein. In certain embodiments, antisense compounds are used to disrupt a TSE and to increase translation of a target protein.

Upstream open reading frames have emerged as an important mechanism by which translation is regulated. Approximately 50% of human transcripts have uORFs and most appear to be functional. When functional, uORFs typically reduce the translation of a polypeptide or protein from the downstream pORF. Characteristics of uORFs such as the strength of Kozak sequence and\or the distance from the 5'cap, affect the effectiveness of each uORF in reducing the translation of the downstream protein. Other factors, such as the secondary structure of the uORF or the number of uORFs per transcript also affect the effectiveness of each uORF in reducing the translation of the downstream protein. Certain embodiments of the present disclosure provide uORF inhibitors (e.g. antisense compounds) that serve to block the initiation of translation from a uORF. In certain embodiments, the uORF inhibitors do not activate RNase H. In certain such embodiments, translation of the protein encoded by a downstream ORF (e.g., the pORF) is enhanced. Certain embodiments of the present invention block the initiation of translation from a uORF with a uORF inhibitor. In certain such embodiments, translation of the protein encoded by the downstream ORF (e.g., the pORF) is enhanced. Certain embodiments of the present disclosure provide TSE inhibitors and/or uORF inhibitors (e.g. antisense compounds) that when bound to a complementary target transcript, do not activate RNase H. Certain embodiments of the present disclosure provide TSE inhibitors and/or uORF inhibitors (e.g. antisense compounds), wherein the antisense compounds are modified oligonucleotides that are not gapmers.

Upstream open reading frames can regulate translation of polypeptides or proteins encoded by pORFs by a variety of mechanisms. The polypeptide or protein encoded by the uORF may be translated, and the resulting uORF polypeptide may block translation of the polypeptide or protein encoded by the pORF on the same mRNA molecule (cis regulation) or on a separate mRNA molecule (trans regulation). In another example of cis regulation, the ribosomal subunits may dissociate from the mRNA following translation of the uORF polypeptide, thus failing to recognize and translate the pORF polypeptide or protein. Alternatively, the uORF stop codon may be recognized as a premature stop codon and initiate nonsense mediated decay. The extent to which a uORF suppresses translation of a pORF polypeptide or protein depends on how often it is recognized by the translational machinery, which is in turn affected by many factors, including the strength of the associated Kozak sequence, the number of uORFs in the 5'-UTR, the position of the stop codon, and the secondary structure of the uORF. uORF inhibitors may be employed to disrupt, alter, or exploit any of these mechanisms. In certain embodiments, uORF inhibitors are antisense compounds, and antisense compounds may be employed to disrupt, alter, or exploit any of these mechanisms. In certain embodiments, uORF inhibitors are antisense compounds, and antisense compounds may be employed to disrupt, alter, or exploit any of these mechanisms to increase expression of a target protein in a cell.

In certain embodiments, a uORF inhibitor (e.g. an antisense compound) disrupts one or more of the factors that contribute to the recognition of a uORF start site by a ribosomal subunit. In certain embodiments, a uORF inhibitor (e.g. an antisense compound) may prevent or decrease one or more of the uORF mediated translational suppressors of pORF polypeptide or protein translation discussed above. For example, in certain embodiments, a uORF inhibitor (e.g. an antisense compound) will disrupt one or more elements of a Kozak sequence, and thereby inhibit recognition of a uORF start site by a ribosomal subunit. For example, in certain embodiments, an antisense compound complementary to a portion of a uORF start site may prevent one or more ribosomal subunits from recognizing a Kozak consensus sequence. In certain embodiments, an antisense compound complementary to a portion of a uORF start site may prevent one or more ribosomal subunits from recognizing a Kozak consensus sequence and would therefore cause the ribosome to pass by the uORF start site and initiate translation at a downstream start site (e.g. the pORF start site). A uORF inhibitor (e.g. an antisense compound) would thereby increase the amount or activity of the target protein encoded by the pORF.

In certain embodiments, an antisense compound complementary to a portion of a target transcript upstream of a uORF start site may prevent one or more ribosomal subunits from recognizing a Kozak consensus sequence. In certain embodiments, an antisense compound complementary to a portion of a target transcript upstream of a uORF start site may prevent one or more ribosomal subunits from recognizing the uORF start site. In certain embodiments, an antisense compound complementary to a portion of a target transcript 10 nucleobases upstream of a uORF start site may prevent one or more ribosomal subunits from recognizing a Kozak consensus sequence. In certain embodiments, an antisense compound complementary to a portion of a target transcript 20 nucleobases upstream of a uORF start site may prevent one or more ribosomal subunits from recognizing a Kozak consensus sequence. In certain embodiments, an antisense compound complementary to a portion of a target transcript 30 nucleobases upstream of a uORF start site may prevent one or more ribosomal subunits from recognizing a Kozak consensus sequence. In certain embodiments, an antisense compound complementary to a portion of a target transcript 40 nucleobases upstream of a uORF start site may prevent one or more ribosomal subunits from recognizing a Kozak consensus sequence. In certain embodiments, an antisense compound complementary to a portion of a target transcript 50 nucleobases upstream of a uORF start site may prevent one or more ribosomal subunits from recognizing a Kozak consensus sequence. In certain embodiments, an antisense compound complementary to a portion of a target transcript 60 nucleobases upstream of a uORF start site may prevent one or more ribosomal subunits from recognizing a Kozak consensus sequence. In certain embodiments, an antisense compound complementary to a portion of a target transcript at least 60 nucleobases upstream of a uORF start site may prevent one or more ribosomal subunits from recognizing a Kozak consensus sequence. Therefore, in certain embodiments, an antisense compound complementary to a portion of a target transcript upstream of a uORF start site would increase the amount or activity the target protein encoded by the pORF.

In certain embodiments, an antisense compound complementary to a portion of a target transcript downstream of a uORF start site may prevent one or more ribosomal subunits from recognizing a Kozak consensus sequence. In certain embodiments, an antisense compound complementary to a portion of a target transcript downstream of a uORF start site may prevent one or more ribosomal subunits from recognizing the uORF start site. Therefore, in certain embodiments, an antisense compound complementary to a portion of a target transcript downstream of a uORF start site would increase the amount or activity the target protein encoded by the pORF.

In certain embodiments, disruption one or more of the factors that contribute to the recognition of a uORF start site by a ribosomal subunit by a uORF inhibitor (e.g. an antisense compound) increases expression of a downstream pORF. For example, a uORF inhibitor (e.g. an antisense compound) may prevent the dissociation of ribosomal submits after uORF polypeptide translation and thereby increase expression of a downstream pORF. For example, a uORF inhibitor (e.g. an antisense compound) may prevent the recognition of the uORF termination codon as premature and prevent nonsense-mediated decay of the transcript comprising the pORF.

In certain embodiments the ribosomal subunits recognize a uORF start site and after translation of all or part of the uORF polypeptide, the ribosomal subunits dissociate from the transcript before recognition of the pORF start site. In certain embodiments, the ribosomal subunits are the 60 s ribosomal subunit and/or the 40 s ribosomal subunit. In certain embodiments, a uORF inhibitor (e.g. an antisense compound) may increase the amount of translation reinitiation at the pORF after uORF polypeptide translation. For example, in certain embodiments, a uORF inhibitor (e.g. an antisense compound) prevents the amount of the 60 s ribosomal subunit and/or the 40 s ribosomal subunit that dissociate from the transcript after translation of all or part of the uORF polypeptide and thereby increases translation of the pORF polypeptide or protein.

In certain embodiments, a uORF inhibitor is a small molecule. In certain embodiments, a uORF inhibitor is an antibody. In certain embodiments, a uORF inhibitor is a polypeptide. In certain embodiments, a uORF inhibitor (e.g. a small molecule, antibody, polypeptide, and/or siRNA) increases the amount or activity a target protein encoded by a pORF via any of the mechanisms described herein.

Upstream open reading frames are one type of translation suppression element. In addition to uORFs, translation can be regulated by other types of translation suppression elements (TSEs) in the 5'-UTR. Translation may be suppressed by structural elements in the 5'-UTR, such as stem-loops and hairpins. In certain embodiments, the extent to which a structural element suppresses translation may be correlated with the sequence and/or stability of the structural element. For example, the extent to which a structural element suppresses translation may increase as the distance between the 5'-cap of the target transcript and the structural element decreases. For another example, in certain embodiments, GC content and/or the number of consecutive GC nucleosides in the structural element may positively correlate with the extent to which translation is suppressed, due to increased stability of the structural element. Thus, in certain embodiments, transcripts with a 5'-UTR containing multiple stretches of at least 3 consecutive GC nucleosides may comprise at least one TSE. In certain embodiments, transcripts with a 5'-UTR containing at least one stretch of at least 7 GC nucleosides may comprise at least one TSE.

TSEs that are structural elements may sterically block one or more ribosomal subunits from accessing the coding region. Without wishing to be bound by mechanism, TSE inhibitors may increase translation of a target protein by relieving such steric blockage. In certain embodiments, antisense compounds that are complementary to at least a portion of a TSE structural element alter the structure of the structural element, resulting in increased translation of the target protein. In certain embodiments, such antisense compounds unfold the structural element. In certain embodiments, antisense compounds that are TSE inhibitors have at least 60% GC content. In certain embodiments, antisense compounds that are TSE inhibitors have at least 70% GC content. In certain embodiments, antisense compounds that are TSE inhibitors have at least 80% GC content. In certain embodiments, antisense compounds that are TSE inhibitors have at least 90% GC content. In certain embodiments, antisense compounds that are TSE inhibitors have 100% GC content. In certain embodiments, antisense compounds that are TSE inhibitors have 3, 4, 5, 6, 7, 8, 9, 10, 11, 12, 13, 14, 15, 16, 17, 18, 19, or at least 20 consecutive GC nucleosides. In certain embodiments, antisense compounds that are TSE inhibitors are complementary to the stem portion of a stem-loop in the 5'-UTR of the target transcript. In certain embodiments, antisense compounds that are TSE inhibitors are complementary to a hairpin in the 5'-UTR of the target transcript.

A third type of TSE is a G quartet. In certain embodiments, the extent to which a G quartet suppresses translation may increase as the distance between the 5'-cap of the target transcript and the G quartet decreases.

A fourth type of TSE is a stem-loop structure. In certain embodiments, transcripts having a stem-loop structure within the 5'-UTR suppress translation of the target protein. In certain embodiments, the extent to which a stem-loop suppresses translation may increase as the distance between the 5'-cap of the target transcript and the stem-loop decreases.

c. Certain Compositions and Methods for Increasing Antisense Activity

In certain embodiments the present disclosure provides methods for increase the activity of an antisense compound in a cell, comprising contact the cell with a translation suppression element inhibitor and thereby increasing the activity of an antisense compound.

In certain embodiments, a translation suppression element inhibitor (e.g. an antisense compound) as described herein increases the amount or activity of a target protein in a cell. In certain embodiments, a uORF inhibitor (e.g. an antisense compound) as described herein increases the amount or activity of a target protein in a cell. In certain embodiments, the target protein plays a role in antisense activity. Therefore, in certain embodiments, increasing the amount or activity of a target protein may also increase the amount or activity of an antisense compound. For example, in certain embodiments, the target protein may play a role in subcellular localization of antisense compounds. In certain embodiments, the target protein may play a role in RNA binding. In certain embodiments, the target protein may play a role in nuclear transport. In certain embodiments, the target protein may play a role in membrane binding. In certain embodiments, the target protein may play a role in DNA binding. In certain embodiments, the target protein may play a role in nuclear import. In certain embodiments, the target protein is a heat shock protein.

In certain embodiments, a translation suppression element inhibitor is used to increase the amount or activity of a target protein that plays a role in antisense activity, thereby increasing the amount or activity of an antisense compound. In this manner, a translation suppression element inhibitor may be used to increase the activity of an antisense compound by contacting a cell with the translation suppression element inhibitor and then contacting the cell with an antisense compound. In certain embodiments, a uORF inhibitor is used to increase the amount or activity of a target protein that plays a role in antisense activity, thereby increasing the amount or activity of an antisense compound. In this manner, a uORF inhibitor may be used to increase the activity of an antisense compound by contacting a cell with the uORF inhibitor and then contacting the cell with an antisense compound.

For example, in certain embodiments, the target protein is RNase H. In certain embodiments, a translation suppression element inhibitor targeted to the 5'-UTR of RNase H increases the amount or activity of RNase H protein in a cell, thereby increasing antisense activity in the cell. In certain embodiments, the target protein is La/SSB. In certain embodiments, a translation suppression element inhibitor targeted to the 5'-UTR of La/SSB increases the amount or activity of La/SSB protein in a cell, thereby increasing antisense activity in the cell. In certain embodiments, the target protein is NPM1. In certain embodiments, a translation suppression element inhibitor targeted to the 5'-UTR of NPM1 increases the amount or activity of NPM1 protein in a cell, thereby increasing antisense activity in the cell. In certain embodiments, the target protein is TCP1-alpha. In certain embodiments, a translation suppression element inhibitor targeted to the 5'-UTR of TCP1-alpha increases the amount or activity of TCP1-alpha protein in a cell, thereby increasing antisense activity in the cell.

In certain embodiments, the target protein is TCP1-epsilon. In certain embodiments, a translation suppression element inhibitor targeted to the 5'-UTR of TCP1-epsilon increases the amount or activity of TCP1-epsilon protein in a cell, thereby increasing antisense activity in the cell. In certain embodiments, the target protein is TCP1-beta. In certain embodiments, a translation suppression element inhibitor targeted to the 5'-UTR of TCP1-beta increases the amount or activity of TCP1-beta protein in a cell, thereby increasing antisense activity in the cell. In certain embodiments, the target protein is HSP90-AA1. In certain embodiments, a translation suppression element inhibitor targeted to the 5'-UTR of HSP90-AA1 increases the amount or activity of HSP90-AA1 protein in a cell, thereby increasing antisense activity in the cell. In certain embodiments, the target protein is HSP90-AB. In certain embodiments, a translation suppression element inhibitor targeted to the 5'-UTR of HSP90-AB increases the amount or activity of HSP90-AB protein in a cell, thereby increasing antisense activity in the cell. In certain embodiments, the target protein is HSPA1L. In certain embodiments, a translation suppression element inhibitor targeted to the 5'-UTR of HSPA1L increases the amount or activity of HSPA1L protein in a cell, thereby increasing antisense activity in the cell. In certain embodiments, the target protein is RAN. In certain embodiments, a translation suppression element inhibitor targeted to the 5'-UTR of RAN increases the amount or activity of RAN protein in a cell, thereby increasing antisense activity in the cell.

In certain embodiments, the target protein is IMP9. In certain embodiments, a translation suppression element inhibitor targeted to the 5'-UTR of IMP9 increases the amount or activity of IMP9 protein in a cell, thereby increasing antisense activity in the cell. In certain embodiments, the target protein is Annexin A2. In certain embodiments, a translation suppression element inhibitor targeted to the 5'-UTR of Annexin A2 increases the amount or activity of Annexin A2 protein in a cell, thereby increasing antisense activity in the cell. In certain embodiments, the target protein is FTCD/58 k. In certain embodiments, a translation suppression element inhibitor targeted to the 5'-UTR of FTCD/58 k increases the amount or activity of FTCD/58 k protein in a cell, thereby increasing antisense activity in the cell.

In certain embodiments, the target protein is PC4/SUB1. In certain embodiments, a translation suppression element inhibitor targeted to the 5'-UTR of PC4/SUB1 increases the amount or activity of PC4/SUB1 protein in a cell, thereby increasing antisense activity in the cell. In certain embodiments, the target protein is VARS. In certain embodiments, a translation suppression element inhibitor targeted to the 5'-UTR of VARS increases the amount or activity of VARS protein in a cell, thereby increasing antisense activity in the cell. In certain embodiments, the target protein is DHX36. In certain embodiments, a translation suppression element inhibitor targeted to the 5'-UTR of DHX36 increases the amount or activity of DHX36 protein in a cell, thereby increasing antisense activity in the cell.

For example, in certain embodiments, the target protein is RNase H. In certain embodiments, a uORF inhibitor targeted to the 5'-UTR of RNase H increases the amount or activity of RNase H protein in a cell, thereby increasing antisense activity in the cell. In certain embodiments, the target protein is La/SSB. In certain embodiments, a uORF inhibitor targeted to the 5'-UTR of La/SSB increases the amount or activity of La/SSB protein in a cell, thereby increasing antisense activity in the cell. In certain embodiments, the target protein is NPM1. In certain embodiments, a uORF inhibitor targeted to the 5'-UTR of NPM1 increases the amount or activity of NPM1 protein in a cell, thereby increasing antisense activity in the cell. In certain embodiments, the target protein is TCP1-alpha. In certain embodiments, a uORF inhibitor targeted to the 5'-UTR of TCP1-alpha increases the amount or activity of TCP1-alpha protein in a cell, thereby increasing antisense activity in the cell.

In certain embodiments, the target protein is TCP1-epsilon. In certain embodiments, a uORF inhibitor targeted to the 5'-UTR of TCP1-epsilon increases the amount or activity of TCP1-epsilon protein in a cell, thereby increasing antisense activity in the cell. In certain embodiments, the target protein is TCP1-beta. In certain embodiments, a uORF inhibitor targeted to the 5'-UTR of TCP1-beta increases the amount or activity of TCP1-beta protein in a cell, thereby increasing antisense activity in the cell. In certain embodiments, the target protein is HSP90-AA1. In certain embodiments, a uORF inhibitor targeted to the 5'-UTR of HSP90-AA1 increases the amount or activity of HSP90-AA1 protein in a cell, thereby increasing antisense activity in the cell. In certain embodiments, the target protein is HSP90-AB. In certain embodiments, a uORF inhibitor targeted to the 5'-UTR of HSP90-AB increases the amount or activity of HSP90-AB protein in a cell, thereby increasing antisense activity in the cell. In certain embodiments, the target protein is HSPA1L. In certain embodiments, a uORF inhibitor targeted to the 5'-UTR of HSPA1L increases the amount or activity of HSPA1L protein in a cell, thereby increasing antisense activity in the cell. In certain embodiments, the target protein is RAN. In certain embodiments, a uORF inhibitor targeted to the 5'-UTR of RAN increases the amount or activity of RAN protein in a cell, thereby increasing antisense activity in the cell.

In certain embodiments, the target protein is IMP9. In certain embodiments, a uORF inhibitor targeted to the 5'-UTR of IMP9 increases the amount or activity of IMP9 protein in a cell, thereby increasing antisense activity in the cell. In certain embodiments, the target protein is Annexin A2. In certain embodiments, a uORF inhibitor targeted to the 5'-UTR of Annexin A2 increases the amount or activity of Annexin A2 protein in a cell, thereby increasing antisense activity in the cell. In certain embodiments, the target protein is FTCD/58 k. In certain embodiments, a uORF inhibitor targeted to the 5'-UTR of FTCD/58 k increases the amount or activity of FTCD/58 k protein in a cell, thereby increasing antisense activity in the cell.

In certain embodiments, the target protein is PC4/SUB1. In certain embodiments, a uORF inhibitor targeted to the 5'-UTR of PC4/SUB1 increases the amount or activity of PC4/SUB1 protein in a cell, thereby increasing antisense activity in the cell. In certain embodiments, the target protein is VARS. In certain embodiments, a uORF inhibitor targeted to the 5'-UTR of VARS increases the amount or activity of VARS protein in a cell, thereby increasing antisense activity in the cell. In certain embodiments, the target protein is DHX36. In certain embodiments, a uORF inhibitor targeted to the 5'-UTR of DHX36 increases the amount or activity of DHX36 protein in a cell, thereby increasing antisense activity in the cell.

In certain embodiments, the target protein is LDLr. Increasing expression of the LDLr protein decreases cholesteral levels.

In certain embodiments, the target protein is CFTR. Mutations in the CFTR gene lead to cystic fibrosis. In certain embodiments, increasing expression of the CFTR protein may ameliorate one or more symptoms of cystic fibrosis.

d. Certain Compositions and Methods for Decreasing Antisense Activity

In certain embodiments, antisense compounds disclosed herein may target microRNAs or other naturally occurring non-coding transcripts that are complementary to a uORF region or a translation suppression element. Certain such antisense compounds would therefore inhibit expression of a target transcript by increasing the effect of a translation suppression element or uORF. For example, in certain embodiments, a non-coding transcript, such as a microRNA may be complementary to a uORF or uORF region and serve to increase expression of a target protein. An antisense compound complementary to the microRNA would sequester the microRNA and the uORF would then suppress translation of the target protein. In such a manner, an antisense compound would inhibit expression of a target protein.

C. Certain Target Genes

The present disclosure provides compounds and methods that may be used to increase expression of any target protein, provided there is at least one uORF on a transcript encoding the target protein. The present disclosure also provides compounds and methods that may be used to increase expression of any target protein, provided there is at least one TSE on a transcript encoding the target protein. In certain embodiments, the at least one TSE comprises a uORF. In certain embodiments, there are at least two TSEs on a transcript encoding a target protein. In certain embodiments neither of the at least two TSEs comprise a uORF. In certain embodiments, one of the at least two TSEs comprises a uORF. In certain embodiments, both of the at least two TSEs comprise a uORF. In certain embodiments, a deficiency of the target protein is associated with disease and so increasing the amount or activity of the protein is expected to ameliorate one or more symptoms of the disease or delay the onset of one or more symptoms of the disease. Table 1 and Table 2, below, list certain genes and associated diseases. In certain embodiments, a target transcript is encoded by a gene listed in Table 1 or Table 2. In certain embodiments, the associated disease or disorder in Table 1 or Table 2 is treated by use of an antisense compound of the present invention targeting such transcript. The diseases associated with each gene in Table 1 include diseases that arise due to or are correlated with an insufficiency of the corresponding uORF-containing gene as well as diseases that could be ameliorated by up-regulation of the corresponding uORF-containing gene. The diseases associated with each gene in Table 2 include diseases that correlate with a mutation or SNP that introduces a uORF in the corresponding gene.

In certain embodiments, antisense compounds are targeted to one or more TSEs in the 5'UTR of a gene in Table 1 or Table 2. In certain embodiments, antisense compounds are not targeted to one or more TSEs in the 5'UTR of a gene in Table 1 or Table 2.

TABLE 1 uORF-containing genes and associated diseases

| Gene | NCBI Gene ID | Associated disease(s) |
|---|---|---|
| ABCA1 | 19 | Cardiovascular, Dry AMD, dyslipidemia, and atherosclerosis |
| ABCB11 | 8647 | Cholestasis, primary sclerosing cholangitis and biliary cirrhosis |
| ABCC2 | 1244 | Dubin-Johnson syndrome-but overexpressed in cancer |
| ABCG5 | 64240 | Cholestasis, primary sclerosing cholangitis and biliary cirrhosis |
| ADAM10 | 102 | Alzheimer's Disease |
| ALB | 213 | liver disease, nephrotic syndrome, renal disease, and analbuminemia |
| ANK1 | 286 | Hereditary spherocytosis |
| APOE | 348 | Cancer, melanoma, pulmonary hypertension, dyslipidemia, atherosclerosis, Alzheimer disease, Lipoprotein glomerulopathy, and Sea-blue histiocyte disease |
| ATP2A2 | 488 | cardiac diseases, congenital heart disease, aortic aneurysms, aortic dissections, arrhythmia, cardiomyopathy, congestive heart failure, Darier-White disease, muscular dystrophy, and Acrokeratosis verruciformis |
| ATP7B | 540 | wilson disease, and menkes disease. |
| ATRX | 546 | alpha-thalassemia myelodysplasia syndrome, somatic, and mental retardation-hypotonic facies syndrome, x-linked. |
| ATXN1 | 6310 | Spinocerebellar ataxia-1 |
| ATXN1L | 342371 | Spinocerebellar ataxia-1 |
| BAX | 581 | Cancer |
| BCL2L11 | 10018 | Cancer, e.g. human T-cell acute lymphoblastic leukemia and lymphoma |
| BDNF | 627 | neurodegeneration diseases, amyotrophic lateral sclerosis, Alzheimer's Disease, Huntington's disease (HD), or Parkinson's Disease (PD) |
| BLM | 641 | bloom syndrome, and rothmund-thomson syndrome. |
| BRCA1 | 672 | Cancer, e.g. breast cancer, pancreatic cancer |
| C/EBPa | 1050 | B-cell maligancy (B-ALL, DLBCL), AML |
| CA2 | 760 | autoimmune retinopathy, and multifocal fibrosclerosis. |
| CASP8 | 841 | CASP8 deficiency, breast cancer, HCC, lung cancer |
| CCBE1 | 147372 | hennekam syndrome, and immune hydrops fetalis. |
| CD36 | 948 | platelet glycoprotein IV deficiency, coronary heart disease, CHDS7 |
| CD3D | 915 | severe combined immune deficiency, autosomal recessive, t cell-negative, b cell-positive, nk cell-positive, cd3d-related, and immunodeficiency 19. |
| CDKN1B | 1027 | cancer, multiple endocrine neoplasia |
| CDKN2A | 1029 | cancer, melanoma |
| CEP290 | 80184 | Leber's congenital amaurosis (LCA), Bardet-Biedl syndrome (BBS), Joubert syndrome, Meckel syndrome, Sior-Loken syndrome |
| CFH | 3075 | C3 glomerulopathy, AMD, PNH, RA etc |
| CFTR | 1080 | Cystic fibrosis, Disseminated bronchiectasis, congenital bilateral absence of vas deferens (CBAVD) |
| CHRNA4 | 1137 | nicotine addiction |
| CHRNA5 | 1138 | nicotine addiction |
| CNTF | 1270 | Multiple Sclerosis |
| CNTFR | 1271 | Multiple Sclerosis |
| COL1A1 | 1277 | Osteogenesis Imperfecta Type I |
| CR1 | 1378 | Alzherimer's Disease |
| CSPP1 | 79848 | joubert syndrome 21, and joubert syndrome with jeune asphyxiating thoracic dystrophy. |
| CTNND2 | 1501 | Cri-du-chat syndrome |
| CTNS | 1497 | intermediate cystinosis, and cystinosis, atypical nephropathic |
| CYP1B1 | 1545 | Glaucoma, Peters anomaly |

TABLE 1-continued uORF-containing genes and associated diseases

| Gene | NCBI Gene ID | Associated disease(s) |
|---|---|---|
| DBT | 1629 | maple syrup urine disease type 2, and maple syrup urine disease type 1a |
| DCAF17 | 80067 | sakati syndrome, and hypogonadism, alopecia, diabetes mellitus, mental retardation, and extrapyramidal syndrome |
| DNASE1 | 1773 | cystic fibrosis, acute bronchitis |
| DDIT3 | 1649 | Myxoid liposarcoma |
| DICER1 | 23405 | DICER1 symdrome, pleuropulmonary blastoma, cystic nephroma, Sertoli-Leydig tumors, multinodular goiter, cancer |
| DRD3 | 1814 | mood disorders |
| EED | 8726 | HIV-1 |
| EFNB1 | 1947 | CFNS |
| EPO | 2056 | erythropoiesis and anemia |
| ESR1 | 2099 | inhibits ERBB1, breast cancer |
| ETHE1 | 23474 | ethylmalonic encephalopathy |
| EZH2 | 2146 | weaver syndrome, ezh2-related overgrowth, lymphomas and leukemias |
| F8 (and F2, 3, 5, 7, 11, 13) | 2147, '52, '53, '55, '57, '60, | Hemophilia, bleeding |
| FAP | 2191 | glomuvenous malformations |
| FMR1 | 2332 | Fragile X syndrome and premature ovarian failure |
| FNDC5 | 252995 | Obesity, Type 2 Diabetes |
| FXN | 2395 | Friedreich's ataxia |
| GALNS | 2588 | mucopolysaccharidosis iv, and kniest dysplasia |
| GATA3 | 2625 | Cancer |
| GBA | 2629 | Synucleinopathies, Gaucher's disease |
| GCH1 | 2643 | gtp cyclohydrolase I deficiency, Parkinson's disease, movement disorders, CNS disease, doparesponsive dystonia, hyperpehnylalaninemia, and atypical severe phenylketonuria |
| GCK | 2645 | Obesity, Type 2 Diabetes, and Hyperinsulinemic hypoglycemia |
| GH2 | 2689 | idiopathic short stature, growth delay |
| GRN | 2896 | autoimmune, inflammatory, dementia, FTD, cancer, e.g. hepatic cancer |
| HBB | 3043 | thallasemia, sickle cell disease, and anemia |
| HBD | 3045 | thallasemia, sickle cell disease, and anemia |
| HBE1 | 3046 | thallasemia, sickle cell disease, and anemia |
| HBG1 | 3047 | Anemia (e.g., Fanconi's anemia), thalassemia (e.g., beta-thalassemia etc.), sickle cell disease, leukemia, cellular dyscrasia, dyserythropoiesis, anisocytosis and poikilocytosis. |
| HBG2 | 3048 | thallasemia, sickle cell disease, and anemia |
| HCRT | 3060 | Narcolepsy/Excessive Daytime Sleepiness |
| HGF | 3082 | Ischemic disease, restenosis after percutaneous transluminal coronary angioplasty (PTCA), arteriosclerosis, insufficiency of peripheral circulation, myocardial infarction, myocardia, peripheral angiostenosis, cardiac insufficiency, nerve degeneration, neuropathy, neurotoxin induced lesions, injury of nerve cell, lesions of nerve cell by infection, epilepsy, head trauma, dementia, cerebral stroke, cerebral infarction, amyotrophic lateral sclerosis, Parkinson's disease, Alzheimer's disease, cancer, tumor, liver cirrhosis, Nonalcoholic fatty liver disease, renal fibrosis, rhabdomyolysis, pulmonary fibrosis, blood coagulopathy, adenosine deaminase deficiency, Chronic Ulcerative Colitis, Crohn's Disease, necrotizing enterocolitis, severe acute gastroenteritis, chronic gastroenteritis, cholera, chronic infections of the bowel, AIDS, pustulous fibrosis, fibrosis, osteoporosis, Arterial sclerosis, chronic glomerulonephritis, cutis keloid formation, progressive systemic sclerosis (PSS), liver fibrosis, pulmonary fibrosis, cystic fibrosis, chronic graft versus host disease, scleroderma (local and systemic), Peyronie's disease, penis fibrosis, inner accretion after surgery, myelofibrosis, idiopathic retroperitoneal fibrosis, hemophilia, decubitus ulcer, scar, atopic dermatitis, or skin damage following a skin graft |
| HNF4a | 3172 | HCC, fibrosis |
| HR | 55806 | atrichia with papular lesions, and hypotrichosis 4 |
| HSD17B4 | 3295 | D-bifunctional protein deficiency |
| IDO1 | 3620 | autoimmune and inflammatory diseases |
| IFNE and other interferon genes | 338376, others | Cancer, HBV, and other virus infection |
| IFRD1 | 3475 | Cystic fibrosis, Chronic obstructive pulmonary disease (COPD), inflammation, lung cancer, sensory/motor neuropathy, a neuronal injury |
| IGF1 | 3479 | CNS diseases, metabolic disease, delayed growth, cancer |
| IGF1R | 3480 | Insulin-like growth factor I resistance |
| IGF2 | 3481 | Russell-Silver syndrome |
| IGF2BP2 | 10644 | Type 2 diabetes, insulin resistance susceptibility |
| IGFBP3 | 3486 | growth delay |
| IGHMBP2 | 3508 | progressive multifocal leukoencephalopathy, and spinal muscular atrophy with respiratory distress 1 |

TABLE 1-continued uORF-containing genes and associated diseases

| Gene | NCBI Gene ID | Associated disease(s) |
|---|---|---|
| IL6 | 3569 | infectious disease, vaccination, and cancer |
| INS | 3630 | Diabetes or related disorders thereof, an insulin resistant non diabetic state, obesity, impaired glucose tolerance (IGT), Metabolic Syndrome, MODY syndrome, Polycystic Ovary Syndrome, cancer, inflammation, hirsuitism, and hypertension. |
| IQGAP1 | 8826 | Cancer, obesity, diabetes, multiple sclerosis, neoplastic transformation, inflammation, Nonsmall cell lung carcinoma (NSCLCs), hypercholesterolemia, liposarcoma, gastric cancer, immunodeficiency, glomerulonephritis, venous thrombosis, glioma |
| IQGAP2 | 10788 | Obesity, diabetes, multiple sclerosis, neoplastic transformation, inflammation, Nonsmall cell lung carcinoma (NSCLCs), hypercholesterolemia, liposarcoma, gastric cancer, immunodeficiency, glomerulonephritis, venous thrombosis, glioma |
| IRF6 | 3664 | van der Woude syndrome |
| IRS2 | 8660 | Alzheimer's disease, Parkinson's disease, amyotrophic lateral sclerosis, insulin resistance, diabetes, Polycystic Ovary Syndrome, atherosclerosis, cancer |
| ITGA7 | 3679 | muscular dystrophy, congenital, due to itga7 deficiency, and congenital muscular dystrophy due to integrin alpha-7 deficiency |
| JAG1 | 182 | Alagille syndrome |
| KCNJ11 | 3767 | Congenital hyperinsulinism, hyperinsulinemic hypoglycemia, 2 |
| KCNMA1 | 3778 | vascular disease, kidney disease, Obesity, Type 2 Diabetes, inflammatory disease, autoimmune disease, and cancer, e.g. kidney, lung, or ovarian cancer |
| KCNMB1 | 3779 | vascular disease, kidney disease, Obesity, Type 2 Diabetes, inflammatory disease, autoimmune disease, and cancer, e.g. kidney, lung, or ovarian cancer |
| KCNMB2 | 10242 | vascular disease, kidney disease, Obesity, Type 2 Diabetes, inflammatory disease, autoimmune disease, and cancer, e.g. kidney, lung, or ovarian cancer |
| KCNMB3 | 27094 | vascular disease, kidney disease, Obesity, Type 2 Diabetes, inflammatory disease, autoimmune disease, and cancer, e.g. kidney, lung, or ovarian cancer |
| KCNQ3 | 3786 | kcnq3-related benign familial neonatal epilepsy, and seizures, benign neonatal, type 2 |
| KLF4 | 9314 | thallasemia, sickle cell disease, and anemia |
| KMT2D | 8085 | Kabuki Syndrome |
| LDLR | 3949 | dyslipidemias, atherosclerosis, and hypercholesterolemia, cardiovascular disease |
| LRP1 | 4035 | Cancer, melanoma |
| LRP5, | 4041, | exudative vitreoretinopathy 4, and hyperostosis, endosteal |
| LRP8 | 7804 | Cancer, melanoma |
| LRPPRC | 10128 | Leigh syndrome Frencn-Canadian type, Cytochrome c oxidase deficiency |
| MBTPS1 | 8720 | Colitis, obesity, diabetes, hypercholesterolemia, dyslipidemia, Crimean-Congo hemorrhagic fever, chondrodysplasia |
| MECP2 | 4204 | Rett Syndrome, MECP2-related severe neonatal encephalopathy, Angelman syndrome, and PPM-X syndrome |
| MSRA | 4482 | cancer, macular degeneration, eye aging, cataract |
| MSX2 | 4488 | tooth agenesis (dentin dysplasia), developmental disorders e.g. Craniosynostosis and Parietal foramina |
| MTR | 4548 | Homocystinuria |
| MUTYH | 4595 | Familial adenomatous polyposis |
| MYCN | 4613 | Feingold syndrome |
| MYF6 | 4618 | Centronuclear Myopathy 3 |
| NAMPT | 10135 | cancer, cytopenia of the myeloid or lymphoid lineage, neutropenia, leukaemia, acute myeloid leukaemia (AML), atherosclerosis, inflammatory bowel disease, Crohn's disease, ulcerative colitis, psoriasis, arthritis, chronic ulcer, ischemic stroke, myocardial infarction, angina and vascular dementia, inflammation, nonalcoholic fatty liver disease |
| NANOG | 79923 | diabetes, osteoarthritis, rheumatoid arthritis, cancer, Duchenne muscular dystrophy, Parkinson's, Alzheimer's, Gaucher disease, type I diabetes, spinal cord injury, burns (tissue regeneration) |
| NEU4 | 129807 | cancer, diabetes, Tay Sachs disease, inflammatory bowel disease, Crohn's disease, ulcerative colitis, psoriasis, arthritis, inflammation, insulin resistance syndrome, hyperlipidemia, fatty liver disease, cachexia, obesity, atherosclerosis, artcriosccrlosis, elevated blood pressure, viral infection |
| NF1 | 4763 | neurofibromatosis and cancer, e.g., neurofibrosarcoma, malignant peripheral nerve sheath tumors, and myelomonocytic leukemia |
| NKX2-3, -5, -8 | 159296, 1482, 26257 | cancer, e.g., lung cancer |
| NOD2 | 64127 | Crohn disease |
| NR5A1 | 2516 | nr5a1-related 46,xy dsd and 46,xy cgd, and adrenocortical insufficiency, without ovarian defect |

TABLE 1-continued uORF-containing genes and associated diseases

| Gene | NCBI Gene ID | Associated disease(s) |
|---|---|---|
| NRF1 | 4899 | Alzheimer's disease, Parkinson's disease, amyotrophic lateral sclerosis, insulin resistance, diabetes, hepatic tumor, non-small cell bronchopulmonary cancer, mitochondrial disease |
| NSD1 | 64324 | Sotos syndrome (cerebral gigantism)autosomal dominant disorder. The cause is haploinsufficiency of the NSD1 gene |
| PAH | 5053 | Phenylketonuria (PKU) |
| PARK2 | 5071 | Parkinson's |
| PKD1 | 5310 | Polycystic kidney disease |
| PLAT | 5327 | ischemic stroke |
| PON1, 2 | 5444, 5445 | diabetes, obesity, hypercholesterolemia, high blood pressure, atherosclerosis, coronary heart disease, autism/autism spectrum disorder, epilepsy, cancer, inflammation, stroke, trauma, a renal disease, rheumatoid arthritis, Fish-Eye disease, purpura, Polycystic Ovary Syndrome, hyperthyroidism, a hepatic diseases, vascular dementia, an infectious disease |
| PPARD | 5467 | Metabolic disease |
| PRKAR1A | 5573 | Carney complex |
| PRPF31 | 26121 | adRP |
| PTEN | 5728 | cancer |
| PYCR1 | 5831 | cystic fibrosis, myocardial fibrosis, myelofibrosis, hepatic fibrosis, interstitial lung fibrosis, neoplastic fibrosis, pancreatic fibrosis, pulmonary fibrosis, subepidermal fibrosis, panmural fibrosis of the bladder, proliferative fibrosis, replacement fibrosis, retroperitoneal fibrosis and root sleeve fibrosis, osteogenesis imperfecta, Ehlers-Danlos syndrome, chondrodysplasias, Marfan syndrome, Alport syndrome, familial aortic aneurysm, achondroplasia, mucopolysaccharidoses, osteoporosis, osteopetrosis, Paget's disease, rickets, osteomalacia, hyperparathyroidism, renal osteodystrophy, osteonecrosis, osteomyelitis, osteoma, osteoid osteoma, osteoblastoma, osteosarcoma, osteochondroma, chondroma, chondroblastoma, chondromyxoid fibroma, chondrosarcoma, fibrous cortical defect, nonossifying fibroma, fibrous dysplasia, fibrosarcoma, malignant fibrous histiocytoma, Ewing's sarcoma |
| RB1, RBL1, RBL2 | 5925, 5933, 5934 | cancer, e.g. bladder cancer, osteosarcoma, retinoblastoma, small cell lung cancer |
| RBBP4 | 5928 | intermediate charcot-marie-tooth neuropathy, retinoblastoma, Alzheimer's |
| RNASEH1 | 246243 | leishmaniasis, a disease or disorder associated with mitochondrial dysfunction, cancer, Aicardi-Goutieres syndrome, AIDS |
| ROR2 | 4920 | brachydactyly, type b1, and brachydactyly type b |
| RPS14 | 6208 | 5q syndrome (myelodysplastic syndrome) |
| RPS19 | 6223 | Diamond-Blackfan Anemia |
| SCN1A | 6323 | convulsion, pain, paralysis, hyperkalemic periodic paralysis, paramyotonia congenita, potassium-aggravated myotonia, long Q-T syndrome 3, motor endplate disease, ataxia, colitis, ileitis, inflammatory bowel syndrome, hypertension, congestive heart failure, benign prostrate hyperplasia, impotence, muscular dystrophy, multiple sclerosis, epilepsy, autism, migraine, severe myoclonic epilepsy of infancy (SMEI or Dravet's syndrome) |
| SCN2A | 6326 | epileptic encephalopathy, early infantile, 11, and benign familial neonatal-infantile seizures |
| SERPINF1 | 5176 | cancer, choroidal neovascularization, cardiovascular disease, diabetes, and osteogenesis imperfecta |
| SERPING1 | 710 | Hereditary Angioedema |
| SHBG | 6462 | disorders of mood and affect, a memory dysfunction disease or disorder, an amnestic disease or disorder, a motor and tic disorder, substance abuse disease or disorder, a psychotic disease or disorder, an anxiety disease or disorder, schizophrenia, schizofreniform disorder, schizoaffective disorder, and delusional disorder, panic disorder, phobias, an obsessive-compulsive disorder, posttraumatic stress disorder, infertility, hirsutism, Tourette's disorder, Asperger syndrome, hypothyroidism, fibromyalgia, chronic fatigue syndrome, hypothalamic-pituitary axis dysregulation, chronic sleep deprivation, alopecia, prostate cancer, breast cancer, polycystic ovary syndrome, osteoporosis, hyperinsulinemia, glucose intolerance, insulin resistance, diabetes |
| SIRT1 | 23411 | cancer, Alzheimer's Disease (AD), Huntington's disease, Parkinson's disease, Amyotrophic Lateral Sclerosis (ALS), Multiple Sclerosis, Duchene muscular dystrophy, skeletal muscle atrophy, Becker's dystrophy, myotonic dystrophy, insulin resistance, diabetes, obesity, Hypercholesterolemia, dyslipidemia hyperlipidemia, sensory neuropathy, autonomic neuropathy, motor neuropathy, retinopathy, hepatitis, fatty liver disease, age-related macular degeneration, osteoporosis, leukemia, bone resorption, dementia, Bell's Palsy, atherosclerosis, cardiac dysrhymias, chronic congestive heart failure, ischemic stroke, coronary artery disease, cardiac muscle disease, chronic renal failure, ulceration, cataract, presbiopia, glomerulonephritis, Guillan-Barre syndrome, hemorrhagic stroke, rheumatoid arthritis, inflammatory bowel disease, SLE, Crohn's disease, osteoarthritis, Chronic Obstructive |

TABLE 1-continued uORF-containing genes and associated diseases

| Gene | NCBI Gene ID | Associated disease(s) |
|---|---|---|
| | | Pulmonary Disease (COPD), pneumonia, urinary incontinence, mitochondrial myopathy, encephalopathy, Leber's disease, Leigh encephalopathia, Pearson's disease, lactic acidosis, mitochondrial encephalopathy, lactic acidosis and stroke like symptoms (MELAS), inflammation |
| SLC1A2 | 6506 | ALS |
| SMAD7 | 4092 | Acute kidney injury (anti-TGFb), colorectal cancer |
| SMCHD1 | 23347 | FSHD |
| SMN1, SMN2 | 6606, 6607 | Spinal muscular atrophy |
| 5NX27 | 81609 | Downs' Syndrome |
| SPINK1 | 6690 | Pancreatits |
| SRB1 | 949 | Cardiovascular disease |
| SRY | 6736 | Gonadal dysgenesis |
| ST7, ST7L | 7982, 54879 | cancer, e.g. myeloid cancer, head and neck squamous cell carcinomas, breast cancer, colon carcinoma, and prostate cancer |
| STAT3 | 6774 | tissue regeneration and Hyper-IgE recurrent infection syndrome |
| TFE3 | 7030 | diabetes, obesity, impaired glucose tolerance (IGT) and Metabolic Syndrome, Polycystic Ovary Syndrome, atherosclerosis, cancer, Alzheimer's disease, Parkinson's disease, amyotrophic lateral sclerosis, diabetic retinopathy, diabetic neuropathy, diabetic amyotrophy, diabetic nephropathy, diabetic cardiomyopathy, angina, myocardial infarction, stroke, a peripheral vascular disease |
| TFEB | 7942 | Lysosomal storage diseases |
| TGFB3 | 7043 | Rienhoff syndrome |
| THPO | 7066 | Myelosuppressive chemo, Bleeding disorders |
| TP63 | 8626 | cancer, tumor, Corneal dystrophy, premature menopause, alopecia, cctrodaclyly-ectodermal dysplasia-cleft syndrome, Hay-Wells syndrome, limb mammary syndrome, acro-dermato-ungual-lacrimal-tooth syndrome, nonsyndromic split-hand/foot malformation, isolated cleft lip/palate, Rapp-Hodgkin syndrome |
| TP73 | 7161 | Cancer |
| UCP2 | 7351 | cancer, obesity, cachexia, anorexia nervosa, bulimia nery osa, diabetes, hyperinsulincmia, glucose intolerance, atherosclerosis, inflammation |
| USP9Y/SP3 | 8287 | Y chromosome infertility |
| UTRN | 7402 | muscular dystrophies, Duchenne muscular dystrophy (DMD), Becker Muscular Dystrophy (BMD), and myotonic dystrophy |
| VEGFA | 7422 | diabetes, coronary artery disease, congestive heart failure, and peripheral vascular disease, cancer, infectious diseases, rheumatoid arthritis, DiGeorge syndrome, HHT, cavernous hemangioma, atherosclerosis, transplant ateriopathy, obesity, psoriasis, warts, allergic dermatitis, scar keloids, pyogenic granulomas, blistering disease, Kaposi sarcoma, persistent hyperplastic vitreous syndrome, Autosomal dominant polycystic kidney disease (ADPKD), diabetic retinopathy, retinopathy of prematurity, macular degeneration, choroidal neovascularization, primary pulmonary hypertension, asthma, nasal polyps, inflammatory bowel disease, Alzheimer's disease, Parkinson's disease, amyotrophic lateral sclerosis, periodontal disease, ascites, peritoneal adhesions, endometriosis, uterine bleeding, ovarian cysts, ovarian hyperstimulation, arthritis, synovitis, osteomyelitis, and/or osteophyte formation, ulceration, verruca vulgaris, angiofibroma of tuberous sclerosis, pot-wine stains, Sturge Weber syndrome, Kippel-Trenaunay-Weber syndrome, Osler-Weber-Rendu syndrome |

TABLE 2

Genes with mutations or SNPs that create uORFs and associated diseases

| Gene | NCBI Gene ID | Associated disease(s) |
|---|---|---|
| ATP7B | 540 | wilson disease, and menkes disease. |
| ATRX | 546 | alpha-thalassemia myelodysplasia syndrome, somatic, and mental retardation-hypotonic facies syndrome, x-linked. |
| BLM | 641 | bloom syndrome, and rothmund-thomson syndrome. |
| BRCA1 | 672 | primary peritoneal carcinoma, and hereditary site-specific ovarian cancer syndrome. |
| CA2 | 760 | autoimmune retinopathy, and multifocal fibrosclerosis. |
| CCBE1 | 147372 | hennekam syndrome, and immune hydrops fetalis. |
| CD3D | 915 | severe combined immune deficiency, autosomal recessive, t cell-negative, b cell-positive, nk cell-positive, cd3d-related, and immunodeficiency 19. |
| CD4 | 920 | okt4 epitope deficiency, and lymphatic system disease. |
| CDKN2A | 1029 | Melanoma predisposition, Melanoma |

TABLE 2-continued

Genes with mutations or SNPs that create uORFs and associated diseases

| Gene | NCBI Gene ID | Associated disease(s) |
|---|---|---|
| CFL2 | 1073 | cfl2-related nemaline myopathy, and nemaline myopathy 7, autosomal recessive. |
| CFTR | 1080 | Cystic fibrosis, Disseminated bronchiectasis |
| CSPP1 | 79848 | joubert syndrome 21, and joubert syndrome with jeune asphyxiating thoracic dystrophy. |
| CTNS | 1497 | intermediate cystinosis, and cystinosis, atypical nephropathic |
| DBT | 1629 | maple syrup urine disease type 2, and maple syrup urine disease type 1a |
| DCAF17 | 80067 | sakati syndrome, and hypogonadism, alopecia, diabetes mellitus, mental retardation, and extrapyramidal syndrome |
| DCLRE1C | 64421 | severe combined immunodeficiency, athabascan type, and artemis deficiency. |
| DFNB31 | 25861 | deafness, autosomal recessive 31, and dfnb31 nonsyndromic hearing loss and deafness. |
| DLG4 | 1742 | schizophrenia. |
| DMD | 1756 | duchenne muscular dystrophy, and becker muscular dystrophy. |
| DNASE1 | 1773 | cystic fibrosis, acute bronchitis |
| ETHE1 | 23474 | ethylmalonic encephalopathy |
| GALNS | 2588 | mucopolysaccharidosis iv, and kniest dysplasia |
| GCH1 | 2643 | Levodopa responsive dystonia |
| HAMP | 57817 | Juvenile hemochromatosis, thalassemia |
| HBB | 3043 | Beta-Thalassemia |
| HMBS | 3145 | histrionic personality disorder, and acute porphyria. |
| HR | 55806 | atrichia with papular lesions, and hypotrichosis 4 |
| IGHMBP2 | 3508 | progressive multifocal leukoencephalopathy, and spinal muscular atrophy with respiratory distress 1 |
| IRF6 | 3664 | Van der Woude syndrome |
| ITGA7 | 3679 | muscular dystrophy, congenital, due to itga7 deficiency, and congenital muscular dystrophy due to integrin alpha-7 deficiency |
| ITGB2 | 3689 | leukocyte adhesion deficiency type 1, and leukocyte adhesion deficiency. |
| KCNJ11 | 3767 | Congenital hyperinsulinism, hyperinsulinemic hypoglycemia, 2 |
| KCNQ3 | 3786 | kcnq3-related benign familial neonatal epilepsy, and seizures, benign neonatal, type 2 |
| LDLR | 3949 | Cardiovascular disease, Familial hypercholesterolemia |
| LRP5, LRP5L | 4041, 91355 | exudative vitreoretinopathy 4, and hyperostosis, endosteal |
| MECP2 | 4204 | autism susceptibility, x-linked 3, and bruxism. |
| MLH1 | 4292 | mlh1-related lynch syndrome, and solitary rectal ulcer syndrome. |
| MSH6 | 2956 | msh6-related lynch syndrome, colorectal cancer, hereditary nonpolyposis, type 5 |
| MUTYH | 4595 | adenomas, multiple colorectal, stomach cancer. |
| NR5A1 | 2516 | nr5a1-related 46,xy dsd and 46,xy cgd, and adrenocortical insufficiency, without ovarian defect |
| PALB2 | 79728 | fanconi anemia, complementation group n, and pancreatic cancer susceptibility 3. |
| PANK2 | 80025 | classic pantothenate kinase-associated neurodegeneration, and harp syndrome. |
| PEX7 | 5191 | peroxisome biogenesis disorder 9b, and rhizomelic chondrodysplasia punctata. |
| PHYH | 5264 | phyh-related refsum disease, and refsum disease. |
| PIK3R5 | 23533 | ataxia-oculomotor apraxia 3, and spinocerebellar ataxia autosomal recessive 1 |
| POMC | 5443 | Proopiomelanocortin deficiency |
| POMT1 | 10585 | pomt1-related muscle diseases, and walker-warburg syndrome. |
| ROR2 | 4920 | brachydactyly, type b1, and brachydactyly type b |
| SCN2A | 6326 | epileptic encephalopathy, early infantile, 11, and benign familial neonatal-infantile seizures |
| SGCA | 6442 | sarcoglycanopathies, and limb-girdle muscular dystrophy, type 2d. |
| SGCD | 6444 | limb-girdle muscular dystrophy type 2f, and delta-sarcoglycanopathy. |
| SLC16A1 | 6566 | erythrocyte lactate transporter defect, and exercise-induced hyperinsulinemic hypoglycemia. |
| SLC19A3 | 80704 | basal ganglia disease, and biotin-responsive basal ganglia disease. |
| SLC2A2 | 6514 | fanconi bickel syndrome, fanconi syndrome |
| SLC7A9 | 11136 | stinuria, and aminoaciduria. |
| SPINK1 | 6690 | Hereditary pancreatitis |
| SRY | 6736 | Gonadal dysgenesis |
| STIL | 6491 | primary autosomal recessive microcephaly type 7, and ideomotor apraxia. |
| TK2 | 7084 | mitochondrial dna depletion syndrome, myopathic form, and tk2-related mitochondrial dna depletion syndrome, myopathic form. |
| TMPRSS3 | 64699 | deafness, autosomal recessive 8/10, and dfnb 8/10 nonsyndromic hearing loss and deafness. |
| TP53 | 7157 | hepatocellular carcinoma, and osteosarcoma |
| TPI1 | 7167 | hemolytic anemia due to triosephosphate isomerase deficiency, and triose phosphate-isomerase deficiency. |

TABLE 2-continued

Genes with mutations or SNPs that create uORFs and associated diseases

| Gene | NCBI Gene ID | Associated disease(s) |
|---|---|---|
| TPM3 | 7170 | nemaline myopathy, and nemaline myopathy 1 |
| TRMU | 55687 | liver failure acute infantile, and melas, mt-th-related. |
| TSEN54 | 283989 | tsen54-related pontocerebellar hypoplasia, and pontocerebellar hypoplasia type 4. |
| ZEB1 | 6935 | corneal dystrophy, posterior polymorphous, 3, and corneal dystrophy, fuchs endothelial, 6. |

In certain embodiments, a uORF inhibitor (e.g. an antisense compound), inhibits ribosomal recognition or uORF activity of a uORF start site on the CDKN2A transcript and thereby increases expression of CDKN2A. In certain embodiments, a uORF inhibitor (e.g. an antisense compound), inhibits ribosomal recognition or uORF activity of a uORF start site on the CFTR transcript and thereby increases expression of CFTR. In certain embodiments, a uORF inhibitor (e.g. an antisense compound), inhibits ribosomal recognition or uORF activity of a uORF start site on the FXII transcript and thereby increases expression of FXII. In certain embodiments, a uORF inhibitor (e.g. an antisense compound), inhibits ribosomal recognition or uORF activity of a uORF start site on the GCH1 transcript and thereby increases expression of GCH1. In certain embodiments, a uORF inhibitor (e.g. an antisense compound), inhibits ribosomal recognition or uORF activity of a uORF start site on the HAMP transcript and thereby increases expression of HAMP.

In certain embodiments, a uORF inhibitor (e.g. an antisense compound), inhibits ribosomal recognition or uORF activity of a uORF start site on the HBB transcript and thereby increases expression of HBB. In certain embodiments, a uORF inhibitor (e.g. an antisense compound), inhibits ribosomal recognition or uORF activity of a uORF start site on the IRF6 transcript and thereby increases expression of IRF6. In certain embodiments, a uORF inhibitor (e.g. an antisense compound), inhibits ribosomal recognition or uORF activity of a uORF start site on the KCNJ11 transcript and thereby increases expression of KCNJ11. In certain embodiments, a uORF inhibitor (e.g. an antisense compound), inhibits ribosomal recognition or uORF activity of a uORF start site on the LDLR transcript and thereby increases expression of LDLR. In certain embodiments, a uORF inhibitor (e.g. an antisense compound), inhibits ribosomal recognition or uORF activity of a uORF start site on the PEX7 transcript and thereby increases expression of PEX7.

In certain embodiments, a uORF inhibitor (e.g. an antisense compound), inhibits ribosomal recognition or uORF activity of a uORF start site on the POMC transcript and thereby increases expression of POMC. In certain embodiments, a uORF inhibitor (e.g. an antisense compound), inhibits ribosomal recognition or uORF activity of a uORF start site on the PRKAR1A transcript and thereby increases expression of PRKAR1A. In certain embodiments, a uORF inhibitor (e.g. an antisense compound), inhibits ribosomal recognition or uORF activity of a uORF start site on the SPINK1 transcript and thereby increases expression of SPINK1. In certain embodiments, a uORF inhibitor (e.g. an antisense compound), inhibits ribosomal recognition or uORF activity of a uORF start site on the SRY transcript and thereby increases expression of SRY.

In certain embodiments, a TSE inhibitor (e.g. an antisense compound) may be used to upregulate a expression of ATM, lipoprotein lipase (LPL), DMD, sphingomyelinase, Factor VIII, insulin, growth hormone, thyroid stimulating hormone, follicle stimulating hormone, or hepcidin.

D. Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

E. Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

Therefore, in certain embodiments, delivery of a compound or composition described herein can affect the pharmacokinetic profile of the compound or composition. In certain embodiments, injection of a compound or composition described herein, to a targeted tissue improves the pharmacokinetic profile of the compound or composition as compared to infusion of the compound or composition. In a certain embodiment, the injection of a compound or composition improves potency compared to broad diffusion, requiring less of the compound or composition to achieve similar pharmacology. In certain embodiments, similar pharmacology refers to the amount of time that a target mRNA and/or target protein is down-regulated (e.g. duration of action). In certain embodiments, methods of specifically localizing a pharmaceutical agent, such as by bolus injection, decreases median effective concentration (EC50) by a factor of about 50 (e.g. 50 fold less concentration in tissue is required to achieve the same or similar pharmacodynamic effect). In certain embodiments, methods of specifically localizing a pharmaceutical agent, such as by bolus injection, decreases median effective concentration (EC50) by a factor of 20, 25, 30, 35, 40, 45 or 50. In certain embodiments the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

In certain embodiments, an antisense compound is delivered by injection or infusion once every month, every two months, every 90 days, every 3 months, every 6 months, twice a year or once a year.

F. Certain Combination Therapies

In certain embodiments, one or more pharmaceutical compositions are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, one or more pharmaceutical compositions and one or more other pharmaceutical agents are administered at the same time. In certain embodiments, one or more pharmaceutical compositions and one or more other pharmaceutical agents are administered at different times. In certain embodiments, one or more pharmaceutical compositions and one or more other pharmaceutical agents are prepared together in a single formulation. In certain embodiments, one or more pharmaceutical compositions and one or more other pharmaceutical agents are prepared separately.

In certain embodiments, pharmaceutical agents that may be co-administered with a pharmaceutical composition of include antipsychotic agents, such as, e.g., haloperidol, chlorpromazine, clozapine, quetapine, and olanzapine; antidepressant agents, such as, e.g., fluoxetine, sertraline hydrochloride, venlafaxine and nortriptyline; tranquilizing agents such as, e.g., benzodiazepines, clonazepam, paroxetine, venlafaxin, and beta-blockers; mood-stabilizing agents such as, e.g., lithium, valproate, lamotrigine, and carbamazepine; paralytic agents such as, e.g., Botulinum toxin; and/or other experimental agents including, but not limited to, tetrabenazine (Xenazine), creatine, conezyme Q10, trehalose, docosahexanoic acids, ACR16, ethyl-EPA, atomoxetine, citalopram, dimebon, memantine, sodium phenylbutyrate, ramelteon, ursodiol, zyprexa, xenasine, tiapride, riluzole, amantadine, [123I]MNI-420, atomoxetine, tetrabenazine, digoxin, detromethorphan, warfarin, alprozam, ketoconazole, omeprazole, and minocycline.

In certain embodiments, the present invention may be used to increase expression of a protein, which sensitizes the cell to other treatment. For example, in certain embodiments, the invention may be used to increase expression of RNase H. Cells with increased RNase H may be more sensitive to subsequent treatment with RNase H-dependent antisense compounds.

NONLIMITING DISCLOSURE AND INCORPORATION BY REFERENCE

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as the "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^m$CGAUCG," wherein $^m$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif And, for example, where a particular high-affinity modification appears at a particular position, other high-affinity modifications at the same position are considered suitable, unless otherwise indicated.

Example 1: Effects of Antisense Oligonucleotides Targeting the uORF of RNase H1 on RNase H1 Protein Expression Human RNase H1 mRNA (GENBANK accession number NM_001286834.1, designated herein as SEQ ID NO: 1) comprises an upstream open reading frame (uORF). Antisense oligonucleotides designed to target the start codon of the uORF of human RNase H1 were tested for their effects on RNase H1 expression in vitro. These antisense oligonucleotides, described in Table 3, were uniformly modified in order to avoid inducing cleavage of the target RNA. The start and stop sites listed in Table 3 indicate the positions on SEQ ID NO: 1 that the antisense oligonucleotides target. The targeted uORF begins at position 86. HeLa cells were transfected with Lipofectamine RNAiMAX (Life Technologies) and one of the antisense oligonucleotides at a final concentration of 25 nM or were mock transfected as a control. Thirty hours after transfection, the cells were lysed, and expression of RNase H1 was analyzed by western blot and RT-PCR. The primary antibody used for the western blot was made as described in Wu et al. *Determination of the Role of the Human RNase H1 in the Pharmacology of DNA-like Antisense Drugs. J. Biol. Chem.* 279, 17181 (2004), and the secondary antibody was purchased from Biorad (catalog #170-6515). The western blot was quantified using Image J, and the results are shown in Table 3 as percent protein levels relative to mock transfected cells following normalization to the Annexin A2 loading control. The RT-PCR results are shown in Table 3 as percent mRNA levels relative to mock transfected cells following normalization to Ribogreen. The results show that antisense oligonucleotides targeting a portion of the RNase H1 uORF that includes the uORF start codon increased RNase H1 expression. Furthermore, certain antisense oligonucleotides did not significantly affect RNase H1 mRNA levels, indicating that the increased RNase H1 expression exhibited by those oligonucleotides occurred mainly via increased translation.

TABLE 4

RNase H1 expression
RNase H1 (% 0 h) following transfection with 25 nM 761909

| 4 h | 8 h | 12 h | 15 h |
|---|---|---|---|
| 143 | 145 | 214 | 176 |

Example 3: Dose Response Effect of an Antisense Oligonucleotide Targeting the uORF of RNase H1 on RNase H1 Protein Expression In Vitro Isis No. 761909 (see Table 3) was tested at five different doses for its effect on RNase H1 expression in vitro. HeLa cells were transfected with 761909 at a concentration listed in Table 5 or were not treated as a control. Fifteen hours after transfection, RNase H1 expression was analyzed as described in Example 1. The results are shown in Table 5 as the percent protein levels relative to untreated control cells following normalization to the Annexin A2 loading control and as mRNA levels relative to untreated control cells following normalization to Ribogreen. The results show that

TABLE 3

RNase H1 expression

| Isis No. | Sequence | Start Site | Stop Site | RNase H1 protein (% mock) | RNase H1 mRNA (% mock) | SEQ ID NO. |
|---|---|---|---|---|---|---|
| 761909 | $C_{mo}A_{mo}U_{mo}U_{mo}U_{mo}C_{mo}G_{mo}A_{mo}C_{mo}U_{mo}C_{mo}C_{mo}C_{mo}G_{mo}G_{mo}C_m$ | 73 | 88 | 166 | 106 | 3 |
| 761910 | $A_{mo}G_{mo}C_{mo}A_{mo}U_{mo}U_{mo}U_{mo}C_{mo}G_{mo}A_{mo}C_{mo}U_{mo}C_{mo}C_{mo}C_{mo}G_m$ | 75 | 90 | 146 | 113 | 4 |
| 761911 | $G_{mo}A_{mo}A_{mo}G_{mo}C_{mo}A_{mo}U_{mo}U_{mo}U_{mo}C_{mo}G_{mo}A_{mo}C_{mo}U_{mo}C_{mo}C_m$ | 77 | 92 | 139 | 114 | 5 |
| 761912 | $G_{mo}G_{mo}G_{mo}A_{mo}A_{mo}G_{mo}C_{mo}A_{mo}U_{mo}U_{mo}U_{mo}C_{mo}G_{mo}A_{mo}C_{mo}U_m$ | 79 | 94 | 106 | 109 | 6 |
| 761913 | $C_{mo}C_{mo}G_{mo}G_{mo}G_{mo}A_{mo}A_{mo}G_{mo}C_{mo}A_{mo}U_{mo}U_{mo}U_{mo}C_{mo}G_{mo}A_m$ | 81 | 96 | 104 | 113 | 7 |

Subscripts:
"m" indicates a 2'-O-methyl modification, and
"o" indicates a phosphodiester internucleoside linkage.

Example 2: Time Course of RNase H1 Protein Expression Following Treatment with an Antisense Oligonucleotide Targeting the uORF In Vitro HeLa cells were transfected with 25 nM Isis No. 761909 (see Table 3). At various time points following transfection, the cells were harvested and RNase H1 expression was analyzed by western blot as described in Example 1. The results are shown in Table 4 as the percent RNase H1 protein expression relative to cells that did not receive antisense oligonucleotide treatment (harvested at the 0 hour time point) following normalization to the Annexin A2 loading control. The results show that the induction of RNase H1 expression was observed within 4 hours following transfection, and maximal expression was observed at approximately 12 hours following transfection.

an antisense oligonucleotide targeting a portion of the RNase H1 uORF increased RNase H1 protein levels in a dose dependent manner; and mRNA levels did not increase, indicating that the antisense oligonucleotide increased RNase H1 expression via increased translation.

TABLE 5

RNase H1 expression following transfection with 761909

| 761909 concentration (nM) | Protein (% untreated cells) | mRNA (% untreated cells) |
|---|---|---|
| 10 | 108 | 100 |
| 15 | 93 | 100 |
| 20 | 183 | 96 |
| 25 | 169 | 92 |
| 30 | 182 | 96 |

Example 4: Effects of Antisense Oligonucleotides Targeting the 5'-Untranslated Region Upstream of the RNase H1 uORF on RNase H1 Protein Expression Antisense oligonucleotides designed to target the 5'-untranslated region upstream of the uORF of human RNase H1 were tested for their effects on RNase H1 protein expression in vitro. These antisense oligonucleotides, described in Table 6, were uniformly modified in order to avoid inducing cleavage of the target RNA. The start and stop sites listed in Table 6 indicate the positions on SEQ ID NO: 1 that the antisense oligonucleotides target. Isis 761909 was included for reference. HeLa cells were transfected with 20 nM antisense oligonucleotide or were mock transfected as a control. Fifteen hours after transfection, RNase H1 expression was analyzed as described in Example 1. The results are shown in Table 6 below as percent protein expression relative to mock transfected cells following normalization to the γ-tubulin loading control and percent mRNA levels relative to mock transfected cells following normalization to Ribogreen. The results show that antisense oligonucleotides do not necessarily need to target the start codon of an uORF in order to induce increased translation of the target. Antisense oligonucleotides that target the 5'-untranslated region upstream of an uORF and antisense oligonucleotides that target at least a portion of the uORF itself can induce translation of the target. Furthermore, the antisense oligonucleotides targeting the 5'-untranslated region upstream of the uORF did not increase mRNA levels, indicating that they increased RNase H1 expression via increased translation.

TABLE 6

RNase H1 expression

| Isis No. | Sequence | Start Site | Stop Site | Protein (% mock) | mRNA (% mock) | SEQ ID NO. |
|---|---|---|---|---|---|---|
| 761918 | $U_{mo}C_{mo}A_{mo}C_{mo}C_{mo}G_{mo}G_{mo}C_{mo}G_{mo}C_{mo}G_{mo}G_{mo}G_{mo}A_{mo}A_{mo}G_{m}$ | 14 | 29 | 155 | 96 | 8 |
| 761919 | $C_{mo}U_{mo}C_{mo}A_{mo}A_{mo}C_{mo}A_{mo}C_{mo}C_{mo}G_{mo}C_{mo}A_{mo}C_{mo}U_{mo}U_{mo}C_{m}$ | 32 | 47 | 214 | 100 | 9 |
| 761917 | $A_{mo}C_{mo}U_{mo}C_{mo}C_{mo}C_{mo}G_{mo}G_{mo}C_{mo}C_{mo}C_{mo}A_{mo}G_{mo}C_{mo}G_{mo}U_{m}$ | 66 | 81 | 116 | 98 | 10 |
| 761916 | $C_{mo}G_{mo}A_{mo}C_{mo}U_{mo}C_{mo}C_{mo}C_{mo}G_{mo}G_{mo}C_{mo}C_{mo}C_{mo}A_{mo}G_{mo}C_{m}$ | 68 | 83 | 142 | 96 | 11 |
| 761915 | $U_{mo}U_{mo}C_{mo}G_{mo}A_{mo}C_{mo}U_{mo}C_{mo}C_{mo}C_{mo}G_{mo}G_{mo}C_{mo}C_{mo}C_{mo}A_{m}$ | 70 | 85 | 218 | 96 | 12 |
| 761909 | $C_{mo}A_{mo}U_{mo}U_{mo}U_{mo}C_{mo}G_{mo}A_{mo}C_{mo}U_{mo}C_{mo}C_{mo}C_{mo}G_{mo}C_{m}$ | 73 | 88 | 151 | 94 | 3 |

Subscripts:
"m" indicates a 2'-O-methyl modification, and
"o" indicates a phosphodiester internucleoside linkage.

Example 5: Effects of Antisense Oligonucleotides of Varying Lengths on RNase H1 Protein Expression Antisense oligonucleotides of varying lengths designed to target at least a portion of the uORF of human RNase H1 were tested for their effects on RNase H1 expression in vitro. These antisense oligonucleotides, described in Table 7, were uniformly modified in order to avoid inducing cleavage of the target RNA. The start and stop sites listed in Table 7 indicate the positions on SEQ ID NO: 1 that the antisense oligonucleotides target. HeLa cells were transfected with 20 nM antisense oligonucleotide or were mock transfected as a control. Fifteen hours after transfection, RNase H1 expression was analyzed as described in Example 1. The results are shown in Table 7 below as the percent protein expression relative to mock transfected cells following normalization to the γ-tubulin loading control and percent mRNA levels relative to mock transfected cells following normalization to Ribogreen. The results show that antisense oligonucleotides of various lengths increased RNase H1 expression mainly via increased translation of the target.

TABLE 7

RNase H1 expression following transfection with 5'-UTR targeting antisense oligonucleotides

| Isis No. | Sequence | Start Site | Stop Site | Length | Protein (% mock) | mRNA (% mock) | SEQ ID NO. |
|---|---|---|---|---|---|---|---|
| 761928 | $C_{mo}A_{mo}U_{mo}U_{mo}U_{mo}C_{mo}G_{mo}A_{mo}C_{mo}U_{mo}C_{mo}C_{m}$ | 77 | 88 | 12 | 143 | 104 | 13 |
| 761927 | $C_{mo}A_{mo}U_{mo}U_{mo}U_{mo}C_{mo}G_{mo}A_{mo}C_{mo}U_{mo}C_{mo}C_{mo}C_{mo}G_{m}$ | 75 | 88 | 14 | 142 | 101 | 14 |
| 761909 | $C_{mo}A_{mo}U_{mo}U_{mo}U_{mo}C_{mo}G_{mo}A_{mo}C_{mo}U_{mo}C_{mo}C_{mo}C_{mo}G_{mo}G_{mo}C_{m}$ | 73 | 88 | 16 | 244 | 94 | 3 |
| 761926 | $C_{mo}A_{mo}U_{mo}U_{mo}U_{mo}C_{mo}G_{mo}A_{mo}C_{mo}U_{mo}C_{mo}C_{mo}C_{mo}G_{mo}G_{mo}C_{mo}C_{mo}C_{m}$ | 71 | 88 | 18 | 187 | 110 | 15 |
| 761925 | $C_{mo}A_{mo}U_{mo}U_{mo}U_{mo}C_{mo}G_{mo}A_{mo}C_{mo}U_{mo}C_{mo}C_{mo}C_{mo}G_{mo}G_{mo}C_{mo}C_{mo}C_{mo}A_{mo}G_{m}$ | 69 | 88 | 20 | 126 | 100 | 16 |

Subscripts:
"m" indicates a 2'-O-methyl modification, and
"o" indicates a phosphodiester internucleoside linkage.

Example 6: Effects of Antisense Oligonucleotides Targeting the uORF of Mouse LRPPRC on LRPPRC Protein Expression Mouse Leucine-Rich PPR-Motif Containing (LRPPRC) mRNA (GENBANK accession number NM_028233.2, designated herein as SEQ ID NO: 2) comprises an upstream open reading frame. Antisense oligonucleotides with various lengths and internucleoside linkages designed to target the start codon of the uORF of mouse LRPPRC were tested for their effects on LRPPRC protein expression in vitro. These antisense oligonucleotides, described in Table 8, were uniformly modified in order to avoid inducing cleavage of the target RNA. The start and stop sites listed in Table 8 indicate the positions on SEQ ID NO: 2 that the antisense oligonucleotides target. The targeted uORF begins at position 70. MHT cells were transfected with Lipofectamine RNAiMAX (Life Technologies) and an antisense oligonucleotide at a concentration listed in Table 8 or were untreated as a control. Fifteen hours after transfection, the cells were lysed, and a western blot was performed with an LRPPRC antibody purchased from Abcam (catalog # ab97505) to analyze expression of LRPPRC. The western blot was quantified using Image J, and the results are shown in Table 8 below as the percent expression relative to untreated control cells following normalization to the loading control (Annexin A2 for 761932 and 761933, and hnRNP K for 759704 and 761930). The results show that antisense oligonucleotides of various lengths targeting the start codon of the uORF of mouse LRPPRC increased LRPPRC expression, including oligonucleotides comprising phosphodiester internucleoside linkages and an oligonucleotide comprising phosphorothioate internucleoside linkages. Thus, the results in Table 8 along with the results in the Examples above show that various antisense oligonucleotides targeting at least a portion of an uORF can increase expression of multiple targets in multiple species.

TABLE 8

LRPPRC expression

| Isis No. | Sequence | Start Site | Stop Site | Concentration (nM) | LRPPRC (% UTC) | SEQ ID NO. |
|---|---|---|---|---|---|---|
| 761932 | $C_{mo}A_{mo}U_{mo}U_{mo}G_{mo}U_{mo}U_{mo}U_{mo}U_{mo}U_{mo}U_{mo}$ $G_{mo}U_{mo}C_{mo}U_{mo}U_{mo}C_{mo}C_{m}$ | 55 | 72 | 10 | 127 | 17 |
| | | | | 20 | 184 | |
| | | | | 30 | 214 | |
| | | | | 40 | 173 | |
| | | | | 50 | 178 | |
| | | | | 60 | 228 | |
| 761933 | $C_{ms}A_{ms}U_{ms}U_{ms}G_{ms}U_{ms}U_{ms}U_{ms}U_{ms}U_{ms}U_{ms}$ $G_{ms}U_{ms}C_{ms}U_{ms}U_{ms}C_{ms}C_{m}$ | 55 | 72 | 10 | 123 | 17 |
| | | | | 20 | 141 | |
| | | | | 30 | 126 | |
| | | | | 40 | 131 | |
| | | | | 50 | 105 | |
| 759704 | $C_{mo}A_{mo}U_{mo}U_{mo}G_{mo}U_{mo}U_{mo}U_{mo}U_{mo}$ $U_{mo}U_{mo}G_{mo}U_{mo}C_{mo}U_{mo}U_{m}$ | 57 | 72 | 10 | 187 | 18 |
| | | | | 20 | 182 | |
| | | | | 30 | 189 | |
| | | | | 40 | 170 | |
| | | | | 50 | 243 | |
| | | | | 60 | 203 | |
| 761930 | $C_{mo}A_{mo}U_{mo}U_{mo}G_{mo}U_{mo}U_{mo}U_{mo}U_{mo}$ $U_{mo}U_{mo}G_{mo}U_{mo}C_{mo}U_{mo}U_{mo}C_{mo}C_{mo}$ $G_{mo}U_{m}$ | 53 | 72 | 10 | 164 | 19 |
| | | | | 20 | 149 | |
| | | | | 30 | 218 | |
| | | | | 40 | 142 | |
| | | | | 50 | 219 | |
| | | | | 60 | 255 | |

Subscripts:
"m" indicates a 2'-O-methyl modification,
"o" indicates a phosphodiester internucleoside linkage, and
"s" indicates a phosphorothioate internucleoside linkage.

Example 7: Effect of Antisense Oligonucleotide Targeting the uORF of Human SFXN3 on SFXN3 Protein Expression Human Sideroflexin 3 (SFXN3) mRNA (GENBANK accession number NM_030971.3, designated herein as SEQ ID NO: 20) comprises an upstream open reading frame. An antisense oligonucleotide designed to target the start codon of the uORF of human SFXN3 was tested for its effect on SFXN3 protein expression in vitro. The antisense oligonucleotide, described in Table 9, was uniformly modified in order to avoid inducing cleavage of the target RNA. The start and stop sites listed in Table 9 indicate the positions on SEQ ID NO: 20 that the antisense oligonucleotide targets. The targeted uORF begins at position 388. HeLa cells were transfected with Lipofectamine RNAiMAX (Life Technologies) and an antisense oligonucleotide at a concentration listed in Table 9 or were untreated as a control. Ten hours after transfection, the cells were lysed, and SFXN3 mRNA and protein expression were analyzed by RT-PCR and western blot, respectively. The western blot was performed with an SFXN3 antibody purchased from Abcam (catalog # ab181163) and quantified using Image J. The results are shown in Table 9 below as the percent protein expression relative to untreated control cells ("UTC") following normalization to the loading control (Ku70, detected with Abcam antibody, catalog # ab3114). SFXN3 mRNA levels normalized to Ribogreen are also shown. The results show that an antisense oligonucleotide targeting the start codon of the uORF of human SFXN3 increased SFXN3 protein expression. SFXN3 mRNA levels did not increase, indicating that the antisense oligonucleotide increased SFXN3 expression via increased translation.

TABLE 9

SFXN3 expression

| Isis No. | Sequence | Start Site | Stop Site | Concentration (nM) | Protein (% UTC) | mRNA (% UTC) | SEQ ID NO. |
|---|---|---|---|---|---|---|---|
| 759677 | $C_{mo}A_{mo}U_{mo}C_{mo}A_{mo}C_{mo}G_{mo}$ $C_{mo}G_{mo}G_{mo}G_{mo}$ $A_{mo}C_{mo}G_{mo}U_{mo}C_{m}$ | 375 | 390 | 10 | 100 | 106 | 21 |
| | | | | 20 | 120 | 102 | |
| | | | | 30 | 124 | 97 | |
| | | | | 40 | 126 | 94 | |
| | | | | 60 | 134 | 109 | |
| | | | | 80 | 133 | 103 | |
| | | | | 100 | 125 | 107 | |

Subscripts:
"m" indicates a 2'-O-methyl modification,
"o" indicates a phosphodiester internucleoside linkage.

Example 8: Effect of Antisense Oligonucleotide Targeting the uORF of Mouse MRPL11 on MRPL11 Protein Expression Mouse Mitochondrial Ribosomal protein L11 (MRPL11) mRNA (GENBANK accession number NM_025553.4, designated herein as SEQ ID NO: 22) comprises an upstream open reading frame. An antisense oligonucleotide designed to target the start codon of the uORF of mouse MRPL11 was tested for its effect on MRPL11 protein expression in vitro. The antisense oligonucleotide, described in Table 10, was uniformly modified in order to avoid inducing cleavage of the target RNA. The start and stop sites listed in Table 10 indicate the positions on SEQ ID NO: 22 that the antisense oligonucleotide targets. The targeted uORF begins at position 24. bEND cells were transfected with Lipofectamine RNAiMAX (Life Technologies) and an antisense oligonucleotide at a concentration listed in Table 10 or were untreated as a control. Ten hours after transfection, the cells were lysed, and MRPL11 mRNA and protein expression were analyzed by RT-PCR and western blot, respectively. The western blot was performed with an MRPL11 antibody purchased from Abcam (catalog # ab2066s) and quantified using Image J. The results are shown in Table 10 below as the percent protein expression relative to untreated control cells ("UTC") following normalization to the loading control (GAPDH, detected with Santa Cruz Biotechnology antibody, catalog # sc-32233). MRPL11 mRNA levels normalized to Ribogreen are also shown. The results show that an antisense oligonucleotide targeting the start codon of the uORF of mouse MRPL11 increased MRPL11 protein expression. MRPL11 mRNA levels did not increase, indicating that the antisense oligonucleotide increased MRPL11 expression via increased translation.

Example 9: Effects of Antisense Oligonucleotides Targeting the uORF of Human THPO on THPO Protein Expression Human Thrombopoietin (THPO) mRNA (GENBANK accession number NM_000460.3, designated herein as SEQ ID NO: 24) comprises seven upstream open reading frames. An antisense oligonucleotide designed to target the start codon of the last uORF of human THPO was tested for its effect on THPO protein expression in vitro. The antisense oligonucleotide, described in Table 11, was uniformly modified in order to avoid inducing cleavage of the target RNA. The start and stop sites listed in Table 11 indicate the positions on SEQ ID NO: 24 that the antisense oligonucleotide targets. The targeted uORF begins at position 210. Hep3B cells were transfected with Lipofectamine RNAiMAX (Life Technologies) and an antisense oligonucleotide at a concentration listed in Table 11 or cells were untreated as a control. Ten hours after transfection, medium was changed to serum-free medium and cells were incubated for an additional 12 hr. Proteins from the medium were precipitated using trichloroacetic acid, and THPO protein expression was analyzed by western blot using a THPO antibody purchased from Abcam (catalog # ab196026) and quantified using Image J. The results are shown in Table 11 below as the percent protein expression relative to untreated control cells ("UTC") following normalization to the loading control (Transferrin). The results show that an antisense oligonucleotide targeting the start codon of the uORF of human THPO increased THPO protein expression.

TABLE 10

MRPL11 expression

| Isis No. | Sequence | Start Site | Stop Site | Concentration (nM) | Protein (% UTC) | mRNA (% UTC) | SEQ ID NO. |
|---|---|---|---|---|---|---|---|
| 773534 | $C_{mo}A_{mo}U_{mo}U_{mo}U_{mo}U_{mo}G_{mo}$ $G_{mo}G_{mo}U_{mo}C_{mo}$ $A_{mo}G_{mo}A_{mo}G_{mo}G_{mo}U_{mo}G_{m}$ | 9 | 26 | 5 | 95 | 93 | 23 |
|  |  |  |  | 10 | 146 | 95 |  |
|  |  |  |  | 20 | 137 | 96 |  |
|  |  |  |  | 40 | 134 | 109 |  |
|  |  |  |  | 80 | 125 | 104 |  |

Subscripts:
"m" indicates a 2'-O-methyl modification,
"o" indicates a phosphodiester internucleoside linkage.

TABLE 11

THPO expression

| Isis No. | Sequence | Start Site | Stop Site | Concentration (nM) | Protein (% UTC) | SEQ ID NO. |
|---|---|---|---|---|---|---|
| 806734 | $C_{mo}A_{mo}U_{mo}G_{mo}G_{mo}A_{mo}G_{mo}$ $G_{mo}C_{mo}G_{mo}G_{mo}$ | 195 | 212 | 5 | 155 | 25 |
|  |  |  |  | 10 | 176 |  |

TABLE 11-continued

THPO expression

| Isis No. | Sequence | Start Site | Stop Site | Concentration (nM) | Protein (% UTC) | SEQ ID NO. |
|---|---|---|---|---|---|---|
| | $C_{mo}U_{mo}U_{mo}A_{mo}G_{mo}G_{mo}C_m$ | | | 20 | 167 | |
| | | | | 40 | 172 | |
| | | | | 60 | 130 | |

Subscripts:
"m" indicates a 2'-O-methyl modification,
"o" indicates a phosphodiester internucleoside linkage.

Example 10: Effects of Mismatched Antisense Oligonucleotides Targeting the uORF of RNase H1 on RNase H1 Protein Expression Antisense oligonucleotides designed to target the start codon of the uORF of human RNase H1 with two mismatches between the antisense oligonucleotide and the target sequence were tested for their effects on RNase H1 expression in vitro. These antisense oligonucleotides, described in Table 12, were uniformly modified in order to avoid inducing cleavage of the target RNA. The start and stop sites listed in Table 12 indicate the positions on SEQ ID NO: 1 that the antisense oligonucleotides target, and the mismatched nucleotides are bolded. The targeted uORF begins at position 86. HeLa cells were transfected with Lipofectamine RNAiMAX (Life Technologies) and an antisense oligonucleotide at a final concentration of 25 nM or were mock transfected as a control. Twenty-four hours after transfection, the cells were lysed, and expression of RNase H1 was analyzed by western blot as described in Example 1. The results are shown in Table 12 as percent protein levels relative to mock transfected cells following normalization to the Ku70 loading control. The results show that antisense oligonucleotides with mismatches to the uORF start codon or near to the uORF start codon had little to no effect on RNase H1 protein expression, whereas antisense oligonucleotides with mismatches further away from the uORF start codon increased RNase H1 protein expression.

TABLE 12

RNase H1 expression

| Isis No. | Sequence | Start Site | Stop Site | RNase H1 protein (% mock) | SEQ ID NO. |
|---|---|---|---|---|---|
| 773519 | $G_{mo}U_{mo}U_{mo}U_{mo}U_{mo}C_{mo}G_{mo}A_{mo}C_{mo}U_{mo}C_{mo}C_{mo}C_{mo}G_{mo}G_{mo}C_m$ | 73 | 88 | 96 | 26 |
| 773520 | $C_{mo}A_{mo}A_{mo}A_{mo}U_{mo}C_{mo}G_{mo}A_{mo}C_{mo}U_{mo}C_{mo}C_{mo}C_{mo}G_{mo}G_{mo}C_m$ | 73 | 88 | 82 | 27 |
| 773521 | $C_{mo}A_{mo}U_{mo}U_{mo}A_{mo}G_{mo}G_{mo}A_{mo}C_{mo}U_{mo}C_{mo}C_{mo}C_{mo}G_{mo}G_{mo}C_m$ | 73 | 88 | 103 | 28 |
| 773522 | $C_{mo}A_{mo}U_{mo}U_{mo}U_{mo}C_{mo}C_{mo}U_{mo}C_{mo}U_{mo}C_{mo}C_{mo}C_{mo}G_{mo}G_{mo}C_m$ | 73 | 88 | 89 | 29 |
| 773523 | $C_{mo}A_{mo}U_{mo}U_{mo}U_{mo}C_{mo}G_{mo}A_{mo}G_{mo}A_{mo}C_{mo}C_{mo}C_{mo}G_{mo}G_{mo}C_m$ | 73 | 88 | 121 | 30 |
| 773524 | $C_{mo}A_{mo}U_{mo}U_{mo}U_{mo}C_{mo}G_{mo}A_{mo}C_{mo}U_{mo}G_{mo}G_{mo}C_{mo}G_{mo}G_{mo}C_m$ | 73 | 88 | 158 | 31 |
| 773525 | $C_{mo}A_{mo}U_{mo}U_{mo}U_{mo}C_{mo}G_{mo}A_{mo}C_{mo}U_{mo}C_{mo}C_{mo}G_{mo}C_{mo}G_{mo}C_m$ | 73 | 88 | 150 | 32 |
| 773526 | $C_{mo}A_{mo}U_{mo}U_{mo}U_{mo}C_{mo}G_{mo}A_{mo}C_{mo}U_{mo}C_{mo}C_{mo}C_{mo}G_{mo}C_{mo}G_m$ | 73 | 88 | 153 | 33 |

Subscripts:
"m" indicates a 2'-O-methyl modification, and
"o" indicates a phosphodiester internucleoside linkage.

Example 11: Effects of Antisense Oligonucleotides Comprising Various Modifications Antisense oligonucleotides targeting the start codon of the uORF in human RNase H1 (SEQ ID NO: 1) or mouse LRPPRC (SEQ ID NO: 2) were designed with various lengths and with various modifications to the internucleoside linkages and to the sugars. These antisense oligonucleotides were tested for their effects on target protein expression in vitro. HEK293 cells (RNase H1 targeting oligonucleotides) or MHT cells (LRPPRC targeting oligonucleotides) were transfected with Lipofectamine RNAiMAX (Life Technologies) and an antisense oligonucleotide at a concentration listed in the tables below. Ten hours after transfection, the cells were lysed, and target protein expression was analyzed by western blot as described in Example 1 (for RNase H1) or Example 6 (for LRPPRC). The results are shown in the tables below as the percent protein expression relative to untreated control cells ("UTC") following normalization to the loading control (Ku70, γ-tubulin, Annexin A2, or a non-specific band detected by the primary antibody). The results show that antisense oligonucleotides of various lengths and with modified internucleoside linkages and various 2'-modifications and bicyclic nucleosides increased target protein expression.

TABLE 13

RNase H1 expression

| Isis No. | Sequence | Start Site | Stop Site | Length | Concentration (nM) | Protein (% mock) | SEQ ID NO. |
|---|---|---|---|---|---|---|---|
| 783683 | $C_{ms}A_{ms}U_{ms}U_{ms}U_{ms}C_{ms}G_{ms}A_{ms}C_{ms}U_{ms}C_{ms}C_m$ | 77 | 88 | 12 | 20 | 191 | 34 |
| 783681 | $C_{ms}A_{ms}U_{ms}U_{ms}U_{ms}C_{ms}G_{ms}A_{ms}C_{ms}U_{ms}C_{ms}C_{ms}C_{ms}G_m$ | 75 | 88 | 14 | 20 | 178 | 35 |
| 783682 | $C_{ms}A_{ms}U_{ms}U_{ms}U_{ms}C_{ms}G_{ms}A_{ms}C_{ms}U_{ms}C_{ms}C_{ms}C_{ms}G_{ms}G_{ms}C_m$ | 73 | 88 | 16 | 20 | 186 | 3 |
| 783679 | $C_{ms}A_{ms}U_{ms}U_{ms}U_{ms}C_{ms}G_{ms}A_{ms}C_{ms}U_{ms}C_{ms}C_{ms}C_{ms}G_{ms}G_{ms}C_{ms}C_{ms}C_m$ | 71 | 88 | 18 | 20 | 149 | 15 |
| 783680 | $C_{ms}A_{ms}U_{ms}U_{ms}U_{ms}C_{ms}G_{ms}A_{ms}C_{ms}U_{ms}C_{ms}C_{ms}C_{ms}G_{ms}G_{ms}C_{ms}C_{ms}C_{ms}A_{ms}G_m$ | 69 | 88 | 20 | 20 | 83 | 16 |

Subscripts:
"m" indicates a 2'-O-methyl modification, and
"s" indicates a phosphorothioate internucleoside linkage.

TABLE 14

RNase H1 expression

| Isis No. 783679 concentration (nM) | Protein (% UTC) |
|---|---|
| 5 | 140 |
| 10 | 179 |
| 20 | 186 |
| 40 | 174 |
| 60 | 195 |

TABLE 15

RNase H1 expression

| Isis No. | Sequence | Start Site | Stop Site | Length | Concentration (nM) | Protein (% mock) | SEQ ID NO. |
|---|---|---|---|---|---|---|---|
| 783674 | $^mC_{es}A_{es}T_{es}T_{es}T_{es}^mC_{es}G_{es}A_{es}^mC_{es}T_{es}^mC_{es}^mC_e$ | 77 | 88 | 12 | 20 | 70 | 36 |
| 783673 | $^mC_{es}A_{es}T_{es}T_{es}T_{es}^mC_{es}G_{es}A_{es}^mC_{es}T_{es}^mC_{es}^mC_{es}^mC_{es}G_e$ | 75 | 88 | 14 | 20 | 104 | 37 |
| 759304 | $^mC_{es}A_{es}T_{es}T_{es}T_{es}^mC_{es}G_{es}A_{es}^mC_{es}T_{es}^mC_{es}^mC_{es}^mC_{es}G_{es}G_{es}^mC_e$ | 73 | 88 | 16 | 20 | 136 | 38 |
| 773517 | $^mC_{es}A_{es}T_{es}T_{es}T_{es}^mC_{es}G_{es}A_{es}^mC_{es}T_{es}^mC_{es}^mC_{es}^mC_{es}G_{es}G_{es}^mC_{es}^mC_{es}^mC_e$ | 71 | 88 | 18 | 20 | 178 | 39 |
| 773516 | $^mC_{es}A_{es}T_{es}T_{es}T_{es}^mC_{es}G_{es}A_{es}^mC_{es}T_{es}^mC_{es}^mC_{es}^mC_{es}G_{es}G_{es}^mC_{es}^mC_{es}^mC_{es}A_{es}G_e$ | 69 | 88 | 20 | 20 | 122 | 40 |

Subscripts:
"e" indicates a 2'-O-methoxyethyl modification, and
"s" indicates a phosphorothioate internucleoside linkage.
Superscript "m" in front of a "C" indicates a 5'-methylcytosine.

TABLE 16

RNase H1 expression

| Isis No. 759304 concentration (nM) | Protein (% UTC) |
|---|---|
| 5 | 137 |
| 10 | 211 |
| 20 | 218 |

TABLE 16-continued

RNase H1 expression

| Isis No. 759304 concentration (nM) | Protein (% UTC) |
|---|---|
| 40 | 208 |
| 60 | 193 |

TABLE 17

RNase H1 expression

| Isis No. | Sequence | Start Site | Stop Site | Length | Concentration (nM) | Protein (% mock) | SEQ ID NO. |
|---|---|---|---|---|---|---|---|
| 783678 | $^mC_{eo}A_{eo}T_{eo}T_{eo}T_{eo}{^m}C_{eo}G_{eo}A_{eo}{^m}C_{eo}T_{eo}{^m}C_{eo}$ $^mC_e$ | 77 | 88 | 12 | 5 | 187 | 36 |
| 783677 | $^mC_{eo}A_{eo}T_{eo}T_{eo}T_{eo}{^m}C_{eo}G_{eo}A_{eo}{^m}C_{eo}T_{eo}{^m}C_{eo}$ $^mC_{eo}{^m}C_{eo}G_e$ | 75 | 88 | 14 | 5 | 144 | 37 |
| 759388 | $^mC_{eo}A_{eo}T_{eo}T_{eo}T_{eo}{^m}C_{eo}G_{eo}A_{eo}{^m}C_{eo}T_{eo}{^m}C_{eo}$ $^mC_{eo}{^m}C_{eo}G_{eo}G_{eo}{^m}C_e$ | 73 | 88 | 16 | 5 | 148 | 38 |
| 783676 | $^mC_{eo}A_{eo}T_{eo}T_{eo}T_{eo}{^m}C_{eo}G_{eo}A_{eo}{^m}C_{eo}T_{eo}{^m}C_{eo}$ $^mC_{eo}{^m}C_{eo}G_{eo}G_{eo}{^m}C_{eo}{^m}C_{eo}{^m}C_e$ | 71 | 88 | 18 | 5 | 101 | 39 |
| 783675 | $^mC_{eo}A_{eo}T_{eo}T_{eo}T_{eo}{^m}C_{eo}G_{eo}A_{eo}{^m}C_{eo}T_{eo}{^m}C_{eo}$ $^mC_{eo}{^m}C_{eo}G_{eo}G_{eo}{^m}C_{eo}{^m}C_{eo}{^m}C_{eo}A_{eo}G_e$ | 69 | 88 | 20 | 5 | 84 | 40 |

Subscripts:
"e" indicates a 2'-O-methoxyethyl modification, and
"s" indicates a phosphorothioate internucleoside linkage.
Superscript "m" in front of a "C" indicates a 5'-methylcytosine.

TABLE 18

RNase H1 expression

| Isis No. | Sequence | Start Site | Stop Site | Concentration (nM) | Protein (% UTC) | SEQ ID NO. |
|---|---|---|---|---|---|---|
| 766733 | $C_{fo}A_{fo}U_{fo}U_{fo}U_{fo}C_{fo}G_{fo}A_{fo}C_{fo}$ $U_{fo}C_{fo}C_{fo}C_{fo}G_{fo}G_{fo}C_f$ | 73 | 88 | 5 | 115 | 3 |
|  |  |  |  | 10 | 126 |  |
|  |  |  |  | 20 | 137 |  |
|  |  |  |  | 40 | 134 |  |
|  |  |  |  | 60 | 127 |  |

Subscripts:
"f" indicates a 2'-fluoro modification,
"o" indicates a phosphodiester internucleoside linkage.

TABLE 19

RNase H1 expression

| Isis No. | Sequence | Start Site | Stop Site | Concentration (nM) | Protein (% UTC) | SEQ ID NO. |
|---|---|---|---|---|---|---|
| 768080 | $^mC_{es}A_{es}T_{es}T_{es}T_{es}{^m}C_{es}G_{es}A_{es}$ $^mC_{es}T_{es}{^m}C_{es}{^m}C_{es}{^m}C_{es}C_{fs}G_{fs}G_{fs}C_f$ | 73 | 88 | 5 | 150 | 38 |
|  |  |  |  | 10 | 125 |  |
|  |  |  |  | 20 | 100 |  |
|  |  |  |  | 40 | 81 |  |
|  |  |  |  | 60 | 78 |  |

Subscripts:
"e" indicates a 2'-O-methoxyethyl modification,
"f" indicates a 2'-fluoro modification,
"s" indicates a phosphorothioate internucleoside linkage.
Superscript "m" in front of a "C" indicates a 5'-methylcytosine.

TABLE 20

RNase H1 expression

| Isis No. | Sequence | Start Site | Stop Site | Concentration (nM) | Protein (% UTC) | SEQ ID NO. |
|---|---|---|---|---|---|---|
| 766741 | $^mC_{es}A_{es}T_{es}T_{es}T_{es}{^m}C_{es}G_{es}A_{es}$ $^mC_{es}T_{es}{^m}C_{es}{^m}C_{es}{^m}C_{es}$ $G_{ks}G_{ks}{^m}C_k$ | 73 | 88 | 5 | 126 | 38 |
|  |  |  |  | 10 | 151 |  |
|  |  |  |  | 20 | 122 |  |

TABLE 20-continued

RNase H1 expression

| Isis No. | Sequence | Start Site | Stop Site | Concentration (nM) | Protein (% UTC) | SEQ ID NO. |
|---|---|---|---|---|---|---|
| | | | | 40 | 121 | |
| | | | | 80 | 62 | |

Subscripts:
"e" indicates a 2'-O-methoxyethyl modification,
"k" indicates a cEt bicyclic nucleoside,
"s" indicates a phosphorothioate internucleoside linkage.
Superscript "m" in front of a "C" indicates a 5'-methylcytosine.

TABLE 21

RNase H1 expression

| Isis No. | Sequence | Start Site | Stop Site | Concentration (nM) | Protein (% mock) | SEQ ID NO. |
|---|---|---|---|---|---|---|
| 806735 | $C_{ms}A_{ms}U_{ms}U_{ms}U_{ms}C_{ms}G_{ms}A_{ms}C_{ms}U_{ms}C_{ms}C_{ms}C_{ms}G_{ms}G_{ks}{}^{m}C_{k}$ | 73 | 88 | 20 | 152 | 3 |
| 806736 | $C_{ms}A_{ms}U_{ms}U_{ms}U_{ms}C_{ms}G_{ms}A_{ms}C_{ms}U_{ms}C_{ms}C_{ms}C_{ms}G_{ks}G_{ks}{}^{m}C_{k}$ | 73 | 88 | 20 | 165 | 3 |
| 806737 | $C_{ms}A_{ms}U_{ms}U_{ms}U_{ms}C_{ms}G_{ms}A_{ms}C_{ms}U_{ms}C_{ms}C_{ms}{}^{m}C_{ks}G_{ks}G_{ks}{}^{m}C_{k}$ | 73 | 88 | 20 | 183 | 3 |
| 806738 | $C_{ms}A_{ms}U_{ms}U_{ms}U_{ms}C_{ms}G_{ms}A_{ms}C_{ms}U_{ms}C_{ms}{}^{m}C_{ks}{}^{m}C_{ks}G_{ks}G_{ks}{}^{m}C_{k}$ | 73 | 88 | 20 | 145 | 3 |

Subscripts:
"m" indicates a 2'-O-methyl modification,
"k" indicates a cEt bicyclic nucleoside, and
"s" indicates a phosphorothioate internucleoside linkage.
Superscript "m" in front of a "C" indicates a 5'-methylcytosine.

TABLE 22

LRPPRC expression

| Isis No. | Sequence | Start Site | Stop Site | Concentration (nM) | Protein (% mock) | SEQ ID NO. |
|---|---|---|---|---|---|---|
| 806739 | $C_{ms}A_{ms}U_{ms}U_{ms}G_{ms}U_{ms}U_{ms}U_{ms}U_{ms}U_{ms}U_{ms}G_{ms}U_{ms}C_{ms}U_{ms}U_{ms}{}^{m}C_{ks}{}^{m}C_{k}$ | 55 | 72 | 20 | 149 | 17 |
| 806740 | $C_{ms}A_{ms}U_{ms}U_{ms}G_{ms}U_{ms}U_{ms}U_{ms}U_{ms}U_{ms}U_{ms}G_{ms}U_{ms}C_{ms}U_{ms}T_{ks}{}^{m}C_{ks}{}^{m}C_{k}$ | 55 | 72 | 20 | 191 | 41 |
| 806741 | $C_{ms}A_{ms}U_{ms}U_{ms}G_{ms}U_{ms}U_{ms}U_{ms}U_{ms}U_{ms}U_{ms}G_{ms}U_{ms}C_{ms}T_{ks}T_{ks}{}^{m}C_{ks}{}^{m}C_{k}$ | 55 | 72 | 20 | 212 | 42 |
| 806742 | $C_{ms}A_{ms}U_{ms}U_{ms}G_{ms}U_{ms}U_{ms}U_{ms}U_{ms}U_{ms}U_{ms}G_{ms}U_{ms}{}^{m}C_{ks}T_{ks}T_{ks}{}^{m}C_{ks}{}^{m}C_{k}$ | 55 | 72 | 20 | 213 | 42 |

Subscripts:
"m" indicates a 2'-O-methyl modification,
"k" indicates a cEt bicyclic nucleoside, and
"s" indicates a phosphorothioate internucleoside linkage.
Superscript "m" in front of a "C" indicates a 5'-methylcytosine.

Example 12: Effects of Antisense Oligonucleotides Targeting the uORF of Mouse LRPPRC In Vivo Isis No. 761933 (see Example 6) was tested for its effect on LRPPRC protein expression in vivo. Groups of three or four male, seven week old BALB/c mice were systemically administered Isis No. 761933, at a dose listed in the tables below, or saline by subcutaneous injection. Animals were sacrificed (Table 23) or received a second dose (Table 24) 48 hours later Animals that received a second dose were sacrificed 48 hours after the second dose. Liver homogenates were prepared, and LRPPRC protein expression was analyzed by western blot, as described in Example 6. The results are shown in the tables below as the percent expression relative to saline treated animals following normalization to the loading control (GAPDH or hnRNP K). The results show that LRPPRC protein expression was increased in vivo following treatment with an antisense oligonucleotide targeting the LRPPRC uORF.

TABLE 23

LRPPRC expression following single dose in vivo

| Isis No. 761933 dose (mg/kg) | Protein (% UTC) |
|---|---|
| 75 | 137 |

TABLE 24

LRPPRC expression following two doses in vivo

| Isis No. 761933 dose (mg/kg) | Protein (% UTC) |
|---|---|
| 3.125 | 109 |
| 6.25 | 124 |
| 12.5 | 136 |

TABLE 24-continued

LRPPRC expression following two doses in vivo

| Isis No. 761933 dose (mg/kg) | Protein (% UTC) |
|---|---|
| 25 | 183 |
| 50 | 169 |
| 100 | 109 |
| 200 | 98 |

Example 13: Effects of Antisense Oligonucleotides Targeting the uORF of Mouse THPO In Vivo Mouse Thrombopoietin (THPO) mRNA (GENBANK accession number NM_009379.2, designated herein as SEQ ID NO: 43) comprises an upstream open reading frame. Isis No. 809793 (see the table below) was designed to target the start codon of the uORF of mouse THPO and tested for its effect on THPO protein expression in vivo. The start and stop sites listed in Table 25 indicate the positions on SEQ ID NO: 43 that the antisense oligonucleotide targets. Groups of three mice were systemically administered Isis No. 809793, at a dose listed in the table below, or saline by subcutaneous injection. The animals were sacrificed 48 hours later, and serum and bone marrow was collected. Serum THPO protein expression was analyzed by western blot, as described in Example 9, and bone marrow THPO mRNA expression was analyzed by RT-PCR. Bone marrow THPO mRNA levels were unaffected by the antisense oligonucleotide treatment (data not shown). The results shown in the table below are the average of two independent experiments and are shown as the percent expression relative to saline treated animals following normalization to the loading control (Transferrin). The results show that THPO protein expression was increased in vivo following treatment with an antisense oligonucleotide targeting the THPO uORF.

TABLE 25

Mouse THPO expression

| Isis No. | Sequence | Start Site | Stop Site | Dose (mg/kg) | THPO protein (% mock) | SEQ ID NO. |
|---|---|---|---|---|---|---|
| 809793 | $C_{ms}A_{ms}U_{ms}G_{ms}G_{ms}A_{ms}G_{ms}G_{ms}C_{ms}G_{ms}G_{ms}C_{ms}U_{ms}U_{ms}G_{ms}A_{ms}G_{m}$ | 309 | 325 | 12.5 | 146 | 44 |
| | | | | 25 | 457 | |
| | | | | 50 | 240 | |
| | | | | 75 | 244 | |

Subscripts:

"m" indicates a 2'-O-methyl modification, and

"s" indicates a phosphorothioate internucleoside linkage.

Example 14: Inhibition of a uORF Targeting Oligonucleotide with a Complementary Oligonucleotide In order to test whether increased translation that is mediated by an oligonucleotide targeting a uORF could be reversed, the effect of an oligonucleotide complementary to the uORF targeting oligonucleotide was tested in vitro. HeLa cells were transfected with 20 nM of Isis No. 761909, as described in Example 1. Five hours later, the cells were transfected with a concentration of Isis No. 761929, which is complementary to Isis No. 761909, listed in the table below. Five hours after the second transfection, cells were lysed and RNase H1 protein expression was analyzed as described in Example 1, with γ-tubulin used as the loading control. The results are shown in the table below as the percent expression relative to mock transfected cells following normalization to the γ-tubulin loading control. The results show that an oligonucleotide targeted to a uORF targeting oligonucleotide blocked the uORF targeting oligonucleotide's ability to increase translation in a dose dependent manner LRPPRC was performed. MHT cells were transfected with Isis No. 761930 for 7 hours, and incubated with pre-warmed medium lacking methionine (Invitrogen, RPMI 1640) at 37° C. for 30 minutes. Cells were then pulse-labeled with 35 µCi/ml $S^{35}$-methionine in RPMI1640 medium for 20 minutes and chased with 1 mM methionine for 40 minutes. Cells were washed with cold PBS containing 10 µg/ml cycloheximide and cell lysate were prepared using IP buffer (Life Technologies). Immunoprecipitation was conducted using anti-LRPPRC antibody (Proteintech) at 4° C. for 3 hours. After 4 washes, the precipitated proteins were analyzed on a 4-12% SDS-PAGE gel, transferred to a membrane, and visualized by autoradiography. The LRPPRC band in the immunoprecipitate from the mock treated cells was significantly lighter than in the immunoprecipitate from the Isis No. 761930 treated cells (data not shown), further confirming that antisense oligonucleotides targeting a uORF increase protein expression via increasing target protein translation. Furthermore, the lysate inputs for both the mock and Isis No. 761930 transfected cells were also analyzed via autoradioagraphy and were very similar, indicating that the increased translation was target specific.

TABLE 26

RNase H1 expression

| Isis No. | Sequence | Concentration 761909 (nM) | Concentration 761929 (nM) | RNase H1 protein (% mock) | SEQ ID NO. |
|---|---|---|---|---|---|
| 761929 | $G_{mo}C_{mo}C_{mo}G_{mo}G_{mo}G_{mo}A_{mo}$ $G_{mo}U_{mo}C_{mo}G_{mo}A_{mo}A_{mo}A_{mo}$ $U_{mo}G_m$ | 20 | 0 | 185 | 45 |
| | | 20 | 10 | 161 | |
| | | 20 | 20 | 120 | |
| | | 20 | 30 | 103 | |
| | | 20 | 40 | 97 | |

Subscripts:
"m" indicates a 2'-O-methyl modification and
"o" indicates a phosphodiester internucleoside linkage.

Example 15: Inhibition of a uORF Targeting Oligonucleotide by Globally Blocking Translation In order to test whether increases in protein expression mediated by antisense oligonucleotides targeting a uORF are due to increased protein stability, translation was blocked following transfection of the oligonucleotide. HeLa cells were transfected with Isis No. 761909 (see Example 1) or mock transfected. Twelve hours later, cells were treated with DMSO or 15 µg/ml cycloheximide at 37° C. Cells were then collected at various time points and cell lysates were prepared and subjected to western analysis, as described in Example 1. A duplicate SDS-PAGE gel was silver-stained and served as loading control. RNase H1 protein levels were calculated relative to mock transfected cells following normalization to the loading control. The results (data not shown) showed that the rates of reduction of RNase H1 protein levels following cycloheximide treatment were similar for mock and Isis No. 761909 transfected cells. Thus, these results, along with the lack of increase in mRNA shown in several above examples, show that increases in protein expression mediated by antisense oligonucleotides targeting a uORF are due to increased protein translation.

Example 16: Effect of a uORF Targeting Antisense Oligonucleotide on Nascent Protein Translation In order to further confirm that antisense oligonucleotides targeting a uORF mediate an increase in translation of new protein, pulse-chase labeling and immunoprecipitation of

Example 17: Effect of an Antisense Oligonucleotide Targeting the uORF of RNase H1 on RNase H1 Activity In order to test whether the increase in RNase H1 protein levels mediated by antisense oligonucleotides targeting a RNase H1 uORF results in an increase in RNase H1 activity, cells were first transfected with Isis No. 761909 (see Example 1) or a control oligonucleotide that does not target RNase H1, Isis No. 759704, then transfected with an antisense oligonucleotide targeting U16 snoRNA or NCL1 mRNA. Ten hours after the first transfection, the cells were reseeded at approximately 50% confluency. Cells were transfected a second time 14 hours later with Isis No. 462026 (U16) or Isis No. 110074 (NCL1) for an additional 4 hours. Cells were then collected, lysed, and U16 snoRNA or NCL1 mRNA levels were analyzed by RT-qPCR using TaqMan primer probe sets. The primer probe set sequences used were: Forward: 5'-CTTGCAATGATGTCG-TAATTTGC-3', SEQ ID NO: 46, Reverse: 5'-TCGTCAAC-CTTCTGTACCAGCTT-3', SEQ ID NO: 47, and Probe: 5"-TTACTCTGTTCTCAGCGACAGTTGCCTGC-3', SEQ ID NO: 48 for U16; and Forward: 5'-GCTTGGCTTCT-TCTGGACTCA-3', SEQ ID NO: 49, Reverse: 5'-TCGC-GAGCTTCACCATGA-3', SEQ ID NO: 50, and Probe: 5'-CGCCACTTGTCCGCTTCACACTCC-3', SEQ ID NO: 51 for NCL1. The results are shown in the tables below as the percent RNA levels relative to untreated control cells that were not transfected with any oligonucleotide, normalized to total RNA as measured using Ribogreen. The results show that Isis No. 761909 targeting a RNase H1 uORF increased the antisense activity of U16 and NCl1 antisense oligonucleotides.

TABLE 27

U16 snoRNA expression

| 1st ASO | | | SEQ | 2nd ASO | | | SEQ |
|---|---|---|---|---|---|---|---|
| Isis No. | Sequence | Concentration (nM) | ID No. | Isis No. | Sequence | Concentration (nM) | mRNA (%) | ID No. |
| Control 759704 | $C_{mo}\ A_{mo}\ U_{mo}\ U_{mo}$ $G_{mo}\ U_{mo}\ U_{mo}\ U_{mo}$ $U_{mo}\ U_{mo}\ U_{mo}\ G_{mo}$ $U_{mo}\ C_{mo}\ U_{mo}\ U_{m}$ | 20 20 20 20 20 | 18 | 462026 | $^mC_{es}A_{es}G_{es}^{\,m}C_{es}A_{es}^{\,G}G_{ds}$ $G_{ds}^{\,m}C_{ds}A_{ds}A_{ds}^{\,m}C_{ds}$ $T_{ds}G_{ds}T_{ds}^{\,m}C_{ds}G_{es}^{\,m}C_{es}$ $T_{es}G_{es}A_{e}$ | 1.25 2.5 5 10 20 | 97 98 97 83 75 | 52 |
| uORF 761909 | $C_{mo}A_{mo}U_{mo}U_{mo}U_{mo}$ $C_{mo}G_{mo}A_{mo}C_{mo}$ $U_{mo}C_{mo}C_{mo}G_{mo}$ $G_{mo}C_{m}$ | 20 20 20 20 20 | 3 | 462026 | $^mC_{es}G_{es}^{\,m}C_{es}A_{es}G_{ds}$ $G_{ds}^{\,m}C_{ds}A_{ds}A_{ds}^{\,m}C_{ds}$ $T_{ds}G_{ds}T_{ds}^{\,m}C_{ds}G_{es}^{\,m}C_{es}$ $T_{es}G_{es}A_{e}$ | 1.25 2.5 5 10 20 | 90 76 70 61 49 | 52 |

Subscripts:
"e" indicates a 2'-O-methoxyethyl modification,
"d" indicates a 2'-deoxynucleoside, and
"s" indicates a phosphorothioate internucleoside linkage.
Superscript "m" in front of a "C" indicates a 5'-methylcytosine.

TABLE 28

NCL1 mRNA expression

| 1st ASO | | | SEQ | 2nd ASO | | | SEQ |
|---|---|---|---|---|---|---|---|
| Isis No. | Sequence | Concentration (nM) | ID No. | Isis No. | Sequence | Concentration (nM) | mRNA (%) | ID No. |
| Control 759704 | $C_{mo}\ A_{mo}\ U_{mo}\ U_{mo}$ $G_{mo}\ U_{mo}\ U_{mo}\ U_{mo}$ $U_{mo}\ U_{mo}\ U_{mo}\ G_{mo}$ $U_{mo}\ C_{mo}\ U_{mo}\ U_{m}$ | 20 20 20 20 20 | 18 | 110074 | $G_{es}T_{es}^{\,m}C_{es}A_{es}T_{es}^{\,m}C_{ds}$ $G_{ds}T_{ds}^{\,m}C_{ds}A_{ds}T_{ds}$ $^mC_{ds}^{\,m}C_{ds}T_{ds}^{\,m}C_{ds}A_{es}$ $T_{es}^{\,m}C_{es}A_{es}T_{e}$ | 1.25 2.5 5 10 20 | 96 95 96 79 45 | 53 |
| uORF 761909 | $C_{mo}A_{mo}U_{mo}U_{mo}U_{mo}$ $C_{mo}G_{mo}A_{mo}C_{mo}$ $U_{mo}C_{mo}C_{mo}C_{mo}G_{mo}$ $G_{mo}C_{m}$ | 20 20 20 20 20 | 3 | 110074 | $G_{es}T_{es}^{\,m}C_{es}A_{es}T_{es}^{\,m}C_{ds}$ $G_{ds}T_{ds}^{\,m}C_{ds}A_{ds}T_{ds}$ $^mC_{ds}^{\,m}C_{ds}T_{ds}^{\,m}C_{ds}A_{es}$ $T_{es}^{\,m}C_{es}A_{es}T_{e}$ | 1.25 2.5 5 10 20 | 93 91 87 62 32 | 53 |

Subscripts:
"e" indicates a 2'-O-methoxyethyl modification,
"d" indicates a 2'-deoxynucleoside, and
"s" indicates a phosphorothioate internucleoside linkage.
Superscript "m" in front of a "C" indicates a 5'-methylcytosine.

Example 18: Effects of Antisense Oligonucleotides Targeting the 5'-Untranslated Region of RNase H1

Antisense oligonucleotides designed to target the 5'-untranslated region upstream of the uORF of human RNase H1 were tested for their effects on RNase H1 protein expression in vitro. The start and stop sites listed in the tables below indicate the positions on SEQ ID NO: 1 that the antisense oligonucleotides target. HEK 293 cells were transfected with 20 nM antisense oligonucleotide or were mock transfected as a control. Ten hours after transfection, RNase H1 protein expression was analyzed as described in Example 1. The results are shown in the tables below as percent protein expression relative to mock transfected cells following normalization to the GAPDH loading control. The results show that many antisense oligonucleotides targeting the 5'-untranslated region upstream of the RNase H1 uORF induced translation of the target.

TABLE 29

RNase H1 expression

| Isis No. | Sequence | Start Site | Stop Site | Protein (% mock) | SEQ ID NO. |
|---|---|---|---|---|---|
| 761772 | $A_{mo}\ A_{mo}\ G_{mo}\ A_{mo}\ U_{mo}\ G_{mo}\ A_{mo}\ C_{mo}\ G_{mo}$ $C_{mo}\ A_{mo}\ C_{mo}\ G_{mo}\ U_{mo}\ C_{mo}\ U_{m}$ | 1 | 16 | 142 | 54 |
| 761773 | $G_{mo}\ G_{mo}\ A_{mo}\ A_{mo}\ G_{mo}\ A_{mo}\ U_{mo}\ G_{mo}\ A_{mo}$ $C_{mo}\ G_{mo}\ C_{mo}\ A_{mo}\ C_{mo}\ G_{mo}\ U_{m}$ | 3 | 18 | 155 | 55 |

TABLE 29-continued

RNase H1 expression

| Isis No. | Sequence | Start Site | Stop Site | Protein (% mock) | SEQ ID NO. |
|---|---|---|---|---|---|
| 761774 | $C_{mo}$ $G_{mo}$ $G_{mo}$ $G_{mo}$ $A_{mo}$ $A_{mo}$ $G_{mo}$ $A_{mo}$ $U_{mo}$ $G_{mo}$ $A_{mo}$ $C_{mo}$ $G_{mo}$ $C_{mo}$ $A_{mo}$ $C_m$ | 5 | 20 | 179 | 56 |
| 761775 | $C_{mo}$ $G_{mo}$ $C_{mo}$ $G_{mo}$ $G_{mo}$ $G_{mo}$ $A_{mo}$ $A_{mo}$ $G_{mo}$ $A_{mo}$ $U_{mo}$ $G_{mo}$ $A_{mo}$ $C_{mo}$ $G_{mo}$ $C_m$ | 7 | 22 | 259 | 57 |

TABLE 30

RNase H1 expression

| Isis No. | Sequence | Start Site | Stop Site | Protein (% mock) | SEQ ID NO. |
|---|---|---|---|---|---|
| 761778 | $C_{mo}$ $A_{mo}$ $C_{mo}$ $C_{mo}$ $G_{mo}$ $G_{mo}$ $C_{mo}$ $G_{mo}$ $C_{mo}$ $G_{mo}$ $G_{mo}$ $G_{mo}$ $A_{mo}$ $A_{mo}$ $G_{mo}$ $A_m$ | 13 | 28 | 132 | 58 |
| 761779 | $G_{mo}$ $U_{mo}$ $C_{mo}$ $A_{mo}$ $C_{mo}$ $C_{mo}$ $G_{mo}$ $G_{mo}$ $C_{mo}$ $G_{mo}$ $C_{mo}$ $G_{mo}$ $G_{mo}$ $G_{mo}$ $A_{mo}$ $A_m$ | 15 | 30 | 164 | 59 |
| 761780 | $C_{mo}$ $C_{mo}$ $G_{mo}$ $U_{mo}$ $C_{mo}$ $A_{mo}$ $C_{mo}$ $C_{mo}$ $G_{mo}$ $G_{mo}$ $C_{mo}$ $G_{mo}$ $C_{mo}$ $G_{mo}$ $G_{mo}$ $G_m$ | 17 | 32 | 182 | 60 |
| 761781 | $U_{mo}$ $U_{mo}$ $C_{mo}$ $C_{mo}$ $G_{mo}$ $U_{mo}$ $C_{mo}$ $A_{mo}$ $C_{mo}$ $C_{mo}$ $G_{mo}$ $G_{mo}$ $C_{mo}$ $G_{mo}$ $C_{mo}$ $G_m$ | 19 | 34 | 226 | 61 |
| 761782 | $A_{mo}$ $C_{mo}$ $U_{mo}$ $U_{mo}$ $C_{mo}$ $C_{mo}$ $G_{mo}$ $U_{mo}$ $C_{mo}$ $A_{mo}$ $C_{mo}$ $C_{mo}$ $G_{mo}$ $G_{mo}$ $C_{mo}$ $G_m$ | 21 | 36 | 229 | 62 |
| 761783 | $G_{mo}$ $C_{mo}$ $A_{mo}$ $C_{mo}$ $U_{mo}$ $U_{mo}$ $C_{mo}$ $C_{mo}$ $G_{mo}$ $U_{mo}$ $C_{mo}$ $A_{mo}$ $C_{mo}$ $C_{mo}$ $G_{mo}$ $G_m$ | 23 | 38 | 259 | 63 |
| 761784 | $C_{mo}$ $C_{mo}$ $G_{mo}$ $C_{mo}$ $A_{mo}$ $C_{mo}$ $U_{mo}$ $U_{mo}$ $C_{mo}$ $C_{mo}$ $G_{mo}$ $U_{mo}$ $C_{mo}$ $A_{mo}$ $C_{mo}$ $C_m$ | 25 | 40 | 237 | 64 |

TABLE 31

RNase H1 expression

| Isis No. | Sequence | Start Site | Stop Site | Protein (% mock) | SEQ ID NO. |
|---|---|---|---|---|---|
| 761785 | $C_{mo}$ $A_{mo}$ $C_{mo}$ $C_{mo}$ $G_{mo}$ $C_{mo}$ $A_{mo}$ $C_{mo}$ $U_{mo}$ $U_{mo}$ $C_{mo}$ $C_{mo}$ $G_{mo}$ $U_{mo}$ $C_{mo}$ $A_m$ | 27 | 42 | 170 | 65 |
| 761786 | $A_{mo}$ $A_{mo}$ $C_{mo}$ $A_{mo}$ $C_{mo}$ $C_{mo}$ $G_{mo}$ $C_{mo}$ $A_{mo}$ $C_{mo}$ $U_{mo}$ $U_{mo}$ $C_{mo}$ $C_{mo}$ $G_{mo}$ $U_m$ | 29 | 44 | 186 | 66 |
| 761787 | $U_{mo}$ $C_{mo}$ $A_{mo}$ $A_{mo}$ $C_{mo}$ $A_{mo}$ $C_{mo}$ $C_{mo}$ $G_{mo}$ $C_{mo}$ $A_{mo}$ $C_{mo}$ $U_{mo}$ $U_{mo}$ $C_{mo}$ $C_m$ | 31 | 46 | 197 | 67 |
| 761788 | $G_{mo}$ $C_{mo}$ $U_{mo}$ $C_{mo}$ $A_{mo}$ $A_{mo}$ $C_{mo}$ $A_{mo}$ $C_{mo}$ $C_{mo}$ $G_{mo}$ $C_{mo}$ $A_{mo}$ $C_{mo}$ $U_{mo}$ $U_m$ | 33 | 48 | 210 | 68 |
| 761789 | $G_{mo}$ $C_{mo}$ $G_{mo}$ $C_{mo}$ $U_{mo}$ $C_{mo}$ $A_{mo}$ $A_{mo}$ $C_{mo}$ $A_{mo}$ $C_{mo}$ $C_{mo}$ $G_{mo}$ $C_{mo}$ $A_{mo}$ $C_m$ | 35 | 50 | 211 | 69 |
| 761790 | $C_{mo}$ $G_{mo}$ $G_{mo}$ $C_{mo}$ $G_{mo}$ $C_{mo}$ $U_{mo}$ $C_{mo}$ $A_{mo}$ $A_{mo}$ $C_{mo}$ $A_{mo}$ $C_{mo}$ $C_{mo}$ $G_{mo}$ $C_m$ | 37 | 52 | 202 | 70 |
| 761791 | $G_{mo}$ $C_{mo}$ $C_{mo}$ $G_{mo}$ $C_{mo}$ $G_{mo}$ $G_{mo}$ $C_{mo}$ $U_{mo}$ $C_{mo}$ $A_{mo}$ $A_{mo}$ $C_{mo}$ $A_{mo}$ $C_{mo}$ $C_m$ | 39 | 54 | 173 | 71 |
| 761792 | $C_{mo}$ $C_{mo}$ $G_{mo}$ $C_{mo}$ $C_{mo}$ $G_{mo}$ $C_{mo}$ $G_{mo}$ $G_{mo}$ $C_{mo}$ $U_{mo}$ $C_{mo}$ $A_{mo}$ $A_{mo}$ $C_{mo}$ $A_m$ | 41 | 56 | 120 | 72 |

TABLE 32

RNase H1 expression

| Isis No. | Sequence | Start Site | Stop Site | Protein (% mock) | SEQ ID NO. |
|---|---|---|---|---|---|
| 761776 | $G_{mo}$ $G_{mo}$ $C_{mo}$ $G_{mo}$ $C_{mo}$ $G_{mo}$ $G_{mo}$ $G_{mo}$ $A_{mo}$ $A_{mo}$ $G_{mo}$ $A_{mo}$ $U_{mo}$ $G_{mo}$ $A_{mo}$ $C_m$ | 9 | 24 | 130 | 73 |
| 761794 | $C_{mo}$ $G_{mo}$ $A_{mo}$ $G_{mo}$ $C_{mo}$ $C_{mo}$ $G_{mo}$ $C_{mo}$ $C_{mo}$ $G_{mo}$ $G_{mo}$ $C_{mo}$ $G_{mo}$ $C_{mo}$ $U_{mo}$ $C_m$ | 45 | 60 | 92 | 74 |
| 761796 | $G_{mo}$ $G_{mo}$ $C_{mo}$ $G_{mo}$ $C_{mo}$ $G_{mo}$ $A_{mo}$ $G_{mo}$ $C_{mo}$ $C_{mo}$ $G_{mo}$ $C_{mo}$ $C_{mo}$ $G_{mo}$ $G_{mo}$ $C_m$ | 49 | 64 | 94 | 75 |
| 761798 | $C_{mo}$ $G_{mo}$ $U_{mo}$ $G_{mo}$ $G_{mo}$ $G_{mo}$ $C_{mo}$ $G_{mo}$ $C_{mo}$ $G_{mo}$ $A_{mo}$ $G_{mo}$ $C_{mo}$ $C_{mo}$ $G_{mo}$ $C_m$ | 53 | 68 | 84 | 76 |
| 761800 | $C_{mo}$ $C_{mo}$ $A_{mo}$ $G_{mo}$ $C_{mo}$ $G_{mo}$ $U_{mo}$ $G_{mo}$ $G_{mo}$ $G_{mo}$ $C_{mo}$ $G_{mo}$ $C_{mo}$ $G_{mo}$ $A_{mo}$ $G_m$ | 57 | 72 | 71 | 77 |

Subscripts: "m" indicates a 2'-O-methyl modification, and "o" indicates a phosphodiester internucleoside linkage.

Example 19: Effects of Antisense Oligonucleotides Targeting the 5'-Untranslated Region of ACP1

Antisense oligonucleotides designed to target the 5'-untranslated region of cytoplasmic phosphotyrosine protein phosphatase (ACP1), which does not comprise a uORF, were tested for their effects on ACP1 protein expression in vitro. The antisense oligonucleotides target the human ACP1 mRNA (GENBANK accession number NM_004300.3, designated herein as SEQ ID NO: 78) and were designed to target at least one stem loop structure in the 5'-untranslated region. The start and stop sites listed in the table below indicate the positions on SEQ ID NO: 78 that the antisense oligonucleotides target. HEK 293 cells were transfected with a concentration of antisense oligonucleotide shown in the table below or were not transfected as a control. Ten hours after transfection, ACP1 protein expression was analyzed by western blot using an Abcam antibody to ACP1 (catalog # ab166896). The results are shown in the tables below as percent protein expression relative to untreated control cells following normalization to the p32 loading control. The results show that the antisense oligonucleotides targeting the 5'-untranslated region of human ACP1 induced translation of the target.

Example 20: Effects of Antisense Oligonucleotides Targeting the 5'-Untranslated Region Downstream of the CFTR uORF Start Codon on CFTR Protein Expression Antisense oligonucleotides designed to target the 5'-untranslated region downstream of the uORF start codon of human cystic fibrosis transmembrane conductance regulator (CFTR) were tested for their effects on CFTR protein expression in vitro. These antisense oligonucleotides, described in the table below, were designed to target the CFTR mRNA (GENBANK accession number NM_000492.3, designated herein as SEQ ID NO: 81) and were uniformly modified in order to avoid inducing cleavage of the target RNA. The start and stop sites listed in the table below indicate the positions on SEQ ID NO: 81 that the antisense oligonucleotides target. One uORF begins at position 13 of SEQ ID NO: 81. Isis No. 786455 targets a portion of the uORF that is just downstream of the uORF start codon. Isis No. 786456 targets a stem loop structure further downstream.

HT-29 cells were transfected with a concentration of antisense oligonucleotide listed in the table below or were mock transfected as a control. Twelve or twenty-two hours after transfection, CFTR expression was analyzed by western blot using Anti-CFTR purchased from EMD Millipore (catalog #05-583, clone M3A7). The results are shown in the

TABLE 33

ACP1 expression

| Isis No. | Sequence | Start Site | Stop Site | Concentration (nM) | Protein (% mock) | SEQ ID NO. |
|---|---|---|---|---|---|---|
| 812652 | $C_{mo}$ $G_{mo}$ $A_{mo}$ $C_{mo}$ $G_{mo}$ $C_{mo}$ $G_{mo}$ $G_{mo}$ $C_{mo}$ $G_{mo}$ $C_{mo}$ $A_{mo}$ $G_{mo}$ $G_{mo}$ $C_{mo}$ $G_m$ | 36 | 51 | 5<br>10<br>20<br>40<br>80 | 112<br>130<br>116<br>165<br>172 | 79 |
| 812658 | $G_{mo}$ $C_{mo}$ $G_{mo}$ $C_{mo}$ $A_{mo}$ $G_{mo}$ $G_{mo}$ $C_{mo}$ $G_{mo}$ $C_{mo}$ $A_{mo}$ $C_{mo}$ $U_{mo}$ $G_{mo}$ $C_{mo}$ $C_{mo}$ $A_{mo}$ $C_m$ | 27 | 44 | 5<br>10<br>20<br>40<br>80 | 121<br>161<br>164<br>119<br>129 | 80 |

Subscripts: "m" indicates a 2'-O-methyl modification and "o" indicates a phosphodiester internucleoside linkage.

table below as percent protein expression relative to mock transfected cells following normalization to the HSP90 loading control. The results show that the antisense oligonucleotides increased CFTR protein expression.

TABLE 34

CFTR expression

| Isis No. | Sequence | Start Site | Stop Site | Time point (h) | Concentration (nM) | Protein (% mock) | SEQ ID NO. |
|---|---|---|---|---|---|---|---|
| 786455 | $U_{ms} U_{ms} C_{ms} U_{ms} C_{ms} U_{ms} G_{ms} A_{ms}$ $C_{ms} C_{ms} U_{ms} G_{ms} C_{ms} U_{ms} G_{ms} U_{ms}$ $G_{ms} A_m$ | 19 | 36 | 12 | 12.5 | 142 | 82 |
|  |  |  |  |  | 25 | 151 |  |
|  |  |  |  |  | 50 | 150 |  |
|  |  |  |  |  | 100 | 86 |  |
|  |  |  |  | 22 | 12.5 | 59 |  |
|  |  |  |  |  | 25 | 93 |  |
|  |  |  |  |  | 50 | 146 |  |
|  |  |  |  |  | 100 | 192 |  |
| 786456 | $C_{ms} C_{ms} A_{ms} A_{ms} A_{ms} G_{ms} A_{ms} C_{ms}$ $C_{ms} U_{ms} A_{ms} C_{ms} U_{ms} A_{ms} C_{ms} U_{ms}$ $C_{ms} U_m$ | 60 | 77 | 22 | 12.5 | 105 | 83 |
|  |  |  |  |  | 25 | 140 |  |
|  |  |  |  |  | 50 | 186 |  |
|  |  |  |  |  | 75 | 186 |  |
|  |  |  |  |  | 100 | 390 |  |
|  |  |  |  |  | 150 | 181 |  |
|  |  |  |  |  | 200 | 262 |  |

Subscripts: "m" indicates a 2'-O-methyl modification, and "s" indicates a phosphorothioate internucleoside linkage.

Example 21: Identification of a Translation Suppression Element that does not Comprise a uORF In order to test the effect of portions of the RNase H1 5'-UTR sequence on RNase H1 expression, the wild type and mutant 5'-UTR sequences were cloned into a plasmid and fused to firefly luciferase. Renila luciferase was cloned into the same plasmids for normalization. The plasmids were transfected into HeLa cells and firefly and Renila luciferase activities were detected using standard methods. The mutants and their firefly luciferase activity relative to the wild type 5'-UTR reporters, normalized to Renila luciferase activity, are shown in the table below. The nucleotide positions reported in the table below refer to the positions of the 5'-UTR of SEQ ID NO: 1 that were mutated or deleted. The results are the averages of multiple experiments and show that the mutation and/or deletion of portions of the 5'-UTR sequence of RNase H1, including portions that do not comprise a uORF, resulted in increased expression in a reporter system, indicating that the mutated portions are part of a translation suppression element.

TABLE 35

Firefly luciferase activity

| Mutation | Deletion | Firefly luciferase activity (%) |
|---|---|---|
| AUG -> UUG (uORF start codon) | n/a | 770 |
| AUG -> UUG (uORF start codon) | Nucleotides 30-60 | 980 |
| GACGGAAGT-> CAGCCTTCA, nucleotides 28-36 | n/a | 1380 |
| CGGTG->GCCAC nucleotides 38-42 | n/a | 680 |
| CGGTG->GCCAC & CGCCG->GCGGC, nucleotides 38-42 & 48-52 | n/a | 600 |

Example 22: Effects of Antisense Oligonucleotides Targeting the uORF of Mouse LRPPRC In Vivo Isis No. 806740 (see Example 11) was tested for its effect on LRPPRC protein expression in vivo. Groups of three, male, seven week old BALB/c mice were systemically administered Isis No. 806740, at a dose listed in the table below, or saline by subcutaneous injection. 48 hours later, the mice received a second dose listed in the table below. Animals were sacrificed 48 hours after the second dose. Liver homogenates were prepared, and LRPPRC protein expression was analyzed by western blot, as described in Example 6. The results are shown in the tables below as the percent expression relative to saline treated animals following normalization to the loading control (PSF). The results show that LRPPRC protein expression was increased in vivo following treatment with an antisense oligonucleotide targeting the LRPPRC uORF and comprising bicyclic nucleic acids.

TABLE 36

LRPPRC expression in vivo

| Isis No. 806740 dose (mg/kg) | Protein (% UTC) |
|---|---|
| 12.5 | 126 |
| 25 | 171 |
| 50 | 113 |
| 100 | 120 |

Example 23: Effects of Antisense Oligonucleotides Targeting the 5'-Untranslated Region of ACP1

Effects of antisense oligonucleotides designed to target the 5'-untranslated region of ACP1, which does not comprise a uORF, are shown above (see Example 19). Additional antisense oligonucleotides designed to target the 5'-untranslation region of ACP1 were tested for their effects on ACP1 protein expression in vitro. The antisense oligonucleotides target the human ACP1 mRNA (GENBANK accession number NM_004300.3, designated herein as SEQ ID NO: 78). The start and stop sites listed in the table below indicate the positions on SEQ ID NO: 78 that the antisense oligonucleotides target. HeLa cells were transfected with 25 nM of an antisense oligonucleotide shown in the table below or were not transfected as a control. Ten hours after transfection, ACP1 protein expression was analyzed by western blot using an Abcam antibody to ACP1 (catalog # ab166896). The results are shown in the tables below as percent protein expression relative to untreated control cells following normalization to the Annexin A2 loading control.

TABLE 37

ACP1 expression

| Isis No. | Sequence | Start Site | Stop Site | Protein (% mock) | SEQ ID NO. |
|---|---|---|---|---|---|
| 812658 | $G_{mo} C_{mo} G_{mo} C_{mo} A_{mo} G_{mo} G_{mo} C_{mo} G_{mo} C_{mo} A_{mo} C_{mo} U_{mo} G_{mo} C_{mo} C_{mo} A_{mo} C_m$ | 27 | 44 | 127 | 80 |
| 812650 | $A_{mo} G_{mo} G_{mo} C_{mo} G_{mo} C_{mo} A_{mo} C_{mo} U_{mo} G_{mo} C_{mo} C_{mo} A_{mo} C_m$ | 27 | 40 | 142 | 84 |
| (XL500) | $G_{mo} C_{mo} A_{mo} G_{mo} G_{mo} C_{mo} G_{mo} C_{mo} A_{mo} C_{mo} U_{mo} G_{mo} C_{mo} C_m$ | 29 | 42 | 147 | 85 |
| 812651 | $G_{mo} C_{mo} G_{mo} C_{mo} A_{mo} G_{mo} G_{mo} C_{mo} G_{mo} C_{mo} A_{mo} C_{mo} U_{mo} G_m$ | 31 | 44 | 107 | 86 |
| (XL502) | $C_{mo} G_{mo} G_{mo} C_{mo} G_{mo} C_{mo} A_{mo} G_{mo} G_{mo} C_{mo} G_{mo} C_{mo} A_{mo} C_m$ | 33 | 46 | 100 | 87 |
| (XL503) | $C_{mo} G_{mo} C_{mo} G_{mo} G_{mo} C_{mo} G_{mo} C_{mo} A_{mo} G_{mo} G_{mo} C_{mo} G_{mo} C_m$ | 35 | 48 | 58 | 88 |
| (XL504) | $G_{mo} A_{mo} C_{mo} G_{mo} C_{mo} G_{mo} G_{mo} C_{mo} G_{mo} C_{mo} A_{mo} G_{mo} G_{mo} C_m$ | 37 | 50 | 107 | 89 |

Subscripts: "m" indicates a 2'-O-methyl modification, and "o" indicates a phosphodiester internucleoside linkage.

Example 24: Effects of Antisense Oligonucleotides Targeting ACP1 Comprising Various Modifications Antisense oligonucleotides designed to target the same or similar site of the 5'-untranslated region of ACP1 as Isis No. 812658 (see Examples 19 and 23) were designed with various modifications and tested for their effects on ACP1 protein expression in vitro. The start and stop sites listed in the table below indicate the positions on SEQ ID NO: 78 that the antisense oligonucleotides target. HeLa cells were transfected with a concentration of an antisense oligonucleotide shown in the tables below or were not transfected as a control. Ten hours after transfection, ACP1 protein expression was analyzed by western blot using an Abcam antibody to ACP1 (catalog # ab166896). The results are shown in the tables below as percent protein expression relative to untreated control cells following normalization to the Annexin A2 or TMED9 loading control.

TABLE 38

ACP1 expression

| Isis No. | Sequence | Start Site | Stop Site | Concentration (nM) | Protein (% mock) | SEQ ID NO. |
|---|---|---|---|---|---|---|
| 812675 | $G_{ms}$ $C_{ms}$ $A_{ms}$ $G_{ms}$ $G_{ms}$ $C_{ms}$ $G_{ms}$ $C_{ms}$ $A_{ms}$ $C_{ms}$ $U_{ms}$ $G_{ms}$ $C_{ms}$ $C_{ms}$ $A_{ms}$ $C_m$ | 27 | 42 | 5 | 161 | 90 |
|  |  |  |  | 10 | 147 |  |
|  |  |  |  | 20 | 227 |  |
|  |  |  |  | 40 | 193 |  |
|  |  |  |  | 80 | 98 |  |
| 812653 | $G_{mo}$ $C_{mo}$ $A_{mo}$ $G_{mo}$ $G_{mo}$ $C_{mo}$ $G_{mo}$ $C_{mo}$ $A_{mo}$ $C_{mo}$ $U_{mo}$ $G_{mo}$ $C_{mo}$ $C_{mo}$ $A_{mo}$ $C_m$ | 27 | 42 | 5 | 87 | 90 |
|  |  |  |  | 10 | 167 |  |
|  |  |  |  | 20 | 182 |  |
|  |  |  |  | 40 | 139 |  |
|  |  |  |  | 80 | 124 |  |

TABLE 39

ACP1 expression

| Isis No. | Sequence | Start Site | Stop Site | Concentration (nM) | Protein (% mock) | SEQ ID NO. |
|---|---|---|---|---|---|---|
| 813860 | $G_{ms}$ $C_{ms}$ $G_{ms}$ $C_{ms}$ $A_{ms}$ $G_{ms}$ $G_{ms}$ $C_{ms}$ $G_{ms}$ $C_{ms}$ $A_{ms}$ $C_{ms}$ $U_{ms}$ $G_{ms}$ $C_{ms}$ $^mC_{ks}$ $A_{ks}$ $^mC_k$ | 27 | 44 | 25 | 87 | 80 |
| 826061 | $G_{ms}$ $C_{ms}$ $G_{ms}$ $C_{ms}$ $A_{ms}$ $G_{ms}$ $G_{ms}$ $C_{ms}$ $G_{ms}$ $C_{ms}$ $A_{ms}$ $C_{ms}$ $U_{ms}$ $G_{ms}$ $C_{ms}$ $^mC_{ko}$ $A_{ks}$ $^mC_k$ | 27 | 44 | 25 | 109 | 80 |
| 826062 | $G_{ms}$ $C_{ms}$ $G_{ms}$ $C_{ms}$ $A_{ms}$ $G_{ms}$ $G_{ms}$ $C_{ms}$ $G_{ms}$ $C_{ms}$ $A_{ms}$ $C_{mo}$ $U_{ms}$ $G_{mo}$ $C_{ms}$ $^mC_{ko}$ $A_{ks}$ $^mC_k$ | 27 | 44 | 25 | 111 | 80 |
| 826063 | $G_{ms}$ $C_{mo}$ $G_{ms}$ $C_{mo}$ $A_{ms}$ $G_{ms}$ $G_{ms}$ $C_{ms}$ $G_{ms}$ $C_{ms}$ $A_{ms}$ $C_{ms}$ $U_{ms}$ $G_{ms}$ $C_{ms}$ $^mC_{ks}$ $A_{ks}$ $^mC_k$ | 27 | 44 | 25 | 111 | 80 |
| 826064 | $G_{ms}$ $C_{ms}$ $G_{ms}$ $C_{ms}$ $A_{ms}$ $G_{ms}$ $G_{mo}$ $C_{ms}$ $G_{mo}$ $C_{ms}$ $A_{ms}$ $C_{ms}$ $U_{ms}$ $G_{ms}$ $C_{ms}$ $^mC_{ks}$ $A_{ks}$ $^mC_k$ | 27 | 44 | 25 | 151 | 80 |
| 826065 | $G_{ms}$ $C_{ms}$ $G_{ms}$ $C_{ms}$ $A_{ms}$ $G_{ms}$ $G_{mo}$ $C_{ms}$ $G_{mo}$ $C_{ms}$ $A_{ms}$ $C_{ms}$ $U_{ms}$ $G_{ms}$ $C_{ms}$ $^mC_{ks}$ $A_{ks}$ $^mC_k$ | 27 | 44 | 25 | 158 | 80 |
| 826066 | $G_{ms}$ $C_{ms}$ $G_{ms}$ $C_{ms}$ $A_{ms}$ $G_{ms}$ $G_{ms}$ $C_{mo}$ $G_{ms}$ $C_{mo}$ $A_{ms}$ $C_{ms}$ $U_{ms}$ $G_{ms}$ $C_{ms}$ $^mC_{ks}$ $A_{ks}$ $^mC_k$ | 27 | 44 | 25 | 140 | 80 |
| 826069 | $G_{ms}$ $C_{ms}$ $G_{ms}$ $C_{ms}$ $A_{ms}$ $G_{ms}$ $G_{ms}$ $C_{ms}$ $G_{ms}$ $C_{ms}$ $A_{ms}$ $C_{ms}$ $U_{ms}$ $G_{ks}$ $C_{ds}$ $^mC_{ks}$ $A_{ds}$ $^mC_k$ | 27 | 44 | 25 | 196 | 80 |

Subscripts: "m" indicates a 2'-O-methyl modification, "o" indicates a phosphodiester internucleoside linkage, "s" indicates a phosphorothioate internucleoside linkage, "k" indicates a cEt bicyclic nucleoside, "d" indicates a 2'-deoxynucleoside.
Superscript "m" preceding a "C" indicates a 5-methylcytosine.

TABLE 40

ACP1 expression

| Isis No. | Start Site | Stop Site | Concentration (nM) | Protein (% mock) | SEQ ID NO. |
|---|---|---|---|---|---|
| 813860 | 27 | 44 | 5 | 130 | 80 |
|  |  |  | 10 | 104 |  |
|  |  |  | 20 | 47 |  |
|  |  |  | 40 | 95 |  |
|  |  |  | 80 | 89 |  |
| 826065 | 27 | 44 | 5 | 143 | 80 |
|  |  |  | 10 | 137 |  |
|  |  |  | 20 | 182 |  |
|  |  |  | 40 | 153 |  |
|  |  |  | 80 | 127 |  |
| 826069 | 27 | 44 | 5 | 127 | 80 |
|  |  |  | 20 | 139 |  |
|  |  |  | 40 | 184 |  |
|  |  |  | 80 | 133 |  |

Example 25: Effects of Antisense Oligonucleotides Targeting the 5'-UTR of Mouse ACP1

Antisense oligonucleotides designed to target the 5'-untranslated region of mouse ACP1 were tested for their effects on ACP1 protein expression in vitro. The antisense oligonucleotides target the mouse ACP1 mRNA (GENBANK accession number NM_021330.4, designated herein as SEQ ID NO: 91) and were designed to target at least one stem loop structure in the 5'-UTR. The start and stop sites listed in the table below indicate the positions on SEQ ID NO: 91 that the antisense oligonucleotides target. MHT cells were transfected with a concentration of antisense oligonucleotide shown in the table below or were not transfected as a control. Ten hours after transfection, ACP1 protein expression was analyzed by western blot. The results are shown in the table below as percent protein expression relative to untreated control cells following normalization to the TCP-1β loading control. The results show that the antisense oligonucleotides targeting the 5'-untranslated region of mouse ACP1 induced translation of the target.

TABLE 41

ACP1 expression

| Isis No. | Sequence | Start Site | Stop Site | Concentration (nM) | Protein (% mock) | SEQ ID NO. |
|---|---|---|---|---|---|---|
| (XL546) | $G_{mo}$ $C_{mo}$ $A_{mo}$ $U_{mo}$ $G_{mo}$ $C_{mo}$ $G_{mo}$ $C_{mo}$ $A_{mo}$ $C_{mo}$ $U_{mo}$ $G_{mo}$ $C_{mo}$ $C_{mo}$ $A_m$ | 20 | 34 | 5 | 88 | 92 |
|  |  |  |  | 10 | 133 |  |
|  |  |  |  | 20 | 153 |  |
|  |  |  |  | 40 | 125 |  |
|  |  |  |  | 80 | 126 |  |
| (XL547) | $G_{ms}$ $C_{ms}$ $A_{ms}$ $U_{ms}$ $G_{ms}$ $C_{ms}$ $G_{ms}$ $C_{ms}$ $A_{ms}$ $C_{ms}$ $U_{ms}$ $G_{ms}$ $C_{ms}$ $C_{ms}$ $A_m$ | 20 | 34 | 5 | 161 | 92 |
|  |  |  |  | 10 | 198 |  |
|  |  |  |  | 20 | 219 |  |
|  |  |  |  | 40 | 227 |  |
|  |  |  |  | 80 | 194 |  |

See above Tables for subscripts legend.

Example 26: Effect of an Antisense Oligonucleotide Targeting the 5'-UTR Mouse ACP1 In Vivo Isis No. 827815 (see the table below) was tested for its effect on mouse ACP1 protein expression in vivo. Groups of three, male, seven week old BALB/c mice were systemically administered Isis No. 827815, at a dose listed in the table below, or saline by subcutaneous injection. Animals were sacrificed 72 hours later. Liver homogenates were prepared, and ACP1 protein expression was analyzed by western blot. The results are shown in the table below as the percent expression relative to saline treated animals following normalization to the TMED9 loading control. The results show that ACP1 protein expression was increased in vivo following treatment with an antisense oligonucleotide targeting the ACP1 5'-UTR.

TABLE 42

ACP1 expression in vivo

| Isis No. | Sequence | Start site | Stop site | Dose (mg/kg) | Protein (% UTC) | SEQ ID NO. |
|---|---|---|---|---|---|---|
| 827815 | $G_{ms}$ $C_{ms}$ $A_{ms}$ $U_{ms}$ $G_{ms}$ $C_{ms}$ $G_{ms}$ $C_{ms}$ $A_{ms}$ $C_{ms}$ $U_{ms}$ $G_{ms}$ $C_{ms}$ $C_{ms}$ $A_{ms}$ $G_m$ | 19 | 34 | 12.5 | 145 | 93 |
|  |  |  |  | 25 | 114 |  |
|  |  |  |  | 50 | 116 |  |
|  |  |  |  | 100 | 94 |  |

See above Tables for subscripts legend.

Example 27: Effect of Antisense Oligonucleotide Targeting the 5'-UTR of Mouse ARF1

An antisense oligonucleotide designed to target the 5'-untranslated region of mouse ADP-ribosylation factor 1 (ARF1) was tested for its effects on ARF1 protein expression in vitro. The antisense oligonucleotide targets the mouse ARF1 mRNA (GENBANK accession number NM_007476.3, designated herein as SEQ ID NO: 94), which does not comprise a uORF, and was designed to target at least one stem loop structure in the 5'-UTR. The start and stop sites listed in the table below indicate the positions on SEQ ID NO: 94 that the antisense oligonucleotide targets. MHT cells were transfected with a concentration of antisense oligonucleotide shown in the table below or were not transfected as a control. Ten hours after transfection, ARF1 protein expression was analyzed by western blot. The results are shown in the table below as percent protein expression relative to untreated control cells following normalization to the TCP-1β loading control. The results show that the antisense oligonucleotide targeting the 5'-untranslated region of mouse ARF1 induced translation of the target.

TABLE 43

ARF1 expression

| Isis No. | Sequence | Start Site | Stop Site | Concentration (nM) | Protein (% mock) | SEQ ID NO. |
|---|---|---|---|---|---|---|
| 814929 | $C_{mo}$ $G_{mo}$ $C_{mo}$ $T_{mo}$ $C_{mo}$ $C_{mo}$ $C_{mo}$ $A_{mo}$ $C_{mo}$ $A_{mo}$ $A_{mo}$ $G_{mo}$ $A_{mo}$ $T_{mo}$ $G_{mo}$ $G_{mo}$ $C_m$ | 44 | 60 | 5 | 112 | 95 |
| | | | | 10 | 179 | |
| | | | | 20 | 215 | |
| | | | | 40 | 181 | |
| | | | | 80 | 122 | |

See above Tables for subscripts legend.

Example 28: Effect of Antisense Oligonucleotide Targeting the 5'-UTR of Mouse USP16

An antisense oligonucleotide designed to target the 5'-untranslated region of mouse ubiquitin processing protease (USP16) was tested for its effects on USP16 protein expression in vitro. The antisense oligonucleotide targets the mouse USP16 mRNA (GENBANK accession number NM_024258.2, designated herein as SEQ ID NO: 96), and was designed to target at least one stem loop structure in the 5'-UTR. The start and stop sites listed in the table below indicate the positions on SEQ ID NO: 96 that the antisense oligonucleotide targets. MHT cells were transfected with a concentration of antisense oligonucleotide shown in the table below or were not transfected as a control. Ten hours after transfection, USP16 protein expression was analyzed by western blot. The results are shown in the table below as percent protein expression relative to untreated control cells following normalization to the β-actin (ACTB) loading control. The results show that the antisense oligonucleotide targeting the 5'-untranslated region of mouse USP16 induced translation of the target.

TABLE 44

USP16 expression

| Isis No. | Sequence | Start Site | Stop Site | Concentration (nM) | Protein (% mock) | SEQ ID NO. |
|---|---|---|---|---|---|---|
| 814928 | $G_{mo}$ $A_{mo}$ $G_{mo}$ $A_{mo}$ $G_{mo}$ $C_{mo}$ $G_{mo}$ $A_{mo}$ $C_{mo}$ $G_{mo}$ $C_{mo}$ $G_{mo}$ $G_{mo}$ $T_{mo}$ $G_{mo}$ $G_{mo}$ $A_m$ | 21 | 37 | 5 | 124 | 97 |
| | | | | 10 | 133 | |
| | | | | 20 | 133 | |
| | | | | 40 | 116 | |
| | | | | 80 | 116 | |

See above Tables for subscripts legend.

Example 29: Effects of Antisense Oligonucleotides Targeting the 5'-UTR of Human LDLr Antisense oligonucleotides designed to target the 5'-untranslated region of human low density lipoprotein receptor (LDLr) were tested for their effects on LDLr protein expression and LDL uptake in vitro. The antisense oligonucleotides target the human LDLr mRNA (GENBANK accession number NM_000527.4, designated herein as SEQ ID NO: 98) and were designed to target at least one stem loop structure in the 5'-UTR. The start and stop sites listed in the table below indicate the positions on SEQ ID NO: 98 that the antisense oligonucleotides target. HEK293 or HeLa cells were transfected with a concentration of antisense oligonucleotide shown in the table below or were not transfected as a control. Ten hours after transfection, LDLr protein expression was analyzed by ELISA (R & D Systems, cat. # DLDLR0). The results are shown in the table below as percent protein expression relative to untreated control cells. The results show that the antisense oligonucleotides targeting the 5'-untranslated region of human LDLr induced translation of the target.

In order to test the effects of the antisense oligonucleotides in the tables below on LDL uptake, HEK 293 or HeLa cells were transfected with an antisense oligonucleotide at a concentration shown in the table below or were not transfected as a control. Approximately fourteen hours after transfection, the medium was changed to lipid-free medium, incubated at 37° C. for one hour, then 5 to 10 µg/mL of Bodipy labeled LDL was added at 4° C. for 30 to 60 minutes to all cells, including untransfected control cells. The cells were then washed with cold PBS, harvested, and lysed with RIPA buffer. The Bodipy fluorescence was measured, and the results in the table below show the percent Bodipy fluorescence relative to untransfected control cells.

TABLE 46

| | | LDL uptake | | |
|---|---|---|---|---|
| Isis No. | Cell type | Bodipy-LDL incubation time (min) | Concentration (nM) | LDL uptake (% UTC) | SEQ ID NO. |
| 814923 | HEK293 | 60 | 40 | 152 | 99 |
| 842196 | HEK293 | 30 | 40 | 115 | 99 |
| | | 60 | 40 | 130 | |
| 842196 | HeLa | 30 | 12.5 | 108 | 99 |
| | | | 25 | 108 | |
| | | | 50 | 127 | |
| | | | 100 | 132 | |

Example 30: Effects of Antisense Oligonucleotides Targeting the 5'-Untranslated Region Downstream of the CFTR uORF Start Codon on CFTR Protein Expression Antisense oligonucleotides designed to target a uORF start codon of human CFTR were tested for their effects on CFTR protein expression in vitro. These antisense oligonucleotides, described in the table below, were designed to target the CFTR mRNA (GENBANK accession number NM_000492.3, designated herein as SEQ ID NO: 81) and were uniformly modified in order to avoid inducing cleavage of the target RNA. The start and stop sites listed in the table below indicate the positions on SEQ ID NO: 81 that the antisense oligonucleotides target.

HT-29 cells were transfected with a concentration of antisense oligonucleotide listed in the table below or were mock transfected as a control. Twenty-four hours after transfection, CFTR expression was analyzed by western blot, as described in Example 20. The results are shown in the table below as percent protein expression relative to mock transfected cells following normalization to a loading control. The results show that the antisense oligonucleotides increased CFTR protein expression.

TABLE 45

LDLr expression

| Isis No. | Sequence | Start Site | Stop Site | Cell type | Concentration (nM) | Protein (% UTC) | SEQ ID NO. |
|---|---|---|---|---|---|---|---|
| 814923 | U$_{mo}$ G$_{mo}$ C$_{mo}$ A$_{mo}$ G$_{mo}$ U$_{mo}$ G$_{mo}$ G$_{mo}$ G$_{mo}$ G$_{mo}$ U$_{mo}$ G$_{mo}$ A$_{mo}$ U$_{mo}$ U$_{mo}$ U$_m$ | 28 | 43 | HEK293 | 5 | 131 | 99 |
| | | | | | 10 | 146 | |
| | | | | | 20 | 169 | |
| | | | | | 40 | 188 | |
| | | | | | 80 | 238 | |
| 814923 | U$_{mo}$ G$_{mo}$ C$_{mo}$ A$_{mo}$ G$_{mo}$ U$_{mo}$ G$_{mo}$ G$_{mo}$ G$_{mo}$ G$_{mo}$ U$_{mo}$ G$_{mo}$ A$_{mo}$ U$_{mo}$ U$_{mo}$ U$_m$ | 28 | 43 | HeLa | 5 | 124 | 99 |
| | | | | | 10 | 154 | |
| | | | | | 20 | 113 | |
| | | | | | 40 | 128 | |
| | | | | | 80 | 106 | |
| 842196? (XL512) | U$_{ms}$ G$_{ms}$ C$_{ms}$ A$_{ms}$ G$_{ms}$ U$_{ms}$ G$_{ms}$ G$_{ms}$ G$_{ms}$ G$_{ms}$ U$_{ms}$ G$_{ms}$ A$_{ms}$ U$_{ms}$ U$_{ms}$ U$_m$ | 28 | 43 | HeLa | 5 | 112 | 99 |
| | | | | | 10 | 111 | |
| | | | | | 20 | 128 | |
| | | | | | 40 | 121 | |
| | | | | | 80 | 137 | |

See above Tables for subscripts legend.

TABLE 47

CFTR expression

| Isis No. | Sequence | Start Site | Stop Site | Concentration (nM) | Protein (% mock) | SEQ ID NO. |
|---|---|---|---|---|---|---|
| 812022 | $U_{mo}$ $G_{mo}$ $C_{mo}$ $U_{mo}$ $G_{mo}$ $U_{mo}$ $G_{mo}$ $A_{mo}$ $U_{mo}$ $G_{mo}$ $U_{mo}$ $C_{mo}$ $A_{mo}$ $U_{mo}$ $U_{mo}$ $U_{mo}$ $G_{mo}$ $C_m$ | 9 | 26 | 50<br>75<br>100<br>150 | 132<br>117<br>125<br>112 | 100 |
| 812023 | $U_{ms}$ $G_{ms}$ $C_{ms}$ $U_{ms}$ $G_{ms}$ $U_{ms}$ $G_{ms}$ $A_{ms}$ $U_{ms}$ $G_{ms}$ $U_{ms}$ $C_{ms}$ $A_{ms}$ $U_{ms}$ $U_{ms}$ $U_{ms}$ $G_{ms}$ $C_m$ | 9 | 26 | 50<br>75<br>100<br>150 | 130<br>126<br>124<br>128 | 100 |

See above Tables for subscripts legend.

Example 31: Effects of Antisense Oligonucleotides Targeting the 5'-UTR of Human LDLr Antisense oligonucleotides designed to target the 5'-untranslated region of human low density lipoprotein receptor (LDLr) were tested for their effects on LDLr protein expression in vitro. The antisense oligonucleotides target the human LDLr mRNA (SEQ ID NO: 98) and were designed to target at least one stem loop structure in the 5'-UTR. The start and stop sites listed in the table below indicate the positions on SEQ ID NO: 98 that the antisense oligonucleotides target. HEK293 cells were transfected with a concentration of antisense oligonucleotide shown in the table below or were not transfected as a control. Sixteen hours after transfection, LDLr protein expression was analyzed by ELISA (R & D Systems, cat. # DLDLR0). The results are shown in the table below as percent protein expression relative to untreated control cells. The results show that the antisense oligonucleotides targeting the 5'-untranslated region of human LDLr induced translation of the target.

TABLE 48

LDLr expression

| Isis No. | Sequence | Start Site | Stop Site | Concentration (nM) | Protein (% UTC) | SEQ ID NO. |
|---|---|---|---|---|---|---|
| 842196 | $U_{ms}$ $G_{ms}$ $C_{ms}$ $A_{ms}$ $G_{ms}$ $U_{ms}$ $G_{ms}$ $G_{ms}$ $G_{ms}$ $G_{ms}$ $U_{ms}$ $G_{ms}$ $A_{ms}$ $U_{ms}$ $U_{ms}$ $U_m$ | 28 | 43 | 20<br>40<br>80 | 125<br>195<br>222 | 99 |
| 842197 | $U_{ms}$ $G_{ms}$ $C_{ms}$ $A_{ms}$ $G_{ms}$ $U_{ms}$ $G_{ms}$ $G_{ms}$ $G_{ms}$ $G_{ms}$ $U_{ms}$ $G_{ms}$ $A_{ms}$ $T_{ks}$ $T_{ks}$ $T_k$ | 28 | 43 | 20<br>40<br>80 | 176<br>266<br>214 | 101 |
| 842198 | $U_{ms}$ $G_{ms}$ $C_{ms}$ $A_{ms}$ $G_{mo}$ $U_{ms}$ $G_{mo}$ $G_{ms}$ $G_{mo}$ $G_{ms}$ $U_{ms}$ $G_{ms}$ $A_{ms}$ $T_{ks}$ $T_{ks}$ $T_k$ | 28 | 43 | 20<br>40<br>80 | 160<br>157<br>194 | 101 |
| 842200 | $U_{ms}$ $G_{ms}$ $C_{ms}$ $A_{ms}$ $G_{mo}$ $U_{ms}$ $G_{mo}$ $G_{ms}$ $G_{mo}$ $G_{ms}$ $U_{mo}$ $G_{ms}$ $A_{ms}$ $U_{ms}$ $U_{ms}$ $U_m$ | 28 | 43 | 20<br>40<br>80 | 131<br>175<br>170 | 99 |
| 842202 | $U_{ms}$ $G_{ms}$ $C_{ms}$ $A_{ms}$ $G_{mo}$ $U_{ms}$ $G_{mo}$ $G_{ms}$ $G_{ms}$ $G_{ms}$ $U_{ms}$ $G_{ms}$ $A_{ms}$ $U_{ms}$ $U_{ms}$ $U_m$ | 28 | 43 | 20<br>40<br>80 | 125<br>132<br>145 | 99 |
| 842205 | $U_{ms}$ $G_{ms}$ $C_{ms}$ $A_{ms}$ $G_{ms}$ $U_{ms}$ $G_{ms}$ $G_{ms}$ $G_{ms}$ $G_{ms}$ $U_{ms}$ $G_{ms}$ $A_{ms}$ $U_{ms}$ $U_{ms}$ $U_{ms}$ $U_{ms}$ $C_m$ | 26 | 43 | 20<br>40<br>80 | 123<br>136<br>107 | 102 |
| 842206 | $U_{ms}$ $G_{ms}$ $C_{ms}$ $A_{ms}$ $G_{ms}$ $U_{ms}$ $G_{ms}$ $G_{ms}$ $G_{ms}$ $G_{ms}$ $U_{ms}$ $G_{ms}$ $A_{ms}$ $U_{ms}$ $U_{ms}$ $T_{ks}$ $T_{ks}$ $^mC_k$ | 26 | 43 | 20<br>40<br>80 | 155<br>173<br>134 | 103 |
| 842207 | $U_{ms}$ $G_{ms}$ $C_{ms}$ $A_{ms}$ $G_{mo}$ $U_{ms}$ $G_{mo}$ $G_{ms}$ $G_{mo}$ $G_{ms}$ $U_{ms}$ $G_{ms}$ $A_{ms}$ $U_{ms}$ $U_{ms}$ $T_{ks}$ $T_{ks}$ $^mC_k$ | 26 | 43 | 20<br>40<br>80 | 125<br>147<br>129 | 103 |
| 842211 | $U_{ms}$ $G_{ms}$ $C_{ms}$ $A_{ms}$ $G_{mo}$ $U_{ms}$ $G_{mo}$ $G_{ms}$ $G_{ms}$ $G_{ms}$ $U_{ms}$ $G_{ms}$ $A_{ms}$ $U_{ms}$ $U_{ms}$ $U_{ms}$ $U_{ms}$ $C_m$ | 26 | 43 | 20<br>40<br>80 | 136<br>143<br>142 | 102 |
| 842212 | $U_{ms}$ $G_{ms}$ $C_{mo}$ $A_{ms}$ $G_{mo}$ $U_{ms}$ $G_{mo}$ $G_{ms}$ $G_{mo}$ $G_{ms}$ $U_{mo}$ $G_{ms}$ $A_{mo}$ $U_{ms}$ $U_{mo}$ $U_{ms}$ $U_{ms}$ $C_m$ | 26 | 43 | 20<br>40<br>80 | 103<br>101<br>120 | 102 |

TABLE 48-continued

LDLr expression

| Isis No. | Sequence | Start Site | Stop Site | Concentration (nM) | Protein (% UTC) | SEQ ID NO. |
|---|---|---|---|---|---|---|
| 842213 | $U_{ms} G_{ms} C_{ms} A_{ms} G_{ms} U_{ms} G_{ms} G_{ms}$ $G_{ms} G_{ms} U_{ms} G_{ms} A_{ms} T_{ks} T_{ds} T_{ks} T_{ds}$ $^{m}C_{k}$ | 26 | 43 | 20<br>40<br>80 | 128<br>135<br>139 | 104 |
| 842214 | $U_{ms} G_{ms} C_{ms} A_{ms} G_{ms} U_{ms} G_{ms} G_{ms}$ $G_{ms} G_{ms} U_{ms} G_{ks} A_{ds} T_{ks} T_{ds} T_{k}$ | 28 | 43 | 20<br>40<br>80 | 134<br>152<br>139 | 101 |

See above Tables for subscripts legend.

Example 32: Time Course of LDLr Protein Expression Following Treatment with an Antisense Oligonucleotide Targeting the 5'-UTR Hep3B cells were transfected with 30 nM Isis No. 842196 (see Table 45) and Lipofectamine 2000 (Life Technologies). At various time points following transfection, the cells were harvested and LDLr protein expression was analyzed by ELISA as described in Examples 30 and 31. The results are shown in Table 49 as the percent LDLr protein expression relative to cells that did not receive antisense oligonucleotide treatment (harvested at the 0 hour time point). The results show that LDLr expression was increased over 4-fold relative to baseline expression by Isis No. 842196, at the 48 hour time point.

TABLE 49

LDLr expression
LDLr (% 0 h) following transfection with 30 nM Isis No. 842196

| 24 h | 36 h | 48 h |
|---|---|---|
| 212 | 230 | 457 |

The invention claimed is:

1. A method of increasing the amount of a target protein in a cell, comprising contacting the cell with an antisense compound comprising a modified oligonucleotide, wherein the target protein is encoded by a target transcript comprising at least one translation suppression element in the 5' untranslated region of the target transcript that is a uORF, wherein the modified oligonucleotide is complementary to a target site comprising the uORF; and thereby increasing the amount of the target protein in the cell.

2. The method of claim 1, wherein at least one translation suppression element in the 5' untranslated region of the target transcript that is a uORF arises from a mutation.

3. The method of claim 1, wherein the modified oligonucleotide consists of 10 to 40 linked nucleosides.

4. The method of claim 1, wherein the modified oligonucleotide comprises a modified region of at least 10 contiguous modified nucleosides.

5. The method of claim 1, wherein the modified oligonucleotide comprises at least one 2'-substituted modified sugar moiety.

6. The method of claim 1, wherein the modified oligonucleotide comprises at least one bicyclic modified sugar moiety.

7. The method of claim 1, wherein the modified oligonucleotide comprises at least one modified internucleoside linkage.

8. The method of claim 7, wherein the at least one modified internucleoside linkage is a phosphorothioate internucleoside linkage.

9. The method of claim 1, wherein the antisense compound comprises at least one conjugate group.

10. The method of claim 1, wherein the antisense compound does not alter the amount of the target transcript.

11. The method of claim 1, wherein the antisense compound is single-stranded.

12. The method of claim 1, wherein the cell is in a subject.

13. The method of claim 1, wherein the modified oligonucleotide is at least 90% complementary to the target site.

14. The method of claim 1, wherein the modified oligonucleotide comprises a plurality of 2'-O-methyl modified sugar moieties.

15. The method of claim 1, wherein the modified oligonucleotide is 100% complementary to the target site.

* * * * *

SEQUENCE LISTING

```
<160> NUMBER OF SEQ ID NOS: 104

<210> SEQ ID NO 1
<211> LENGTH: 1862
<212> TYPE: DNA
<213> ORGANISM: Homo sapiens

<400> SEQUENCE: 1
cgtgcgtcat cttcccgcgc cggtgacgga agtgcggtgt tgagcgccgg cggctcgcgc      60
ccacgctggg ccgggagtcg aaatgcttcc cggtgccggg agtgagcgat gagctggctt     120
ctgttcctgg cccacagagt cgccttggcc gccttgccct gccgccgcgg ctctcgcggg     180
ttcgggatgt tctatgccgt gaggaggggc cgcaagaccg gggtctttct gacctggaat     240
gagtgcagag cacaggtgga ccggtttcct gctgccagat ttaagaagtt tgccacagag     300
gatgaggcct gggcctttgt caggaaatct gcaagcccgg aagtttcaga agggcatgaa     360
aatcaacatg gacaagaatc ggaggcgaaa gccagcaagc gactccgtga gccactggat     420
ggagatggac atgaaagcgc agagccgtat gcaaagcaca tgaagccgag cgtggagccg     480
gcgcctccag ttagcagaga cacgttttcc tacatgggag acttcgtcgt cgtctacact     540
gatggctgct gctccagtaa tgggcgtaga aggccgcgag caggaatcgg cgtttactgg     600
gggccaggcc atcctttaaa tgtaggcatt agacttcctg ggcggcagac aaaccaaaga     660
gcggaaattc atgcagcctg caaagccatt gaacaagcaa agactcaaaa catcaataaa     720
ctggttctgt atacagacag tatgtttacg ataaatggta taactaactg ggttcaaggt     780
tggaagaaaa atgggtggaa gacaagtgca gggaaagagg tgatcaacaa agaggacttt     840
gtggcactgg agaggcttac ccaggggatg gacattcagt ggatgcatgt tcctggtcat     900
tcgggattta taggcaatga agaagctgac agattagcca gagaaggagc taaacaatcg     960
```

```
gaagactgag ccatgtgact ttagtccttg ggagaacttg agccagcggc tgtcttgctg    1020
cctgtactta ctggtgtgga aaatagcctg caggtaggac cattgcagtg atgggcagat    1080
gcgtctttca cacggaatca ggcacagtgg ccttctgtga catgtgttta taaaaaatgg    1140
ttaagtatat aataaattga acatctttga gattggagaa ttatgtgaga tttccacatt    1200
atgtttactg ggttcaatac tgtccttgct tgttttattg caggcaagca aggcaaatgg    1260
cctaaaatgc tgtggcttat attttgataa gaaatcaaaa aaccattggt taaaagatgc    1320
aactcagaag tctggaagta ttctgaaagc atccatttac cgtccagttg acaggtttga    1380
gtctcctgct tgtataggtg acttgtgccc atgggtacat taaaggaaca tgctgcccag    1440
ggcctgggcg gacagctcag tgggcaggat gtgtgctggg tctcagcccc atgtgcctgc    1500
ttgctgggca gttagtatag ggcaaagcct gcctgcggcg accctggctg ctaggccatt    1560
ctctaggaac agctgcgact cataaagacc aagaagcata aataaacttt caaaaattta    1620
tttggctctt tcgttaaaaa ctgtgcaaat taaaaaaaaa aaaaaaaaag taagacaccg    1680
gctgggcaca gtggctcact tctgtaatcc tagcactttg ggaggccaag gcgggcagat    1740
cacttgaggt caggagtttg agaccagctt ggccaacatg acgaaaccct gtctctacta    1800
aaattacaaa aattatccag gtgtggtggc acgggcttgt agtcccagct acttgggagg    1860
ct                                                                  1862

<210> SEQ ID NO 2
<211> LENGTH: 4638
<212> TYPE: DNA
<213> ORGANISM: Mus musculus

<400> SEQUENCE: 2
gccaggctcg ctgagagccg ggcgctgga caagggaaca gggacactgt gaacggaaga      60
caaaaaacaa tgtatagtaa aacagaaggc ggatccaggg tatcccgcga actcggcttg     120
cctctcccgt gagccttggc ggggatctgc tcctcctcc gctggacgcc ctcggtcctt      180
agtttgtccc actaggggcg accgggtcgt cacgtgctcc tccaggtcct ctgcaggagc     240
gtgcatccta tcctgccttg gtacgctga gccatggcag ccctgctgag acccgcgcgt      300
tggctgctcg gggccgcggc ggccccgcgc ctcccgctgt ccctgcgcct cctgcgggc      360 gtcccgggcc ggctgtcctc cgtcgtccgg gtcgcggctg ttggtagccg gccggctgca     420
ggagagcgtc tgagccaagc cagattgtat gccatcgttg ctgagaaaag ggatcttcaa     480
gaggagcctc ctcctgtgag aaagaacagc agtcaatttg actgggctct gatgagactg     540
gataattctg tccggagaac aggccgcatc acaaaggggc ttctgcagag agtctttgag     600
agcacgtgta gctcaggtag cccagggagc aatcaagctc tgcttctgct gcgcagctgt     660
ggctcgctcc tgcccgaact gagtctcgcc gagaggacag agtttgctca caagatctgg     720
gacaaacttc agcagttagg tgtcgtatat gatgtcagtc attacaatgc tttacttaaa     780
gtatatcttc aaaatgaata caaattttca cctactgact tcctggcaaa gatggaggga     840
gcaaacatcc aaccaaatcg agtaacatac cagaggctga tagctgccta ctgtaatgtt     900
ggggacattg aaggtgccag caagatcctt ggatttatga aaacgaaaga ccttccgatc     960
acagaggccg tgttcagtgc tctcgtcaca gggcatgcga gagctgggga tatggaaaat    1020
gcagaaaata ttctcacagt gatgaaacag gccggcattg agcctggccc agacacgtat    1080
ctggccttgt tgaatgcaca tgctgagagg ggtgacattg ccaggttag gcagattctg    1140 gagaaagtgg agaagtcaga ccattacttc atggaccgcg acttcttgca ggttattttt    1200
```

```
agcttcagta aggctggcta ccctcagtat gtctcagaaa tactggagaa gattacctat    1260
gagagacggt ctattccaga tgcaatgaac ctcatttgt ttttagccac tgagaagtta    1320
gaagacactg cgttccaggt tttattggca ttacccctgt ccaaggacga gagctccgat    1380
aactttggca gtttcttttt gcggcactgt gtgactctgg atttgccccc tgagaagctg    1440
atagactact gtcggaggct gagggacgcc aagctgcaca gctcctcact gcagttcacg    1500
ctgcactgtg ctcttcaagc caataggaca gctttggcaa agcagtgat ggaggctttg     1560 agggaagaag ggtttcctat ccgaccgcac tatttctggc cgttgcttgc tgggcatcag    1620
aaaacaaaaa atgttcaagg aataatagat atcctcaaaa taatgaacaa agtgggagtg    1680
gatcctgatc aggaaacata tataaactat gtgtttccgt gctttgatag tgcacagtca    1740
gttcgagctg ctttgcagga aaatgaatgt ctcctcgcaa gtagtacctt tgctcaagct    1800
gaagtgaaga atgaagcaat aaatgggaac ttacagaaca ttttgtcatt tttggaatcg    1860
aatacattgc ctttctcgtt tagttctttg agaaacagcc taatcctagg cttcaggagg    1920
tcgatgaaca tagatctttg gagcaagata acagaattgt tgtacaagga tgaacgctat    1980
tgctcaaagc ctccgggacc agcggaagct gttggctatt ttctttataa cttgattgac    2040
agcatgagtg actcagaggt acaggccaag gaggagcgtt tgagacaata cttccatcag    2100
ctgcaggaga tgaatgttaa agttcctgaa aacatctaca aaggcatttg taatttgctg    2160
aatacctacc atgttcctga attgattaag gatattaagg ttctggttga cagagagaag    2220
gtagattctc aaaaaacttc tcaagttacc tcatctgatt tggaatcaac acttgagaaa    2280
ctcaaagctg aaggccaacc tgtaggatct gccctgaagc agctcctgct gctgctctgc    2340
tcagaggaga atatgcaaaa ggcccttgag gtgaaagcaa aatatgagtc agacatggtt    2400
attggtggct atgcagcatt aataaatttg tgctgtcgac atgataatgc agaagatgcg    2460
tggaacttga acaagaagt tgaccgctta gatgcttcgg ctattcttga cactgccaag    2520
tacgtagccc ttgtaaaagt actgggaaag cacagcagac tccaagatgc tattaacatt    2580
ctaaaggaga tgaaagagaa ggatgttgtt atcaaagatg caacagtctt gtccttttc    2640 cacatcctca atggtgcagc tttaagaggt gaaattgaaa cagtaaaaca gctgcatgaa    2700
gccatcgtga ctcttgggtt ggcaaagccg tccagcaaca taagcttccc gttggtcact    2760
gtgcacctgg aaaagggtga cttacctgct gctcttgaag ccagcattgc ctgccataaa    2820
aaatataaag tgttacccag gattcatgat gtcttatgta agctagtaga gaaaggcgag    2880
actgatttga tccagaaagc aatggacttt gtgagccaag aacaagggga gatgacgatg    2940
ctctacgacc tcttctttgc tttcctgcag acggggaatt acaaagaagc taagaagatc    3000
attgagactc caggcattag agctcggcct acaagactcc agtggttttg tgatcgatgc    3060
attgccagta atcaggttga agctcttgag aagttggtag agctgactga gaagctgttt    3120
gagtgtgaca gagaccagat gtactacaac ttactgaagc tatacaaaat aagcagtgac    3180
tggcaaagag cggatgctgc gtggaccaaa atgcaagaag agaacattat ccctcgagag    3240
cggacactgc ggctcttagc cgagatcttg aaaaccagca accaggaagt tccttttcgac    3300 gttccggagt tgtggttttgg agatgacaga ccttccctga gtccatcctc acgctcagca    3360
ggagaggacg ttactgagaa gacgttgttg tctaactgca aactaaagaa gagtaaagat    3420
gcatataata tcttccttaa agccgaaaag caaaacgttg tatttagcag tgaaacttat    3480
agcaccttga taggcttgct gctgagtaag gacgacttca cccaagcaat gcacgtgaag    3540
```

-continued

```
gatttcgctg agacccacat caagggcttc acactgaacg atgctgccaa cagcctcctc    3600
atcataaggc aagttaggcg ggattatttg aaagggctc tggcaactct gagagcagcc     3660
ttggatttga agcaggttcc gtcccagatc gccgtgaccc gcctcatcca ggcgttggcc    3720
ttgaagggtg atgtgaaag catagaggcc attcagagaa tggtggctgg acttgacacg     3780
attggactct caaaaatggt ttttatcaat aacatcgctt tggcccagat gaagaataat    3840
aaacttgatg ctgccataga aaacattgag cacctgcttg cttccgagaa ccaagccata    3900
gaacctcagt actttggctt gtcgtatcta ttcagaaaag tgatcgaaga gcagatggaa   3960
ccagcgctag agaagttaag catcatgtct gagagaatgg cgaatcagtt tgcactttac    4020
aagcccgtca ctgatctatt cctgcagctt gtggattcag gcaaggtgga tgaggccaga    4080
gctctcttag agagatgcgg tgccattgcc gagcagagct cgcttctgtc ggtgttctgt    4140
ctgaggactt ctcagaaacc gaaaaaggca ccagttctga agactttgtt agaactgatt    4200
cctgagttac gtgataacga taaagtatat tcttgcagca tgaaaagcta tgccttagac    4260
aaagatgtgg cctcggctaa agcactgtat gagtatttga cagccaagaa cttgaagcta    4320
gatgacctgt ttctcaagcg ctatgcagct ttgctcaagg atgtcggcga accagtcccc    4380
ttccccgagc cccctgaaag ctttgcattt tatataaagc aactaaagga agcaagggaa    4440
agcccttcat gagagaagca gcgcggctgt gtgtgtgtct atgtgtgtgt gtgtctgtgt    4500
gtgtgtctgt gtgtgtgtct gtgtgtgtgt gtctatgtgt gtatatgcgc gcgcacatgc    4560
ctatgtctaa atgttatttc taaaatgtac ttgagaggaa aataaaccaa tgaaaatgta    4620
aaaaaaaaaa aaaaaaaa                                                  4638
```

<210> SEQ ID NO 3
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 3
cauuucgacu cccggc                                                    16

<210> SEQ ID NO 4
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 4
agcauuucga cucccg                                                    16

<210> SEQ ID NO 5
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 5
gaagcauuuc gacucc                                                    16

<210> SEQ ID NO 6
<211> LENGTH: 16
<212> TYPE: RNA
<213> ORGANISM: Artificial sequence

```
<220> FEATURE:
<223> OTHER INFORMATION: Synthetic oligonucleotide

<400> SEQUENCE: 6
gggaagcauu ucgacu                                                  16

<210> SEQ ID NO 7
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 7
ccgggaagca uuucga                                                  16

<210> SEQ ID NO 8
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 8
ucaccggcgc gggaag                                                  16

<210> SEQ ID NO 9
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 9
cucaacaccg cacuuc                                                  16

<210> SEQ ID NO 10
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 10
acucccggcc cagcgu                                                  16

<210> SEQ ID NO 11
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 11
cgacucccgg cccagc                                                  16

<210> SEQ ID NO 12
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 12
uucgacuccc ggccca                                                  16
```

```
<210> SEQ ID NO 13
<211> LENGTH: 11
<212> TYPE: RNA
<213> ORGANISM: Artificial sequence
<220> FEATURE:
<223> OTHER INFORMATION: Synthetic oligonucleotide

<400> SEQUENCE: 13
cauuucgacu c                                                              11

<210> SEQ ID NO 14
<211> LENGTH: 14
<212> TYPE: RNA
<213> ORGANISM: Artificial sequence
<220> FEATURE:
<223> OTHER INFORMATION: Synthetic oligonucleotide

<400> SEQUENCE: 14
cauuucgacu cccg                                                           14

<210> SEQ ID NO 15
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 15
cauuucgacu cccggccc                                                       18

<210> SEQ ID NO 16
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 16
cauuucgacu cccggcccag                                                     20

<210> SEQ ID NO 17
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 17
cauuguuuuu ugucuucc                                                       18

<210> SEQ ID NO 18
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 18
cauuguuuuu ugucuu                                                         16

<210> SEQ ID NO 19
<211> LENGTH: 20
<212> TYPE: RNA
<213> ORGANISM: Artificial sequence
<220> FEATURE:
<223> OTHER INFORMATION: Synthetic oligonucleotide
```

<400> SEQUENCE: 19
cauuguuuuu ugucuuccgu                                            20

<210> SEQ ID NO 20
<211> LENGTH: 3129
<212> TYPE: DNA
<213> ORGANISM: Homo sapiens

<400> SEQUENCE: 20

| | | | | | |
|---|---|---|---|---|---|
| ggcacctccc | ttaggcgcca | gggacagccg | agcgttacct | ggtcccgggc | agcggagttc | 60 |
| tttacccacc | ccagttctgg | ttctgacgcc | ctagctcatt | ccgcaaattt | agggcttggg | 120 |
| tctggcttgt | tcccctccgg | ctcgaaccac | ctcttctctg | agccgagcca | gctaccgggg | 180 |
| ctcctggaat | tgccacccct | ccctgggcac | ccttgaggcc | tccgtggagg | gacgtcacgg | 240 |
| ggcagagcgg | gacgtgagcc | tgagtttgct | gcaggcgtgc | tctgtgtggt | ggctgggttc | 300 |
| tgccaatccc | cgtgcccacc | gggtgggcgc | ggccgggaag | ctcctgcccc | tccctgctgg | 360 |
| tcggcgtcac | gcgtgacgtc | ccgcgtgatg | gctgggaggg | cccggcggcg | acagcggagg | 420 |
| cagagaggaa | ggcggttctg | agagcttcag | agagcgatgg | aaagcaaaat | gggtgaattg | 480 |
| cctttagaca | tcaacatcca | ggaacctcgc | tgggaccaaa | gtactttcct | gggcagagcc | 540 |
| cggcactttt | tcactgttac | tgatcctcga | aatctgctgc | tgtccggggc | acagctggaa | 600 |
| gcttctcgga | acatcgtgca | gaactacagg | gccggcgtgg | tgacccccagg | gatcaccgag | 660 |
| gaccagctgt | ggagggccaa | gtatgtgtat | gactccgcct | tccatccgga | cacaggggag | 720 |
| aaggtggtcc | tgattggccg | catgtcagcc | caggtgccca | tgaacatgac | catcactggc | 780 |
| tgcatgctca | cattctacag | gaagacccca | accgtggtgt | tctggcagtg | ggtgaatcag | 840 |
| tccttcaatg | ccattgttaa | ctactccaac | cgcagtggtg | acactccat | cactgtgagg | 900 |
| cagctgggga | cagcctatgt | gagtgccacc | actggagctg | tggccacggc | cctgggactc | 960 |
| aaatccctca | ccaagcacct | gccccccttg | gtcggcagat | ttgtgccctt | tgcagcagtg | 1020 |
| gcagctgcca | actgcatcaa | catcccctg | atgaggcaga | gagagctgca | ggtgggcatc | 1080 |
| ccggtggctg | atgaggcagg | tcagaggctt | ggctactcgg | tgactgcagc | caagcaggga | 1140 |
| atcttccagg | tggtgatttc | aagaatctgc | atggcgattc | ctgccatggc | catcccacca | 1200 |
| ctgatcatgg | acactctgga | gaagaaagac | ttcctgaagc | gccgccctg | gctggggca | 1260 |
| ccctgcagg | tgggactggt | gggcttctgc | ctggtatttg | caaccccct | gtgctgtgcc | 1320 |
| ctattccccc | agaagagctc | catacacata | agcaacctgg | aaccagagct | gagagctcag | 1380 |
| atccatgagc | aaaaccccag | cgttgaagtg | gtctactaca | acaaggggct | ttgaggaggg | 1440 |
| tcagcctctg | tcccctccct | cacttccttg | ggctgctgct | ttagtggagt | catgtcaccc | 1500 |
| ctaccacttg | gctatctgcc | tagcactggg | caggggcctt | ggtgggcaga | tggcaattga | 1560 |
| gggtagcaac | ctattagggt | gggggaggga | cctccataag | gcttttcctc | ccttctctgg | 1620 |
| tttcaaagat | cagagcacat | aaccctcct | gtgcttgagt | gtccatgcat | atacatacat | 1680 |
| gatacacatg | tgtatgtgta | cattgggtcc | tgaaagctag | aagcaggcat | gctagcctag | 1740 |
| tatgttctga | catctggctt | cccttctcag | cctcatgtcc | acctgcctgc | cagccaggct | 1800 |
| acaggtgtga | cttccttctc | taaactgtta | caccagccaa | gttatttttg | atggcacctc | 1860 |
| atcccttcta | gaaataggag | gagccccagg | atccaggac | agagacttat | agacactagt | 1920 |
| aggacaaagc | gggctgaatc | cttcaggttt | ctgataccta | gctccccaag | ctgactgggc | 1980 |

| | |
|---|---|
| tggcagagga gaacatgttg agacaaggga ggcagggac ttatgcatcc ctcagtgcca | 2040 |
| tcccttgtat cctggaatag ctccatttcc cctcctcctc tctaccagac aaaggagtgc | 2100 |
| ctgtgtcctg tactgccctc gctgtctccc ccaccaccct acttgacagc gtgggcatct | 2160 |
| tcaggcacag ccttgggagt tcctggtgtg ctctgacatc atgacctcaa atctaaatcc | 2220 |
| tccaatccca actcccttc ccaaacaaaa agccacagag gcagagcaag cattcccctt | 2280 |
| taagagcttc cactgcaccc cctcccaagg gacacagcgg taggaatggt gcttaaactc | 2340 |
| cacaggtatc agagagggtg taactaggac atcctcaagg gcagctaggc cccgaatgta | 2400 |
| caatgttaag acagggaatt tgtgttcca ttgactttt tttttttttt taatggagtt | 2460 |
| tcactatttt gcccaggctg gagtgcgatg gtgcgatctt ggctcactgc aacctctgcc | 2520 |
| tcctgggttc aagtgattct cttgcctcag tctcccgagt agtggaaatt acaggtgtgt | 2580 |
| gctaccacat cttgctagtt ttgtattttt agcagagatg ggggtttcac catgttggcc | 2640 |
| aggctagtct cgaactcctg acctcaggtg atccacctgc cttggcctcc caaagcactg | 2700 |
| ggattacaag catgagccac tgtgcccagc ctgttccact gacatttctt agacattcag | 2760 |
| caaaaccccc accttaacct cttttctttc ttgagggttg gtcctgtccc cacctccacc | 2820 |
| ctcccacccc ctggaagagg aagggcccgg gcatcagtgg ctagtccaaa taaaatatgg | 2880 |
| gcttggggat ggaatgggtg gtggtaagtt cacagagtgt agttagatcc caactcccat | 2940 |
| gacctctggc ttcagtggtg ggtggggcag ggcagatgaa agggcttcag tgggaacctc | 3000 |
| tgagagcatt ttcctgttcc ccctatcaac cgcccccagt gataacatct gtgaagccag | 3060 |
| ccattactca ataaactgca aacttgtcta aaaaaaaaa aaaaaaaaaa aaaaaaaaa | 3120 |
| aaaaaaaaa | 3129 |

<210> SEQ ID NO 21
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 21

| | |
|---|---|
| caucacgcgg gcaguc | 16 |

<210> SEQ ID NO 22
<211> LENGTH: 2882
<212> TYPE: DNA
<213> ORGANISM: Mus musculus

<400> SEQUENCE: 22

| | |
|---|---|
| gggcccttca cctctgaccc aaaatggccg cgcccagagc gtagttcttt gcttctccga | 60 |
| ggcgagctaa gattaaaatc ctacatcatg tccaagctaa gccgggccac tcggaccctc | 120 |
| aagaagcccg aggccggcgg cgtgatccgg tccatcgtgc gagcaggcca agctattcct | 180 |
| gggcctccac taggtcccat cttgggtcag cgaggtgtct ctatcaacca gttctgcaaa | 240 |
| gagttcaacg agaagacaaa ggacatcaaa gaaggcattc ccctgcctac aaaaattttt | 300 |
| ataaagcccg acaggacatt tgagctcaag attgggcagc ccactgtttc ttacttttg | 360 |
| aaggcagctg ctgggatcga aaggggggcc cggcatacag ggaaagaggt ggcaggcctg | 420 |
| gtgagtttga agcacgtata tgagattgcc tgtgtcaaag ctaaggatga tgcttttgcc | 480 |
| atgcaagatg tgcccctgtc ttctgtggtc cgttccatca ttggctctgc ccgttccctg | 540 |
| ggcattcgag tggtgaagga cctcagtgca gaagaactgg aggctttcca gaaggaacga | 600 |

-continued

```
gctgtgtttt tggctgctca gaaagaggca gatttggcag cccaggcaga agctgccaag      660
aagtgacccc aactttctac actctgagaa tttgaagtga gaggctgaga aaggggggcca     720 cagaggaagc tgagccaaag gacttcatgg caacccgatt tctagtttcc tgacatgttt      780
ctgtacattt gctgtgccag gggatcaagc ctgaataaat atcctttgtc atcaactctc      840
agcttctctc ctgagacccc agagatgggg accaatactg acagttccca gccttcacag      900
gtgtgagctg ccctacaggt gaacgcagcc tcaaccaagc aaattatcat gcccagtgcc      960
ttggtcagcc ttgtattata tcaaaataac caaagcttgg tgcttttataa agaaaaggta    1020 ttgatttggc ttctgattca tggtgctgga gtatggcaag gctcacttgc tgtatgacag     1080
catggtacag tggaaacagt cacatacata gggccatctg tgtgaggtag cctcacctgg     1140
accagtcccc gccttaaggc caacattagt gaaggttgga ctcccagacc cctccgccag     1200
accacacttt gatttattca ttttatatgt gactgttttg cctgcatata tgtgagtgca     1260
ctgtgtgcat gcttggtgtc tgtcagaaga gggtattgga tcccctggag ctggatttat     1320
gggtagttgt gaaccagtat gtggatcctg gagttgaacc tgggttctct gtaagagcaa     1380
caaacaagtg ctcttacctc ctgagccatc tctctactct atcccccttt tttgagatag     1440
gatctctgga tatccttgaa ctcacggaga tccacctgcc tctgccttcc acattgctgg     1500
gactaaagct tgcaccacca tacagggcat agcccccact tcttaaggat tccaccacct     1560
tccacactgg gaagcaagcc ttcagcccat gagcctccgg ggcacgtgtc gtaacattca     1620
ggctctgagt aggtacaagt ggagtagagc ccagggagaa atcctatgtt cagggttgaa     1680
gatgttgttt cctgatggag ctgctcctta cacaaagcct caacttctat tcccaacact     1740
tcagagcaca taagcctgtg ctcttccctc ggggatgaga gaaggcacag tcgatggggt     1800
ccacagacac taaggcttgg ctgtgttgct tgtcttttct tagtataact gttggggagt     1860
ttgtatctga gaagcaggag cctgacagag aattcagacc acagataggg ttatccttta     1920
tccaggggca gcttcaggcc tccctgctga gttgacatga ttgtttctga ggcagaatct     1980
cattatttag ccttggctgg cctgaaactg gctggctagg ctacagcctg acctctcagt     2040
gctccagtta aaggtgtgca ttaccccacc cggctcctta ctaagtttgg ttatttgctt     2100 tttaaaact tgccatttgg ggctggagag atggctcaga ggttaagagc actagctgct     2160
cttccagagg tcctgtgttc agttcccagc aaccacatgg tagctcatca ccatatatag     2220
tgagatctgg tgccctcctc tggcttgcag gtatacatgc aggcaaaaca ctacgtagta     2280
aatctataaa acaaaacttg ctggttttt tgttttttgtt tgttttgtt ttgttttaat      2340 gctgttggag atgaaaccca gggcctcatt cagccagagc caggactgtg tccctctcag     2400
ctctgcctct gccaagcttg tgaatctacc ctgggtcagg gagaacagcc gaatcacagc     2460
ccagacctac ataagtgaaa ttccagtaga cacctgcctg agaagtcctt gtggacccttt    2520 gacctgcctg agaagtcctt ggggacccct ggtctgcctg agaagtcctt ggggacccct     2580
ggtctgcctg agaagtcctt ggggacccct ggtctgcctg aaaagtcctt ggggggccctt    2640 gacctgcctg agaagtcctt ggggggccctt gacctcctgt tttcccattc tacaaaacat    2700
caagtgttct ctcagaagag aggcagaatt gacaggaaag atgaagtctg tgtttgccgt     2760
gtgttgcatg ctgggcatta tttttttgctt gttaacattc tgaacaattt agtcaaattt    2820
tcacatagta ttaatagttc aacattgttt actaatacaa ttaaaacttt tattacgtgt     2880
at                                                                    2882
```

<210> SEQ ID NO 23
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 23 cauuugggu cagaggug                                                    18

<210> SEQ ID NO 24
<211> LENGTH: 1923
<212> TYPE: DNA
<213> ORGANISM: Homo sapiens

<400> SEQUENCE: 24

| | | | | | |
|---|---|---|---|---|---|
| cagaagtggc | ccaggcaggc | gtatgacctg | ctgctgtgga | ggggctgtgc | cccaccgcca | 60 |
| catgtcttcc | tacccatctg | ctccccagag | ggctgcctgc | tgtgcacttg | ggtcctggag | 120 |
| cccttctcca | cccggataga | ttcttcaccc | ttggcccgcc | tttgccccac | cctactctgc | 180 |
| ccagaagtgc | aagagcctaa | gccgcctcca | tggccccagg | aaggattcag | gggagaggcc | 240 |
| ccaaacaggg | agccacgcca | gccagacacc | ccggccagaa | tggagctgac | tgaattgctc | 300 |
| ctcgtggtca | tgcttctcct | aactgcaagg | ctaacgctgt | ccagcccggc | tcctcctgct | 360 |
| tgtgacctcc | gagtcctcag | taaactgctt | cgtgactccc | atgtccttca | cagcagactg | 420 |
| agccagtgcc | cagaggttca | ccctttgcct | acacctgtcc | tgctgcctgc | tgtggacttt | 480 |
| agcttgggag | aatggaaaac | ccagatggag | gagaccaagg | cacaggacat | ctgggagca | 540 |
| gtgacccttc | tgctggaggg | agtgatggca | gcacggggac | aactgggacc | cacttgcctc | 600 |
| tcatccctcc | tggggcagct | ttctggacag | gtccgtctcc | tccttgggc | cctgcagagc | 660 |
| ctccttggaa | cccagcttcc | tccacagggc | aggaccacag | ctcacaagga | tcccaatgcc | 720 |
| atcttcctga | gcttccaaca | cctgctccga | ggaaaggtgc | gttcctgat | gcttgtagga | 780 |
| gggtccaccc | tctgcgtcag | gcgggcccca | cccaccacag | ctgtcccag | cagaacctct | 840 |
| ctagtcctca | cactgaacga | gctcccaaac | aggacttctg | gattgttgga | gacaaacttc | 900 |
| actgcctcag | ccagaactac | tggctctggg | cttctgaagt | ggcagcaggg | attcagagcc | 960 |
| aagattcctg | gtctgctgaa | ccaaaacctcc | aggtccctgg | accaaatccc | cggatacctg | 1020 |
| aacaggatac | acgaactctt | gaatggaact | cgtggactct | ttcctggacc | ctcacgcagg | 1080 |
| accctaggag | ccccggacat | ttcctcagga | acatcagaca | caggctccct | gccacccaac | 1140 |
| ctccagcctg | gatattctcc | ttccccaacc | catcctccta | ctggacagta | tacgctcttc | 1200 |
| cctcttccac | ccaccttgcc | caccctgtg | gtccagctcc | acccctgct | tcctgaccct | 1260 |
| tctgctccaa | cgcccaccccc | taccagcct | cttctaaaca | catcctacac | ccactcccag | 1320 |
| aatctgtctc | aggaagggta | aggttctcag | acactgccga | catcagcatt | gtctcgtgta | 1380 |
| cagctcccctt | ccctgcaggg | cgcccctggg | agacaactgg | acaagatttc | ctactttctc | 1440 |
| ctgaaaccca | aagccctggt | aaaagggata | cacaggactg | aaaagggaat | cattttcac | 1500 |
| tgtacattat | aaaccttcag | aagctatttt | tttaagctat | cagcaatact | catcagagca | 1560 |
| gctagctctt | tggtctattt | tctgcagaaa | tttgcaactc | actgattctc | tacatgctct | 1620 |
| ttttctgtga | taactctgca | aaggcctggg | ctggcctggc | agttgaacag | agggagagac | 1680 |
| taaccttgag | tcagaaaaca | gagaaagggt | aatttccttt | gcttcaaatt | caaggccttc | 1740 |
| caacgccccc | atccccttta | ctatcattct | cagtgggact | ctgatcccat | attcttaaca | 1800 |

-continued

```
gatctttact cttgagaaat gaataagctt tctctcagaa atgctgtccc tatacactag    1860
acaaaactga gcctgtataa ggaataaatg ggagcgccga aaagctccct aaaaagcaaa    1920
aaa                                                                 1923
```

<210> SEQ ID NO 25
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 25
cauggaggcg gcuuaggc                                                 18

<210> SEQ ID NO 26
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 26 guuucgacu cccggc                                                    16

<210> SEQ ID NO 27
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 27
caaaucgacu cccggc                                                   16

<210> SEQ ID NO 28
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 28
cauuaggacu cccggc                                                   16

<210> SEQ ID NO 29
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 29 cauuccucu cccggc                                                    16

<210> SEQ ID NO 30
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 30
cauuucgaga cccggc                                                   16

<210> SEQ ID NO 31
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 31
cauuucgacu ggcggc                                                     16

<210> SEQ ID NO 32
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 32
cauuucgacu ccgcgc                                                     16

<210> SEQ ID NO 33
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 33
cauuucgacu cccgcg                                                     16

<210> SEQ ID NO 34
<211> LENGTH: 12
<212> TYPE: RNA
<213> ORGANISM: Artificial sequence
<220> FEATURE:
<223> OTHER INFORMATION: Synthetic oligonucleotide

<400> SEQUENCE: 34
cauuucgacu cc                                                         12

<210> SEQ ID NO 35
<211> LENGTH: 14
<212> TYPE: RNA
<213> ORGANISM: Artificial sequence
<220> FEATURE:
<223> OTHER INFORMATION: Synthetic oligonucleotide

<400> SEQUENCE: 35
cauuucgacu cccg                                                       14

<210> SEQ ID NO 36
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 36
catttcgact cc                                                         12

<210> SEQ ID NO 37
<211> LENGTH: 14
<212> TYPE: DNA
<213> ORGANISM: Artificial sequence
<220> FEATURE:
<223> OTHER INFORMATION: Synthetic oligonucleotide

```
<400> SEQUENCE: 37
catttcgact cccg                                                      14

<210> SEQ ID NO 38
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 38
catttcgact cccggc                                                    16

<210> SEQ ID NO 39
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 39
catttcgact cccggccc                                                  18

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
catttcgact cccggcccag                                                20

<210> SEQ ID NO 41
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: bases at these positions are RNA
<220> FEATURE:
<221> NAME/KEY: misc_feature
<222> LOCATION: (17)..(18)
<223> OTHER INFORMATION: bases at these positions are RNA

<400> SEQUENCE: 41
cauuguuuuu ugucutcc                                                  18

<210> SEQ ID NO 42
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(14)
<223> OTHER INFORMATION: bases at these positions are RNA
<220> FEATURE:
<221> NAME/KEY: misc_feature
<222> LOCATION: (17)..(18)
<223> OTHER INFORMATION: bases at these positions are RNA

<400> SEQUENCE: 42
```
cauuguuuuu ugucuucc                                                            18

<210> SEQ ID NO 43
<211> LENGTH: 2419
<212> TYPE: DNA
<213> ORGANISM: Mus musculus

<400> SEQUENCE: 43

```
gggtcctgtc agcagcgcca caaagtcttc gagaagagaa gatggcctga gcactgtcaa      60
gccttgccgc gggactcaaa cttcatcagg cccacctcca ccccagccta cctgtgtggc     120
catcagcacg ggtccgctcc ccaacgccgg gttcccctcg atcactgtaa ctgcgatgct     180
ctggatccct tggatactcg aagaccaggc cagcgggctg tggatctaga ttgctgcgct     240
ctgcatccgg ggacagagtc cttggcccac ctctctccca cccgactctg ccgaaagaag     300
cacagaagct caagccgcct ccatggcccc aggaaagatt caggggagag gccccataca     360
gggagccact tcagttagac accctggcca aatggagct gactgatttg ctcctggcgg     420
ccatgcttct tgcagtggca agactaactc tgtccagccc cgtagctcct gcctgtgacc     480
ccagactcct aaataaactg ctgcgtgact cccacctcct tcacagccga ctgagtcagt     540
gtcccgacgt cgacccttg tctatccctg ttctgctgcc tgctgtggac tttagcctgg     600
gagaatggaa acccagacg gaacagagca aggcacagga cattctaggg gcagtgtccc     660
ttctactgga gggagtgatg gcagcacgag gacagttgga accctcctgc ctctcatccc     720
tcctgggaca gctttctggg caggttcgcc tcctcttggg ggccctgcag ggcctcctag     780
gaacccagct tcctctacag ggcaggacca cagctcacaa ggaccccaat gccctcttct     840
tgagcttgca caactgctt cggggaaagg tgcgcttcct gcttctggta aaggtcccaa     900
ccctctgtgt cagacggacc ctgccaacca cagctgtccc aagcagtact tctcaactcc     960
tcacactaaa caagttccca acaggacttt ctggattgtt ggagacgaac ttcagtgtca    1020
cagccagaac tgctggccct ggacttctga gcaggcttca gggattcaga gtcaagatta    1080
ctcctggtca gctaaatcaa acctccaggt ccccagtcca aatctctgga tacctgaaca    1140
ggacacacgg acctgtgaat ggaactcatg ggctcttttgc tggaacctca cttcagaccc    1200
tggaagcctc agacatctcg cccggagctt tcaacaaagg ctccctggca ttcaacctcc    1260
agggtggact tcctccttct ccaagccttg ctcctgatgg acacacaccc ttccctcctt    1320
cacctgcctt gcccaccacc catggatctc caccccagct ccaccccctg tttcctgacc    1380
cttccaccac catgcctaac tctaccgccc tcatccagt cacaatgtac cctcatccca    1440
ggaatttgtc tcaggaaaca tagcgcgggc actgggccag tgagcgtctg cagcttctct    1500
cggggacaag cttccccagg aaggctgaga ggcagctgca tctgctccag atgttctgct    1560
ttcacctaaa aggccctggg aagggatac acagcactgg agattgtaaa attttaggag    1620
ctatttttt ttaacctatc agcaatattc atcagagcag ctagcgatct ttggtctatt    1680
ttcggtataa atttgaaaat cactaattct ctatatgtgc tttcatacat taagtctgca    1740
aatgcctagg caggtcttgc cttttaaccc aggtagatgc tacaccatat cagaaaacaa    1800
aagggaactt tcctttgctt caagtttaag ccttcccgcg cctccaacac ccccacaatg    1860
ccctccttcc cttcactgta attctcagtg agactgtatg gtcctcgaga tatactgctc    1920
ttgataaaga attaacaggc tatcacttag aaagactgtc cctacttaag agacaaaact    1980
gaacctgtaa gagaataact gggagcaccc aaaagccaat aaaaatcagg gaccaatgtt    2040
cttcactggg gcaacagagc tcctggaccc tgcctcccaa gaaagctaac aggaagcctg    2100
```

```
ggagctccac accccaggta aggctgtgca gctggctcag taaagagcag acttggatgt    2160
ggcagctgag caaagagcat cagcagctca gcagggctc agccaggcct gggctcctgc     2220
ttccctcctg tggaggtcag gcggaagtgc aggaagtggc aagaggcagg ctcctcggct    2280
cacacagcag gacaagcaca gagcgcttga aggctcttta taatttccac aaatgcacct    2340
aaaaagcagc cctgtgtggc cactccaaac tttattggaa ccctcccaaa tgaaggcaga    2400
cttataggac tttccaacc                                                 2419
```

```
<210> SEQ ID NO 44
<211> LENGTH: 17
<212> TYPE: RNA
<213> ORGANISM: Artificial sequence
<220> FEATURE:
<223> OTHER INFORMATION: Synthetic oligonucleotide

<400> SEQUENCE: 44
cauggaggcg gcuugag                                                   17

<210> SEQ ID NO 45
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 45
gccgggaguc gaaaug                                                    16

<210> SEQ ID NO 46
<211> LENGTH: 23
<212> TYPE: DNA
<213> ORGANISM: Artificial sequence
<220> FEATURE:
<223> OTHER INFORMATION: Primer

<400> SEQUENCE: 46
cttgcaatga tgtcgtaatt tgc                                            23

<210> SEQ ID NO 47
<211> LENGTH: 23
<212> TYPE: DNA
<213> ORGANISM: Artificial sequence
<220> FEATURE:
<223> OTHER INFORMATION: Primer

<400> SEQUENCE: 47
tcgtcaacct tctgtaccag ctt                                            23

<210> SEQ ID NO 48
<211> LENGTH: 29
<212> TYPE: DNA
<213> ORGANISM: Artificial sequence
<220> FEATURE:
<223> OTHER INFORMATION: Probe

<400> SEQUENCE: 48
ttactctgtt ctcagcgaca gttgcctgc                                      29

<210> SEQ ID NO 49
<211> LENGTH: 21
<212> TYPE: DNA
<213> ORGANISM: Artificial sequence
<220> FEATURE:
```

```
<223> OTHER INFORMATION: Primer

<400> SEQUENCE: 49
gcttggcttc ttctggactc a                                               21

<210> SEQ ID NO 50
<211> LENGTH: 18
<212> TYPE: DNA
<213> ORGANISM: Artificial sequence
<220> FEATURE:
<223> OTHER INFORMATION: Primer

<400> SEQUENCE: 50
tcgcgagctt caccatga                                                   18

<210> SEQ ID NO 51
<211> LENGTH: 24
<212> TYPE: DNA
<213> ORGANISM: Artificial sequence
<220> FEATURE:
<223> OTHER INFORMATION: Probe

<400> SEQUENCE: 51
cgccacttgt ccgcttcaca ctcc                                            24

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
cagcaggcaa ctgtcgctga                                                 20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
gtcatcgtca tcctcatcat                                                 20

<210> SEQ ID NO 54
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 54
aagaugacgc acgucu                                                     16

<210> SEQ ID NO 55
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 55
ggaagaugac gcacgu                                                     16
```

```
<210> SEQ ID NO 56
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 56
cgggaagaug acgcac                                                      16

<210> SEQ ID NO 57
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 57
cgcgggaaga ugacgc                                                      16

<210> SEQ ID NO 58
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 58
caccggcgcg ggaaga                                                      16

<210> SEQ ID NO 59
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 59
gucaccggcg cgggaa                                                      16

<210> SEQ ID NO 60
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 60
ccgucaccgg cgcggg                                                      16

<210> SEQ ID NO 61
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 61
uuccgucacc ggcgcg                                                      16

<210> SEQ ID NO 62
<211> LENGTH: 16
<212> TYPE: RNA
<213> ORGANISM: Artificial sequence
<220> FEATURE:
<223> OTHER INFORMATION: Synthetic oligonucleotide
```

```
<400> SEQUENCE: 62
acuuccguca ccggcg                                                      16

<210> SEQ ID NO 63
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 63
gcacuuccgu caccgg                                                      16

<210> SEQ ID NO 64
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 64
ccgcacuucc gucacc                                                      16

<210> SEQ ID NO 65
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 65
caccgcacuu ccguca                                                      16

<210> SEQ ID NO 66
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 66
aacaccgcac uuccgu                                                      16

<210> SEQ ID NO 67
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 67
ucaacaccgc acuucc                                                      16

<210> SEQ ID NO 68
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 68
gcucaacacc gcacuu                                                      16

<210> SEQ ID NO 69
<211> LENGTH: 16
```

```
<212> TYPE: RNA
<213> ORGANISM: Artificial sequence
<220> FEATURE:
<223> OTHER INFORMATION: Synthetic oligonucleotide

<400> SEQUENCE: 69
gcgcucaaca ccgcac                                                    16

<210> SEQ ID NO 70
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 70
cggcgcucaa caccgc                                                    16

<210> SEQ ID NO 71
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 71
gccggcgcuc aacacc                                                    16

<210> SEQ ID NO 72
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 72
ccgccggcgc ucaaca                                                    16

<210> SEQ ID NO 73
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 73
ggcgcgggaa gaugac                                                    16

<210> SEQ ID NO 74
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 74
cgagccgccg gcgcuc                                                    16

<210> SEQ ID NO 75
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 75
```
ggcgcgagcc gccggc 16

<210> SEQ ID NO 76
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 76
cgugggcgcg agccgc 16

<210> SEQ ID NO 77
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 77
ccagcguggg cgcgag 16

<210> SEQ ID NO 78
<211> LENGTH: 1568
<212> TYPE: DNA
<213> ORGANISM: Homo sapiens

<400> SEQUENCE: 78
actgcgcagg cgcgcgggc aagagggtgg cagtgcgcct gcgccgcgtc ggcgtgcgga 60
acgccgcggt gtctcggcgc ctctgcgcgc gggaagatgg cggaacaggc taccaagtcc 120
gtgctgtttg tgtgtctggg taacatttgt cgatcaccca ttgcagaagc agttttcagg 180
aaacttgtaa ccgatcaaaa catctcagag aattggaggg tagacagcgc ggcaacttcc 240
gggtatgaga tagggaaccc ccctgactac cgagggcaga gctgcatgaa gaggcacggc 300
attcccatga gccacgttgc ccggcagatt accaaagaag attttgccac atttgattat 360
atactatgta tggatgaaag caatctgaga gatttgaata gaaaaagtaa tcaagttaaa 420
acctgcaaag ctaaaattga actacttggg agctatgatc cacaaaaaca acttattatt 480
gaagatccct attatgggaa tgactctgac tttgagacgg tgtaccagca gtgtgtcagg 540
tgctgcagag cgttcttgga gaaggccac tgaggcaggt tcgtgccctg ctgcggccag 600
cctgactaga ccccacccctg aggtcctgca tttctcagtc ggtgtgtaat cacgttccag 660
ggcccaaagc ccagctcttt gttcagttga cttactgttt cttaccttaa aaagtaattg 720
tagatggaaa tcagttgtgt ttggcaggag aatcaataaa aatctttgat tcagacagct 780
tatggggtat tttaagcatt cttagactag ttgaacatct cactttgccc cagttacaaa 840
aatagtagaa caagcaacat aaaacaatga aggaaaacct cacttgaagg cccaggtcaa 900
catctaagcc tgttgagact tagataatcg agtctacctc ttcagtaggt ttgtgtggat 960
ggcctggagg gcaggtgccc tctgctcccc agtgctacct ctctcttccc tagggccttt 1020
tgtggattga cagtagtccc ctccgtagga gctcacagtc tagattagaa gtgtttttaat 1080
ttctacacac ccatagtgca cacttgtata ttgaaaagat agggaagaga gaaacattta 1140
tggaatcagt cgttggcacc ttcaatactt catgatttt gtcgagttta cttcatgagg 1200
aggtcagccc attggctccc atctgaacca ctttgcctct gaaacttaat tacatccaga 1260
aagaaggaca cttgtatgct agtctatggt cagttgagga atatgactgt ttttatatgc 1320
acatgtaacc caaatgtcca atataaattg gcttattttt taaaataatt ttaaaagttg 1380

```
ggaaaagtgt tattatttgg catgcttaaa tattgaataa gtattcttca tcagcattta    1440
ataaatgtat aggcagatgt aaggtaattt ctgtgtattt tgagataatg tcaaaatcat    1500
gaatatttca aaataaactg gggagttata aaaatacaac tagagatata aaaaaaaaaa    1560
aaaaaaaa                                                             1568
```

<210> SEQ ID NO 79
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 79

```
cgacgcggcg caggcg                                                      16
```

<210> SEQ ID NO 80
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 80

```
gcgcaggcgc acugccac                                                    18
```

<210> SEQ ID NO 81
<211> LENGTH: 6132
<212> TYPE: DNA
<213> ORGANISM: Homo sapiens

<400> SEQUENCE: 81

```
aattggaagc aaatgacatc acagcaggtc agagaaaaag ggttgagcgg caggcaccca      60
gagtagtagg tctttggcat taggagcttg agcccagacg gccctagcag ggaccccagc     120
gcccgagaga ccatgcagag gtcgcctctg gaaaaggcca gcgttgtctc caaactttt     180 ttcagctgga ccagaccaat tttgaggaaa ggatacagac agcgcctgga attgtcagac    240
atataccaaa tcccttctgt tgattctgct gacaatctat ctgaaaaatt ggaaagagaa    300
tgggatagag agctggcttc aaagaaaaat cctaaactca ttaatgccct tcggcgatgt    360
tttttctgga gatttatgtt ctatggaatc tttttatatt taggggaagt caccaaagca    420
gtacagcctc tcttactggg aagaatcata gcttcctatg acccggataa caaggaggaa    480
cgctctatcg cgatttatct aggcataggc ttatgccttc tctttattgt gaggacactg    540
ctcctacacc cagccatttt tggccttcat cacattggaa tgcagatgag aatagctatg    600
tttagtttga tttataagaa gactttaaag ctgtcaagcc gtgttctaga taaataagt    660 attggacaac ttgttagtct cctttccaac aacctgaaca aatttgatga aggacttgca    720
ttggcacatt tcgtgtggat cgctcctttg caagtgcac tcctcatggg gctaatctgg    780
gagttgttac aggcgtctgc cttctgtgga cttggtttcc tgatagtcct tgccctttt    840 caggctgggc tagggagaat gatgatgaag tacagagatc agagagctgg gaagatcagt    900
gaaagacttg tgattacctc agaaatgatt gaaaatatcc aatctgttaa ggcatactgc    960
tgggaagaag caatggaaaa aatgattgaa aacttaagac aaacagaact gaaactgact   1020
cggaaggcag cctatgtgag atacttcaat agctcagcct tcttcttctc agggttcttt   1080
gtggtgtttt tatctgtgct tccctatgca ctaatcaaag gaatcatcct ccggaaaata   1140
```

```
ttcaccacca tctcattctg cattgttctg cgcatggcgg tcactcggca atttccctgg    1200
gctgtacaaa catggtatga ctctcttgga gcaataaaca aaatacagga tttcttacaa    1260
aagcaagaat ataagacatt ggaatataac ttaacgacta cagaagtagt gatggagaat    1320
gtaacagcct tctgggagga gggatttggg gaattatttg agaaagcaaa acaaaacaat    1380
aacaatagaa aaacttctaa tggtgatgac agcctcttct tcagtaattt ctcacttctt    1440
ggtactcctg tcctgaaaga tattaatttc aagatagaaa gaggacagtt gttggcggtt    1500
gctggatcca ctggagcagg caagacttca cttctaatgg tgattatggg agaactggag    1560
ccttcagagg gtaaaattaa gcacagtgga agaatttcat tctgttctca gttttcctgg    1620
attatgcctg gcaccattaa agaaaatatc atctttggtg tttcctatga tgaatataga    1680
tacagaagcg tcatcaaagc atgccaacta gaagaggaca tctccaagtt tgcagagaaa    1740
gacaatatag ttcttggaga aggtggaatc acactgagtg gaggtcaacg agcaagaatt    1800
tctttagcaa gagcagtata caaagatgct gatttgtatt tattagactc tccttttgga    1860
tacctagatg ttttaacaga aaaagaaata tttgaaagct gtgtctgtaa actgatggct    1920
aacaaaacta ggattttggt cacttctaaa atggaacatt taaagaaagc tgacaaaata    1980
ttaattttgc atgaaggtag cagctatttt tatgggacat tttcagaact ccaaaatcta    2040
cagccagact ttagctcaaa actcatggga tgtgattctt tcgaccaatt tagtgcagaa    2100
agaagaaatt caatcctaac tgagaccctta caccgtttct cattagaagg atgctcct    2160 gtctcctgga cagaaacaaa aaaacaatct tttaaacaga ctggagagtt tggggaaaaa    2220
aggaagaatt ctattctcaa tccaatcaac tctatacgaa aatttccat tgtgcaaaag    2280 actcccttac aaatgaatgg catcgaagag gattctgatg agcctttaga gagaaggctg    2340
tccttagtac cagattctga gcagggagag gcgatactgc ctcgcatcag cgtgatcagc    2400
actggcccca cgcttcaggc acgaaggagg cagtctgtcc tgaacctgat gacacactca    2460
gttaaccaag gtcagaacat tcaccgaaag acaacagcat ccacacgaaa agtgtcactg    2520
gcccctcagg caaacttgac tgaactggat atatattcaa gaaggttatc tcaagaaact    2580
ggcttggaaa taagtgaaga aattaacgaa gaagacttaa aggagtgctt ttttgatgat    2640
atggagagca taccagcagt gactacatgg aacacatacc ttcgatatat tactgtccac    2700
aagagcttaa ttttttgtgct aatttggtgc ttagtaattt ttctggcaga ggtggctgct    2760
tctttggttg tgctgtggct ccttggaaac actcctcttc aagacaaagg gaatagtact    2820
catagtagaa ataacagcta tgcagtgatt atcaccagca ccagttcgta ttatgtgttt    2880
tacatttacg tgggagtagc cgacactttg cttgctatgg gattcttcag aggtctacca    2940
ctggtgcata ctctaatcac agtgtcgaaa atttttacacc acaaaatgtt acattctgtt    3000
cttcaagcac ctatgtcaac cctcaacacg ttgaaagcag gtgggattct taatagattc    3060
tccaaagata tagcaatttt ggatgacctt ctgcctctta ccatatttga cttcatccag    3120
ttgttattaa ttgtgattgg agctatagca gttgtcgcag ttttacaacc ctacatcttt    3180
gttgcaacag tgccagtgat agtggctttt attatgttga gagcatattt cctccaaacc    3240
tcacagcaac tcaaacaact ggaatctgaa ggcaggagtc caattttcac tcatcttgtt    3300
acaagcttaa aaggactatg gacacttcgt gccttcggac ggcagcctta ctttgaaact    3360
ctgttccaca agctctgaa tttacatact gccaactggt tcttgtacct gtcaacactg    3420
cgctggttcc aaatgagaat agaaatgatt tttgtcatct tcttcattgc tgttaccttc    3480
atttccattt taacaacagg agaaggagaa ggaagagttg gtattatcct gactttagcc    3540
```

```
atgaatatca tgagtacatt gcagtgggct gtaaactcca gcatagatgt ggatagcttg    3600
atgcgatctg tgagccgagt ctttaagttc attgacatgc aacagaagg taaacctacc    3660 aagtcaacca aaccatacaa gaatggccaa ctctcgaaag ttatgattat tgagaattca    3720
cacgtgaaga aagatgacat ctggccctca ggggggccaaa tgactgtcaa agatctcaca    3780
gcaaaataca cagaaggtgg aaatgccata ttagagaaca tttccttctc aataagtcct    3840
ggccagaggg tgggcctctt gggaagaact ggatcaggga gagtactttt gttatcagct    3900
tttttgagac tactgaacac tgaaggagaa atccagatcg atggtgtgtc ttgggattca    3960
ataactttgc aacagtggag gaaagccttt ggagtgatac cacagaaagt atttattttt    4020
tctggaacat ttagaaaaaa cttggatccc tatgaacagt ggagtgatca agaaatatgg    4080
aaagttgcag atgaggttgg gctcagatct gtgatagaac agtttcctgg aagcttgac    4140 tttgtccttg tggatggggg ctgtgtccta agccatggcc acaagcagtt gatgtgcttg    4200
gctagatctg ttctcagtaa ggcgaagatc ttgctgcttg atgaacccag tgctcatttg    4260
gatccagtaa cataccaaat aattagaaga actctaaaac aagcatttgc tgattgcaca    4320
gtaattctct gtgaacacag gatagaagca atgctgaat gccaacaatt tttggtcata    4380
gaagagaaca aagtgcggca gtacgattcc atccagaaac tgctgaacga gaggagcctc    4440
ttccggcaag ccatcagccc ctccgacagg gtgaagctct tccccaccg gaactcaagc    4500 aagtgcaagt ctaagcccca gattgctgct ctgaaagagg agacagaaga agaggtgcaa    4560
gatacaaggc tttagagagc agcataaatg ttgacatggg acatttgctc atggaattgg    4620
agctcgtggg acagtcacct catggaattg gagctcgtgg aacagttacc tctgcctcag    4680
aaaacaagga tgaattaagt ttttttttaa aaagaaaca tttggtaagg ggaattgagg    4740
acactgatat gggtcttgat aaatggcttc ctggcaatag tcaaattgtg tgaaaggtac    4800
ttcaaatcct tgaagattta ccacttgtgt tttgcaagcc agattttcct gaaaacccctt    4860 gccatgtgct agtaattgga aaggcagctc taaatgtcaa tcagcctagt tgatcagctt    4920
attgtctagt gaaactcgtt aatttgtagt gttggagaag aactgaaatc atacttctta    4980
gggttatgat taagtaatga taactggaaa cttcagcggt ttatataagc ttgtattcct    5040
ttttctctcc tctccccatg atgtttagaa acacaactat attgtttgct aagcattcca    5100
actatctcat ttccaagcaa gtattagaat accacaggaa ccacaagact gcacatcaaa    5160
atatgcccca ttcaacatct agtgagcagt caggaaagag aacttccaga tcctggaaat    5220
cagggttagt attgtccagg tctaccaaaa atctcaatat ttcagataat cacaatacat    5280
cccttacctg ggaaagggct gttataatct ttcacagggg acaggatggt tcccttgatg    5340
aagaagttga tatgcctttt cccaactcca gaaagtgaca agctcacaga cctttgaact    5400
agagtttagc tggaaaagta tgttagtgca aattgtcaca ggacagccct tctttccaca    5460
gaagctccag gtagagggtg tgtaagtaga taggccatgg gcactgtggg tagacacaca    5520
tgaagtccaa gcatttagat gtataggttg atggtggtat gttttcaggc tagatgtatg    5580
tacttcatgc tgtctacact aagagagaat gagagacaca ctgaagaagc accaatcatg    5640
aattagtttt tatgcttct gttttataat tttgtgaagc aaaatttttt ctctaggaaa    5700
tatttatttt taataatgttt caaacatata taacaatgct gtattttaaa agaatgatta    5760
tgaattacat ttgtataaaa taattttat atttgaaata ttgacttttt atggcactag    5820
tatttctatg aaatattatg ttaaaactgg gacaggggag aacctagggt gatattaacc    5880
```

```
aggggccatg aatcaccttt tggtctggag ggaagccttg gggctgatgc agttgttgcc    5940
cacagctgta tgattcccag ccagcacagc ctcttagatg cagttctgaa gaagatggta    6000
ccaccagtct gactgtttcc atcaagggta cactgccttc tcaactccaa actgactctt    6060
aagaagactg cattatattt attactgtaa gaaaatatca cttgtcaata aaatccatac    6120
atttgtgtga aa                                                        6132

<210> SEQ ID NO 82
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 82
uucucugacc ugcuguga                                                  18

<210> SEQ ID NO 83
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 83
ccaaagaccu acuacucu                                                  18

<210> SEQ ID NO 84
<211> LENGTH: 14
<212> TYPE: RNA
<213> ORGANISM: Artificial sequence
<220> FEATURE:
<223> OTHER INFORMATION: Synthetic oligonucleotide

<400> SEQUENCE: 84
aggcgcacug ccac                                                      14

<210> SEQ ID NO 85
<211> LENGTH: 14
<212> TYPE: RNA
<213> ORGANISM: Artificial sequence
<220> FEATURE:
<223> OTHER INFORMATION: Synthetic oligonucleotide

<400> SEQUENCE: 85
gcaggcgcac ugcc                                                      14

<210> SEQ ID NO 86
<211> LENGTH: 14
<212> TYPE: RNA
<213> ORGANISM: Artificial sequence
<220> FEATURE:
<223> OTHER INFORMATION: Synthetic oligonucleotide

<400> SEQUENCE: 86
gcgcaggcgc acug                                                      14

<210> SEQ ID NO 87
<211> LENGTH: 14
<212> TYPE: RNA
<213> ORGANISM: Artificial sequence
<220> FEATURE:
<223> OTHER INFORMATION: Synthetic oligonucleotide

<400> SEQUENCE: 87
```

```
cggcgcaggc gcac                                                        14

<210> SEQ ID NO 88
<211> LENGTH: 14
<212> TYPE: RNA
<213> ORGANISM: Artificial sequence
<220> FEATURE:
<223> OTHER INFORMATION: Synthetic oligonucleotide

<400> SEQUENCE: 88
cgcggcgcag gcgc                                                        14

<210> SEQ ID NO 89
<211> LENGTH: 14
<212> TYPE: RNA
<213> ORGANISM: Artificial sequence
<220> FEATURE:
<223> OTHER INFORMATION: Synthetic oligonucleotide

<400> SEQUENCE: 89
gacgcggcgc aggc                                                        14

<210> SEQ ID NO 90
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 90
gcaggcgcac ugccac                                                      16

<210> SEQ ID NO 91
<211> LENGTH: 3107
<212> TYPE: DNA
<213> ORGANISM: Mus musculus

<400> SEQUENCE: 91
atgtccacgg tcagaaccct ggcagtgcgc atgcgcctcg tcccgacgcg gtttctgggc      60
gccagggtct gcaccgaaac atggcagagg ttgggtccaa gtcagtgctg ttcgtgtgtc     120
tcggtaacat ttgccggtca cccattgcag aagcagtatt caggaaactg gtaactgatg     180
aaaaggtttc agataattgg aggatagaca gtgcggctac atccacctat gaagtgggga     240
accctcctga ctatcgaggg cagaactgca tgagaaaaca tggcatccac atgcagcaca     300
ttgcacggca gattacaaaa gaagactttg ccacattcga ttatatacta tgtatggatg     360
aaagcaatct gagagatctc aatagaaaaa gtaatcaagt taaaaactgc aaagctaaaa     420
ttgagctact tgggagctat gatccacaga acagctcat cattgaagat ccctattatg      480
gcaatgactc tgacttcgag gtggtgtacc agcaatgcct taggtgctgc aaggccttcc     540
tggagaagac ttactagctg gtcctaagcc ccaccattga gcagctcact catcagtgct     600
gtgcccaagg gtggtggcag tccttagccc catacccac ctctcttttc agctgactta      660
ctgtatatct ttaaaataat tgtaggtggg aattaggcat atgttcagaa ggataaaagc     720
atttgagtca gacagtttga ggtgtggcta agcattctta gactaactaa acctctgacc     780
ttgcggtgat tacaaaacag tggaacaagc aaatatggaa caaagaaaaa caaaacaaa      840 aacaaaaacc cagaaagtaa gagtgaccta gaaggtccat atcagcctct gagctcggca     900
agcctgggtc gtctggtcta agtggagtgt gtgcatgacc cgcacccagt gtgccgtttg     960
```

```
cttgccgtgt actctcttct ctaggctctc gttgtgacaa tagctccatt cacggcagcc    1020
ttccagttaa cactggcagt ttaagctcag acacactgag ggtgttgagg gatttgagag    1080
aggagacgct ggatgtgctg atgggcctgg gactccagca ggccgtcctg ggctggacag    1140
tgacaccctg tctaaaaggg gaacaaaaat aacaacggat gggagcagca gatggataaa    1200
gttaccatct tcagtcttac ttggttttg tctactttcc tgagctttgt tcttgtttga    1260
gccactttgc tttaaaaaaa aagtaagtgt gcttaaatac tggtatgtgt ttgtaagtgt    1320
tctctcatgg gcaatttaca aagttatagg caagcaagag taattttgt gtattttcag    1380 aaaagagacc tcaaatttat atgaatgtat gtcagaaagg aacatgaatt caactgggaa    1440
gttatcaaat acaactgaga tacaaatcca gtgtctgcct gcttcttact gacaagtgaa    1500
caagatacct aaatgttgcc tccatgtgcc tttttatttg cttgagtgtg aagtttgggc    1560
tctcagcctc tgtgttagaa agtaaagtga tgagatggat acacacaatg ctgtgttgga    1620
tggcgatggg tgtctaattg agagactcca ggcactatcc ttatccttgg gccttcttca    1680
tgtagctggt gctccctacc cgcttcccag ctgaaaaggt ggtaactgtc tgtcttagcc    1740
tgtcttagct caggtcacta ctggtgagct ccagtcacgc agaacttgta gttagaagag    1800
ccatcctgac gtctgaaagg aaggaagccc aggggcctag gaatatgcag tctcttcttg    1860
gccagggctc ctctctcgaa ggaggaaagc ttacacctga ctcttccaga agaaagcagc    1920
tatcccagca ccctctcaca gaaaggccat gatgtcccag caaaggcaga cacttcagct    1980 gccttttgg gctcctgtgg ggttttggtc agagtcttca caaaattaaa accgaggaag    2040
ggagaggaca ggtagtcagc cacaaggagg aaatggatta agtcaaagct ctccaccta    2100 cttcagtgct tgcttcagaa tctcagattt ctctttcagg tcataagatc ctattgtttt    2160
cttgaaattt tacctgtgta tcttacacgc agatccttgg aatgtcaggt tctgctttgt    2220
tctacggctg tctcaaacag cacagtgtgt ttataagggc tcatgaacag agaaattaac    2280
tttttacatt caatcaaatt acatttgttt aaaatacagc cattaaattt taaaactgtt    2340
ctcagggtgc ttcttggtttt gacattctct tacaatcagg tagagatggt agatgtggag    2400
tattgatggc taaatgagac caagcgatca ggagtttatg ttattcagta cttagtcaca    2460
tctacacaca cacacacgca cacgtgtata tatatagtga acaatgtgta tgtatgttta    2520
tatatacata tattctgagc cttgacattg ttatttaaga gtcattctga agactgttca    2580
ttattccaaa cacttcattt atttccttgt atttattcac agtatttaca tattgtacaa    2640
tacctggaat gtacttttac atttacagag gacaagtggg actggccttg gcatagccac    2700
agatacatat gccactgttt tcaacacaac tgaggttttt ttggttttca ttaaaatttt    2760
tcatgcagtt ccaaactata ctttgggatt ttaattgtag aatacaaaat gtcaaatcat    2820
actatatgct ctatgaaaat acagtttaat gttctgccta tgtttctaaa gaaatattcc    2880
ttgtggttcc acctaatctt aaaagaaaa tacctcattt tacagaacaa tacatcaaat    2940
gtggaatgtt gtctgttttt acaatcataa gagtggcaaa tctcactgac agatacactg    3000
attcactgaa tgcatatttg taaactgtca gcaacataga aaatgcaaag gaattatgga    3060
agagtgcaaa aataaatctc tgtccacagg aagtgggcat gaagatg                 3107
```

<210> SEQ ID NO 92
<211> LENGTH: 15
<212> TYPE: RNA
<213> ORGANISM: Artificial sequence
<220> FEATURE:
<223> OTHER INFORMATION: Synthetic oligonucleotide

<400> SEQUENCE: 92
gcaugcgcac ugcca    15

<210> SEQ ID NO 93
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 93
gcaugcgcac ugccag    16

<210> SEQ ID NO 94
<211> LENGTH: 1799
<212> TYPE: DNA
<213> ORGANISM: Mus musculus

<400> SEQUENCE: 94

```
ggcgtgcccc gcggcaggcg ctgacgtggc tgccgtcagc gccgccatct tgtgggagcg      60
aaaccaacgc ctggctggga gcagccgccg cggaggtctt tggccagtat cgattccacc     120
tgtccacaaa catggggaat atctttgcaa acctcttcaa gggccttttt ggcaaaaaag     180
aaatgcgcat tctcatggtg ggcctggatg ctgcagggaa gacaacaatt ctatacaaac     240
ttaagctggg cgaaattgtg accaccattc ccaccattgg tttcaatgtg gagactgttg     300
aatacaagaa tatcagcttc accgtgtggg atgtgggcgg ccaggacaag atccggccgc     360
tgtggcgcca ctacttccag aacacccaag cttgatctt cgtagtggac agcaatgaca     420
gagagcgtgt gaacgaggcc cgtgaagagc tcatgaggat gctagctgaa gatgagctcc     480
gagatgctgt tctcttggtg tttgccaaca gcaggacct ccccaatgcc atgaatgcgg      540
ccgaaatcac agacaagctg gggctgcact ctctacgcca caggaactgg tacattcagg     600
ccacctgtgc caccagcggg gacgggctct atgaaggact agattggctg tctaatcagc     660
tccggaacca gaagtgaacc agaccctctc ctcccctca cttcctcttc tccgccctca      720
gctttcctct catgtggcaa acgtgcgact ctgtggtcct gagtgccaga agctgtctcc     780
atgggttggt cacagtgtgc atcgcaccgt gctgtacatg tgcagacgca gcctgcagcc     840
aggttttat ttaatgtaaa tagtttctgt ttccactgag gcagtttctg gtactcctat      900
gcaatattac ttagcttttt tattgtaaaa agagaatcaa ctcaactgtc agtactgaga     960
agggatttgg gtgtagggc acctggcctc cgggagccat tgggctgtag actggtgtcg    1020
gtatccattt ggtggttggt ttttaaccca aactcagtgc atttttaaa aatagttaaa    1080
aatacaggac aagaacactt gaacacacag aacgagact atgcctagtg taggttttgc    1140
agttaatggc ctgaatgcta gatatcagat cacctgtttc gctgtgggaa caggagagaa    1200
ggtgatgaac aaaccaccat ccgctgcatg gtcacagtag agccccgtg actcgcctgt    1260
ctttgggtca cctgcattcc atagcattgt gcttgtactt gtgctcacac ggttacctag    1320
ggtaggctgg gagccattgt ggggtgcagg gcctggcttg tacttggtgt gtgcaaggcc    1380
caatggcagc ctgcataccc agcctactct tgggcccact tggacgcgct ggcaggaggc    1440
ctgggtctca ccagcaggag tgcgtgcaag gtgggagggt cggtccatta cagacccaca    1500
tcctggagca ccccccatctc catgtgtgaa gtagcttcct ccctcagcct gcaagggtcc    1560
gatttgccat cgaaagacga cctctacttt tttcttttgt atttttgataa acactgaaga    1620
```

-continued

| | |
|---|---|
| agctggagct gttaaattta tcttggggaa atctcagaac tggtttattt ggtgtcgtgg | 1680 |
| aacctcttac cgctttcaat acacaattag taatcaactg ttttgtatac ttgttttcag | 1740 |
| ttttcatttc gacaagcact gtaattatag ctgttagaat aaagtctctt aactatttg | 1799 |

<210> SEQ ID NO 95
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 95

| | |
|---|---|
| cgctcccaca agatggc | 17 |

<210> SEQ ID NO 96
<211> LENGTH: 2926
<212> TYPE: DNA
<213> ORGANISM: Mus musculus

<400> SEQUENCE: 96

| | |
|---|---|
| tctccgggag ggtggctggt tccaccgcgt cgctctctct gcgtcacctg gaggaagcgg | 60 |
| agctggcggc cggctccggg cccgtcgcgg gaggcagtta tgggcgccgt cgccccggat | 120 |
| tgtaactttg tgtcagcgtg cagtccataa agtgccagca tggggaagaa acggaccaag | 180 |
| gggagaagtg ctccagacac ggtggcctca gagtctgcag aaccagtgtg cagacacctt | 240 |
| agaaaagggt tggaacaagg taatttgaaa aaagctttag taaatgtgga gtggaatatc | 300 |
| tgccaagact gtaagactga caataaagtg aaagataaac ctgaggagga agcagaagac | 360 |
| ccttcggttt ggctctgtct taaatgtggc catcagggct gtggcagaga ttctcaggag | 420 |
| cagcatgcct tgaagcacta cacgacaccg agatccgagc tcactaccct ggtgctcagt | 480 |
| ctggacaact ggagcgtctg gtgctacaag tgtgacgagg aagtcaagta ctgtagctca | 540 |
| aaccgattgg gccaagtggt tgattatgtt agaaaacaag ctggcgtaag aacttcaaaa | 600 |
| ccagcagaga aaataatgg acacattgag ctcgaaaata aaaattgga gaagagagt | 660 |
| aaaaatgaac aagagagaga gaaatcggaa aacctggcta agaaaactat tcccatggac | 720 |
| tctgcttccc agataactgt gaaaggactc agtaatttgg ggaatacttg ttcttcaat | 780 |
| gcagttatgc agaacttgtc acaaacgcca gtgcttagag aactactaaa agaagtgaag | 840 |
| atgtctggaa cgattgtaaa aatagagcca cctgatctgg cactaacaga acctttagaa | 900 |
| gtaaacctcg agcctccagg tcctcttact ttagccatga gccagtttct cagtgagatg | 960 |
| caagagaaca aaaagcgagt tgtgacacct aaagagctct tttctcaggt ctgtaaaaaa | 1020 |
| gcaacacgtt ttaagggta ccagcaacaa gacagccagg agctgcttcg ctacctactg | 1080 |
| gatgggatga gagcggaaga acaccaaaga gtgagtaaag gaattcttaa agcatttggt | 1140 |
| aattctactg aaaaattgga tgaagaagta aaaaataaag ttaaagatta tgaaaagaaa | 1200 |
| aaggcaatcc cgagttttgt ggaccgcatc tttggtggcg agctgactag tacgatcatg | 1260 |
| tgtgatgaat gcaggactgt ctccttagtg catgaatcgt tccttgattt gtctcttcca | 1320 |
| gttttagatg atcagagtgg taagaaaagt ataaatgata aaaatgtgaa aatgacaatg | 1380 |
| gaggaagaag ataaagacag tgaggaagag aaagatgaca gctacatgaa atcaaggagc | 1440 |
| gatcttccgt cagggacaag caagcaccta cagaaaaagg caagaagca ggccaaaaag | 1500 |
| caggccaaga accaacgaag gcaacaaaaa attcaagaaa gatttcttca cttcaatgag | 1560 |
| ctctgcgcca ctgactacac ggaagacaat gaacgtgaag ctgacacagc acttgcggga | 1620 |

```
gaagtggaag tggataccga ctccacccat ggttctcaag aggaggccac acagatagag    1680
ctgtctgtta accagaagga tttggatggc caagagagca tgatagaaag gacacctgat    1740
gtgcaggaaa gcccagagga cctaggagtg aaaagtgcta acaccgagag tgatctgggg    1800
attgtgacgc ctgctcctga atgtcctagg gatttcaatg gtgccttcct ggaagaaagg    1860
accagtggag aactagacat tatcaatggt ttaaaaaacc ttaatttgaa tgctgctgtt    1920
gatcctgatg aaataaatat agagattccg aatgacagtc attctgcacc caaggtatat    1980
gaggtcatga acgaggaccc agaaactgct ttctgtaccc tcgcgaaccg agaagcgttt    2040
agtactgatg agtgttccat tcaacattgc ttatatcagt tcacccggaa tgagaaactt    2100
caagatgcca ataaactgct ttgtgaagtg tgttcaagac ggcagtgtaa tggaccaaag    2160
gcaaatataa aaggtgacag agacatgtt tacaccaatg ccaagaagca gatgctggtc    2220
tccctcgcgc tcctgtcct cactctgcat ttaaagcgat tccagcaggc tggttttaac    2280
ctgcgcaaag ttaacaaaca cataaagttt ccagaaatct tagatttggc tccttttgt    2340 acccttaaat gtaagaatgt tgctgaagaa agtacacgag tgctgtattc cttatatgga    2400
gttgttgaac acagtggtac tatgaggtca gggcattaca ctgcctatgc gaaggagaga    2460
actgcaagct gtcacctctc caatcttgtt cttcacggtg acattccaca agattgtgaa    2520
atggaatcaa ccaaagggca gtggtttcac atcagcgata cacatgtgca agctgtgcct    2580
ataactaaag tactgaactc acaagcgtat ctcctatttt atgagagaat actgtgataa    2640 caaaagtgc tttctctgga aatacaccta tggcttttat actggctatt ataacaataa    2700
aaagttaaac tataaattat gttcacctaa gtaaatgaca gaaaaaaaat catgtttatt    2760
tatttaaata caggcaaaat aatttacagc ggttttgtat tagcatactg gttttattc    2820 cttctagttt caactttagg aaggatttga ataactaagt tctgtgctta ctctgactgg    2880
gtggtagtgc ttgacacatc aataaactga tattcccaaa aaaaaa    2926

<210> SEQ ID NO 97
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 97
gagagcgacg cggtgga                                                    17

<210> SEQ ID NO 98
<211> LENGTH: 5292
<212> TYPE: DNA
<213> ORGANISM: Homo sapiens

<400> SEQUENCE: 98
ctcttgcagt gaggtgaaga catttgaaaa tcaccccact gcaaactcct ccccctgcta      60
gaaacctcac attgaaatgc tgtaaatgac gtgggccccg agtgcaatcg cgggaagcca     120
gggtttccag ctaggacaca gcaggtcgtg atccgggtcg ggacactgcc tggcagaggc     180
tgcgagcatg gggccctggg gctggaaatt gcgctgacc gtcgccttgc tcctcgccgc     240
ggcggggact gcagtgggcg acagatgcga aagaaacgag ttccagtgcc aagacgggaa     300
atgcatctcc tacaagtggg tctgcgatgg cagcgctgag tgccaggatg gctctgatga     360
gtcccaggag acgtgcttgt ctgtcacctg caaatccggg gacttcagct gtggggcg      420
```

```
tgtcaaccgc tgcattcctc agttctggag gtgcgatggc caagtggact gcgacaacgg    480
ctcagacgag caaggctgtc cccccaagac gtgctcccag gacgagtttc gctgccacga    540
tgggaagtgc atctctcggc agttcgtctg tgactcagac cgggactgct tggacggctc    600
agacgaggcc tcctgcccgg tgctcacctg tggtcccgcc agcttccagt gcaacagctc    660
cacctgcatc ccccagctgt gggcctgcga caacgacccc gactgcgaag atggctcgga    720
tgagtggccg cagcgctgta ggggtcttta cgtgttccaa ggggacagta gcccctgctc    780
ggccttcgag ttccactgcc taagtggcga gtgcatccac tccagctggc gctgtgatgg    840 tggcccccgac tgcaaggaca aatctgacga ggaaaactgc gctgtggcca cctgtcgccc    900
tgacgaattc cagtgctctg atggaaactg catccatggc agccggcagt gtgaccggga    960
atatgactgc aaggacatga gcgatgaagt tggctgcgtt aatgtgacac tctgcgaggg    1020
acccaacaag ttcaagtgtc acagcggcga atgcatcacc ctggacaaag tctgcaacat    1080
ggctagagac tgccgggact ggtcagatga acccatcaaa gagtgcggga ccaacgaatg    1140
cttggacaac aacggcggct gttcccacgt ctgcaatgac cttaagatcg gctacgagtg    1200
cctgtgcccc gacggcttcc agctggtggc ccagcgaaga tgcgaagata tcgatgagtg    1260
tcaggatccc gacacctgca gccagctctg cgtgaacctg gagggtggct acaagtgcca    1320
gtgtgaggaa ggcttccagc tggaccccca cacgaaggcc tgcaaggctg tgggctccat    1380
cgcctacctc ttcttcacca accggcacga ggtcaggaag atgacgctgg accggagcga    1440
gtacaccagc ctcatcccca acctgaggaa cgtggtcgct ctggacacgg aggtggccag    1500
caatagaatc tactggtctg acctgtccca gagaatgatc tgcagcaccc agcttgacag    1560
agcccacggc gtctcttcct atgacaccgt catcagcaga gacatccagg ccccgacgg    1620 gctggctgtg gactggatcc acagcaacat ctactggacc gactctgtcc tgggcactgt    1680
ctctgttgcg gataccaagg gcgtgaagag gaaaacgtta ttcagggaga cggctccaa    1740 gccaagggcc atcgtggtgg atcctgttca tggcttcatg tactgggctg actggggaac    1800
tcccgccaag atcaagaaag ggggcctgaa tggtgtggac atctactcgc tggtgactga    1860
aaacattcag tggcccaatg gcatcaccct agatctcctc agtggccgcc tctactgggt    1920
tgactccaaa cttcactcca tctcaagcat cgatgtcaac gggggcaacc ggaagaccat    1980
cttggaggat gaaagaggc tggcccaccc cttctccttg gccgtctttg aggacaaagt    2040
attttggaca gatatcatca cgaagccat tttcagtgcc aaccgcctca caggttccga    2100
tgtcaacttg ttggctgaaa acctactgtc cccagaggat atggttctct tccacaacct    2160
cacccagcca agaggagtga actggtgtga aggaccacc ctgagcaatg gcggctgcca    2220
gtatctgtgc ctccctgccc cgcagatcaa ccccactcg cccaagttta cctgcgcctg    2280
cccggacggc atgctgctgg ccagggacat gaggagctgc ctcacagagg ctgaggctgc    2340
agtggccacc caggagacat ccaccgtcag gctaaaggtc agctccacag ccgtaaggac    2400
acagcacaca accacccgac ctgttcccga cacctcccgg ctgcctgggg ccaccctggg    2460
gctcaccacg gtggagatag tgacaatgtc tcaccaagct ctgggcgacg ttgctggcag    2520
aggaaatgag aagaagccca gtagcgtgag ggctctgtcc attgtcctcc ccatcgtgct    2580
cctcgtcttc ctttgcctgg gggtcttcct tctatggaag aactggcggc ttaagaacat    2640
caacagcatc aactttgaca accccgtcta tcagaagacc acagaggatg aggtccacat    2700
ttgccacaac caggacggct acagctaccc ctcgagacag atggtcagtc tggaggatga    2760
cgtggcgtga acatctgcct ggagtcccgt ccctgcccag aaccctcct gagacctcgc    2820
```

```
cggccttgtt ttattcaaag acagagaaga ccaaagcatt gcctgccaga gctttgtttt    2880
atatatttat tcatctggga ggcagaacag gcttcggaca gtgcccatgc aatggcttgg    2940
gttgggattt tggtttcttc ctttcctcgt gaaggataag agaaacaggc ccgggggggac   3000 caggatgaca cctccatttc tctccaggaa gttttgagtt tctctccacc gtgacacaat    3060
cctcaaacat ggaagatgaa aggggagggg atgtcaggcc cagagaagca gtggctttc     3120 aacacacaac agcagatggc accaacggga cccctggcc ctgcctcatc caccaatctc     3180
taagccaaac ccctaaactc aggagtcaac gtgtttacct cttctatgca agccttgcta    3240
gacagccagg ttagccttg ccctgtcacc cccgaatcat gacccaccca gtgtctttcg     3300
aggtgggttt gtaccttcct taagccagga aagggattca tggcgtcgga atgatctgg    3360 ctgaatccgt ggtggcaccg agaccaaact cattcaccaa atgatgccac ttcccagagg    3420
cagagcctga gtcactggtc acccttaata tttattaagt gcctgagaca cccggttacc    3480
ttggccgtga ggacacgtgg cctgcaccca ggtgtggctg tcaggacacc agcctggtgc    3540
ccatcctccc gacccctacc cacttccatt cccgtggtct ccttgcactt tctcagttca    3600
gagttgtaca ctgtgtacat ttggcatttg tgttattatt ttgcactgtt ttctgtcgtg    3660
tgtgttggga tgggatccca ggccagggaa agcccgtgtc aatgaatgcc ggggacagag    3720
aggggcaggt tgaccgggac ttcaaagccg tgatcgtgaa tatcgagaac tgccattgtc    3780
gtctttatgt ccgcccacct agtgcttcca cttctatgca aatgcctcca agccattcac    3840
ttccccaatc ttgtcgttga tgggtatgtg tttaaaacat gcacggtgag gccgggcgca    3900
gtggctcacg cctgtaatcc cagcactttg ggaggccgag gcgggtggat catgaggtca    3960
ggagatcgag accatcctgg ctaacacgtg aaacccgtc tctactaaaa atacaaaaaa     4020
ttagccgggc gtggtggcgg gcacctgtag tcccagctac tcgggaggct gaggcaggag    4080
aatggtgtga acccgggaag cggagcttgc agtgagccga gattgcgcca ctgcagtccg    4140
cagtctggcc tgggcgacag agcgagactc cgtctcaaaa aaaaaaaaca aaaaaaacc     4200 atgcatggtg catcagcagc ccatggcctc tggccaggca tggcgaggct gaggtgggag    4260
gatggtttga gctcaggcat ttgaggctgt cgtgagctat gattatgcca ctgctttcca    4320
gcctgggcaa catagtaaga ccccatctct taaaaaatga atttggccag acacaggtgc    4380
ctcacgcctg taatcccagc actttgggag gctgagctgg atcacttgag ttcaggagtt    4440
ggagaccagg cctgagcaac aaagcgagat cccatctcta caaaaccaa aaagttaaaa     4500 atcagctggg tacggtggca cgtgcctgtg atcccagcta cttgggaggc tgaggcagga    4560
ggatcgcctg agcccaggag gtggaggttg cagtgagcca tgatcgagcc actgcactcc    4620
agcctgggca acagatgaag accctatttc agaaatacaa ctataaaaaa ataaataaat    4680
cctccagtct ggatcgtttg acgggacttc aggttctttc tgaaatcgcc gtgttactgt    4740
tgcactgatg tccggagaga cagtgacagc ctccgtcaga ctcccgcgtg aagatgtcac    4800
aagggattgg caattgtccc cagggacaaa acactgtgtc ccccccagtg cagggaaccg    4860
tgataagcct ttctggtttc ggagcacgta aatgcgtccc tgtacagata gtggggatt     4920 tttgttatgt ttgcacttg tatattggtt gaaactgtta tcacttatat atatatatat    4980
acacacatat atataaaatc tatttatttt tgcaaccct ggttgctgta tttgttcagt     5040
gactattctc ggggccctgt gtaggggggt attgcctctg aaatgcctct tctttatgta    5100
caaagattat ttgcacgaac tggactgtgt gcaacgcttt tgggagaat gatgtccccg     5160
```

-continued

```
ttgtatgtat gagtggcttc tgggagatgg gtgtcacttt ttaaaccact gtatagaagg    5220
tttttgtagc ctgaatgtct tactgtgatc aattaaattt cttaaatgaa ccaatttgtc    5280
taaaaaaaaa aa                                                         5292
```

```
<210> SEQ ID NO 99
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 99
ugcagugggg ugauuu                                                     16

<210> SEQ ID NO 100
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 100
ugcugugaug ucauuugc                                                   18

<210> SEQ ID NO 101
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(13)
<223> OTHER INFORMATION: bases at these positions are RNA

<400> SEQUENCE: 101
ugcagugggg ugattt                                                     16

<210> SEQ ID NO 102
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 102
ugcagugggg ugauuuuc                                                   18

<210> SEQ ID NO 103
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: bases at these positions are RNA
<220> FEATURE:
<221> NAME/KEY: misc_feature
<222> LOCATION: (18)..(18)
<223> OTHER INFORMATION: bases at these positions are RNA

<400> SEQUENCE: 103
ugcagugggg ugauuttc                                                   18
```

```
<210> SEQ ID NO 104
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(13)
<223> OTHER INFORMATION: bases at these positions are RNA
<220> FEATURE:
<221> NAME/KEY: misc_feature
<222> LOCATION: (18)..(18)
<223> OTHER INFORMATION: bases at these positions are RNA

<400> SEQUENCE: 104
ugcagugggg ugattttc                                                 18
```